US012509699B2

(12) United States Patent
Törjék et al.

(10) Patent No.: US 12,509,699 B2
(45) Date of Patent: Dec. 30, 2025

(54) **BEETS COMPRISING A GENE CONFERRING RESISTANCE TO *CERCOSPORA BETICOLA***

(71) Applicant: KWS SAAT SE & Co. KGaA, Einbeck (DE)

(72) Inventors: Otto Törjék, Einbeck (DE); Dietrich Borchardt, Einbeck (DE); Margaret Rekoske, Shakopee, MN (US); Wolfgang Mechelke, Einbeck (DE); Britta Schulz, Einbeck (DE); Jens Christoph Lein, Göttingen (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 0 days.

(21) Appl. No.: 19/055,088

(22) Filed: Feb. 17, 2025

(65) Prior Publication Data

US 2025/0223608 A1 Jul. 10, 2025

Related U.S. Application Data

(63) Continuation of application No. 18/161,613, filed on Jan. 30, 2023, which is a continuation of application No. 17/005,903, filed on Aug. 28, 2020, now Pat. No. 11,597,944, which is a continuation of application No. 16/793,503, filed on Feb. 18, 2020, now Pat. No. 10,767,191, which is a continuation of application No. PCT/EP2019/054008, filed on Feb. 18, 2019.

(30) Foreign Application Priority Data

Feb. 18, 2019 (EP) .................................... 19157888

(51) Int. Cl.
*C12N 15/82* (2006.01)
*A01H 6/02* (2018.01)

(52) U.S. Cl.
CPC ......... *C12N 15/8282* (2013.01); *A01H 6/024* (2018.05)

(58) Field of Classification Search
None
See application file for complete search history.

(56) References Cited

U.S. PATENT DOCUMENTS

| | | | | |
|---|---|---|---|---|
| 4,067,141 | A | 1/1978 | Matsunaga et al. | |
| 7,335,816 | B2 | 2/2008 | Kraus et al. | |
| 7,435,874 | B2 | 10/2008 | Gebhardt et al. | |
| 8,321,147 | B2 | 11/2012 | Bink et al. | |
| 9,029,635 | B2 | 5/2015 | Harms et al. | |
| 10,633,670 | B2 | 4/2020 | Kock et al. | |
| 10,767,191 | B1 * | 9/2020 | Törjék | A01H 6/024 |
| 11,597,944 | B2 * | 3/2023 | Törjék | A01H 5/06 |
| 2002/0139046 | A1 | 10/2002 | Weber et al. | |
| 2013/0227721 | A1 | 8/2013 | Becker | |
| 2014/0206850 | A1 | 7/2014 | Bundock | |
| 2014/0212877 | A1 | 7/2014 | Manley et al. | |
| 2016/0152999 | A1 | 6/2016 | Torjek et al. | |
| 2023/0227841 | A1 * | 7/2023 | Törjék | A01H 6/024 800/301 |

FOREIGN PATENT DOCUMENTS

| | | | |
|---|---|---|---|
| CN | 1555414 | A | 12/2004 |
| DE | 26 07 785 | A1 | 9/1976 |
| DE | 3442317 | A1 | 5/1986 |
| EP | 3696188 | A1 | 8/2020 |
| GB | 2 323 766 | A | 10/1998 |
| WO | 2018/202800 | A1 | 11/2018 |
| WO | 2020/064687 | A1 | 4/2020 |
| WO | 2020/152117 | A1 | 7/2020 |

OTHER PUBLICATIONS

International Search Report and Written Opinion issued in PCT/EP2019/054008 dated Apr. 15, 2019.

Third Party Observation in EP Application No. 20191416 mailed Dec. 12, 2024, submitted Dec. 6, 2024.

The European applications for Plant Variety Protection (PVP) and/or Seed Marketing Authorization of KWS sugar beet varieties Fiammetta KWS dated Dec. 14, 2017 (with machine translation).

The European applications for Plant Variety Protection (PVP) and/or Seed Marketing Authorization of KWS sugar beet varieties Giacomina KWS dated Dec. 14, 2017 (with machine translation).

Sugar Beet epsp synthase, GenBank accession No. XP_010692222.1, published Nov. 2016.

Singh et al., "Primer Premier: Program for Design of Degenerate Primers from a Protein Sequence", BioTechniques, 1998, vol. 24, No. 2, pp. 318-319.

Matsuda, "PCR-Based Detection Methods for Single-Nucleotide Polymorphism or Mutation: Real-Time PCR and Its Substantial Contribution Toward Technological Refinement", Chapter 2, 2017, Editor(s) Gergory S. Makowski, Advances in Clinical Chemistry, Elsevier, vol. 80, pp. 45-72.

Bae et al., "Cas-OFFinder: a fast and versatile algorithm that searches for potential off-target sites of Cas9 RNA-guided endonucleases"; Bioinformatics Application Notes, vol. 30, No. 10, 2014, pp. 1473-1475.

Depicker et al., "Nopaline Synthase: Transcript Mapping and DNA Sequence", Journal of Molecular and Applied Genetics, vol. 1, No. 6, 1982, pp. 561-573.

(Continued)

*Primary Examiner* — Cathy Kingdon

(74) *Attorney, Agent, or Firm* — Troutman Pepper Locke LLP

(57) ABSTRACT

A more efficient breeding against *Cercospora* leaf spot disease, or the development of new resistant lines, is enabled via the provision of the *Cercospora* resistance-mediating gene according to the invention; in particular, a dominant resistance effect in the target plant is evoked by the property of the identified gene alone. The *Cercospora* resistance-mediating gene, and embodiments of the present invention that are described in the preceding, offer additional applications, e.g., the use of the resistant gene allele in cis-genetic or trans-genetic approaches, with the goal of developing new resistant cultivars.

17 Claims, 7 Drawing Sheets

Specification includes a Sequence Listing.

(56) References Cited

OTHER PUBLICATIONS

Dixon et al., "The Tomato Cf-2 Disease Resistance Locus Comprises Two Functional Genes Encoding Leucine-Rich Repeat Proteins", Cell, vol. 84, 1996, pp. 451-459.
Henikoff et al., "Tilling. Traditional Mutagenesis Meets Functional Genomics", Plant Physiology, vol. 135, Jun. 2004, pp. 630-636.
Holtschulte, "Cercospora beticola: World-wide Distribution and Incidence" 2000, pp. 1-12.
Lindsey et al., "Transformation of Sugarbeet (*Beta vulgaris*) by Agrobacterium tumefaciens", Journal of Experimental Botany, vol. 41, No. 226, May 1990, pp. 529-536.
Martin et al., "Understanding The Functions Of Plant Disease Resistance Proteins", Annu. Rev. Plant Biol. vol. 54, 2003, pp. 23-61.
Odell et al., "Identification of DNA sequences required for activity of the cauliflower mosaic virus 35S promoter" Nature, vol. 313, 1985, pp. 810-812.
Osakabe et al., "Genome Editing with Engineered Nucleases in Plants", Plant Cell Physiol, vol. 56, No. 3, 2015, pp. 389-400.
Park et al., "Cas-Designer: a web-based tool for choice of CRISPR-Cas9 target sites", Bioinformatics, vol. 31 No. 24, 2015, pp. 4014-4016.
Rushton et al., "Interaction of elicitor-induced DNA-binding proteins with elicitor response elements in the promoters of parsley PR1 genes" The EMBO Journal, vol. 15 No. 20, 1996, pp. 5690-5700.
Sambrook et al, eds. Molecular Cloning: A Laboratory Manual, vol. 2, "Analysis of Genomic DNA by Southern Hybridization", 1989, pp. 9.31-9.59.
Steinrucken, "Die Zuchtung von Cercospora-resistenten Zuckerruben" Vortr. Pflanzenzuchtg, 1997, vol. 37, pp. 76-91.
Steinrucken, "Cultivation of Cercospora-resistant sugar beet", Lectures on Plant Breeding, 1997, pp. 1-7. (English translation of NPL).
Tang et al., "A CRISPR-Cpf1 system for efficient genome editing and transcriptional repression in plants" Nature Plants, vol. 3, Article No. 17018, 2017, pp. 1-5.
UniProtKB-Q41397 "Cf-2.1—*Solanum pimpinellifolium* (Currant tomato)" https://www.uniprot/org/uniprot/Q41397, Oct. 18, 2018, pp. 1-6.
Weiland et al., "Sugarbeet leaf spot disease (*Cercospora beticola* Sacc.)", Molecular Plant Pathology, vol. 5 No. 3, 2004, pp. 157-166.
Weltmeier et al., "Transcript Profiles in Sugar Beet Genotypes Uncover Timing and Strength of Defense Reactions to Cercospora beticola Infection", Molecular Plant-Microbe Interactions (MPMI), vol. 24 No. 7, 2011, pp. 758-772.
Predicted: LRR receptor-like serine/threonine-protein kinase RCH1 [*Beta vulgaris* subsp. *vulgaris*], NCBI Reference Sequence: XP_010676066.1, 4 pages, https://www.ncbi.nlm.nih.gov/protein/XP_010676066 accessed on Mar. 15, 2019.
Hunger et al., "Cf-like resistance gene analogue, mRNA sequence", EM_EST:BU089571, 1 page, http://ibis.internal.epo.org/exam/dbfetch.jsp?id=EM_EST:BU089571 accessed on Mar. 15, 2019.
Stevanato et al., "The Sea Beet (*Beta vulgaris* L. ssp. *maritima*) of the Adriatic Coast as Source of Resistance for Sugar Beet", Sugar Tech, 2001, vol. 3, No. 3, pp. 77-82.
Larbi et al., "Effects of Cd and Pb in sugar beet plants grown in nutrient solution: induced Fe deficiency and growth inhibition", Funct. Plant Biol., 2002, vol. 29, pp. 1453-1464.
Wyse, "Sucrose uptake by sugar beet tap root tissue", Plant Physiol, 1979, vol. 64, pp. 837-841.
Frese, "Chapter 13: Combining static and dynamic management of PGR: a case study of Beta genetic resources" Engels (eds). Managing Plant Genetic Diversity, IPGR. 2002, pp. 133-147.
Lytvyn et al., "Creation of transgenic sugar beet lines expressing insect pest resistance genes cry1C and cry2A", Cytology and Genetics, 2014, vol. 48, No. 2, pp. 69-75.
Nilsson et al., "QTL analysis of Cercospora leaf spot resistance in sugar beet", Plant Breeding, 1999, vol. 118, pp. 327-334.
Heijbroek et al., "Fungicides and insecticides applied to pelleted sugar-beet seeds—II. Control of pathogenic fungi in soil", Crop Protection, 1995, vol. 14, No. 5, pp. 363-366.
Rochalska et al., "Influence of alternating magnetic field on respiration of sugar beet seeds", International Agrophysics, 2008, vol. 22, pp. 255-259.
Trkulja et al. "Molecular and experimental evidence of multi-resistance of Cercospora beticola field populations to MBC, DMI and Qol fungicides", European Journal of Plant Pathology, 2017, vol. 149, No. 4, pp. 895-910.
International Search Report and Written Opinion issued in PCT/EP2021/071944 dated Oct. 18, 2021.
All, "Rapid detection and quantification of Cercospora beticola in soil using PCR and ELISA assays", Dissertation, 2012, 144 pages.
Bilgen et al., "Transferring Cercospora Leaf Spot Resistance From Beta Maritima to Sugarbeet by Backcrossing", Journal of the A.S.S.B.T., 1969, vol. 15, No. 5, pp. 444-449.
Panella et al., "USDA-ARS Sugarbeet Releases and Breeding Over the Past 20 years", 2015, Journal of Sugar Beet Research, vol. 52, Nos. 3 & 4, pp. 40-85.
Guo et al., "Protein tolerance to random amino acid change", PNAS, 2004, vol. 101, No. 25, pp. 9205-9210.
GenBank:JY463144.1 [on-line], 2013, [Search Date Jan. 26, 2023 ], Internet : < URL :https://www.ncbi.nlm.nih.gov/nuccore/jy463144 >.
GenBank:JY461792.1 [on-line], 2013, [Search Date Jan. 26, 2023 ], Internet : < URL : https://www.ncbi.nlm.nih.gov/nuccore/jy461792 >.
Third Party Observation in EP Application No. 20191416 mailed Apr. 24, 2023, submitted Apr. 19, 2023.
Printout from the PINTO Database; printed Dec. 9, 2022.
Reformatted Table of PINTO Database of Dec. 9, 2022.
Material Transfer Agreement; https://www.geves.fr/wp-content/uploads/PROTOVATEPLANTESDESERVICES20182019; French-language original; date unknown.
Material Transfer Agreement; https://www.geves.fr/wp-content/uploads/PROTOVATEPLANTESDESERVICES20182019; English-language translation; date unknown.
Marketing Materials from KWS; Mar. 28, 2020.
Third Party Observation in EP Application No. 19704637 mailed Apr. 24, 2023, submitted Apr. 19, 2023.
Third Party Observation in EP Application No. 19157888 mailed Apr. 24, 2023, submitted Apr. 19, 2023.
Proof of personal handover of Fiametta KWS to Mrs. Fattori Declaration dated Sep. 30, 2024.
Declaration of Hendrik Tschoep dated Oct. 10, 2024 including Sequence information of BETA 1859.
Use without restriction status of varieties—public summary of results; "Barbabietola da Zucchero e CVS 2020", established Feb. 13, 2020.
MTA IPK Gatersleben; date unknown.
Third Party Observation in EP Application No. 19704637.8 mailed Dec. 12, 2024, submitted Dec. 6, 2024.
Third Party Observation in EP Application No. 19157888.9 malled Dec. 12, 2024, submitted Dec. 6, 2024.
Rose, "Introns as Gene Regulators: A Brick on the Accelerator", Frontiers in Genetics, 2019, vol. 9, Article 672, 6 pages.
Afzal et al., "Seed Production technologies of Some Major Field Crops", In: Hasanuzzaman M. (eds) Agronomic Crops, 2019, pp. 655-678.

* cited by examiner

BEETS COMPRISING A GENE CONFERRING RESISTANCE TO *CERCOSPORA BETICOLA*

CROSS-REFERENCE TO RELATED APPLICATIONS

This application is a continuation of U.S. patent application Ser. No. 18/161,613, filed on Jan. 30, 2023, which is a continuation of U.S. Patent application Ser. No. 17/005,903, filed on Aug. 28, 2020, now issued as U.S. Pat. No. 11,597,944 on Mar. 7, 2023, which is a continuation of U.S. patent application Ser. No. 16/793,503, filed on Feb. 18, 2020, now issued as U.S. Pat. No. 10,767,191 on Sep. 8, 2020, which claims priority to European Patent Application No. 19157888.9, filed Feb. 18, 2019 under 35 U.S.C. § 119 and to PCT Patent Application No. PCT/EP2019/054008, filed Feb. 18, 2019 under 35 U.S.C. § 365, the entire contents of these applications are incorporated herein by reference in their entirety.

SEQUENCE LISTING

This application contains a Sequence Listing which has been submitted in XML format via EFS-Web and is hereby incorporated by reference herein in its entirety. The XML text file was created on Jan. 25, 2023, is named 245761_000198_SL.xml and is 267,637 bytes in size.

FIELD OF THE INVENTION

The present invention relates to a nucleic acid molecule which encodes a polypeptide, which nucleic acid molecule is able to confer a resistance to *Cercospora*—in particular, to the fungus *Cercospora beticola* in a plant, and, in particular, in a plant of the species *Beta vulgaris* in which the polypeptide is expressed—as well as to the polypeptide encoded by the nucleic acid molecule according to the invention. In particular, the nucleic acid molecule according to the invention is characterized in that the resistance effect to *Cercospora* that is conferred by the polypeptide is dominant. Furthermore, the invention relates to a *Cercospora*-resistant plant, plant cell, plant organ, plant tissue, plant part, or a seed or descendant of a plant, which comprises the nucleic acid molecule or portions thereof as an endogenous gene, as an edited gene, or as a transgene. Furthermore, the present invention also encompasses methods for increasing the resistance to *Cercospora* in a plant of the species *Beta vulgaris*, as well as methods for producing or identifying and possibly selecting a *Cercospora*-resistant plant. The present invention also encompasses methods for monitoring an infestation by the pathogen *Cercospora beticola*, as well as oligonucleotide probes and primers for hybridization with the nucleic acid molecule according to the invention.

BACKGROUND OF THE INVENTION

*Cercospora* leaf spot is one of the most important, globally prevalent leaf diseases of plants from the species *Beta vulgaris* and *Spinacia oleracea*. It is caused by the fungus *Cercospora beticola*. Plants infested by this disease typically form small, relatively round leaf spots (2-3 mm) that are light gray in the middle and are surrounded by a red-brown border. In a severe infestation, the leaf spots overlap, so that entire portions of the leaf blade dry out. Small black dots (pseudostromata) are visible within the fully formed spots, and a gray, felt-like covering (conidia bearers with conidia) forms under damp conditions—predominantly, on the leaf underside. Severely infested leaves first turn yellow, then turn brown and die. New leaf growth occurs in parallel, wherein the leaves become diseased again and die, however. At first, damage symptoms only on individual plants are visible; however, with spread of the disease, formation of persistent infestation nests often occurs. The further propagation over the entire field takes place via rain and wind.

The pathogen *Cercospora beticola* was first described in the second half of the 19th century, in Italy. Up to 40% crop losses may occur due to a severe infestation, which may be triggered by humid weather, early row closure, a high infection potential from previous years, or strong irrigation. These losses result from a reduced beet crop and reduced sugar content; see Holtschulte ((2000) "*Cercospora beticola*—worldwide distribution and incidence," pp. 5-16, in "*Cercospora beticola* Sacc. Biology, Agronomic Influence and Control Measures in Sugar Beet," vol. 2 (M. J. C. Asher, B. Holtschulte, M. R. Molard, F. Rosso, G. Steinrcken, R. Beckers, eds.). International Institute for Beet Research, Brussels, Belgium, 215 pp.). In order to fight back against the disease, intercropping or fungicides are often used. A chemical control of *Cercospora beticola* via fungicides incurs costs to the farmer and pollutes the environment. Repeated applications of fungicides additionally increase the selection pressure on fungicide-tolerant *Cercospora beticola* strains. This is contrary to a sustainable agricultural practice. It is worth mentioning that during the last few years stems of *Cercospora beticola* occurred which showed resistance against one or more fungicides; see for Trkulja, Nenad R., et al. "Molecular and experimental evidence of multi-resistance of *Cercospora beticola* field populations to MBC, DMI and QoI fungicides." *European Journal of Plant Pathology* 149.4 (2017): 895-910. The problem became such severe that the German Federal Office of Consumer Protection and Food Safety (BVL) approved the exemptional admission of copper-based fungicides for combating *Cercospora*. However, copper-based fungicides are generally regarded (depending on the dosage) as harmful for humans and environment. Copper is a heavy metal which may accumulate in the soil.

Indirect combat is done via the selection of cultivars with healthy leaves and cultivation of the beets with at least a 3-year crop rotation. Markedly better control of the infestation may be achieved with a combination of tolerant or resistant cultivars. Less susceptible *Cercospora*-tolerant beet cultivars have been offered on the market since 2000 (Steinrücken 1997, "Die Züchtung von *Cercospora*-resistenten Zuckerrüben." ["The breeding of *Cercospora*-resistant sugar beets." ], Vorträge far Pflanzenzüchtung [Lectures on Plant Breeding], Volume 37, Lecture symposium, Mar. 4-5, 1997, Kiel). These cultivars are furnished with a quantitative resistance to *Cercospora beticola*. The resistance of these cultivars is based upon several genes and is quantitatively passed down, wherein the exact number of the genes that are responsible for the resistance is not known; see Weiland and Koch (2004), Sugarbeet leaf spot disease (*Cercospora beticola* Sacc.), *The Plant Journal,* 5(3), 157-166. The complex quantitative heredity was confirmed via several Quantitative Trait Loci (QTL) analyses. This method allows the mapping of polygenic inherited resistances and is a reliable technique for identifying the number and position of genetic resistance factors on the genetic linkage map of a host plant. In this way, multiple causative QTL's could be determined on each chromosome of the sugar beet.

The mappings were performed with different *Cercospora*-resistance donors, wherein the observed QTL effects were, for the most part, small. The maximum declared phenotypical values were at 5%.

In continuative studies, lists of differentially expressed genes have been described. In a study by Weltmeier et al., ((2011) Transcript profiles in sugar beet genotypes uncover timing and strength of defense reactions to *Cercospora beticola* infection, *Molecular plant-microbe interactions,* 24(7), 758-772), a genome-side expression profile for various genotypes of sugar beet (i.e., *Cercospora*-resistant, -tolerant, -susceptible, etc.) was created with the aid of a microarray-based technology during the pathogen infection in order to analyze transcriptional changes in the expression profile in connection with leaf spot. Via these analyses, the authors were in a position to create a pathogen-induced transcription profile in various tested genotypes of sugar beet and to determine potential candidate genes. However, these genes have not yet been characterized in detail. The genetic and functional background of *Cercospora* resistance and the identity of the resistance genes have until now been entirely unclear.

However, with the quantitative heredity of QTL, not only is the desired resistance to *Cercospora beticola* introduced into the plant, but, rather, often unwanted features as well, such as, for example, reduced yield, due to the inheritance of additional genes that are linked with the positive feature of *Cercospora* resistance. This phenomenon is also known by the term, "linkage drag." Furthermore, the enormous breeding cost that is required in order to select for multiple resistance loci without thereby reducing the yield may have negative effects on the vitality of the plants; see Weiland and Koch, 2004.

Breeding companies have offered *Cercospora*-tolerant cultivars on the market for more than a decade. The resistance of these cultivars is inherited via multiple resistance genes with small effect. However, a disadvantage of these cultivars consists in the cultivar development being very laborious and complicated due to the complicated heredity, and in such cultivars having a markedly poorer yield performance relative to normal cultivars, in the absence of an infestation. Among other things, this may be linked to the epigenetic interaction of some resistance genes with genes that are responsible for sugar production, which leads to reduced fitness of the plants, in the absence of the pathogen. Furthermore, *Cercospora* shows the tendency to overcome the tolerance of long-established cultivars. Moreover, the so far available resistance scores of non-adapted, wild genetic resources is usually not reliable and not comparable among each other as the underlying studies took place at different environment conditions, under different infestation pressure and with different pathogenic stems of *Cercospora*. In this regard it should be mentioned that environmental parameters like moisture, temperature, wind etc. (which tend to be unstable) have significant influence on the progress of the *Cercospora* disease after infection. It is common that a specific genetic resource shows high level of tolerance/resistance in one study and tends to be completely susceptible in another study. Due to the above given factors it was so far not possible to identify a dominant resistance gene having a major effect towards *Cercospora* although there is a strong demand for such a gene which could be easily transferred into already existing cultivars and varieties to establish resistance towards *Cercospora*.

The use of new breeding techniques based upon gene editing, e.g., by means of TALE nucleases or CRISPR systems, and of transgenic approaches, is not applicable on the so far available genetic material due to the complicated heredity and the multitude of the genes which are involved in the resistance development, the majority of which have not yet been identified and characterized.

For sustainable breeding against *Cercospora* leaf spot that is to counteract the danger of *Cercospora* variants that overcome resistance, it is necessary to continuously identify new resistance genes and integrate these into the gene pools of cultivated plants such as sugar beets. In particular, the aim consisted in the provision of suitable resistance genes that, after expression in the plant, on their own already produce a very large, dominant resistance effect against *Cercospora beticola.*

According to the invention, this aim is achieved via the embodiments characterized in the claims and in the specification.

SUMMARY OF THE INVENTION

The present invention relates to a nucleic acid molecule that is able to confer a resistance to *Cercospora*—in particular, to the fungus *Cercospora beticola*—in a plant, and, in particular, in *Beta vulgaris* subsp. *vulgaris*. The polypeptide which is encoded by the nucleic acid molecule is thereby produced in the plant. The nucleic acid molecule, after whose expression the polypeptide is produced, on its own, already produces in the plant a very large, dominant resistance effect against *Cercospora beticola.*

Furthermore, the invention relates to a *Cercospora*-resistant plant, plant cell, plant organ, plant tissue, plant part, a seed, seed stock, or descendant of a plant, which endogenously or transgenically comprises the nucleic acid molecule or portions thereof. According to a specific optional embodiment, those plants and their components that have been obtained via an essentially biological process are excluded.

Methods for increasing the resistance to *Cercospora* in a plant of the species *Beta vulgaris*, as well as methods for producing or identifying and possibly selecting a *Cercospora*-resistant plant, are likewise encompassed by the present invention. The present invention also encompasses methods for monitoring an infestation of the pathogen *Cercospora beticola*, as well as oligonucleotides as probes and primers for hybridization with the nucleic acid molecule according to the invention.

The present invention therefore relates to the embodiments that are listed in the following points and illustrated in the examples and figures.

[1] Nucleic acid molecule encoding a polypeptide that is able to confer resistance to *Cercospora* in a plant in which the polypeptide is expressed, characterized in that the nucleic acid molecule comprises a nucleotide sequence which is selected from
- (a) a nucleotide sequence encoding a polypeptide having an amino acid sequence according to SEQ ID No. 3;
- (b) a nucleotide sequence that comprises the DNA sequence according to SEQ ID No. 2;
- (c) a nucleotide sequence that comprises a DNA sequence selected from the group consisting of SEQ ID No. 1 or SEQ ID No. 53;
- (d) a nucleotide sequence that hybridizes to a nucleotide sequence which is complementary to the nucleotide sequence according to (a), (b), or (c), under stringent conditions;
- (e) a nucleotide sequence encoding a polypeptide which, via substitution, deletion, and/or addition of one or more amino acids of the amino acid sequence, differs from a polypeptide encoded by the nucleotide sequence according to (a), (b), or (c);

(f) a nucleotide sequence encoding a polypeptide which has an amino acid sequence that is at least 70% identical to an amino acid sequence according to SEQ ID No. 3;

(g) a nucleotide sequence that is at least 70% identical to a DNA sequence according to SEQ ID No. 1 or SEQ ID No. 2;

wherein the resistance to *Cercospora* is preferably a resistance to *Cercospora beticola*, or wherein the plant is preferably a plant of the subspecies *Beta vulgaris* subsp. *vulgaris*, and is, particularly preferably, sugar beet.

[2] Nucleic acid molecule according to [1], characterized in that the resistance effect to *Cercospora* that is conferred by the polypeptide is dominant in the plant—preferably, wherein the polypeptide confers a resistance effect of at least one rating score, and, preferably, of more than one rating score, particularly preferably, of at least two rating scores, particularly preferably, of at least three rating scores, and, especially preferably, of at least four rating scores.

[3] Nucleic acid molecule according to [1] or [2], characterized in that the nucleic acid molecule originates from *Beta vulgaris* subsp. *maritima.*

[4] Polypeptide encoded by the nucleic acid molecule according to one of [1] through [3].

[5] Vector or expression cassette comprising the nucleic acid molecule according to one of [1] through [3], wherein the nucleic acid molecule is preferably heterologous to the vector or to the expression cassette.

[6] Cell which comprises the nucleic acid molecule according to one of [1] through [3], or the vector or the expression cassette according to [5], wherein the nucleic acid molecule or the expression cassette are preferably present as an endogene or transgene.

[7] *Cercospora*-resistant plant or a portion thereof, characterized in that the plant or its portion contains the nucleic acid molecule according to one of [1] through [3], endogenously or transgenically, or the vector or the expression cassette according to [5], wherein the plant which endogenously contains the nucleic acid molecule is a plant of the species *Beta vulgaris*—but not *Beta vulgaris* subsp. *maritima*—or of *Beta vulgaris* subsp. *vulgaris.*

[8] Plant according to [7], characterized in that the plant is a hybrid plant.

[9] Plant according to [7] or [8], characterized in that the nucleic acid molecule is present heterozygously or homozygously in the genome of the plant.

[10] Seeds or descendants of the plant according to one of [7] through [9], wherein the seed or the descendant transgenically or endogenously comprises the nucleic acid molecule according to one of [1] through [3], or the vector or the expression cassette according to [5].

[11] Method for increasing the resistance to *Cercospora* in a plant, including the following steps:

(i) integration of the nucleic acid molecule according to one of [1] through [3], or of the vector or of the expression cassette according to [5], by means of homology-directed repair or homologous recombination—preferably, supported by a site-directed nuclease—into the genome of at least one cell of a plant, and optional regeneration of a plant from the at least one plant cell; or (ii) increase in the expression of the nucleic acid molecule according to one of [1] through [3] in at least one cell of the plant—preferably, via modification of the native promoter, e.g., comprising a DNA sequence according to SEQ ID No. 7, or via linking of the nucleic acid molecule according to one of [1] through [3] with a heterologous promoter that has a higher level of activity in comparison to the native promoter, e.g., comprising a DNA sequence according to SEQ ID No. 7—in particular, after *Cercospora* infection—and optional regeneration of a plant from the at least one plant cell; or (iii) increase in the activity and/or stability of the polypeptide according to [4] via modification of the nucleotide sequence of the nucleic acid molecule according to one of [1] through [3] in at least one cell of the plant, and optional regeneration of a plant from the at least one plant cell; or (iv) transformation of a plant cell with the nucleic acid molecule according to one of [1] through [3], or the vector or the expression cassette according to [5], and optional regeneration of a (transgenic) plant from the transformed plant cell;

wherein the resistance to *Cercospora* is preferably a resistance to *Cercospora beticola*, or the plant is preferably a plant of the species *Beta vulgaris*—preferably, *Beta vulgaris* subsp. *vulgaris*—and, in particular, is sugar beet.

[12] Method for producing a *Cercospora*-resistant plant according to one of [7] through [9], including the following steps:

(a) transformation of a plant cell with the nucleic acid molecule according to one of [1] through [3], or the vector or the expression cassette according to [5]; and (b) regeneration of the transgenic plant from the transformed plant cell; or (i) introduction of a site-directed nuclease and a repair matrix into a cell of a plant of the species *Beta vulgaris*, wherein the site-directed nuclease is able to generate at least one double-strand break of the DNA in the genome of the cell—preferably, upstream and/or downstream of a target region—and the repair matrix comprises the nucleic acid molecule according to one of [1] through [3];

(ii) cultivation of the cell from (i) under conditions that allow a homology-directed repair or a homologous recombination, wherein the nucleic acid molecule is incorporated from the repair matrix into the genome of the plant; and (iii) regeneration of a plant from the cell modified in (ii).

[13] Method according to [12], characterized in that the target region comprises an allelic variant of the nucleic acid molecule according to one of [1] through [3], wherein the allelic variant encodes a polypeptide not conferring resistance or a slight resistance to *Cercospora.*

[14] Method according to [12] or [13], characterized in that the at least one double-strand break occurs at a position that is at most 10,000 base pairs upstream and/or downstream of the target region, or that is at most 10,000 base pairs distant from the allelic variant as defined in [13].

[15] Method according to [12] or [13], characterized in that the allelic variant of the nucleic acid molecule comprises a nucleotide sequence which is selected from (a) a nucleotide sequence that encodes a polypeptide having an amino acid sequence according to SEQ ID No. 6;
(b) a nucleotide sequence that comprises the DNA sequence according to SEQ ID No. 5;
(c) a nucleotide sequence that comprises a DNA sequence according to SEQ ID No. 4;
(d) a nucleotide sequence that hybridizes to a nucleotide sequence which is complementary to the nucleotide sequence according to (a), (b), or (c), under stringent conditions;
(e) a nucleotide sequence that encodes a polypeptide which, via substitution, deletion, and/or addition of one or more amino acids of the amino acid sequence, differs from a polypeptide that is encoded by the nucleotide sequence according to (a), (b), or (c); or
(f) a nucleotide sequence that encodes a polypeptide which has an amino acid sequence that is at least 80% identical to an amino acid sequence according to SEQ ID No. 6.

[16] Plant, or a portion thereof, obtained or obtainable according to a method according to one of [12] through [15].

[17] Method for identifying, and optionally providing, a plant of the species *Beta vulgaris* that is resistant to *Cercospora*, characterized in that the method includes at least step (i) or (ii):
(i) detection of the presence and/or expression of the nucleic acid molecule according to one of [1] through [3], or the presence of the polypeptide according to [4], in the plant or a portion of the plant; and/or
(ii) detection of at least one marker locus in the nucleotide sequence of the nucleic acid molecule according to one of [1] through [3] or in a cosegregating region; and
(iii) possible selection of the *Cercospora beticola*-resistant plant.

[18] Method for identification of a nucleic acid molecule which encodes a polypeptide that is able to confer a resistance to *Cercospora* in a plant of the species *Beta vulgaris* in which the polypeptide is expressed, characterized in that the method includes the following steps:
(i) comparison of the amino acid sequence of the polypeptide according to [4] with amino acid sequences from a sequence database, or identification of allelic variants which encode the polypeptide according to [4] in genotypes of the species *Beta vulgaris;*
(ii) identification of the amino acid sequence, or an allelic variant, encoding an amino acid sequence, wherein the amino acid sequence is at least 80% identical to the amino acid sequence of the polypeptide according to [4];
(iii) introduction of a nucleic acid molecule, or the allelic variant, encoding the identified amino acid sequence into a plant of the species *Beta vulgaris*, and expression of the nucleic acid molecule in the plant; and
(iv) detection of the resistance to *Cercospora.*

[19] Method for farming of plants of the species *Beta vulgaris*, including
(i) the provision of plants according to one of [7] through [9], the planting of a pelleted seed of a sugar beet plant or of a plant of the genus *Beta* according to one of [26]-[39], the production of plants of the species *Beta vulgaris* with the aid of a method according to one of [12] through [15], or the identification and selection of plants of the genus *Beta* with the aid of a method according to [17], and
(ii) cultivation of the plants from (i) or descendants thereof,
wherein the method counteracts an infestation of the cultivated plants with *Cercospora.*

[20] Oligonucleotide of at least 15, 16, 17, 18, 19, or 20—preferably, at least 21, 22, 23, 24, or 25, particularly preferably, at least 30, 35, 40, 45, or 50, and, especially preferably, at least 100, 200, 300, or 500—nucleotides in length, which oligonucleotide hybridizes with a nucleotide sequence as defined in one of [1] through [3].

[21]A pair of oligonucleotides—preferably, oligonucleotides according to [20] or a kit containing these oligonucleotides—wherein the oligonucleotides are suitable for hybridization as forward primer and reverse primer to a region in the *Beta vulgaris* genome that, in *Beta vulgaris*, has a cosegregation with the *Cercospora* resistance conferred by the polypeptide according to [4], or with the nucleic acid molecule according to one of [1] through [3].

[22] Use of the nucleic acid molecule according to one of [1] through [3] in the production of *Cercospora*-resistant plants of the subspecies *Beta vulgaris* subsp. *vulgaris.*

[23] Method for the production of an organism which comprises a mutated version according to [1] and/or a mutated version of a promoter comprising a nucleic acid sequence selected from
(a) SEQ ID NO: 7
(b) a nucleotide sequence, which hybridizes under stringent conditions with a sequence which is complementary to the sequence according to (a)
(c) a nucleotide sequence which is at least 70% identical to a sequence according to SEQ ID NO: 7
wherein the method includes the following steps:
(I) Provision of an organism or a cell comprising the nucleic acid molecule and/or the promoter
(II) Increase of the mutation rate of the organism or the cell or mutagenesis of the organism or the cell
(III) Phenotypic selection of an organism, which as a result of a mutation exhibits an altered resistance or altered resistance level towards *Cercospora beticola* or Genotypic selection of an organism or a cell which comprises a mutation in the nucleic acid molecule and/or the promoter wherein the mutation has been created via step (II) and optionally
(IV) Regeneration of the organism from the cell obtained via step (III).

[24] Method according to [23], wherein the organism is a plant.

[25] Method according to [24] wherein the plant is a *Beta vulgaris*, preferably a *Beta vulgaris* subsp. *vulgaris*, more preferably a sugar beet.

[26]A pelleted seed of a sugar beet plant or a plant of the genus *Beta* comprising a nucleic acid molecule according to [1].

[27] The pelleted seed according to [26], wherein the beet body is suitable as raw material for industrial sugar production.

[28] The pelleted seed according to [26] or [27], wherein the pelleted seed is a monogerm seed.

[29] The pelleted seed according to [26] to [28], wherein the sugar beet plant is harvestable before bolting.

[30] The pelleted seed according to [26] to [29], wherein the resistance to *Cercospora* is a resistance to *Cercospora beticola.*

[31] The pelleted seed according to [26] to [30], wherein the sugar beet plant is biannual.

[32] The pelleted seed according to [26] to [31], which has been technically treated, wherein the technical treatment is selected from the group consisting of:
(a) polishing;
(b) dressing;
(c) incrustation; and
(d) coloring.

[33] The pelleted seed according to [26] to [32], wherein the pellet comprises at least one chemical selected from the group selected of:
(a) insecticide;
(b) fungicide; and
(c) fertilizer.

[34] The pelleted seed according to [26] to [33], wherein the seed has been subjected to priming or pre-germination before or during pelleting.

[35] The pelleted seed according to [26] to [34], wherein the sugar beet plant is a hybrid sugar beet plant.

[36] The pelleted seed according to [26] to [35] wherein the nucleotide sequence includes at least one mutation.

[37] The pelleted seed according to [36] wherein the at least one mutation is a mutation relative to SEQ ID No. 1 or SEQ ID No 2.

[38] The pelleted seed according to [36] or [37] wherein the nucleotide sequence including the at least one mutation encodes a polypeptide which has an amino acid sequence that is at least 99% identical to an amino acid sequence according to SEQ ID No. 3.

[39] The pelleted seed according to [38] wherein the nucleotide sequence including the at least one mutation encodes a polypeptide having an amino acid sequence according to SEQ ID No. 3.

[40]A packing containing the pelleted seed according to [26] to [39] or containing seed stock comprising the nucleic acid molecule according to [1] wherein the seed stock preferable is seed stock of a plant of the genus *Beta*.

[41]A mixture of a pelleting mass and a sugar beet plant seed wherein the sugar beet plant seed comprises a nucleic acid sequence which encodes a polypeptide that is able to confer resistance to *Cercospora*, wherein the nucleotide sequence is selected from the group consisting of
(a) a nucleotide sequence encoding a polypeptide having an amino acid sequence according to SEQ ID No. 3;
(b) a nucleotide sequence that comprises the DNA sequence according to SEQ ID No. 2;
(c) a nucleotide sequence that comprises a DNA sequence selected from the group consisting of SEQ ID No. 1 or SEQ ID No. 53;
(d) a nucleotide sequence that hybridizes to a nucleotide sequence which is complementary to the nucleotide sequence according to (a), (b), or (c), under stringent conditions;
(e) a nucleotide sequence encoding a polypeptide which, via substitution, deletion, and/or addition of one or more amino acids of the amino acid sequence, differs from a polypeptide encoded by the nucleotide sequence according to (a), (b), or (c);
(f) a nucleotide sequence encoding a polypeptide which has an amino acid sequence that is at least 70% identical to an amino acid sequence according to SEQ ID No. 3;
(g) a nucleotide sequence that is at least 70% identical to a DNA sequence according to SEQ ID No. 1 or SEQ ID No. 2.

[42]A method for producing the pelleted sugar beet plant seed according to [26] to [39] comprising the following steps:
a) providing a sugar beet plant seed comprising a nucleic acid sequence which encodes a polypeptide that is able to confer resistance to *Cercospora,*
wherein the nucleotide sequence which is selected from the group consisting of
(i) a nucleotide sequence that encodes a polypeptide which has an amino acid sequence that is at least 95% identical to an amino acid sequence according to SEQ ID No. 3; and
(ii) a nucleotide sequence that is at least 95% identical to a DNA sequence according to SEQ ID No. 1 or SEQ ID No. 2
b) embedding the sugar beet plant seed in a pelleting mass
c) allow the pelleting mass to dry or dry the pelleting mass.

[43] The pelleted seed according to [36] to [39] wherein the nucleotide sequence including the at least one mutation is an artificial nucleotide sequence which does not occur naturally.

[44] The method according to [23] wherein during step (II) a mutagenizing chemical like EMS or mutagenizing radiation is applied.

[45]A variety or cultivar of the genus *Beta* comprising the nucleic acid molecule according to [1] or a pelleted seed the variety or cultivar.

First, some of the terms used in this application are explained in detail in the following: What is understood by "rating score" in the sense of the present invention is a qualitative assessment of the resistance to a *Cercospora* infestation that is represented using a scale from 1 to 9 (with 1=strong resistance and 9=no resistance).

TABLE 1A 9-level resistance rating for Cercospora

| Rating score | Leaf phenotype | Whole plant phenotype |
|---|---|---|
| 1 | Healthy leaf | Healthy leaf, whole |
| 3 | Diseased leaf, spots on the outer leaves | Whole plant, beginning of disease, spots on the outer leaves |
| 5 | Diseased leaf, merging of the spots into dying areas | Whole plant, advanced disease, merging of the spots into dying areas |
| 7 | Diseased leaf, large part of the leaf brown and dead, only lower lamina is still alive | Whole diseased plant, large portions of the outer leaves are dying off |
| 9 | Diseased leaves, lamina and petiole are dead and dried | Whole diseased plant, outer leaves have died, inner leaves with severe damage, strong new leaf growth |

The genus *Cercospora* encompasses various species, e.g., the species *Cercospora arachidicola, Cercospora ariminiensis, Cercospora asparagi, Cercospora bertoreae, Cercospora beticola, Cercospora bizzozeriana, Cercospora canescens, Cercospora carotae, Cercospora chenopodii,*

*Cercospora cistinearum, Cercospora cladosporioides, Cercospora diazu, Cercospora dulcamarae, Cercospora erysimi, Cercospora hayi, Cercospora kikuchii, Cercospora malvacearum, Cercospora malvicola, Cercospora medicaginis, Cercospora oryzaem, Cercospora personata, Cercospora plantaginis, Cercospora ricinella, Cercospora setariae, Cercospora unamunoi, Cercospora violae*, or *Cercospora zeae-maydis.*

In conjunction with the specification of a length of a nucleotide sequence, the term, "approximately," means a deviation by +/−200 base pairs—preferably, by +/−100 base pairs, and, particularly preferably, by +/−50 base pairs.

A "plant of the genus *Beta*" belongs to the amaranth family (Amaranthaceae). Numbering among these plants are plants of the species *Beta macrocarpa, Beta vulgaris, Beta lomatogona, Beta macrorhiza, Beta corolliflora, Beta trigyna*, and *Beta nana*. A plant of the species *Beta vulgaris* is, in particular, a plant of the subspecies *Beta vulgaris* subsp. *vulgaris*. For example, numbering among these are *Beta vulgaris* subsp. *vulgaris* var. *altissima* (sugar beet in a narrower sense), *Beta vulgaris* ssp. *vulgaris* var. *vulgaris* (chard), *Beta vulgaris* ssp. *vulgaris* var. conditiva (beetroot/red beet), *Beta vulgaris* ssp. *vulgaris* var. *crassa/alba* (fodder beet). It is noted that the nucleic acid according to the invention does not naturally occur in sugar beet, chard, beetroot, or fodder beet, but may be introduced into these via human action.

A "plant of the genus *Spinacia*" belongs to the amaranth family (Amaranthaceae). This genus especially encompasses *Spinacia oleracea.*

A "functional fragment" of a nucleotide sequence means a segment of a nucleotide sequence which has a functionality identical or comparable to that of the complete nucleotide sequence from which the functional fragment originates. As such, the functional fragment may possess a nucleotide sequence which is identical or homologous to the total nucleotide sequence over a length of at least 50%, 55%, 60%, 65%, 70%, 75%, 80%, 85%, 90%, 92%, 94% 96%, 97%, 98%, or 99%. This also explicitly encompasses the range of 90-100%. Furthermore, a "functional fragment" of a nucleotide sequence may also mean a segment of a nucleotide sequence which modifies the functionality of the entire nucleotide sequence, e.g., in the course of post-transcriptional or transcriptional gene silencing. As such, the functional fragment of a nucleotide sequence may comprise at least 14, 15, 16, 17, 18, 19, 20, 21, 22, 23, 24, or 25—preferably, at least 30, 35, 40, 45, 50, 60, 70, 80, 90, 100, 120, or 140, and, particularly preferably, at least 160, 180, 200, 250, 300, 350, 400, 450, 500, 600, 700, 800, 900, or 1,000—successive nucleotides of the total nucleotide sequence. This also explicitly encompasses the range of 21 to 50 nucleotides.

A "functional part" of a protein means a segment of a protein, or a section of the amino acid sequence, that encodes the protein, wherein the segment may exert functionality identical or comparable to that of the entire protein in a plant cell. Over a length of at least 50%, 55%, 60%, 65%, 70%, 75%, 80%, 85%, 90%, 92%, 94% 96%, 97%, 98%, or 99%, a functional part of a protein has an amino acid sequence that is identical or, with consideration of conservative and semi-conservative amino acid exchanges, similar to the protein from which the functional part originates.

The term, "heterologous," means that the introduced polynucleotide originates from a cell or an organism with a different genetic background, of the same species or a different species, or is homologous to the prokaryotic or eukaryotic host cell, but is then located in a different genetic environment and thus differs from a corresponding polynucleotide that is possibly naturally present. A heterologous polynucleotide may be present in addition to a corresponding endogenous gene.

In the sense of the invention, what is understood by a "homolog" is a protein of the same phylogenetic origin; what is understood by an "analog" is a protein which exerts the same function, but has a different phylogenetic origin; what is understood by an "ortholog" is a protein from a different species that exerts the same function; and what is understood by a "paralog" is a protein that has appeared within a species due to duplication, wherein this copy either retains the same protein function, alters its expression template, but not the function, changes its protein function, or divides up the original gene function between both copies.

What is to be understood by "hybridizing" or "hybridization" is a process in which a single-stranded nucleic acid molecule binds to a nucleic acid strand that is complementary to the greatest possible extent, i.e., forms base pairs with this. Standard methods for hybridization are described in, for example, Sambrook et al., Molecular Cloning: A Laboratory Manual, 3rd ed., Cold Spring Harbor Laboratory Press, Cold Spring Harbor, NY, 2001. What is preferably understood by this is that at least 60%—more preferably, at least 65%, 70%, 75%, 80%, or 85%, and, particularly preferably, 90%, 91%, 92%, 93%, 94%, 95%, 96%, 97%, 98%, or 99%—of the bases of the nucleic acid molecule form a base pairing with the nucleic acid strand that is complementary to the greatest possible extent. The possibility of such an annealing depends upon the stringency of the hybridization conditions. The term, "stringency," relates to the hybridization conditions. High stringency is present when a base pairing is made more difficult; low stringency is present if a base pairing is made easier. For example, the stringency of the hybridization conditions depends upon the salt concentration or ionic strength and the temperature. In general, the stringency may be increased by increasing the temperature and/or decreasing the salt content. What are to be understood by "stringent hybridization conditions" are those conditions given which a hybridization predominantly occurs only between homologous nucleic acid molecules. The term, "hybridization conditions," thereby relates not only to the conditions prevailing in the actual addition of the nucleic acids, but also to the conditions prevailing in the following washing steps. For example, stringent hybridization conditions are conditions under which, predominantly, only those nucleic acid molecules hybridize that have at least 70%—preferably, at least 75%, at least 80%, at least 85%, at least 90%, or at least 95%—sequence identity. Stringent hybridization conditions are, for example: hybridization in 4×SSC at 65° C., and subsequent repeated washing in 0.1×SSC at 65° C. for approximately 1 hour in total. A hybridization preferably occurs under stringent conditions.

In relation to a nucleic acid in the form of a double-stranded DNA, "complementary" nucleotide sequence means that the second DNA strand complementary to the first DNA strand has the nucleotides that correspond to the bases of the first strand, in accordance with the base pairing rules. A complementary sequence is, preferably, entirely complementary to the counter-sequence, and thus preferably has the same length.

What is understood by an "isolated nucleic acid molecule" is a nucleic acid molecule extracted from its natural or original environment. The term also encompasses a synthetically-produced nucleic acid molecule. What is understood by an "isolated polypeptide" is a polypeptide extracted from its natural or original environment. The term also encompasses a synthetically-produced polypeptide.

A "molecular marker" is a nucleic acid that is polymorphic in a plant population and is used as a reference or orientation point. A marker for the detection of a recombination event should be suitable for monitoring differences or polymorphisms within a plant population. Such a marker is thus able to detect and differentiate between various allelic states (alleles). The term, "molecular marker," also relates to nucleotide sequences which are complementary or at least largely complementary or homologous to genomic sequences—for example, nucleic acids which are used as probes or primers. These differences at the DNA level are to be found as markers and are, for example, polynucleotide sequence differences, e.g., SSR's (simple sequence repeats), RFLP's (restriction fragment length polymorphisms), FLP's (fragment length polymorphisms) or SNP's (single nucleotide polymorphisms). The markers may be derived from genomic or expressed nucleic acids, e.g., spliced RNA, cDNA, or ESTs, and may also relate to nucleic acids that are used as probes or primer pairs and as such are suitable for amplifying a sequence fragment using PCR-based methods. Markers that describe genetic polymorphisms (between parts of a population) may be detected using well-established methods from the prior art (An Introduction to Genetic Analysis, 7th edition, Griffiths, Miller, Suzuki, et al., 2000). For example, among these are DNA sequencing, PCR-based, sequence-specific amplification, verification of RFLP's, verification of polynucleotide polymorphisms by means of allele-specific hybridization (ASH), detection of amplified variable sequences of the plant genome, detection of a 3SR (self-sustained sequence replication), detection of SSR's, SNP's, RFLP's, or AFLP's (amplified fragment length polymorphisms). Furthermore, the methods for detection of ESTs (expressed sequence tags) and SSR markers derived from EST sequences and RAPD (randomly amplified polymorphic DNA) are also known. Depending upon the context, the term, "marker," in the description may also mean a specific chromosome position in the genome of a species where a specific marker (SNP, for example) may be found.

Markers also include synthetic oligonucleotides that may be connected with one or more detection molecules, wherein the detection molecules may be used for a detection reaction or the generation of a signal within the scope of a verification method. Synthetic oligonucleotides also include labeled primers. Synthetic oligonucleotides and labeled primers are artificial compounds, do not occur in nature, and cannot be isolated from nature. The production of such compounds is explained further below.

A "promoter" is a non-translated, regulatory DNA sequence, typically upstream of a coding region, which contains the binding point for the RNA polymerase and initiates the transcription of the DNA. A promoter additionally contains other elements that act as a regulator gene for gene expression (for example, cis-regulatory elements). A "core or minimal promoter" is a promoter that has the basic elements which are needed for transcription initiation (for example, TATA box and/or initiator).

A "pathogen" means an organism that, in interactions with a plant, leads to disease symptoms in one or more organs in the plant. For example, animal, fungal, bacterial, or viral organisms or oomycetes number among these pathogens.

What is to be understood by a "pathogenic infection" is the earliest point in time at which a pathogen interacts with a plant host tissue. In this sense, "infestation" means the occurrence of contact between pathogen and host. With an anchorage of a pathogen at a host, e.g., of a fungal spore on a leaf surface of a plant, mechanisms of pathogen detection and signal relaying begin in the plant host cell. In the case of *Cercospora beticola*, conidia are formed in humid, warm weather and transferred to neighboring plants by rain and wind. New infections most often show individual leaf spots first at the physiologically older outer leaves. These are most often quite clearly delimited from the healthy leaf tissue by a brown ring. The brown conidia carriers of the fungus in the middle part of the spots may be observed with the aid of a magnifying glass (rating score 3). The number of these brown spots increases rapidly, wherein the sporocarps initially overlap even smaller dead areas (rating score 5). In the further course of the disease, which now also spans to the inner leaves, dying-off of the outer leaves finally occurs for the first time (rating score 7), and, then, of practically all leaves (rating score 9). Course of disease and symptom severity are strongly dependent upon the site and on the annually fluctuating weather conditions.

Plant "organs" means, for example, leaves, shoot, stem, roots, hypocotyl, vegetative buds, meristems, embryos, anthers, ovula, seeds, or fruits. "Plant parts" include, but are not limited to, the shoot or the stalk, leaves, blossoms, inflorescence, roots, fruits, and seeds, as well as the pollen. The term, "plant parts," also means an association of multiple organs, e.g., a blossom or a seed, or a part of an organ, e.g., a cross-section through the plant shoot. Plant "tissues" are, for example, callus tissue, storage tissue, meristematic tissue, leaf tissue, shoot tissue, root tissue, plant tumor tissue, or reproductive tissue, as well as the cambium, parenchyma, vascular tissue, sclerenchyma, and epidermis. However, the tissue is not limited to this listing. For example, what are to be understood by plant "cells" are, for example, isolated cells having a cell wall or aggregates thereof, or protoplasts.

"Variety" means a plant grouping within a single botanical taxon of the lowest known rank, which grouping, irrespective of whether the conditions for the grant of a breeder's right are fully met, can be—defined by the expression of the characteristics resulting from a given genotype or combination of genotypes, distinguished from any other plant grouping by the expression of at least one of the said characteristics and considered as a unit with regard to its suitability for being propagated unchanged.

In conjunction with the present invention, the term, "regulatory sequence," relates to a nucleotide sequence which influences the specificity and/or the expression strength, e.g., in that the regulatory sequence confers a defined tissue specificity. Such a regulatory sequence may be located upstream of the transcription initiation point of a minimal promoter, but also downstream thereof, e.g., in a transcribed, but not translated, leader sequence or within an intron.

The term, "resistance," is to be understood broadly and covers the range of the protection from a retardation up to a complete blocking of the development of the disease. One example of an important pathogen is *Cercospora beticola*. A resistant plant cell of the invention or resistant plant of the invention preferably achieves a resistance to *Cercospora beticola*. A resistance to a pathogen is to be equated to a resistance to the disease which this pathogen causes; for example, a resistance to *Cercospora beticola* is also a resistance to leaf spot disease. For example, an increase in the resistance can be measured via a reduced fungal biomass on the host plant; for this, the fungal DNA may be determined with the aid of quantitative PCR in comparison to the plant DNA in the infested plant tissue. An additional approach to the measurement of resistance is optical rating, wherein rating scores of 1 (not susceptible) to 9 (very susceptible) are awarded. "Transgenic plant" relates to a plant into whose genome is integrated at least one polynucleotide.

It may thereby be a heterologous polynucleotide. The polynucleotide is, preferably, stably integrated, which means that the integrated polynucleotide is stably preserved in the plant, is expressed, and also may be stably passed on to the descendants. The stable introduction of a polynucleotide into the genome of a plant also includes the integration into the genome of a plant of the preceding parental generation, wherein the polynucleotide may be stably passed on further. The term, "heterologous," means that the introduced polynucleotide originates from a cell or an organism with a different genetic background, of the same species or a different species, or is homologous to the prokaryotic or eukaryotic host cell, for example, but then is located in a different genetic environment and thus differs from a corresponding polynucleotide that is possibly naturally present. A heterologous polynucleotide may be present in addition to a corresponding endogenous gene.

"Raw material for industrial sugar production" means plant material which can be fed into a sugar production facility which is specialized in the extraction of sugar from sugar beets. Such raw material is typically the beet body (taproot) of the harvested sugar beet. To ensure the conformity with the extraction process the beet body needs to have sufficient mass, volume and a conical shape so that the raw material can be mechanically cut into shreds (beet strips). These beet strips maximize the surface area for sugar extraction and should have a low content of Sodium, Potassium and Nitrogen to allow an efficient extraction. After the extraction remaining beet pulp is pressed, dried and used as animal feed.

"Saccharose concentration" is expressed as percentage of the fresh weight of the root.

"Monogerm" means that a seed grows into exactly one plant whereas a polygerm or multigerm seed (also called "seed ball") grows into several plants.

"Bolting" is the production of a flowering stem (or stems) on a sugar beet in a natural attempt to produce seeds and reproduce. Bolting is triggered in sugar beet due to vernalization, i.e. a chilling stress which might occur e.g. during overwintering. However, commercially grown sugar beets are harvested before bolting as the bolting process and subsequent seed setting reduces the saccharose content in the beet body.

"Introgression" means that a nucleotide sequence has been transferred into the genome of a plant wherein this nucleotide sequence originates from a plant that does not belong to the same species or subspecies. This can for example mean that a nucleotide sequence deriving from a plant of the subspecies *Beta vulgaris maritima* has been transferred into a plant of the subspecies *Beta vulgaris vulgaris*.

BRIEF DESCRIPTION OF THE FIGURES

Designs and embodiments of the present invention are described by way of example with reference to the pending sequences and figures.

DETAILED DESCRIPTION OF THE INVENTION

Figure 1:
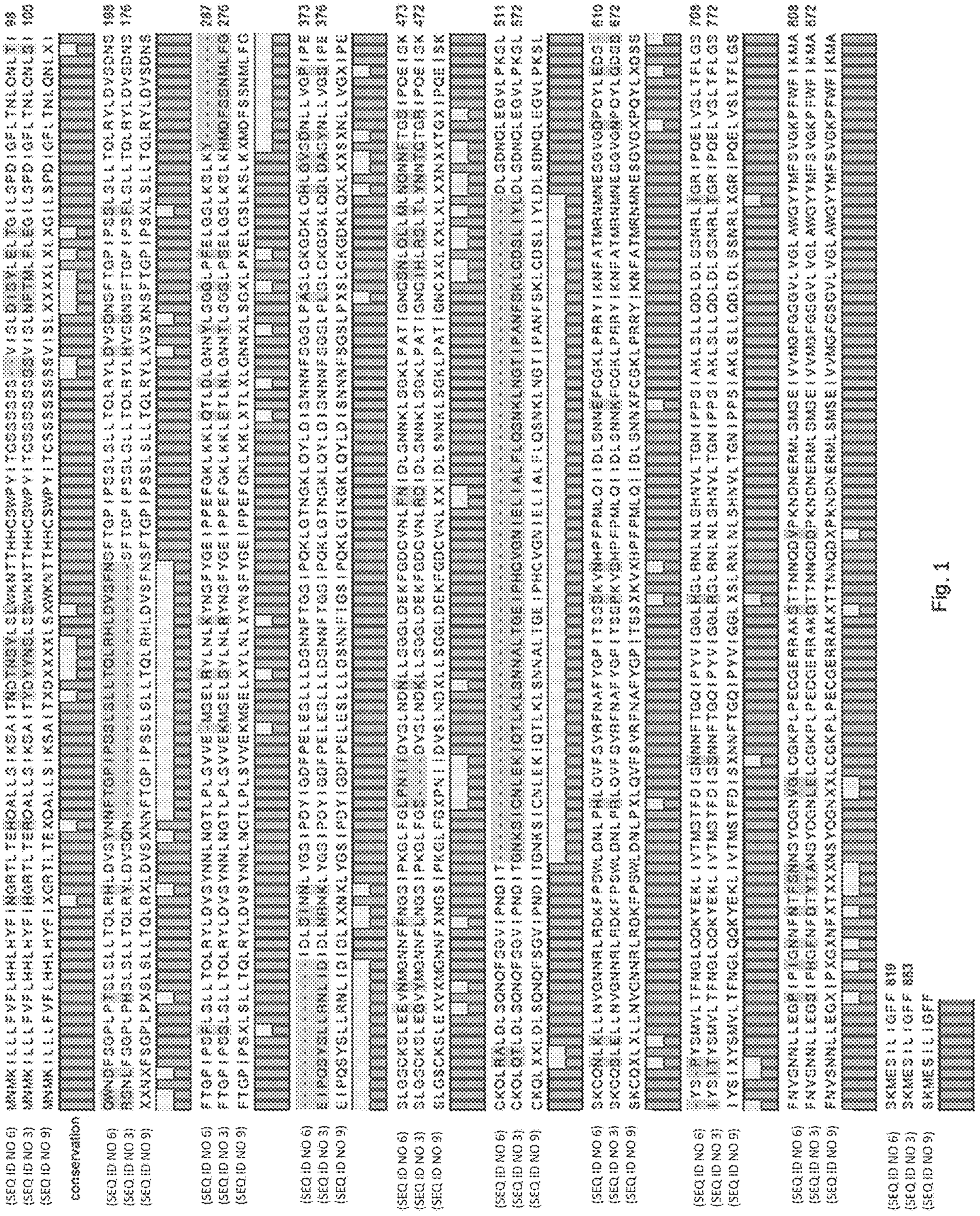
FIG. 1: Protein sequence alignment between the resistant protein (protein which confers *Cercospora* resistance in a plant) and the sensitive protein (protein which does not confer *Cercospora* resistance in a plant). The polymorphisms are highlighted in gray.

The present invention relates to a nucleic acid molecule that is able to confer a resistance to *Cercospora* in a plant—in particular, in *Beta vulgaris* subsp. *vulgaris*—in which the polypeptide which is encoded by the nucleic acid molecule is expressed. According to a preferred embodiment of the invention, the pathogen is the fungus *Cercospora beticola*, which is among the most important and destructive leaf pathogens of sugar beets, beetroot, and chard, among others, and may cause crop losses of over 40%. The fungus produces the secondary metabolite cercosporin, which reacts with oxygen in the presence of light and leads to the formation of reactive oxygen species (ROS). The ROS cause massive cell damage in the leaf tissue of the infested plant that visible in the form of necroses.

The present invention is based upon the genetic fine mapping, identification, isolation, and characterization of a gene or of a gene locus that originates from the donor *Beta vulgaris* subsp. *maritima*, whose presence in a plant—in particular, in *Beta vulgaris* subsp. *vulgaris*—correlates with or is causative of the resistance of the plant concerned to *Cercospora* leaf spot disease. Initial material was a *Beta vulgaris* subsp. *maritima* population which was developed from 37 *Beta vulgaris* subsp. *maritima* accessions from different sources.

The nucleotide and amino acid encoding sequence of the nucleic acid molecule according to the invention is characterized by numerous polymorphisms, which differentiates the NPS-LRR gene identified according to the invention from the "sensitive" variant of the gene, i.e., the variant of the gene that does not confer resistance to *Cercospora*. Examples of polymorphisms are presented in FIG. 1.

The nucleic acid molecule according to the invention may be an isolated nucleic acid molecule. It is preferably DNA, and, particularly preferably, cDNA (coding DNA). The polypeptide which is encoded by the nucleic acid molecule according to the invention preferably confers a resistance to the pathogen *Cercospora beticola*, which causes the plant disease *Cercospora* leaf spot. Furthermore, the polypeptide which is encoded by the nucleic acid molecule according to the invention confers—in particular, in a plant of the genus *Beta*—a resistance to this pathogen. The plant is preferably a plant of the species *Beta vulgaris*—particularly preferably, a plant of the subspecies *Beta vulgaris* subsp. *vulgaris*;

among these are, for example, the cultivars sugar beet, beetroot, fodder beet, chard, and Swiss chard.

In one embodiment of the present invention, the nucleic acid molecule according to the invention comprises a nucleotide sequence that encodes a polypeptide with an amino acid sequence according to SEQ ID No. 3 and/or the coding DNA sequence according to SEQ ID No. 2. Furthermore, the present invention provides a nucleotide sequence that comprises the DNA sequences according to SEQ ID No. 1 and SEQ ID No. 53.

The gene identified according to the invention is a resistance gene/protein of the type NBS-LRR, which is characterized by specific structural motifs. The general structure of such resistance proteins in plants has already been well-examined (Martin et al., Annual Review Plant Biology 54 (2003), 23-61). However, the principle of the structural embodiment—in particular, of what is known as the LRR domain, which applies as a potential detection domain for most unknown pathogenic effectors—is unpredictable, and the functional background of the resistance genes i.e., the genetic structure, is generally largely unknown. The identification of a *Cercospora* resistance-conferring gene or protein solely on the basis of the known structural motif is, consequently, impossible. Furthermore, the sequence region has turned out to be a highly repetitive region that contains, among other things, tandem repeats with very high sequence homology, which makes the development of diagnostic markers, as well as the assembly of sequence data, especially difficult.

With the aid of the setup of a population of over 4,000 dividing descendants and the development of special recombination screens, the target region was reduced, and thus ever further isolated, via analysis of informative recombinants (genotypical and phenotypical) in a series of resistance tests. This genetic mapping, as well as the creation of physical maps accompanied by WHG sequencing ("whole genome sequencing"), comparative BAC (Bac-by-Bac) sequencing, and bioinformatic analyses, led to the identification of three recombinant genotypes that confirmed the resistance gene (1 recombinant in the neighboring gene, on the one hand, and 2 recombinants in the neighboring gene, on the other). In light of particular requirements, the inventors placed the highly repetitive structure in the target region, which, among other things, contains tandem repeats with very high sequence homology, which made the marker development, and thus the identification of informative recombinants, enormously more difficult. The following steps were particularly decisive for the location of the genetic structure of the resistance gene:

- development of the markers s4p0264s01, s4p2271s01, sxh0678s01, s4p4293s01, s4p4295s01, s4p4301s01 (see Table 1B).
- Fine mapping coupled with intensive phenotyping. The phenotypes were verified with 90-180 descendants per plant in a greenhouse test, and with intensive statistical methods (for example, t-test, power analysis, etc.).
- BAC clone identification and sequencing from BAC pools of the resistant genotype.
- Sequence evaluation, as well as sequence and protein comparison between RR (i.e., resistant) and ss (i.e., sensitive) genotypes; an unambiguous assembly of the RR and ss sequence data was thereby not always possible, due to the sequence complexity.

TABLE 1B

Marker in the target region relating to sensitive genotype, resistant genotype and consensus sequence.

| Marker | Sequences: sensitive/ resistant/consensus | Position on genetic map [cM] | Position on physical map [bp] |
|---|---|---|---|
| s4p0264s01 | SEQ ID No. 54/SEQ ID No. 55/SEQ ID No. 10 | 62,79590373 | 57208510 |
| s4p2271s01 | SEQ ID No. 56/SEQ ID No. 57/SEQ ID No. 11 | 62,81185523 | 57212240 |
| s4p4293s01 | SEQ ID No. 58/SEQ ID No. 59/SEQ ID No. 12 | 62,84491806 | 57219956 |
| s4p4295s01 | SEQ ID No. 60/SEQ ID No. 61/SEQ ID No. 13 | 62,85399055 | 57222060 |
| s4p4301s01 | SEQ ID No. 62/SEQ ID No. 63/SEQ ID No. 14 | 62,94635089 | 57243521 |
| sxh0678s01 | SEQ ID No. 64/SEQ ID No. 65/SEQ ID No. 15 | 62,97474964 | 57250119 |

The compounds provided in Table 1B can be used as molecular markers according to the invention.

Analyses yielded that the LRR gene has a moderate protein homology to the Cf-2 resistance protein from the tomato (UNIPROT|Q41397_SOLPI P. Cf-2.1)(sequence identity 322/830=38%). In fact, the identified *Cercospora* resistance-conferring protein is the best sugar beet protein homolog to the Cf-2 tomato resistance protein. The Cf-2 resistance protein from the tomato confers a resistance to *Cladosporium fulvum*—a type of black mold fungus (U.S. Pat. No. 6,287,865 B1)—via interaction with the avirulence protein Avr2 from *C. fulvum*. This leads to the activation of the plant immune defense against the pathogen; see Dixon et al., 1996 (Dixon, Mark S., et al., "The tomato Cf-2 disease resistance locus comprises two functional genes encoding leucine-rich repeat proteins." Cell 84.3 (1996): 451-459). Due to the sequence homology between the Cf-2 gene and the identified LRR gene, it is to be assumed—but without thereby being bound to one theory—that a similar defense mechanism forming the basis of *Cercospora* resistance also occurs in the case of the sugar beet. However, a different mechanism is not to be precluded, due to the moderate sequence homology.

Furthermore, substitutions, deletions, insertions, additions, and/or any other change may be introduced into the nucleotide sequence according to the invention that, alone or in combinations, do in fact change the nucleotide sequence, wherein the modified nucleotide sequence may, however, perform the same function as the initial sequence. The present case deals with the coding of an amino acid sequence which confers resistance to *Cercospora* leaf spot disease. In a further embodiment, the invention therefore includes a nucleotide sequence that encodes a polypeptide which represents a derivative of the polypeptide which is encoded by the nucleotide sequence according to the invention, or which includes the amino acid sequence according to the invention. A derived amino acid sequence which has at least one substitution, deletion, insertion, or addition of one or more amino acids, wherein the functionality of the encoded polypeptide/protein is preserved, represents a derivative of the polypeptide. Substitutions, deletions, insertions, additions, and/or any other change, either solely or in combinations, that do in fact change the nucleotide sequence, but perform the same function as the initial sequence, may thereby be introduced into the nucleotide sequence using conventional methods that are known in the prior art, e.g., via site-directed mutagenesis, PCR-mediated mutagenesis, transposon mutagenesis, genome editing, etc.

The substitution of one amino acid by a different amino acid having the same or equivalent or similar chemical/physical properties is referred to as a "conservative substitution" or "semi-conservative substitution." Examples of physical/chemical properties of an amino acid are, for example, hydrophobia or the charge. Which amino acid substitution represents a conservative or semi-conservative substitution is known to the person skilled in the art. Moreover, general expertise allows the person skilled in the art to recognize, identify, and detect which amino acid deletions and additions are harmless to the functionality of the resistance protein, and at which positions these are possible. The person skilled in the art is aware that, in the case of the present NBS-LRR protein for modifications of the amino acid sequence (substitutions, deletions, insertion, or additions of one or more amino acids), the functionality, in particular, of the conserved domains must be preserved, and that therefore only limited preceding modifications are possible in these domains.

The invention thus includes a functional fragment of the nucleotide sequence according to the invention. The term, "fragment," thereby includes genes with a nucleotide sequence sufficiently similar to the aforementioned nucleotide sequence. The term, "sufficiently similar," means that a first nucleotide sequence or amino acid sequence has a sufficient or minimum number of identical or equivalent nucleotides or amino acid groups relative to a second nucleotide sequence or a second amino acid sequence.

With regard to the amino acid sequence, after modification via an aforementioned method, this also has a common structural domain and/or possesses common functional activity. Nucleotide sequences or amino acid sequences that have an identity of at least approximately 70%, at least approximately 75%, at least approximately 80%, at least approximately 85%, at least approximately 90%, at least approximately 91%, at least approximately 92%, at least approximately 93%, at least approximately 94%, at least approximately 95%, at least approximately 96%, at least approximately 97%, at least approximately 98%, at least approximately 99%, or at least approximately 100% with the nucleotide sequence or amino acid sequence according to the invention are defined here as being sufficiently similar. This also explicitly encompasses the range of 90% to 100%. For the functional fragments, a sufficient similarity is established if the nucleotide sequence or amino acid sequence generally has the same property as the previously-named nucleotide sequence or amino acid sequence of the present invention. Those nucleotide sequences which encode a derivative or for a derived amino acid sequence are generated either directly or indirectly (for example, via amplification or replication steps) from an initial nucleotide sequence which corresponds to the nucleotide sequence according to the invention over the entire length, or at least in part.

Accordingly, the present invention includes a nucleotide sequence that is able to hybridize, under stringent conditions, with a nucleotide sequence complementary to a nucleotide sequence according to the invention or to the nucleotide sequence that encodes the amino acid sequence according to the invention.

In a further embodiment, the nucleic acid molecule according to the invention is characterized in that, after expression in a plant, it already, on its own, confers a dominant resistance effect against a pathogen—preferably, against *Cercospora beticola*—or that it encodes for a polypeptide that is able to confer a dominant resistance effect against *Cercospora*. In a preferred embodiment, the nucleic acid molecule or the polypeptide confers a resistance effect of at least one rating score—preferably, of at least two rating scores, and, particularly preferably, of three to four rating scores. Such a gene that already, on its own, confers such a strongly pronounced resistance to *Cercospora* in a plant, or that encodes a polypeptide that is able to confer such a pronounced resistance, is not known from the prior art. As was already described above, in previously available varieties on the market, the *Cercospora* resistance is transmitted via many resistance genes having little effect, and a disadvantage of such varieties is that their development is very slow and expensive due to the complicated transmission, and that such varieties have a markedly poorer crop yield relative to normal varieties, in the absence of an infestation. Among other things, this may be linked to the epigenetic interaction of some resistance genes with genes that are responsible for sugar production, which leads to reduced fitness of the plants, in the absence of the pathogen.

The inventors could thus for the first time provide a *Cercospora* resistance gene that may be used for markedly simplified breeding. Via the incorporation of this gene in elite lines, it is now possible to very quickly develop very high-yield varieties with a high *Cercospora* resistance. Accordingly, in the framework of the present invention there are provided for the first time a sugar beet plant, a chard plant, a red beet or beetroot plant, a fodder beet plant having the resistance according to the invention against *Cercospora beticola* and thus being encompassed by the present invention. As the listed plants are all cultivated plants, crops or plants which are suitable for the agricultural cultivation and which have the resistance according to the invention, are part of the invention.

Especially such crops are part of the invention which comprise a subterrestrial storage organ usable as food, raw material or industrial source of sugar and which comprise the resistance according to the invention are a further aspect of the present invention. The storage organ can be for example the sugar containing beet body of the sugar beet, the consumable beet body of the red beet or the feedable beet body of the fodder beet. The subterrestrial storage organ can sum up to more than 50% and for the sugar beet even to more than 70% of the total mass of the full-grown plant. Furthermore, also seeds or seeding material of these plants are part of the invention. The seeds or the seeding material can be technically treated as described further below. Part of the invention are also plants of the genus *Spinacia* comprising the resistance gene according to the invention. Especially plants of the species *Spinacia oleracea* and their varieties comprising the resistance gene according to the invention are included.

In this context, the invention also includes a nucleic acid that encodes the protein according to SEQ ID No. 3, wherein, in a specific embodiment, the naturally occurring nucleic acid according to SEQ ID No. 1 is excluded.

Furthermore, the present invention relates to a recombinant and/or heterologous DNA molecule that comprises the sequences of the nucleic acid molecule according to the invention. This DNA molecule, furthermore, preferably has a regulatory sequence. It may thereby be operatively linked with this regulatory sequence or be under the influence of this regulatory sequence. This regulatory sequence is preferably a promoter sequence and/or other sequences of transcription or translation control elements—for example, cis-elements. The regulatory sequence, which controls the expression of a gene that includes the nucleic acid molecule according to the invention, is preferably a sequence that is able to confer or modulate the expression, as a result of a pathogenic infection. This promoter is preferably able to control the expression of the DNA sequence specifically in leaves of the plant. The regulatory sequence may be heterologous to the expressing sequence. Such an approach has the advantage that the person skilled in the art may better adjust the expression rate of the expressing sequence, the tissue in which the expression occurs, and the point in time at which the expression occurs, in that he selects that regulatory sequence which is best suited to the respective use case. The heterologous DNA sequence preferably includes a nucleotide sequence which encodes a component of the plant pathogen defense (example: resistance genes (R-genes) or genes which encode enzymes involved in signal transfer, such as kinases or phosphatases, and for G-protein, or which encode a pathogenic effector (what are known as avirulence genes (avr))). The heterologous DNA sequence may be one of the DNA sequences according to the invention. The heterologous DNA sequence may also additionally encode further components of the plant pathogen defense. The heterologous DNA sequence may therefore be designed such that a polycistronic mRNA is created after its transcription.

The present invention furthermore also relates to a polypeptide which can be encoded by the nucleic acid molecule according to the invention and a functionally and/or immunologically active fragment thereof, as well as an antibody that specifically binds to the polypeptide or to its fragment. The polypeptide particularly preferably has an amino acid sequence according to SEQ ID No. 3. The recombinant production of proteins, polypeptides, and fragments is familiar to the person skilled in the art (Sambrook et al., Molecular Cloning: A Laboratory Manual, 3rd ed., Cold Spring Harbor Laboratory Press, Cold Spring Harbor, NY, 2001, or Wingfield, P. T., 2008, Production of Recombinant Proteins, Current Protocols in Protein Science, 52:5.0:5.0.1-5.0.4). Polyclonal or monoclonal antibodies to the protein according to the invention may be produced by the person skilled in the art according to known methods (E. Harlow et al., editor, Antibodies: A Laboratory Manual (1988)). The production of monoclonal antibodies, as well as of Fab and F(ab')2 fragments that are also useful in protein detection methods, may be performed via various conventional methods (Goding, Monoclonal Antibodies: Principles and Practice, pp. 98-118, New York: Academic Press (1983)). The antibodies may then be used for the screening of expression cDNA libraries in order to identify identical, homologous, or heterologous genes by means of immunological screening (Sambrook et al., Molecular Cloning: A Laboratory Manual, Cold Spring Harbor Laboratory Press, Cold Spring Harbor, NY, 1989, or Ausubel et al., 1994, "Current Protocols in Molecular Biology." John Wiley & Sons), or may be used for western blot analyses. In particular, the present invention relates to antibodies that selectively detect a polypeptide encoded by the *Cercospora* resistance-conferring allele according to the invention, and essentially do not detect the polypeptide encoded by the correspondingly sensitive allele, i.e., that they detect less, by a factor of 2—preferably, a factor of 5, and, more preferably, a factor or 10 or more—of the polypeptide encoded by the correspondingly sensitive allele than the polypeptide encoded by the *Cercospora* resistance-conferring allele according to the invention.

In a preferred embodiment, the antibody according to the invention is characterized in that it is a synthetic polypeptide which does not occur in nature.

Furthermore, the antibodies according to the invention may be linked with a fluorescent dye in order to be usable in an immunohistochemical method, for example, and evoke an antibody coloration. The fluorescent dye may be fluorochrome. The antibodies according to the invention may also be present linked with other signaling molecules. Among these are, for example, biotin, radioisotopes, reporter enzymes such as alkaline phosphatase, or oligonucleotides.

An additional subject matter of the invention is vectors or expression cassettes that include the nucleic acid molecule or the recombinant DNA molecule according to the invention—possibly under control of regulatory elements and, in particular, under control of functional regulatory elements in plants, as well as negative and/or positive selection markers. The vector backbone is thereby heterologous to the nucleic acid molecule according to the invention, which means that such a vector does not occur in nature and cannot be isolated from nature. The vector is a plasmid, a cosmid, a phage or an expression vector, a transformation vector, shuttle vector or cloning vector; it may be double-stranded or single-stranded, linear or circular; or it may transform a prokaryotic or eukaryotic organism either via integration into its genome or extrachromosomally. The nucleic acid molecule or DNA molecule according to the invention in an expression vector or expression cassette is, preferably, operatively linked with one or more regulatory sequences which allow the transcription and, optionally, the expression in a prokaryotic or eukaryotic cell; (Sambrook et al., Molecular Cloning: A Laboratory Manual, 3rd ed., Cold Spring Harbor Laboratory Press, Cold Spring Harbor, NY, 2001). These regulatory sequences are preferably promoters or terminators—in particular, a transcription initiation starting point, a ribosome binding location, an RNA-processing signal, a transcription termination location, and/or a polyadenylation signal. For example, the nucleic acid molecule is here under the control of a suitable promoter and/or a terminator. Suitable promotors may be constitutive promotors (example: 35S promoter from the "Cauliflower mosaic virus" (Odell et al., Nature 313 (1985), 810-812); those promoters which are pathogenically inducible are especially suitable (example: PR1 promoter from parsley (Rushton et al., EMBO J. 15 (1996), 5,690-5,700)). Particularly suitable pathogenically-inducible promoters are synthetic or chimeric promoters which do not occur in nature, are composed of multiple elements, and contain a minimal promoter, and have at least one cis-regulatory element upstream of the minimal promoter, which at least one cis-regulatory element serves as a binding location for special transcription factors. Chimeric promoters are designed according to the desired requirements and are induced or repressed via different factors. Examples of such promoters are found in WO 00/29592, WO 2007/147395, and WO 2013/091612. For example, a suitable terminator is the nos-terminator (Depicker et al., J. Mol. Appl. Genet. 1(1982), 561-573). Suitable promoters and terminators may also be the native promoter and the native terminator, whose DNA sequences are reproduced in SEQ ID Nos. 7 and 8. The vectors or expression cassettes additionally contain for conventional indicator/reporter genes or resistance genes for the detection of the transfer of the desired vector or DNA molecule/nucleic acid molecule, and for selection of the individuals that contain these, since a direct detection via the expression of the gene is for the most part rather difficult. Since the nucleic acid molecule according to the invention here itself encodes for a polypeptide which confers resistance to *Cercospora* leaf spot disease, it is not essential for the expression in plant cells to provide an additional resistance gene; however, it is recommended, in order to allow a rapid selection.

Examples of indicator/reporter genes are, for example, the luciferase gene and the gene encoding green fluorescent protein (GFP). These, furthermore, also allow tests for the activity and/or regulation of a promoter of the gene. Examples of resistance genes—especially, for plant transformations—are the neomycin phosphotransferase gene, the bygromycin phosphotransferase gene, or the gene encoding phosphinothricin acetyltransferase. Additional positive selection markers may be enzymes which provide the transformed plant a selection advantage over the non-transformed plant—in particular, a nutrient advantage, e.g., the mannose-6-phosphate isomerase or the xylose isomerase. However, this does not preclude additional indicator/reporter genes or resistance genes known to the person skilled in the art. In a preferred embodiment, the vector is a plant vector. Furthermore, the expression cassette may be present as integrated into a plant genome.

In a further aspect, the present invention relates to cells that include the vectors, recombinant DNA molecules, and/or nucleic acid molecules according to the invention. A cell in the sense of the invention may be a prokaryotic (for example, bacterial) or eukaryotic cell (for example, a plant cell or a yeast cell). The cell is preferably an *agrobacterium* such as *Agrobacterium tumefaciens* or *Agrobacterium rhizogenes*, an *Escherichia coli* cell, or a plant cell; the plant cell is particularly preferably a cell of a plant of the genus *Beta*, the species *Beta vulgaris*, or the subspecies *Beta vulgaris* subsp. *vulgaris*. The cell may also be present as a culture. The invention also consequently covers a cell culture which contains such cells. The cell culture is preferably a pure culture or an isolate that contains no cells of another type.

Known to the person skilled in the art are both numerous methods, such as conjugation or electroporation, with which he may introduce the nucleic acid molecule according to the invention, the recombinant DNA molecule, and/or the vector or the expression cassette of the present invention into an *agrobacterium*, and methods such as diverse transformation methods (biolistic transformation, *agrobacterium*-mediated transformation) with which he may introduce the nucleic acid molecule according to the invention, the DNA molecule, and/or the vector of the present invention into a plant cell (Sambrook et al., Molecular Cloning: A Laboratory Manual, 3rd ed., Cold Spring Harbor Laboratory Press, Cold Spring Harbor, NY, 2001.

Furthermore, the present invention preferably relates to a *Cercospora*-resistant plant—preferably, a plant of the species *Beta vulgaris* subsp. *vulgaris* or a portion thereof—that contains the nucleic acid molecule according to the invention which confers the *Cercospora* resistance. The *Cercospora*-resistant plant may contain the nucleic acid molecule according to the invention as a transgene or as an endogene. Within the scope of the invention, for the first time, plants of the subspecies *Beta vulgaris* subsp. *vulgaris* were produced which contain the nucleic acid molecule according to the invention. The invention here also includes plants of the subspecies *Beta vulgaris* subsp. *vulgaris* which contain the nucleic acid molecule according to the invention as an endogene.

A portion may thereby be a cell, a tissue, an organ, or a combination of multiple cells, tissues, or organs. A combination of multiple organs is, for example, a blossom or a seed. A *Cercospora*-resistant plant of the present invention preferably shows a higher resistance to *Cercospora*—in particular, *Cercospora beticola*—than a corresponding plant that does not contain the nucleic acid molecule according to the invention (control plant). The control plant ideally has the identical genotype as the transgenic plant, and has been cultured under identical conditions, but does not contain the resistance-conferring nucleic acid molecule. The level of the resistance, e.g., to *Cercospora beticola*, may be qualitatively established in plants of the genus *Beta* by determining rating scores. A higher resistance manifests in an improvement in the resistance by at least one rating score, by at least two rating scores, and, preferably, by at least three or more rating scores.

A plant cell or plant or portion thereof of the present invention that contains the nucleic acid molecule according to the invention—in particular, a plant of the genus *Beta*—preferably shows a higher resistance to a pathogen—in particular, to *Cercospora beticola*—than a corresponding plant cell or plant or portion thereof that does not contain the nucleic acid molecule according to the invention, or contains a sensitive allelic variant of the nucleic acid molecule. The level of the resistance, e.g., to *Cercospora beticola*, may be qualitatively established in plants of the genus *Beta* by determining rating scores. A higher resistance manifests in an improvement in the resistance by at least one rating score, by at least two rating scores, and, preferably, by at least three or more rating scores.

In the case of a transgenic plant cell, or plant or portion thereof, this comprises the nucleic acid molecule or DNA molecule according to the invention as a transgene or the vector or the expression cassette of the present invention. Such a transgenic plant cell or plant or portion thereof is, for example, one that is transformed—preferably, stably—with the nucleic acid molecule, DNA molecule according to the invention, or with the vector or the expression cassette of the present invention. In a preferred embodiment, the nucleic acid molecule is operatively linked with one or more regulatory sequences which allow the transcription and, optionally, the expression in the plant cell. The total structure made up of the nucleic acid molecule according to the invention and the regulatory sequence(s) then represents the transgene. Such regulatory sequences are, for example, a promoter or a terminator. Numerous functional promoters and terminators that are applicable in plants are known to the person skilled in the art.

The invention also includes a vacuole of the cell according to the invention, and the content substances stored therein.

Furthermore, the invention also relates to the cell extract from a cell—preferably, from a plant cell, particularly preferably, from a cell of *Beta vulgaris*, and, especially preferably, from a cell of one of the following crops: sugar beet, chard, or beetroot. No plant can be regenerated from the cell extract.

Likewise encompassed by the invention is a plant genome containing the nucleic acid according to the invention.

The sugar concentration from the cell extract may thereby be increased relative to a cell that is not a cell according to the invention, but that belongs to the same species or crop. This applies, in particular, under the conditions when infested by *Cercospora*.

Also encompassed by the invention is the use of the cell extract for the production of sugar (saccharose) or for the production of juice—preferably, beetroot juice.

Likewise encompassed by the invention is the sugar—in particular, saccharose—contained in the cells according to the invention and their vacuoles.

An additional aspect of the invention is seed stock comprising seeds that contain the nucleic acid according to the invention. The nucleic acid according to the invention may be present transgenically or endogenously. The seed stock and the seeds may be technically treated. The invention thus also comprises technically-treated seed stock and technically-treated seeds. The various embodiments of technically-treated seed stock are explained in detail in the following whereby the term seed stock also includes seeds: Technically-treated seed stock may be present in polished form. The outermost layer of the seed is thereby removed, so that the seed assumes a more rounded form. This is helpful in sowing, where an optimally uniform shape leads to a uniform distribution of the seed stock grains. Technically-treated seed stock furthermore encompasses pelleted seed stock. The seed stock is thereby embedded in a pelleting mass that protects the seed stock contained therein and leads to a larger mass, such that the pelleted seed stock shows a greater resistance capability with regard to wind drift and is thus less susceptible to being blown away by the wind, and, at the same time, a more precise positioning during sowing is enabled. In a preferred embodiment of the invention, all pelleted seed stock grains of a batch or unit designated for sale have essentially the same shape and the same mass. Deviations of 5% in diameter and mass are possible. However, the deviations preferably do not exceed 1%. As one of the main components, the pelleting mass may contain for example a mineral compound such as clay, bentonite, kaolin, humus and/or peat, for example. It is possible to add an adhesive material like polyacylamide. Additional possible components are cited in U.S. Pat. No. 4,067,141. Moreover, the pelleting mass may contain additional chemical agents that positively influence the cultivation in practice. These may here be substances that are counted among fertilizing agents. These include compounds rich of one or more of the following elements: Nitrogen, Phosphorus and Potassium (macronutrients). Therefore, the fertilizing ingredients may contain for example Nitrate nitrogen, Ammonium nitrogen, Magnesium Nitrate, Calcium Ammonium Nitrate, Mono Ammonium Phosphate, Mono Potassium Phosphate and Potassium Nitrate. Furthermore, pelleting mass may contain fungicides, insecticides, and/or antifeedants.

The fungicides may be thiram and/or hymexazol and/or other fungicides. The insecticide may be a substance from the neonicotinoid group. The substance from the neonicotinoid group is preferably imidacloprid (ATC Code: QP53AX17) and/or clothianidin (CAS number 210880-92-5). Furthermore, the insecticide may also be cyfluthrin (CAS number 68359-37-5), beta-cyfluthrin or tefluthrin. It is worth mentioned that the compound included in the dressing or pelleting mass are taken up by the plant and show systemic effect thereby providing suitable protection of the whole plant. Plants resulting from pelleted seed including one or more pesticides therefore differ from naturally occurring plants and show better performance under biotic stress conditions. In this context the invention also encompasses a mixture of a pelleting mass and a seed according to the invention. Furthermore, the invention also encompasses a method for producing a pelleted seed according to the invention comprising the following steps:

a) providing a sugar beet plant seed comprising the nucleic acid according to the invention,
b) embedding the sugar beet plant seed in a pelleting mass, and
c) allowing the pelleting mass to dry or drying the pelleting mass, wherein the seed may be optionally a primed or pregerminated seed or the seed may be allowed to be primed during step b).

The pelleted seed stock is a specific embodiment of dressed seed stock. In this context technically-treated seed stock encompasses also the dressed seed stock. However, the invention is not limited to pelleted seed stock, but, rather, may be applied with any form of dressed seed stock. The invention thus also relates to dressed seed stock, which includes pelleted seed stock, but is not limited to this. Dry dressing, wet dressing, and suspension dressing are thus also encompassed. The dressing may thereby also contain at least one dye (coloring), such that the dressed seed stock may be quickly differentiated from undressed seed stock, and, furthermore, good visibility in the environment is ensured after sowing. The dressing may also contain those agrochemicals which are described in the context of the pilling mass. The invention includes thus such dressed seed stock whereby the dressing contains at least one anti-feedant such as an insecticide and/or at least one fungicide. Optionally, so called electronic dressing (dressing by application of electric energy) may be applied. Electronic dressing is not a dressing in the strict sense of the word but is very suitable to destroy plant pathogens which adhere to the seed or seed stock before planting the seed or seed stock. It is also beneficial that seeds or seed stock which have only been treated by use of electronic dressing (without using agrochemicals) can be fed to animals in case more seed or seed stock is available than needed to till a field.

An additional form of technically-treated seed stock is encrusted seed stock. What is known as coating is also spoken of in this context as well as of seed stock treated with a coating. The difference to pelleted seed stock is that the seed grains retain their original shape, wherein this method is especially economical. The method is described in EP 0 334 258 A1, for example. An additional form of technically-treated seed stock is sprouted or primed seed stock. Sprouted seed stock is pretreated via a pre-germination, whereas primed seed stock has been pretreated via a priming ("germination"). Pre-germinated and primed seed stock have the advantage of a shorter emergence time. The point in time of the emergence after sowing is, at the same time, more strongly synchronized. This enables better agrotechnical processing during cultivation and especially during the harvest, and, additionally, increases the yield quantity. In pre-germination, the seed stock is germinated until the radicle exits the seed stock shell, and the process is subsequently stopped. In the priming, the process is stopped before the radicle exits the seed stock shell. Compared to pre-germinated seed stock, seed stock that has been subjected to a priming is insensitive to the stress of a re-drying and, after such a re-drying, has a longer storage life in comparison to pre-germinated seed stock, for which a re-drying is generally not advised. In this context, technically pretreated seed stock also includes primed and re-dried seed stock. The process of pre-germination is explained in U.S. Pat. No. 4,905,411 A. Various embodiments of priming are explained in EP 0 686 340 A1. In addition to this, it is also possible to simultaneously pill and prime seed stock in one process. This method is described in EP 2 002 702 B1. Primed seed stock which is moreover pelleted, is encompassed by the present invention.

The technically-treated seed stock may additionally be furnished with one or more of the herbicide resistances explained above. This allows a further-improved agrotechnical cultivation, since the technically-treated seed stock may be deployed on a field that has previously been treated with weed killer, and that therefore is weed-free.

In addition to this, the invention also encompasses a mixture containing the seed stock according to the invention or the seeds according to the invention, and a dressing mass as defined above. The dressing mass is thereby preferably embodied as a pelleting mass, as defined above.

With storage of seed stock according to the invention, storage conditions are preferably to be chosen that do not negatively affect the stability or storage life of the seed stock. Fluctuations in humidity may, especially, have a disadvantageous effect here. Part of the invention is a method for the storage of the seed stock in a bag or container that is via simultaneously water-repellent and breathable. Such a bag or container may be designed as a carton or packing. Such a carton or packing may optionally possess an inner vapor barrier. If the carton or packing is designed as a duplex carton, its stability increases. A container, bag, carton or packing comprising the seed stock according to the invention, or technically-treated seed stock according to the invention, is likewise a part of the invention. It is likewise part of the invention to store seed stock according to the invention or technically-treated seed stock according to the invention in such a bag, container, box, packing or carton.

The present invention also encompasses varieties comprising the resistance gene according to the invention. Furthermore, plants, seeds and seedstock of such a variety are included. The seeds and seedstock of such a variety may be subject to a technical treating as described herein (e.g. pelleting). Suitable sugar beet varieties for the introduction of the resistance gene are for example BTS 7300 N, BTS 2045, BTS 3750, DAPHNA, KORTESSA KWS or SABATINA KWS. Sugar beet plants of the named varieties are also examples of hybrid sugar beet plants. Suitable red beet varieties for the introduction of the resistance gene are for example Jolie, Scarlett (PV-9503) or Diaz wherein Jolie and Diaz are also examples of hybrid red beet plants. Suitable Swiss Chard varieties for the introduction of the resistance gene are for example Fluence, Ion or Tesla/PV-9022. Suitable varieties of *Spinacia oleracea* (spinach) for the introduction of the resistance gene are for example PV-9210, PV-1194 or La Paz/PV-1237. Hybrid plants take advantage from the heterosis effect.

In one embodiment, the plant according to the invention is a hybrid plant or a double haploid plant. Hybrid plants and double haploid plants do not occur in nature and cannot be isolated from nature. In a further embodiment of the plant according to the invention, the nucleic acid molecule according to the invention is present in heterozygous or homozygous form. In the case of a hybrid plant, the nucleic acid molecule may also be present in hemizygous form. The invention also encompasses hybrid seeds and double haploid seeds which contain a nucleic acid according to the invention or a polypeptide according to the invention.

A further embodiment of the present invention comprises a plant—preferably, of the species *Beta vulgaris*—that is characterized in that the resistance to *Cercospora* in this plant is further increased. For example, this may be realized by means of"gene stacking," i.e., the resistance is increased using this dose effect. For this, the plants according to the invention that contain the *Cercospora* resistance-conferring allele are over-transformed with this resistance allele in order to increase the amount of the transcription of the gene in the plant. An alternative approach includes the gene editing/site-directed mutagenesis or TILLING-mediated modification of the native promoter of the resistance-conferring allele, in order to increase its expression rate, or the modification of the resistance-conferring LRR gene allele itself, in order to increase its activity or stability. Such a method for increasing the activity by means of modification of a resistance gene is described in WO 2006/128444 A2, for example, and may be performed by means of the techniques known to the person skilled in the art. An additional approach may include the fusion of the nucleic acid molecule according to the invention with a heterologous promoter that exhibits a higher activity in comparison to the native promoter—in particular, after *Cercospora* infection.

An additional embodiment of the present invention relates to a sugar beet plant or a portion thereof or a pelleted seed of such a plant which is harvestable before bolting because no bolting of the sugar beet plant occurs during the first 10, 11, 12, 13, 14 or 15 months after germination and the development of a beet body is finished during this period. Suitable varieties to create a sugar beet plant according to this paragraph by introduction of the resistance according to the invention are for example DAPHNA, KORTESSA KWS or SABATINA KWS.

In one embodiment of the present invention the sugar beet plant or a portion thereof or a pelleted seed of such a plant has agenome allowing the development of a beet body having a mass summing up to at least 50%, 60%, 70%, 80% or even 90% of the total mass of the full-grown plant. Suitable varieties to create a sugar beet plant according to this paragraph by introduction of the resistance according to the invention are for example DAPHNA, KORTESSA KWS or SABATINA KWS.

In another embodiment of the present invention the sugar beet plant or a portion thereof or a pelleted seed of such a plant has a genome allowing the development of a beet body having a minimum mass of 200 g, 250 g, 300 g, 350 g, 400 g, 450 g or 500 g and a maximum mass of 1000 g, 1100 g, 1200 g, 1300 g, 1400 g, 1500 g, 1600 g, 1700 g, 1800 g, 1900 g or even 2000 g via photosynthesis. Suitable varieties to create a sugar beet plant according to this paragraph by introduction of the resistance according to the invention are for example DAPHNA, KORTESSA KWS or SABATINA KWS.

An additional embodiment of the present invention is directed to a sugar beet plant or a portion thereof or a pelleted seed of such a plant wherein the genome of the sugar beet plant allows development of a beet body having a saccharose concentration of at least 10%, 11%, 12%, 13%, 14%, 15%, 16%, 17%, 18%, 19% or even 20%. Suitable varieties to create a sugar beet plant according to this paragraph by introduction of the resistance according to the invention are for example DAPHNA, KORTESSA KWS or SABATINA KWS.

In one embodiment of the present invention the sugar beet plant or a portion thereof or a pelleted seed of such a plant includes at least one, at least two, at least three, at least four, at least five, at least ten, at least twenty or even at least thirty mutation(s) relative to SEQ ID No. 1, 2 or 4.

The method for the production of an organism which comprises a mutated version of the nucleic acid molecule according to the above given embodiment [1] and/or a mutated version of a promoter comprising a nucleic acid sequence selected from the group consisting of (a) SEQ ID NO: 7, (b) a nucleotide sequence, which hybridizes under stringent conditions with a sequence which is complementary to the sequence according to (a), and (c) a nucleotide sequence which is at least 70% identical to a sequence according to SEQ ID NO: 7, wherein the method includes the following steps:

(I) Provision of an organism or a cell comprising the nucleic acid molecule and/or the promoter (II) Increase of the mutation rate of the organism or the cell or mutagenesis of the organism or the cell (III) Phenotypic selection of an organism, which as a result of a mutation exhibits an altered resistance or altered resistance level towards *Cercospora beticola* or Genotypic selection of an organism or a cell which comprises a mutation in the nucleic acid molecule and/or the promoter wherein the mutation has been created via step (II) and optionally (IV) Regeneration of the organism from the cell obtained via step (III).

The organism can be a plant. Preferably the plant is a *Beta vulgaris*. However, it is also possible to use unicellular organisms as bacteria. The bacterium can be *E. coli*. If the organism is a plant then the method can be applied in vivo as well as in vitro. If the organism is a plant and the method is applied in vitro, a cell culture of the plant may be established and the increase of the mutation rate or the mutagenization may occur in the cell culture. The increase of the mutation rate encompasses for example the application of mutagenic agents like for example 5-bromouracil or ethylmethane sulfonate (EMS) or the application of physical mutagens like ionizing radiation or UV light. The mutagenization encompasses also the targeted mutagenesis. The targeted mutagenesis can be achieved by precise methods as gene editing (as explained further below). The regeneration of organism out of cells is explained in various standard references of the cell biology. The regeneration of plants is for example explained in the standard reference "Plant biotechnology: comprehensive biotechnology, second supplement" (Michael W. Fowler, Graham Warren, Murray Moo-Young—Pergamon Press—1992). The regeneration of *Beta vulgaris* out of the cell culture is described in Lindsey & Gallois "Transformation of sugarbeet (*Beta vulgaris*) by *Agrobacterium tumefaciens*." Journal of experimental botany 41.5 (1990): 529-536.

These references also describe how plant cell cultures are established. As explained further above the mutated version of the nucleic acid molecule respectively the promoter characterizes themselves preferably due to the expression rate of the resistance imparting nucleic acid molecule which is increased by the mutation. Such an effect can also rely on the presence of several mutations. For example, it is possible to introduce two, three, four, five or more mutations in the promoter or the nucleic acid molecule.

By the introduction of mutations thus more resistance imparting protein can be built in the cell or the protein has a better effect. Thereby, the resistance in comparison to a control plant comprising the unaltered nucleic acid according to the invention can be increased for example by at least 1, 2, 3, 4, 5 or more percent. The increase can be measured as explained further below. Moreover, the resistance due to the mutation or mutations can be increased by at least one rating score. The determination of rating scores is explained elsewhere herein. Furthermore, the resistance protein can impart—as a result of the mutations—an altered effect and in some circumstances can exhibit effect against such pathogens which have adapted themselves to the initial resistance mechanism. In this context the invention encompasses also such mutated variants of the nucleic acids according to the invention and mutated variants of the protein according to the invention. Preferably the invention encompasses such variants which do not occur in nature and cannot be isolated from nature to make sure that the pathogen had no opportunity to adapt itself to such variants. The above described method for the production of an organism which comprises a mutated version of the nucleic acid molecule may furthermore include a further step, in which those organisms or respectively plants are identified, which have a further increased resistance due to the mutation or mutations. If an increase of resistance has taken place may be determined by the herein explained rating scores or the measuring of the resistance level.

Besides the above described method for the production of organisms which comprise a mutated version of the nucleic acid molecule or of the promoter it is also possible to modify the according nucleic acids chemically in an isolated state to achieve the desired effects (as for example those which are described above). The advantage of this approach is that the compounds can be edited even more precisely. For this purpose, the following method is offered:

Production of a chemically modified nucleic acid molecule according to the above given embodiment [1] and/or a chemically modified promoter comprising a nucleotide sequence which is chosen from (a) SEQ ID NO: 7;

(b) a nucleotide sequence which hybridizes under stringent conditions to a nucleotide sequence according to (a);

(c) a nucleotide sequence which is at least 70% identical to a sequence according to SEQ ID NO: 7;

wherein the method comprises the following steps:

(I) Provision of the nucleic acid molecule as stated above in isolated form (II) chemical modification of the nucleic acid molecule or the promoter by one of the following steps:

(IIa) Mutagenization (IIb) Gene editing (IIc) Restriction and ligation respectively insertion or deletion.

Furthermore, chemical modifications can be generated by such approaches as stated elsewhere herein in context of allelic variants. The gene editing given under step (H) above is equal to the term "Genome-Editing". Optionally the chemically modified nucleic acid molecule or the chemically modified promoter can be subsequently introduced into a cell or can be stably integrated. With the help of such a cell, the chemically modified nucleic acid molecule and the modified promoter can be propagated in context of the cell proliferation. They can be subsequently isolated in vast number and expression analyses may be performed. Expression analyses are especially suitable when the chemical modification concerns the promoter. It is possible to harvest the cells and to isolate the chemically modified resistance protein for chemical analyses. If the cell which comprises the chemically modified nucleic acid molecule or the modified promoter is a plant cell, a complete plant may be regenerated out of this cell. The approaches described within this passage can be performed subsequently to the above given method for the production of a modified form of the nucleic acid molecule and/or a modified promoter and the obtained variants are also a part of this invention. Moreover, a plant comprising the chemically modified nucleic acid molecule or the modified promoter are also part of the invention. Thus, the invention is also related to a plant obtained by this method. Furthermore, the invention relates also to the chemically modified nucleic acid molecules obtained by this method and to the encoded polypeptides. These compounds may be optimized versions of the original (not modified) compounds, wherein the resulting resistance level—as explained further above—may be increased by at least by 1, 2, 3, 4, 5, or more percent or may be increased by at least one rating score. In this regard the method for the production of a chemically modified nucleic acid molecule is also a method for the optimization of the nucleic acid molecule. The method for optimization may furthermore contain an additional step, in which those modified variants of the nucleic acid molecule are identified which lead in comparison to the unamended variants to an increased resistance in a plant.

In a further embodiment, the plant of the present invention additionally, transgenically or endogenously, comprises a second nucleic acid molecule at a different position in the genome, which encodes a polypeptide that is able to confer a resistance to *Cercospora* in the plant in which the polypeptide is expressed. For example, one or more of the resistance genes or resistance loci that are described in the prior art may—insofar as they are not already present in the initial genotype—be introduced into the present plant by means of crossing, transformation, homology-directed repair, or homologous recombination in the plant. Among these are, for example, the rhizomania resistance RZ1 (Lewellen, R. T., I. O. Skoyen, and A. W. Erichsen, "Breeding sugar beet for resistance to rhizomania: Evaluation of host-plant reactions and selection for and inheritance of resistance." 50*th Winter Congress of the International Institute for Sugar Beet Research, Brussels* (*Belgium*), Feb. 11-12, 1987. IIRB. Secretariat General, 1987), or the rhizomania resistance RZ3 (WO 2014/202044).

The present invention additionally relates to a method for increasing the resistance to *Cercospora* in a plant of the species *Beta vulgaris*, wherein the increase in the resistance takes place without the resistance-conferring gene according to the invention, in comparison to an isogenic plant. The increase in the resistance may take place via integration of the nucleic acid molecule according to the invention into the genome of at least one cell of a plant of the species *Beta vulgaris*, as well as possible regeneration of a plant from the plant cell. The integration may take place both by means of sexual crossing, e.g., with one of the aforementioned *Beta vulgaris* subsp. *maritima* and subsequent selection, or by means of homology-directed repair or homologous recombination. The two latter methods cited are preferably supported by site-directed nucleases which may be selected from, but are not limited to, the following: CRISPR nuclease, including Cas9, CasX, CasY, or Cpf1 nuclease, TALE nuclease, zinc finger nuclease, meganuclease, Argonaut nuclease, restriction endonuclease, including FokI or a variant thereof, recombinase, or two, site-specific, nicking endonucleases. The introduction of the resistance-conferring gene by means of CRISPR-mediated homologous recombination in *Beta vulgaris* subsp. *vulgaris* is shown in Example 1.

Moreover, the invention encompasses also a method of producing an agronomically sugar beet plant of the genus *Beta* that displays improved resistance to *Cercospora beticola*, the method comprising introgressing into said plant a chromosomal interval that confers the improved resistance to *Cercospora beticola*, wherein the chromosomal interval maps to a position between a sequence represented by a marker selected from the group consisting of s4p4293s01 and s4p4295s01 and a sequence represented by a marker selected from the group consisting of s4p4301s01 and sxh0678s01, characterized in that the chromosomal interval comprises a nucleotide sequence encoding a polypeptide that is able to confer resistance to *Cercospora beticola* in a plant in which the polypeptide is expressed wherein the nucleotide sequence is selected from (a) a nucleotide sequence encoding a polypeptide having an amino acid sequence according to SEQ ID No. 3;
(b) a nucleotide sequence that comprises the DNA sequence according to SEQ ID No. 2;
(c) a nucleotide sequence that comprises a DNA sequence selected from the group consisting of SEQ ID No. 1 or SEQ ID No. 53;
(d) a nucleotide sequence that hybridizes to a nucleotide sequence which is complementary to the nucleotide sequence according to (a), (b), or (c), under stringent conditions;
(e) a nucleotide sequence encoding a polypeptide which, via substitution, deletion, and/or addition of one or more amino acids of the amino acid sequence, differs from a polypeptide encoded by the nucleotide sequence according to (a), (b), or (c);
(f) a nucleotide sequence encoding a polypeptide which has an amino acid sequence that is at least 70% identical to an amino acid sequence according to SEQ ID No. 3;
(g) a nucleotide sequence that is at least 70% identical to a DNA sequence according to SEQ ID No. 1 or SEQ ID No. 2;

An alternative approach includes the increase in the expression of the nucleic acid molecule according to the invention in the plant. This may take place via modification of the native promoter, wherein the modification preferably takes place by means of gene editing or site-directed mutagenesis which is mediated via site-directed nucleases, and, optionally, repair models. Examples of such nucleases have already been cited above. The increase in the expression of the nucleic acid molecule according to the invention may likewise take place via fusion of the nucleic acid molecule with a heterologous promoter, which exhibits a higher activity in comparison to the native promoter—in particular, after *Cercospora* infection. The fusion may likewise take place via site-directed nuclease and repair models, but also by means of direct insertion after double-strand break.

As has already been mentioned above, a method for increasing the *Cercospora* resistance, may also result in the increase in the activity and/or stability of the polypeptide according to the invention, via modification of the nucleotide sequence of the nucleic acid molecule according to the invention. Such a method for increasing the activity by means of modification of a resistance gene is described in WO 2006/128444 A2, for example, and may be performed by means of the techniques known to the person skilled in the art. This approach is explained in detail further below.

Alternatively, a *Cercospora*-resistant genotype may be produced from a *Cercospora*-sensitive genotype by means of random or directed mutagenesis of the nucleic acid sequence of the sensitive gene, and thus the *Cercospora* resistance may be increased. Examples of polymorphisms which differentiate the sensitive allele from the resistant allele are presented in FIG. 1.

For example, the sensitive allele may be modified via gene mutation by means of TALE nucleases (TALEN's) or zinc finger nucleases (ZFN's), as well as CRISPR/Cas systems, which—among other things—are described by way of example in WO 2014/144155 A1 (Engineering plant genomes using CRISPR/Cas systems) and in Osakabe & Osakabe, Plant Cell Physiol., 56 (2015), 389-400. This may also be achieved via use of the method designated as TILLING (Targeted Induced Local Lesions in Genomes), wherein it is described, e.g., in the German patent application DE 10 2013 101 617, how point mutations are caused in the sensitive gene, and plants are subsequently selected that exhibit a suitable, i.e., resistance-conferring, mutation, e.g., a barley resistant to yellow mosaic virus; see DE 10 2013 101 617 on pp. 4, 8, and 12, in paragraphs [0014], [0026], and [0038]. The TILLING method is also described in detail in the publication by Henikoff et al. (Henikoff et al., Plant Physiol. 135, 2004, 630-636).

These methods preferably lead to an improvement in the resistance by at least one rating score—particularly preferably, to an improvement in the resistance by at least two, three, or more rating scores. After mutagenesis of the plant cells and subsequent regeneration of plants from the mutagenized plant cells, or mutagenesis of plants, the plants may then be identified that exhibit one or more mutations, as depicted in FIG. 1, in an endogenous nucleic acid molecule. In this context the already mentioned plant according to the invention may be characterized by that the resistance is increased by at least one rating score, preferably by at least two or more rating scores.

Alternatively, the resistance of the plants according to the invention may be increased for example by at least 1, 2, 3, 4, 5 or more percent in comparison to a control plant, which does not comprise the nucleic acid according to the invention. The increase can be measured by inoculation of respectively one healthy leaf with an isolate of the pathogen and the determination of the infested surface after 15 days. A reduce of 5% of the infested surface corresponds to an increase of the resistance of 5%. Further parameters for the conduction of the measuring can be derived from the below given embodiment "resistance rest".

An additional embodiment of the present invention is a method for producing a *Cercospora*-resistant plant, which may take place via transformation of a plant cell with the nucleic acid molecule according to the invention, the recombinant DNA molecule, or with the vector or the expression cassette, and regeneration of the transgenic plant from the transformed plant cell (see Example 2), as well as, as described above, by means of random or targeted mutagenesis of the nucleic acid sequence of the sensitive gene to generate a *Cercospora*-resistant genotype, or via crossing and selection, e.g., with one of the aforementioned *Beta vulgaris* subsp. *maritima*. Vectors or expression cassettes, as well as methods for transforming plants, have already been described above.

The method for production of a *Cercospora*-resistant plant alternatively includes, as described above, the introduction of a site-directed nuclease and a repair matrix into a cell of a plant of the species *Beta vulgaris*, wherein the site-directed nuclease is able to generate at least one double-strand break of the DNA in the genome of the cell—preferably, upstream and/or downstream of a target region—and the repair matrix comprises the nucleic acid molecule according to the invention. The method furthermore includes the cultivation of this cell under conditions that allow a homology-directed repair or a homologous recombination, wherein the nucleic acid molecule is incorporated from the repair matrix into the genome of the plant. Furthermore, the regeneration of a plant from the modified plant cell is encompassed (see Example 1).

In a preferred embodiment, the target region is an allelic variant of the nucleic acid molecule according to the invention, wherein the allelic variant encodes a polypeptide which does not confer resistance to *Cercospora*. In a further preferred embodiment, this allelic variant comprises a nucleotide sequence that encodes a polypeptide with an amino acid sequence according to SEQ ID No. 6 and/or comprises the encoded DNA sequence according to SEQ ID NO: 5 or the genomic DNA sequence according to SEQ ID No. 4.

As described in connection with the nucleic acid molecule according to the invention, substitutions, deletions, insertions, additions, and/or any other change may be introduced that, either alone or in combinations, do in fact change the nucleotide sequence, but perform the same function as the initial sequence—here, the nucleotide sequence of the allelic variant of the nucleic acid molecule according to the invention. Therefore, in a further embodiment, the invention includes a nucleotide sequence that encodes a polypeptide which represents a derivative of the polypeptide which is encoded by the allelic variant of the nucleic acid molecule according to the invention, or which comprises the amino acid sequence of the allelic variant of the nucleic acid molecule according to the invention. A derived amino acid sequence which has at least one substitution, deletion, insertion, or addition of one or more amino acids, wherein the functionality of the encoded polypeptide/protein is preserved, represents a derivative of the polypeptide. The nucleotide sequence, using conventional methods that are known in the prior art, e.g., via site-directed mutagenesis, PCR-mediated mutagenesis, transposon mutagenesis, genome editing, etc., substitutions, deletions, insertions, additions, and/or any other change, either solely or in combinations with the gene, may thereby be introduced, which do in fact change the nucleotide sequence, but perform the same function as the initial sequence.

With regard to the amino acid sequence, after modification via an aforementioned method, this also has a common structural domain and/or possesses common functional activity. Nucleotide sequences or amino acid sequences that at least approximately 80%, at least approximately 85%, at least approximately 90%, at least approximately 91%, at least approximately 92%, at least approximately 93%, at least approximately 94%, at least approximately 95%, at least approximately 96%, at least approximately 97%, at least approximately 98%, at least approximately 99%, or at least approximately 100% identical to the nucleotide sequence or amino acid sequence of the cited allelic variant of the nucleic acid molecule according to the invention are defined here as being sufficiently similar. Accordingly, the present invention includes a nucleotide sequence that is able to hybridize, under stringent conditions, with a nucleotide sequence that is complementary to a nucleotide sequence of the allelic variant of the nucleic acid molecule according to the invention or to the nucleotide sequence that encodes the corresponding amino acid sequence.

In a further preferred embodiment, the method according to the invention is characterized in that the double strand break occurs in an allelic variant of the nucleic acid molecule according to embodiment [1] or that the at least one double strand break occurs at a position which is at least 10,000 base pairs upstream or downstream of the allelic variant, wherein the allelic variant codes for a polypeptide which does not impart a resistance towards *Cercospora*.

For the person skilled in the art, it is obvious that numerous, different sensitive sequences may occur that derive from the nucleic acid molecule according to the invention, but do not confer resistance to *Cercospora*, such that the sequences listed above (SEQ ID Nos. 4, 5, and 6) should only be considered as an example of sequences, and the present invention is not limited to the aforementioned allelic variant of the nucleic acid molecule according to the invention. Such an allelic variant can comprise a nucleotide sequence, which is selected from:

(a) a nucleotide sequence encoding a polypeptide having an amino acid sequence according to SEQ ID No. 6;
(b) a nucleotide sequence that comprises the DNA sequence according to SEQ ID No. 5;
(c) a nucleotide sequence that comprises a DNA sequence according to SEQ ID No. 4;

(d) a nucleotide sequence that hybridizes with the complementary sequence according to (a), (b), or (c), under stringent conditions;

(e) a nucleotide sequence encoding a polypeptide which, via substitution, deletion, and/or addition of one or more amino acids of the amino acid sequence, differs from a polypeptide encoded by the nucleotide sequence according to (a), (b), or (c);

(f) a nucleotide sequence encoding a polypeptide which has an amino acid sequence that is at least 70%, 75%, 80%, 85%, 90%, 95%, 96%, 97%, 98% or 99% identical to an amino acid sequence according to SEQ ID No. 6;

(g) a nucleotide sequence that is at least 70%, 75%, 80%, 85%, 90%, 95%, 96%, 97%, 98% or 99% identical to a DNA sequence according to SEQ ID No. 4 or SEQ ID No. 5;

As described above, with quantitative heredity of QTL, not only is the desired resistance to often introduced into the plant, but, rather, also often unwanted features such as, for example, reduced yield, due to the inheritance of additional genes that are not linked with the positive feature of the resistance. This increasingly occurs if, as in the case of *Cercospora* resistance, the resistance is inherited in previously available cultivars via many resistance genes with small effect. Therefore, in a preferred embodiment, the introduction of the nucleic acid molecule according to the invention, which already shows, on its own, a dominant resistance effect, or of the vector or the expression cassette, is not linked with the introduction of unwanted features, wherein the yield is, preferably, not negatively affected. Furthermore, encompassed by the invention is the plant that is obtained via such a method.

Although the QTL analyses with that have previously been known from the prior art could detect actual QTL's, the underlying genomic regions that had shown a QTL effect also mediated the disadvantages described above, which is why "linkage drag" is also discussed in this context. At the same time, the QTL's and the effects connected therewith were not described uniformly in the respective prior art, and merely mediated a weak effect, such that the utilization of these results in the breeding of *Cercospora*-resistant plants was possible to only a limited extent, and was largely uncertain. Targeted breeding and controlled integration of the resistance gene into the gene pool of the sugar beet are now enabled by means of the identification of the resistance gene described herein. This ensures the breeding and generation of entirely new *Cercospora*-resistant cultivars that exhibit a high resistance to the pathogen, without negatively affecting the sugar yield.

The present invention likewise relates to a method for the identification, and possibly the provision, of a plant of the species *Beta vulgaris* that is resistant to the pathogen *Cercospora*, characterized in that the method includes a step of the detection of the presence and/or of the expression of a nucleic acid molecule according to the invention or of the polypeptide according to the invention in the plant or a sample/portion thereof. The presence and/or the expression of a nucleic acid molecule according to the invention, or of the polypeptide according to the invention, may be tested by means of standard methods known to the person skilled in the art, e.g., by means of PCR, RT-PCR, or western blot.

Furthermore, the identification method according to the invention also includes the detection of the nucleic acid molecule according to the invention by means of detection of at least one polymorphism between resistant and sensitive sequences, i.e., between the sequences of the nucleic acid molecule according to the invention and the sequences of the allelic variant of the nucleic acid molecule according to the invention that is described above, using molecular markers that detect one or more polymorphisms. As has already been described above, it is obvious to the person skilled in the art that numerous sensitive sequences exist, i.e., numerous sequences that encode the allelic variant of the nucleic acid molecule according to the invention. One of these is presented by way of example in the sequence comparison with the nucleotide sequence of the nucleic acid molecule according to the invention in FIG. 1. A preferred embodiment of the method according to the invention consequently includes the detection of at least one polymorphism that is presented in FIG. 1 using molecular markers which detect the polymorphisms—in particular, diagnostic polymorphisms. This detection preferably occurs using at least one molecular marker per polymorphism—in particular, per diagnostic polymorphism. It is known to the person skilled in the art which marker techniques are to be applied to detect a corresponding polymorphism, and how molecular markers for this are constructed (see Advances in Seed Science and Technology Vol. I, Vanangamudi et al., 2008). Furthermore, the present invention encompasses molecular markers which describe or detect a polymorphism according to FIG. 1, such as the use of a molecular marker for detection of a polymorphism according to FIG. 1. It is thereby also possible to use markers that do not differentiate between various polymorphisms, as long as the markers are able to detect such a polymorphism as it occurs in the nucleic acid molecule according to the invention, but is not contained the sensitive allelic variant.

Alternatively, or additionally, the identification method according to the invention includes a step of detecting at least one marker locus in the nucleotide sequence of the nucleic acid molecule according to the invention or in a cosegregating regions thereof. Preferably the cosegregating region is a genomic region in *Beta vulgaris* which cosegregates with the *Cercospora* resistance conferred by the polypeptide according to the present invention, or with the nucleic acid molecule according to the present invention, more preferably the cosegregating region comprises and is flanked by markers sxh0678s01 and s4p0264s01, by markers s4p4301s01 and s4p2271s01, by markers s4p4301s01 and s4p4293s01, or by markers s4p4301s01 and s4p4295s01. The detection may thereby take place via a method step in which at least one marker or at least one primer pair binds at the locus according to SEQ ID No. 74 or 75—preferably, at the locus according to SEQ ID No. 76 or 77—and, optionally as a result of this, a signal is generated, e.g., a fluorescence signal or a sequence amplificate. Thus, alternatively or additionally the cosegregating region may comprise a sequence according to SEQ ID NO 74 and/or 75, or SEQ ID NO: 76 and/or 77. Furthermore, the preceding identification methods also represent methods for selection of a plant which exhibits the resistance to *Cercospora* according to the invention. The method for selection includes a concluding step of selecting a resistant plant.

In this context, the present invention also includes the development or production of molecular markers that are suitable for detecting the aforementioned polymorphisms between the nucleic acid molecule according to the invention (resistant allele) and the sensitive allelic variant, wherein the markers are preferably suitable for detecting the polymorphisms presented in FIG. 1 or the construction of hybridization probes that specifically bind to the nucleotide sequence of the nucleic acid molecule according to the invention, or the production of a pair of nucleic acid molecules that is suitable for amplifying, in a PCR, a region that is specific to the nucleic acid molecule according to the invention, and thus for detecting these in a plant or plant cell.

The invention preferably includes a method for producing oligonucleotides of at least 15, 16, 17, 18, 19, or 20—preferably, at least 21, 22, 23, 24, or 25, particularly preferably, at least 30, 35, 40, 45, or 50, and, especially preferably, at least 100, 200, 300, 500 or 1,000—nucleotides in length that specifically hybridize with a nucleotide sequence of the nucleic acid molecule according to the invention or the nucleic acid molecule that is complementary thereto, or a pair of nucleic acid molecules—preferably, in the form of oligonucleotides—that is suitable for attachment as a forward and reverse primer to a region that is specific to the nucleic acid molecule according to the invention, and for amplifying this in a polymerase chain reaction (PCR), or that is suitable for hybridization as a forward and reverse primer to a region in the *Beta vulgaris* genome that, in *Beta vulgaris*, has a cosegregation with the *Cercospora* resistance conferred by the polypeptide according to the invention or with the nucleic acid molecule according to the invention. An example for suitable primers for the detection of a resistance-mediating nucleotide sequence according to the invention are given by SEQ ID NO 98 and SEQ ID NO 99. These two sequences build a primer pair which can be used in the PCR. The invention also includes a kit comprising oligonucleotides or molecular markers according to the invention.

The method for the production of oligonucleotides initially includes: the comparison of the nucleotide sequence of the nucleic acid molecule according to the invention with the nucleotide sequence of the corresponding nucleic acid molecule that does not confer resistance or of the sensitive allelic variant, which preferably has a nucleotide sequence according to SEQ ID No. 4 or 5; the identification of the sequence differences between the two nucleotide sequences; and the generation of nucleic acid molecules—here, meaning oligonucleotides—that specifically bind to the nucleic acid molecule according to the invention, but not to the nucleic acid molecule that does not mediate resistance.

Furthermore, the oligonucleotide according to the invention may be connected to a fluorescent dye in order to generate a fluorescence signal, e.g., under excitation via light of the corresponding wavelength. The fluorescent dye may be fluorochrome. The oligonucleotides according to the invention may be coupled with other compounds that are suitable for generating a signal. Such oligonucleotides do not occur in nature and also cannot be isolated from nature. The following is executed to produce such marked oligonucleotides: DNA may be marked bio-orthogonally. For this, DNA may be marked in vivo or in vitro with nucleoside analogs, which, for example, may subsequently be coupled with a fluorophore per Staudinger reaction. In addition to this, DNA may also be chemically provided with fluorophores. Oligonucleotides may be marked via a phosphoramidite synthesis with fluorophores that, for example, are used in QPCR, DNA sequencing, and in situ hybridization. Furthermore, DNA may be generated enzymatically in the course of a polymerase chain reaction with fluorescent nucleotides, or be marked with a ligase or a terminal deoxynucleotidyl transferase. DNA may also be detected indirectly via a biotinylation and fluorescent avidin. For couplings, fluorescein, fluorescent lanthanides, gold nanoparticles, carbon nanotubes, or quantum dots, among other things, are used as fluorophores. One of the most commonly used fluorescent substances is FAM (carboxyfluorescein). Consequently, oligonucleotides and, in particular, primers that possess a FAM marking are encompassed by the invention. FAM is preferably present as 6-FAM, wherein—depending upon the desired wavelength of the emission and excitation—other FAM variants, e.g., 5-FAM, may, however, also be used. Examples of additional fluorescence markers are AlexaFluor, ATTO, Dabcyl, HEX, Rox, TET, Texas Red, and Yakima Yellow. Depending upon the field of use, the oligonucleotides may be furnished with modifications of the bases or of the sugar phosphate spine. Among these are, among others, amino-dT, azide-dT, 2-aminopurine, 5-Br-dC, 2'-deoxyinosine (INO), 3'-deoxy-A, C, G, 5-Met-dC, 5-OH-Met-dCN6-Met-dA, and others.

Furthermore, the present invention also relates to a marker chip (“DNA chip”, “assay” or microarray) which contains at least one oligonucleotide according to the invention that is suitable for detection. The marker chip is suitable for application in one or more detection methods according to the invention.

The invention likewise includes a method for production of the protein according to the invention. The method includes the provision or cultivation of a cell culture which contains the SEQ ID No. 2, and the subsequent expression of the protein encoded by SEQ ID No. 2.

Furthermore, the present invention also relates to a *Cercospora*-resistant plant or a portion thereof which was identified, and, if applicable, selected, via a method as described in the preceding. In particular, the present invention relates to a population of plants comprising plants that are available according to one of the methods according to the invention as described in the preceding, and that preferably are resistant to *Cerospora* leaf spot disease or *Cercospora* infestation, and are characterized by the presence of a nucleic acid molecule according to the invention. The population preferably has at least 10—preferably, at least 50, more preferably, at least 100, particularly preferably, at least 500, and, particularly in agricultural farming, preferably at least 1,000—plants. The proportion of plants in the population that do not carry the nucleic acid molecule according to the invention and/or are susceptible to *Cercospora* leaf spot disease is preferably below 25% —preferably, below 20%, more preferably, below 15%, even more preferably, 10%, and, in particular, preferably below 5%, if present at all.

With the fine mapping described above, the position of the *Cercospora* resistance-conferring gene in the genome of *Beta vulgaris* subsp. *maritima* could be determined, and the gene itself and the surrounding sequence regions could be identified. This in turn represents the basis for the development of DNA hybridization probes or genetic markers in the target region, with the aid of which the *Cercospora* resistance-mediating gene could be detected, or could be differentiated from the gene that does not confer resistance.

DNA hybridization probes may be derived from the sequence of the *Cercospora* resistance-conferring gene and be used for the screening of genomic and/or cDNA banks of the desired organism. The probes may be used to amplify identified homologous genes via the known process of polymerase chain reaction (PCR), and to check whether the *Cercospora* resistance-conferring gene is present endogenously in an organism, or has been successfully introduced as heterologous genetic element.

The person skilled in the art may here resort to customary hybridization, cloning, and sequencing methods, which, for example, are listed in Sambrook et al., Molecular Cloning: A Laboratory Manual, 3rd ed., Cold Spring Harbor Laboratory Press, Cold Spring Harbor, NY, 2001. The person skilled in the art may also synthesize and use oligonucleotide primers to amplify sequences of the *Cercospora* resistance-conferring gene. In order to achieve a specific hybridization, such probes should be specific and have at least a length of 15 nucleotides—preferably, at least 20 nucleotides. A detailed guide to hybridization of nucleic acids may be found in Tijssen, Laboratory Techniques in Biochemistry and Molecular Biology—Hybridization with Nucleic Acid Probes, Part 1, Chapter 2, "Overview of principles of hybridization and the strategy of nucleic acid probe assays." Elsevier, New York (1993); and in Current Protocols in Molecular Biology, Chapter 2, Ausubel et al., eds., Greene Publishing and Wiley Interscience, New York (1995).

Therefore, a nucleic acid molecule of at least 15, 16, 17, 18, 19, or 20—preferably, at least 21, 22, 23, 24, or 25, particularly preferably, at least 30, 35, 40, 45, or 50, and, especially preferably, at least 100, 200, 300, 500, or 1,000—nucleotides in length is the subject matter of the present invention, wherein this nucleic acid molecule specifically hybridizes with a previously-described nucleotide sequence according to the invention that comprises the *Cercospora* resistance-conferring gene. This also explicitly encompasses the range of 15 to 35 nucleotides.

The present invention thus also relates to markers as oligonucleotides—in particular, primer oligonucleotides. These comprise a nucleic acid molecule of at least 15 nucleotides in length that specifically hybridizes with a nucleotide sequence defined as in the preceding.

In particular, the present invention encompasses a pair of nucleic acid molecules—preferably, in the form of oligonucleotides or a kit containing this pair of oligonucleotides—that is suitable for hybridization as a forward and reverse primer to a region that is specific to the nucleic acid molecule according to the invention, and for amplifying this in a polymerase chain reaction (PCR), or that is suitable as a forward and reverse primer for hybridization to a region in the *Beta vulgaris* genome that, in *Beta vulgaris*, exhibits a cosegregation with the *Cercospora* resistance conferred by the polypeptide according to the invention, or with the nucleic acid molecule according to the invention.

The following advantages for the breeding and development of new resistant plant lines of the genus *Beta* may also be achieved via the present invention. Sequence information, as well as the identified polymorphisms which allow a differentiation between resistant and susceptible alleles of the disclosed gene, i.e., between the alleles that confer a *Cercospora* resistance and the alleles that are not capable of conferring this resistance, make possible the marker development directly in the gene, as described above, as well as in the regions situated upstream and downstream, which represents an important facilitation for the plant breeder—in particular, with regard to the development of optimized elite lines without "linkage drag." Moreover, knowledge about the sequential structure may be used for the identification of additional resistance genes—in particular, against *Cercospora*—which are homologous or orthologous, for example.

Therefore, the present invention also encompasses a method for the identification of additional nucleic acid molecules encoding polypeptides or additional proteins that are able to confer a resistance to *Cercospora* in a plant in which the polypeptide is expressed. The person skilled in the art may thereby use databases, employing suitable search profiles and computer programs for the screening for homologous sequences or for sequence comparisons. Moreover, by means of conventional molecular biology techniques, the person skilled in the art may himself derive additional DNA sequences encoding *Cercospora* resistance proteins, and use these within the scope of the present invention. For example, suitable hybridization probes may be derived from the sequence of the nucleic acid molecule according to the invention and be used for the screening of genomic and/or cDNA banks of the desired organism. The person skilled in the art may here resort to customary hybridization, cloning, and sequencing methods, which, for example, are listed in Sambrook et al., Molecular Cloning: A Laboratory Manual, 3rd ed., Cold Spring Harbor Laboratory Press, Cold Spring Harbor, NY, 2001. Using known sequences, the person skilled in the art may also synthesize and use oligonucleotide primers to amplify sequences of *Cercospora* resistance-conferring nucleic acid molecules.

In one embodiment, the present invention therefore encompasses a method for the identification of a nucleic acid molecule which encodes a polypeptide that is able to confer a resistance to *Cercospora* in a plant of the species *Beta vulgaris* in which the polypeptide is expressed. The method thereby includes the comparison of the amino acid sequence of the polypeptide according to the invention which, in *Beta vulgaris* subsp. *vulgaris*, confers a *Cercospora* resistance with amino acid sequences from a sequence database, or with sequences of allelic variants of the polypeptide according to the invention in genotypes of the species *Beta vulgaris*. Furthermore, the method according to the invention includes the identification of an amino acid sequence or of an allelic variant that is at least 80% identical to the amino acid sequence of the polypeptide according to the invention, as well as the introduction of a nucleic acid molecule encoding the identified amino acid sequence or allelic variant in a plant of the species *Beta vulgaris*; expression of the nucleic acid molecule in the plant; and, optionally, subsequent verification of the resistance to *Cercospora*.

As described in the preceding, additional *Cercospora* resistance-conferring proteins or their coding genes, i.e., homologs, analogs, and orthologs, that are at least 70%—preferably, at least 80%, particularly preferably, at least 90%, especially preferably, at least 95%, or even 98%—identical to the amino acid sequence of the polypeptide which is encoded by the nucleic acid molecule according to the invention may be identified via classical bioinformatic approaches (database searches and computer programs for screening for homologous sequences).

The term, homolog(s), thereby means that the genes concerned (from two different plant species) have essentially the same function and a common ancestor, and therefore typically show a significant identity in their nucleic acid or coded amino acid sequences. However, there are also many genes that are homologous to one another, without protein sequences resulting in a meaningful paired alignment. In contrast to this, the term, analog(s), describes genes or proteins that (likewise) have an identical or similar function, but are not created from the same structure, i.e., have no common ancestor. In this case, often, no significant identity can be established in their nucleic acid or encoded amino acid sequence, or, in the best case, in specific functional domains.

In the context of genome sequencing, homologs are, for annotation, more finely classified. The terms, orthology and paralogy, have been introduced for this. Orthologs are genes that are connected via a speciation event. Paralogs are genes that trace back to a duplication event A gene is, then, fundamentally a homolog or analog or ortholog in the sense of the present invention if it is able to confer *Cercospora* resistance in a plant. To check, methods, which have already been described in the preceding, known to the person skilled in the art are used, e.g., the amplification of the identified homolog or analog or ortholog by means of PCR, cloning in expression vectors, introduction into the target plant or plant cell, and checking the resistance.

As described above, the usage disclosed here of the resistant gene allele in cis- or transgenic approaches opens up the possibility of new resistant species of the genus *Beta* which, using the dose effect, exhibit a higher resistance, or in which a resistance break may be avoided and the resistance development optimized via the stacking of the disclosed gene with other resistance genes. Modifications of the gene by means of tilling or targeted engineering to optimize the codon selection for an increased expression or for the development of new or modified resistance alleles are also possible. According to a preferred embodiment the codon-optimized sequences or the modified resistance alleles are not occurring in nature but are artificial. An example of a modified genomic sequence is provided by SEQ ID No. 94 in which the codon at position 16-18 is modified but the encoded amino acid sequence is unchanged and corresponds to SEQ ID No. 3. An example of a modified cDNA sequence is provided by SEQ ID No. 95 in which the codon at position 55-57 is modified but the encoded amino acid sequence is unchanged and corresponds to SEQ ID No. 3. SEQ ID No. 94 and SEQ ID No. 95 are also examples for hybridizing sequences. An example of a modified resistance conferring allele is given by the amino acid sequence according to SEQ ID No. 96 in which the amino acid valine has been replaced with the amino acid leucine at position 209 (SEQ ID NO: 100). The amino acid sequence according to SEQ ID No. 96 is encoded by the modified cDNA according to SEQ ID No. 97. These sequences do not occur in nature but are artificial. When replacing amino acids in for example the resistance-mediating Sequence according to SEQ ID No. 3 it is recommended to exchange amino acids within the following groups:

a) glycine, alanine, valine, leucine, isoleucine
b) serine, cysteine, selenocysteine, threonine, methionine
c) phenylalanine, tyrosine, tryptophan
d) histidine, lysine, arginine
e) aspartate, glutamate, asparagine, glutamine.

The present invention also relates to the use in a plant of the identified *Cercospora* resistance-conferring gene allele in a genetic or molecular stack with other genetic elements which may confer agronomically advantageous properties. The economic value of cultivated plants may thereby be markedly increased, in that, for example, the yield performance is increased in comparison to plants that possess the same genetics, but have not been furnished with the nucleic acid according to the invention. Furthermore, new crop areas for a plant may be opened up that were not previously accessible to the cultivation of this plant due to biotic factors such as strong pathogen pressure. In particular, the present invention relates to the use of the identified *Cercospora* resistance-conferring gene allele in methods for controlling an infestation with the pathogen *Cercospora beticola* in the agricultural or horticultural cultivation of plants of the genus *Beta*, e.g., encompassing the identification and selection of plants of the genus *Beta* with the aid of one of the methods described in the preceding and/or the cultivation of the plants so selected or descendants thereof. The present invention thus includes a method for the cultivation of plants of the species *Beta vulgaris*, including, in a first step, the provision of *Cercospora*-resistant plants of the species *Beta vulgaris* according to the invention, or the production of plants of the species *Beta vulgaris* with the aid of the production method according to the invention, or the identification and selection of plants of the species *Beta vulgaris* with the aid of the identification method according to the invention that has been described in the preceding; and including, in a second step, the cultivation of the plants from the first step, or the deployment of seed stock of the plants from the first step, or the raising of plants from the first step. The cultivation method thereby counteracts an infestation of the cultivated plants by *Cercospora*. The cultivation method may be part of a method for producing sugar. The method for the production of sugar includes the steps of the cultivation method, and additionally, as a penultimate step, the harvesting of the cultivated plants, and, as a last step, the extraction of sugar from the aforesaid plants.

The cultivation method may also be part of a method for producing seed stock. The method for the production of seed stock includes the steps of the cultivation method, and additionally, as a penultimate step, the vernalization of the cultivated plants, and, as a last step, the extraction of seeds from the aforesaid plants.

The extracted seeds may optionally be pelleted, in order to obtain pelleted seed stock of the species *Beta vulgaris*. In this instance, it is a method for the production of pelleted seed stock.

Moreover, the method for the production of seed stock may be designed as a method for the production of *Cercospora*-resistant seed stock. The method for the production of *Cercospora*-resistant seed stock includes the steps of the method described above for the production of seed stock, and additionally, as a last step, the verification of the nucleic acid according to the invention according to a method described herein in at least one of the extracted seeds—preferably, in at least 0.1% or in at least 1% of the extracted seeds. The verification is particularly preferably implemented so that the seed remains germinable. This means that the extraction of the DNA required for verification from the seed does not neutralize the germinability of the seed. In such an instance, the verification of the nucleic acid according to the invention may have taken place in an especially large proportion of all extracted seeds. For example, the verification may take place in at least 2%—preferably, at least 3%, particularly preferably, at least 4%—of all extracted seeds.

The plants according to the invention, their cells, or seeds or seed stock according to the invention may possess additional, agronomically advantageous properties, or be furnished with such. One example is the tolerance or resistance to an herbicide such as glyphosate, glufosinate, or ALS inhibitors. The tolerance to glyphosate or an ALS-inhibitor herbicide is preferred. A specific embodiment of the glyphosate resistance is disclosed in U.S. Pat. No. 7,335,816 B2. Such a glyphosate resistance is, for example, available from seed stock stored at the NCIMB, Aberdeen (Scotland, UK), under the access number, NCIMB 41158 or NCIMB 41159. Such seeds may be used in order to obtain a glyphosate-tolerant sugar beet plant. The glyphosate resistance may also be introduced into other species of the genus *Beta* via crossing.

The invention thus also encompasses plants, their cells, or seeds or seed stock, characterized in that these contain the nucleic acid according to the invention, and furthermore in that a) a DNA fragment of the genomic DNA of the plant, portions, or seeds thereof may be amplified via polymerase chain reaction with a first primer that has the nucleotide sequence of SEQ ID No. 81, and a second primer that has the nucleotide sequence of SEQ ID No.

82, wherein the DNA fragment is at least 95%—preferably, 100%—identical to the nucleotide sequence of SEQ ID No. 83, and/or b) a DNA fragment of the genomic DNA of the plant, portions, or seeds thereof may be amplified via polymerase chain reaction with a first primer that has the nucleotide sequence of SEQ ID No. 84, and a second primer that has the nucleotide sequence of SEQ ID No. 85, wherein the DNA fragment is at least 95% identical—preferably, 100% identical—to the nucleotide sequence of SEQ ID No. 86, and/or c) a DNA fragment of the genomic DNA of the plant, portions, or seeds thereof may be amplified via polymerase chain reaction with a first primer that has the nucleotide sequence of SEQ ID No. 87, and a second primer that has the nucleotide sequence of SEQ ID No. 88, wherein the DNA fragment is at least 95% identical—preferably, 100% identical—to the nucleotide sequence of SEQ ID No. 89.

A specific embodiment of the ALS-inhibitor herbicide resistance is disclosed in the document, WO2012/049268 A1. For example, such an ALS-inhibitor herbicide resistance is available from a deposit of NCIMB, Aberdeen, UK, under the number NCIMB 41705. Furthermore, such an ALS-inhibitor resistance may be produced via tilling or site-directed mutagenesis, e.g., via gene editing, such as through the use of CRISPR/Cas, CRISPR/Cpf1, TALENS or zinc finger nucleases. The invention thus also encompasses plants, their cells, or seeds or seed stock, characterized in that these contain the nucleic acid according to the invention, and furthermore in that these exhibit a mutation in an endogenous acetolactate synthase gene, wherein the acetolactate synthase gene encodes an acetolactate synthase protein which, as a result of the mutation at position 569, has a different amino acid than tryptophan. As a result of the mutation, the amino acid at position 569 is preferably alanine, glycine, isoleucine, leucine, methionine, phenylalanine, proline, valine, or arginine. Position 569 is preferably defined via the position 569 of SEQ ID No. 90. Furthermore, the specific sequence of the mutated acetolactate synthase gene SEQ ID No. 91 is preferred. The mutated sequence of the acetolactate synthase gene, or the sequence according to SEQ ID No. 91, does not occur in nature and cannot be isolated from nature. Furthermore, the mutation may be present both heterozygously and homozygously in the plants, their cells or seeds, or the seed stock. We recommend the homozygous presence of the mutation, since this promotes a more stable or more intensive phenotypical occurrence of the resistance.

Numerous additional herbicides and their applicability are known to the person skilled in the art from the prior art. He may resort to the prior art in order to achieve knowledge of which genetic elements are to be used in what manner in order to implement a corresponding tolerance in plants.

Moreover, an herbicide tolerance has the synergistic effect that the occurrence of weeds is reduced via the use of herbicides. This is advantageous in combating *Cercospora*, because it is known that the conidia (asexual spores) or the pseudostroma (mycelium) of *Cercospora beticola* can survive for up to 2 years on plant material.

A further example of an agronomically advantageous property is an additional pathogen resistance, wherein pathogens may be insects, viruses, nematodes, bacteria, or fungi, for example. For example, a broad pathogen defense for a plant may be achieved via combination of different pathogen resistances/tolerances, since genetic elements may exhibit additive effects among one another. For example, numerous resistance genes for this are known to the person skilled in the art as genetic elements. For example, US20160152999A1 discloses an RZ resistance gene against the disease Rhizomania. This disease is caused by the agent, "Beet Necrotic Yellow Vein Virus." Several disease resistances contained in one plant have synergistic effects upon one another. If a plant is infested for the first time by a pathogen, its immune system is normally weakened, and the epidermis as an outer barrier is often damaged, such that the probability of further infections is increased. An additional example of an agronomically advantageous property is cold tolerance or frost tolerance. Plants which exhibit this property may already be shown earlier in the year, or may remain in the field longer, which may lead to increased yields, for example. Here, the person skilled in the art may also resort to the prior art to find suitable genetic elements. Additional examples of agronomically advantageous properties are water usage efficiency, nitrogen usage efficiency, and yield. Genetic elements which may be used to confer such properties might be found in the prior art.

Furthermore, numerous modifications for pathogen defense are known to the person skilled in the art. In addition to the families of the R-genes that are often described, the Avr/R approach, the Avr gene complementation (WO 2013/127379), the autoactivation of an R-gene (WO 2006/128444), or the HIGS (host-induced gene silencing) approach (e.g., WO2013/050024) may be advantageously used. In particular, the autoactivation of an R-gene might be important to the present invention. For this, a nucleic acid is to be created that encodes an autoactivated resistance protein for generation of a resistance to pathogens in plants. This nucleic acid then has only a limited portion of an NBS-LRR resistance gene, such as the wb-R-gene, which extends downstream from the 5' end of the coding region of the NBS-LRR resistance gene to the beginning of the coding for the NBS domain of the NBS-LRR resistance gene.

In this context, a method is also encompassed which contains the step of the removal of that region of the nucleic acid according to the invention which encodes the N-terminal region and which begins with the p-loop in the NBS domain, and extends up to the end of the N-terminal region.

The resistance proteins that are encoded for by such shortened nucleic acids are generally autoactivated, in that these resistance proteins trigger an immune reaction in the plant, even in the absence of the associated pathogen, and thus increase the base immunity of the plant. Furthermore, such a shortened nucleic acid according to the invention, and the polypeptide that is encoded by this, are encompassed.

Furthermore, the invention also includes the use of the *Cercospora* resistance-conferring gene allele, identified with a method described above, for combination with one of the preceding modifications, or with a genetic element described in the preceding which may convey in a plant one or more agronomically advantageous properties.

In addition to relating to the plant according to the invention, the present invention also relates to seeds or descendants, or to an organ, a plant part, a tissue, or a cell thereof in the production of products that are typically produced from sustainable raw materials, such as foodstuffs and animal feed—preferably, sugar or syrup (molasses), wherein the molasses is also used for industrial applications, e.g., in alcohol production or as a growing medium for the production of biotechnological products, in the production of materials or substances for the chemical industry, e.g., refined chemicals, pharmaceuticals or precursors thereof, diagnostics, cosmetics, bioethanol, or biogas. An example of the use of sugar beet as a biogenic raw material in biogas plants is described in the application DE 10 2012 022 178 A1; see, for example, paragraph 10.

The following examples explain the invention, but without limiting the subject matter of the invention. Unless indicated otherwise, standard molecular biology methods have been used; see, for example, Sambrook et al., Molecular Cloning: A Laboratory Manual, 3rd ed., Cold Spring Harbor Laboratory Press, Cold Spring Harbor, NY, 2001, Fritsch et al., Cold Spring Harbor Laboratory Press: 1989; Mayer et al., Immunochemical Methods in Cell and Molecular Biology, eds., Academic Press, London, 1987, and Weir et al., Handbook of Experimental Immunology, Volumes I-IV, Blackwell, eds., 1986.

Some of the most important sequences according to the invention are explained in detail in the following:

SEQ ID No. 1: genomic DNA sequence of the *Cercospora* resistance-conferring gene from *Beta vulgaris* subsp. *maritima*.

SEQ ID No. 2: cDNA sequence of the *Cercospora* resistance-conferring gene as it does not occur in nature.

SEQ ID No. 3: amino acid sequence of the *Cercospora* resistance-conferring protein as it is encoded by SEQ ID No. 1 or SEQ ID No. 2.

SEQ ID No. 4: genomic DNA sequence of the sensitive Variant of the *Cercospora* resistance-conferring gene SEQ ID No. 5: cDNA of the sensitive Variant of the *Cercospora* resistance-conferring gene SEQ ID No. 6: Amino acid sequence of the sensitive Variant of the *Cercospora* resistance-conferring gene SEQ ID No. 7: native promoter of the *Cercospora* resistance-conferring gene from *Beta vulgaris* subsp. *maritima*.

SEQ ID No. 8: native terminator of the *Cercospora* resistance-conferring gene from *Beta vulgaris* subsp. *maritima*.

SEQ ID No. 53: sequence of the locus from *Beta vulgaris* subsp. *maritima* containing the *Cercospora* resistance-conferring gene according to SEQ ID No. 1.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Introduction of the Resistance-Conferring Gene by Means of CRISPR-Mediated Homologous Recombination in *Beta vulgaris* Subsp. *vulgaris*

Design and Selection of the crRNA:

Suitable crRNA's for Cpf1-mediated induction of double-strand breaks have been designed with the aid of CRISPR RGEN Tools (Park J., Bae S., and Kim J.-S. Cas-Designer: A web-based tool for choice of CRISPR-Cas9 target sites. *Bioinformatics* 31, 4014-4016 (2015); Bae S., Park J., and Kim J.-S. Cas-OFFinder: A fast and versatile algorithm that searches for potential off-target sites of Cas9 RNA-guided endonucleases. *Bioinformatics* 30, 1473-1475 (2014)). For this, suitable protospacers were sought within the genomic DNA sequences having a length of 500-1,300 bp which flank the 5'- and 3'-end of the *Cercospora* resistance gene from *Beta vulgaris* subsp. *maritima*. In order to ensure the functionality of the endonuclease Cpf1 from *Lachnospiraceae bacterium* ND2006 (Lb), protospacers having a length of 24 nt were selected whose genomic binding sequence at the 5'-end was flanked by an essential protospacer adjacent motif (PAM) having the sequence 5'-IT TV-3' (V=G or Cor A). Suitable protospacers were selected according to the predetermined quality criteria of the tool and reconciled as to potential off-targets with a reference genome of *B. vulgaris* subsp. *vulgaris*. For the continuing tests, crRNA's, exclusively, were selected that, in addition to the actual target sequence, have at most 15 identical bases with a functional PAM. Since the first 18 nt of the protospacer are essential to the detection and cutting of the target sequence, an unwanted cutting within other genomic sequences could be precluded in this way (Tang, X., L. G. Lowder, T. Zhang, A. A. Malzahn, X. Zheng, D. F. Voytas, Z. Zhong, Y. Chen, Q. Ren, Q. Li, E. R. Kirkland, Y. Zhang, and Y. Qi (2017), "A CRISPR-Cpf1 system for efficient genome editing and transcriptional repression in plants." Nat Plants 3: 17018). In this way, four potential crRNAs at the 5'-flanking region (5' crRNA #1-4) and three crRNA's at the 3'-flanking region (3' crRNA #1-3) of the resistance gene could be identified (see Table A).

TABLE A

Selected target sequences within the 5'- and 3'-flanking DNA sequences of the resistance gene in *B. vulgaris*. The PAM is underlined.

| Name of the crRNA | Genomic target sequence with 5'-flanking PAM (underlined) | Binding at the +/- strand |
|---|---|---|
| 5'crRNA#1 | TTTATTTCGATTTCGATTCTTGGATTAT (SEQ ID No. 16) | - |
| 5'CrRNA#2 | TTTCAACCCAGTATCCTTATCCGTCACT (SEQ ID No. 17) | - |
| 5'crRNA#3 | TTTATTTAAACATGATACGTATCATATT (SEQ ID No. 18) | + |
| 5'crRNA#4 | TTTAAACATGATACGTATCATATTGAGT (SEQ ID No. 19) | + |
| 3'crRNA#1 | TTTGTGGGTGGGTGGTTTTCACGTGTGT (SEQ ID No. 20) | - |
| 3'crRNA#2 | TTTCCCCTCCCTTTGCCGCTGCGAAGTT (SEQ ID No. 21) | - |
| 3'crRNA#3 | TTTCTTCTTCTTGCTTCCACCATAACAC (SEQ ID No. 22) | - |

Cloning of the genetic elements: For the cloning of the cpf1-expression cassette and the crRNA-expression cassette, first, a detection sequence of the restriction enzyme of BbsI that prevents cloning was removed from the target vector pZFNnptII via introduction of a point mutation (T to G). The mutagenesis was performed with a mutagenesis kit according to the specification of the manufacturer, using two mutagenesis primers (see Table B).

TABLE B

| Mutagenesis primer used to introduce a point mutation (T to G, underlined) to remove the BbsI detection sequence. | |
|---|---|
| Name | Sequence 5'→3' |
| Mutagenesis primer 1 | TCAGTGCAGCCGTCGTCTGAAAACGACA (SEQ ID No. 23) |
| Mutagenesis primer 2 | TGTCGTTTTCAGACGACGGCTGCACTGA (SEQ ID No. 24) |

Figure 2:
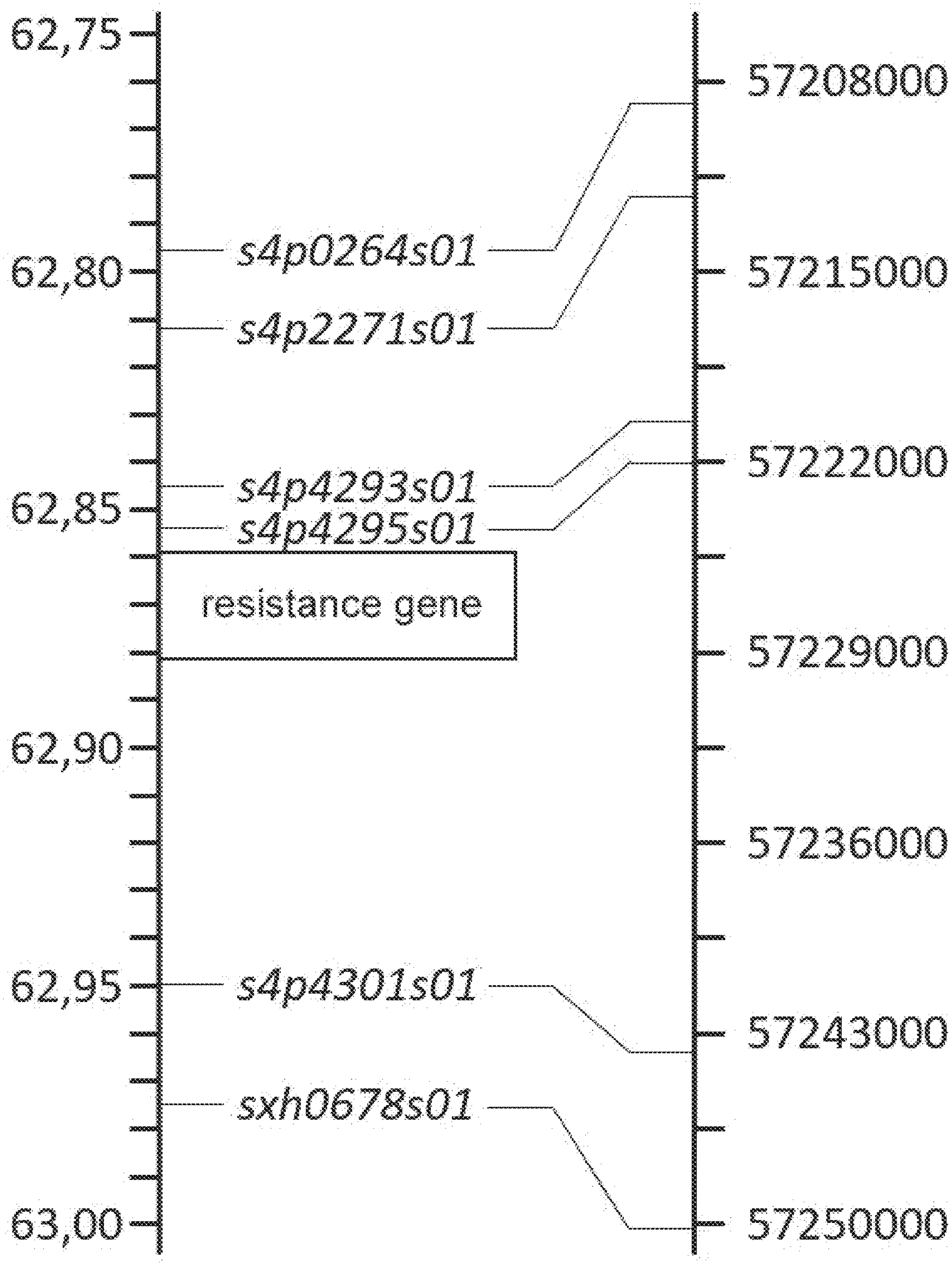
FIG. 2: Protein sequence alignment between the resistant protein (protein which confers *Cercospora* resistance in a plant) and the sensitive protein (protein which does not confer *Cercospora* resistance in a plant). The polymorphisms are highlighted in gray.

For the expression of the Lbcpf1 gene in *B. vulgaris*, a DNA sequence codon-optimized for A. *thaliana*, with 5'-flanking PcUbi promoter sequence from *Petroselinum crispum* (SEQ ID No. 79) and a 3'-flanking 3A terminator sequence from *Pea* sp. as a DNA fragment, was synthetically produced. The restriction interface (HindIII) that is relevant to cloning within the Lbcpf1-coding sequence (CDS) [SEQ ID No. 78] were removed via the introduction of a silent mutation (base exchange, without modifying the amino acid sequence), in order to avoid an unintended cutting within the coding region. The codon optimization was performed with the aid of the GeneArt algorithm from Invitrogene/ThermoScientific. In order to enable the transport of the Cpf1 in the cell nucleus, the coding sequence of the nucleus location signal (NLS) of the SV40 was integrated into the cpf1 CDS at the 5'-end, and the NLS of the nucleoplasmin was integrated at the 3'-end. For the ligation in the binary target vector pZFNnptII (FIG. 2), the expression cassette was flanked by two HindIII restriction interfaces and subsequently ligated to pZFNnptII_LbCpf1. The successful insertion of the PcUbi::Cpf1::TPea expression cassette was verified by means of sequencing, wherein the binding regions of the primers used for the sequencing were situated both in the flanking vector regions and within the expression cassette (see Table C).

TABLE C

| Primer used for the sequencing of the PcUbi::Cpf1::TPea expression cassette integrated into pZFNnptII | |
|---|---|
| Name | Sequence 5'→3' |
| pSeq_CRBM_F1 | SEQ ID No. 25 |
| pSeq_CRBM_R1 | SEQ ID No. 26 |
| pSeq_CRBM_F2 | SEQ ID No. 27 |
| pSeq_CRBM_R2 | SEQ ID No. 28 |
| pSeq_CRBM_F3 | SEQ ID No. 29 |
| pSeq_CRBM_R3 | SEQ ID No. 30 |
| pSeq_CRBM_F4 | SEQ ID No. 31 |
| pSeq_CRBM_R4 | (SEQ ID No. 32) |

After transcription into the plant cell, the crRNA's should be cut out via two flanking ribozymes. For this, the precursor crRNA was flanked by the coding sequences of a hammerhead ribozyme and an HDV ribozyme (Tang, X, L. G. Lowder, T. Zhang, A. A. Malzahn, KX. Zheng, D. F. Voytas, Z. Zhong, Y. Chen, Q. Ren, Q. Li, E. R. Kirkland, Y. Zhang, and Y. Qi (2017), "A CRISPR-Cpf1 system for efficient genome editing and transcriptional repression in plants." Nat Plants 3: 17018).

For a perfect ligation of the individual protospacers at the coding sequence of the crRNA repeat, two BbsI detection sequences were integrated between crRNA repeat and HDV ribozyme, wherein the overhangs that were used for the cloning were adapted accordingly. In order to ensure an identical expression strength of the cpf1 and the crRNA's, the crRNA ribozyme cassette was bounded, at the 5-end, by the PcUbi promoter sequence and, at the 3'-end, by [a/the] 3A terminator sequence. For the later ligation in the target vector pZFNnptII_Cpf1, the crRNA expression cassette was flanked by two PstI interfaces and ordered as a synthetic DNA fragment. The protospacers were synthesized as complementary oligonucleotides and annealed according to a standard protocol. The 24-bp-long DNA fragment that was generated in this way was flanked by the 4-nt overhangs that are relevant to the ligation (see Table D).

TABLE D

| Sequence of oligonucleotides that were used for the generation of short 24-bp protospacers. The 4-nt overhangs that are used for the ligation are the respective four first nucleotides of each listed sequence. | |
|---|---|
| Name of the crRNA | Sequence 5'→3' |
| 5'crRNA#1 | SEQ ID No. 33<br>SEQ ID No. 34 |
| 5'crRNA#2 | SEQ ID No. 35<br>SEQ ID No. 36 |
| 5'crRNA#3 | SEQ ID No. 37<br>SEQ ID No. 38 |
| 5'crRNA#4 | SEQ ID No. 39<br>SEQ ID No. 40 |
| 3'crRNA#1 | SEQ ID No. 41<br>SEQ ID No. 42 |
| 3'crRNA#2 | SEQ ID No. 43<br>SEQ ID No. 44 |
| 3'crRNA#3 | SEQ ID No. 45<br>SEQ ID No. 46 |

The efficiency of the four crRNA's was tested by means of agrobacteria-mediated gene transfer in leaves of *B. vulgaris*. The pZFNtDTnptII plasmid was co-transformed in order to check the transformation efficiency. The transformation of the leaf explant took place via vacuum infiltration according to a standard protocol. The fluorescence of the tDT was checked after six days by means of fluorescence microscopy, and leaf explants with heterogeneous fluorescence were discarded. Ten days after infiltration took place, the leaf explants were quick-frozen in liquid nitrogen, pestled, and the genomic DNA was isolated by means of the CTAB method (Clarke, Joseph D., "Cetyltrimiethyl ammonium bromide (CTAB) DNA miniprep for plant DNA isolation." Cold Spring Harbor Protocols 2009.3 (2009): pdb-prot5177). The efficiency of the individual crRNA's was determined by an external service provider, using the frequency of the inserted editions (e.g., insertions, deletions, or base exchange) in comparison to unedited sequences in the genomic DNA, by means of NGS.

As a synthetic DNA construct, the most efficient crRNA's—5' crRNA #3 and 3'crRNA #1—with the previously described ribozymes, promoter, and terminator sequences, were ordered as reverse-oriented expression cassettes. The entire DNA construct was flanked by two PstI restriction interfaces for cloning in the target vector pZFNnptII_LbCpf1. After insertion of the crRNA's has taken place, the LbCpf1 and crRNA expression cassettes were ligated from the vector pZFNnptII_LbCpf1_crRNA into the pUbitDTnptII vector via HindIII.

As a repair template which should be integrated into the genome of *B. vulgaris* via homologous recombination, the resistance gene expression cassette was flanked, at the 5'-end, by the 5'crRNA #3 and, at the 3'-end, by the 3'crRNA #1 binding sequence. This enabled the excision of the resistance gene expression cassette from the plasmid via Cpf1. The entire DNA template was synthesized as an 87,326-bp-long synthetic DNA fragment (SEQ ID No. 80) and used directly in the vector backbone for the transformation. The resistance gene plasmid and the pUbitDTnptII LbCpf1_crRNA plasmid were introduced into *B. vulgaris* callus cultures with the aid of a gene cannon.

The transformation efficiency was determined using the transient tDT fluorescence, one day after the transformation, by means of fluorescence microscopy. The callus cultures were cultivated on shoot induction medium without selection pressure (without Kanamycin), and the regenerated shoots were subsequently checked for the site-directed integration of the resistance-conferring resistance gene cassette. For this, the genomic DNA was isolated by means of CTAB. The integration of the resistance-conferring gene was amplified by means of PCR using the primers pCRBM_F1 according to SEQ ID No. 47 and pCRBM_R1 according to SEQ ID No. 48 (see Table E), and the PCR products were subsequently sequenced with both primers. Shoots, in which the successful insertion of the expression cassette could be verified in this manner, were identified in the following analyses of the integration site of the resistance gene. In order to verify the insertion within the desired target sequence in the genome, the flanking regions of the resistance gene expression cassette were amplified by means of PCR. The binding of a primer here took place within the resistance gene DNA sequence; the binding of the second primer took place outside of the 5'- or 3'-flanking homologous region of the inserted expression cassette (see Table E). The amplified DNA sequences were sequenced using the same primers, and the integration at the desired location was confirmed in this way. In order to preclude the binding of the primers pCRBM_F1 (SEQ ID No. 47), pCRBM_R1 (SEQ ID No. 48), pCRBM_R2 (SEQ ID No. 50) and pCRBM_F3 (SEQ ID No. 51) in sequence-similar regions of the genome, all primer sequences were compared beforehand with the *B. vulgaris* genome. For the primer pCRBM_F3 (SEQ ID No. 51), it was not possible to select the nucleotide sequence such that a binding to the wild-type sequence could be precluded. Therefore, the 3'-flanking region was amplified in all shoots that tested positive for the resistance gene, and the site-specific insertion was verified exclusively via the subsequent sequencing. The generated PCR product thereby differs by 18 bp from the wild-type sequence. In order to enable the complete sequencing of the amplified sequences, the PCR products were additionally sequenced via a third primer with a binding location within the amplified sequence (pCRBM_S2, pCRBM_S3; see Table E). In order to preclude the nonspecific binding of the primers pCRBM_F1 (SEQ ID No. 47), pCRBM_R1 (SEQ ID No. 48) and pCRBM_R2 (SEQ ID No. 50) within the wild-type genome, the nucleotide sequences were compared with an internal reference genome of *B. vulgaris*. The primers were additionally tested by means of PCR for the binding in genomic sequences of *B. vulgaris* wild-type plants.

In order to preclude the integration of the resistance gene in other regions of the genome, a targeted amplification of the target location was performed (Targeted Locus Amplification, TLA).

TABLE E

Primer used to verify the insertion of the resistance gene expression cassette at the desired integration site.

| Name | Sequence 5'→3' | Size of the PCR product | Binding |
|---|---|---|---|
| pCRBM_F1 | SEQ ID No. 47 | 450 bp | within the resistance gene expression cassette |
| pCRBM_R1 | SEQ ID No. 48 | | within the resistance gene expression cassette |
| pCRBM_F2 | SEQ ID No. 49 | 1,140 bp | up-strand of the 5'-flanking homologous region |
| pCRBM_R2 | SEQ ID No. 50 | | within the resistance gene promoter sequence |
| pCRBM_S2 | SEQ ID No. 66 | | |
| pCRBM_F3 | SEQ ID No. 51 | 1,280 | within the resistance gene terminator sequence |
| pCRBM_R3 | SEQ ID No. 52 | | down-strand of the 3'-flanking homologous region |
| pCRBM_S3 | SEQ ID No. 67 | | |

In addition to the verification and the successful insertion of the resistance gene expression cassette into the genome of *B. vulgaris*, the unwanted integration of plasmid DNA was also checked. For this, genomic DNA, in which the verification had already yielded a successful insertion of the resistance gene at the desired target site, was checked for the presence of plasmid DNA by means of PCR. Sequence regions within the cpf1, the crRNA ribozyme cassette, and the tDT were thereby amplified using the primers listed in Table F, and subsequently sequenced.

TABLE F

Primers used to verify stably-integrated, plasmid-specific sequences in the genome of the regenerated *B. vulgaris* shoots

| Name | Sequence 5'→3' | Size of the PCR product | Binding |
|---|---|---|---|
| pSeq_LbCpf1_F4 | SEQ ID No. 68 | 214 | Cpf1 |
| pSeq_LbCpf1_R3 | SEQ ID No. 69 | | |
| pSeq_Ribozyme_F | SEQ ID No. 70 | 172 | crRNA ribozyme cassette |
| pSeq_Ribozyme_R | SEQ ID No. 71 | | |
| pSeq_tDT_F | SEQ ID No. 72 | 400 | tDT |
| pSeq_tDT_R | SEQ ID No. 73 | | |

Example 2: Introduction of the Resistance-Conferring Gene as a Transgene by Means of Gene Transformation in *Beta vulgaris* Subsp. *vulgaris*

The transgenic approach to the production of *Cercospora*-resistant plants served not only for the alternative validation of the LRR gene as the resistance-conferring gene, but also as a means of producing transgenic resistance events that confers a novel *Cercospora* resistance or improve already existing *Cercospora* resistances.

The binary vector pZFN-nptII-LRR was generated by means of the following standard cloning procedures: Within the T-DNA of this vector, the cDNA of the resistance gene according to SEQ ID NO 2 was cloned together with its native promoter sequence. The T-DNA furthermore included the neomycin phosphotransferase II (nptII) gene, which confers resistance to a bandwidth of aminoglycoside antibiotics such as kanamycin or paromomycin. These antibiotic resistances were used for the selection of the transgenic plant cells and tissues. The NOS promoter and the pAG7 terminator flanked the nptII gene. The backbone of the binary vector furthermore contained the colE1 and the pVSI origin for the plasmid replication in *Escherichia coli* or *Agrobacterium tumefaciens*. The aadA gene confers streptomycin/spectinomycin resistance for bacteria selection. The pZFN-nptII-LRR plasmid was transformed in *agrobacterium* strain AGL-1 by means of standard procedure.

Figure 3:
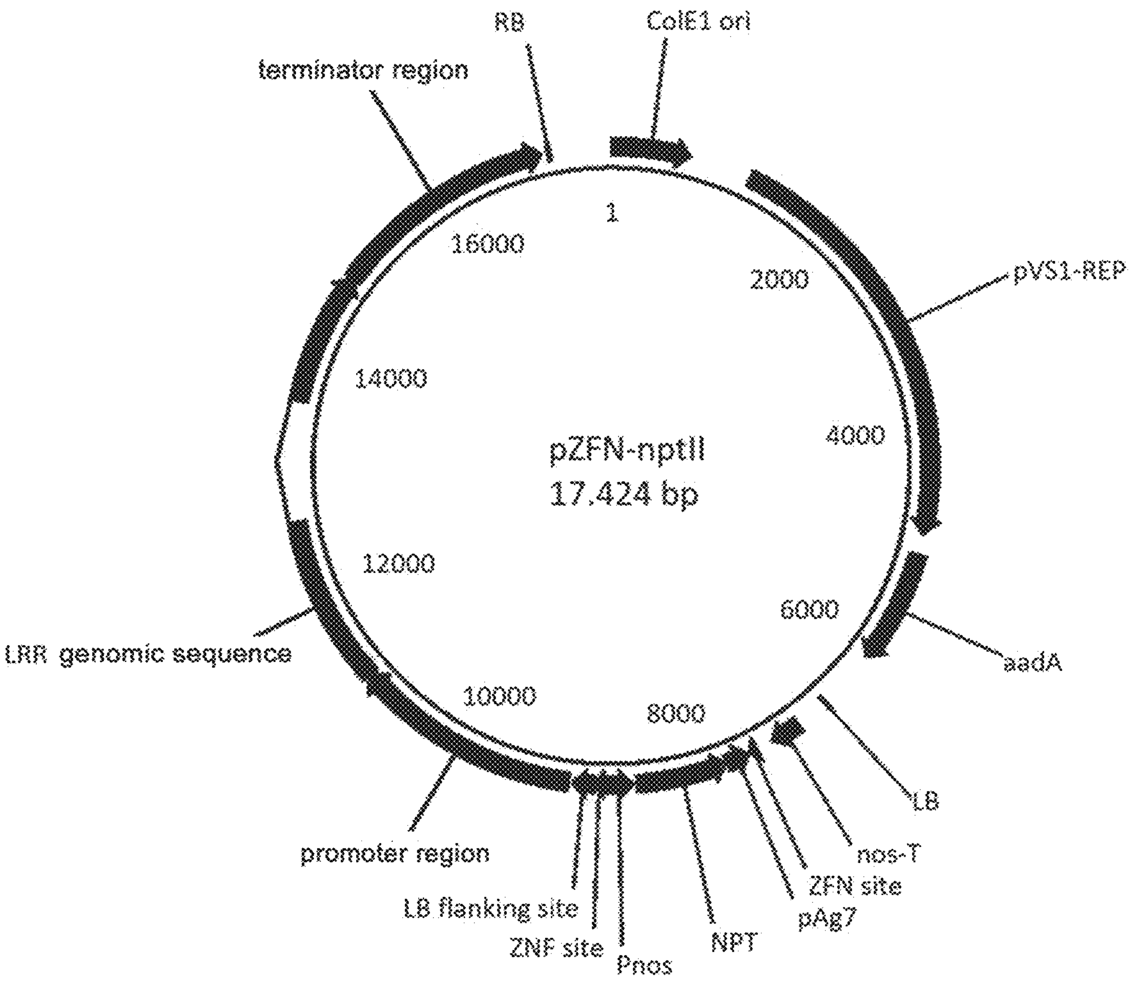
FIG. 3: Vector map of the vector pZFN-nptII including the LRR region.
Figure 4:
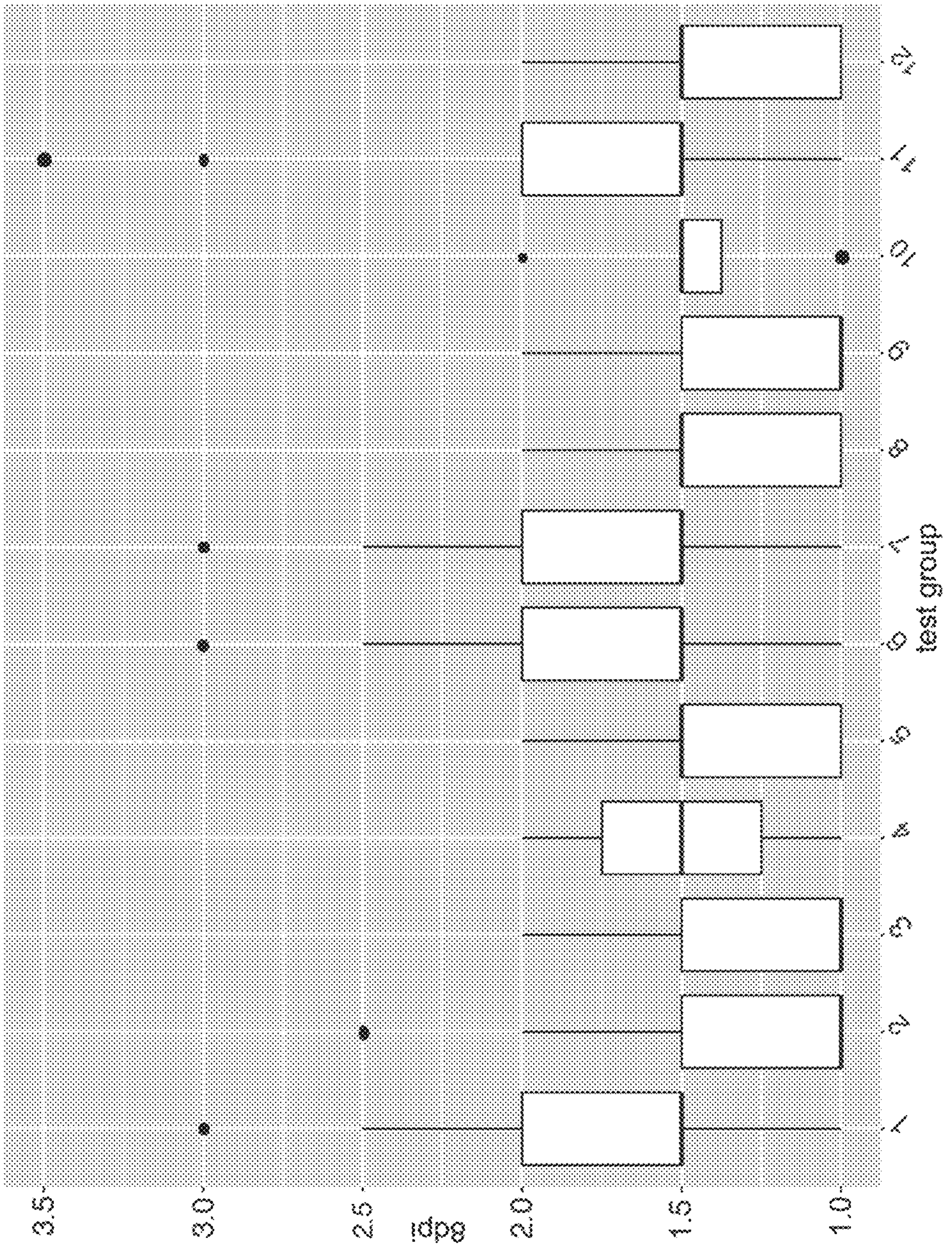
FIG. 4: Statistical box-plot evaluation of the data generated eight days post infection during the transgenic verification of the resistance gene.
Figure 5:
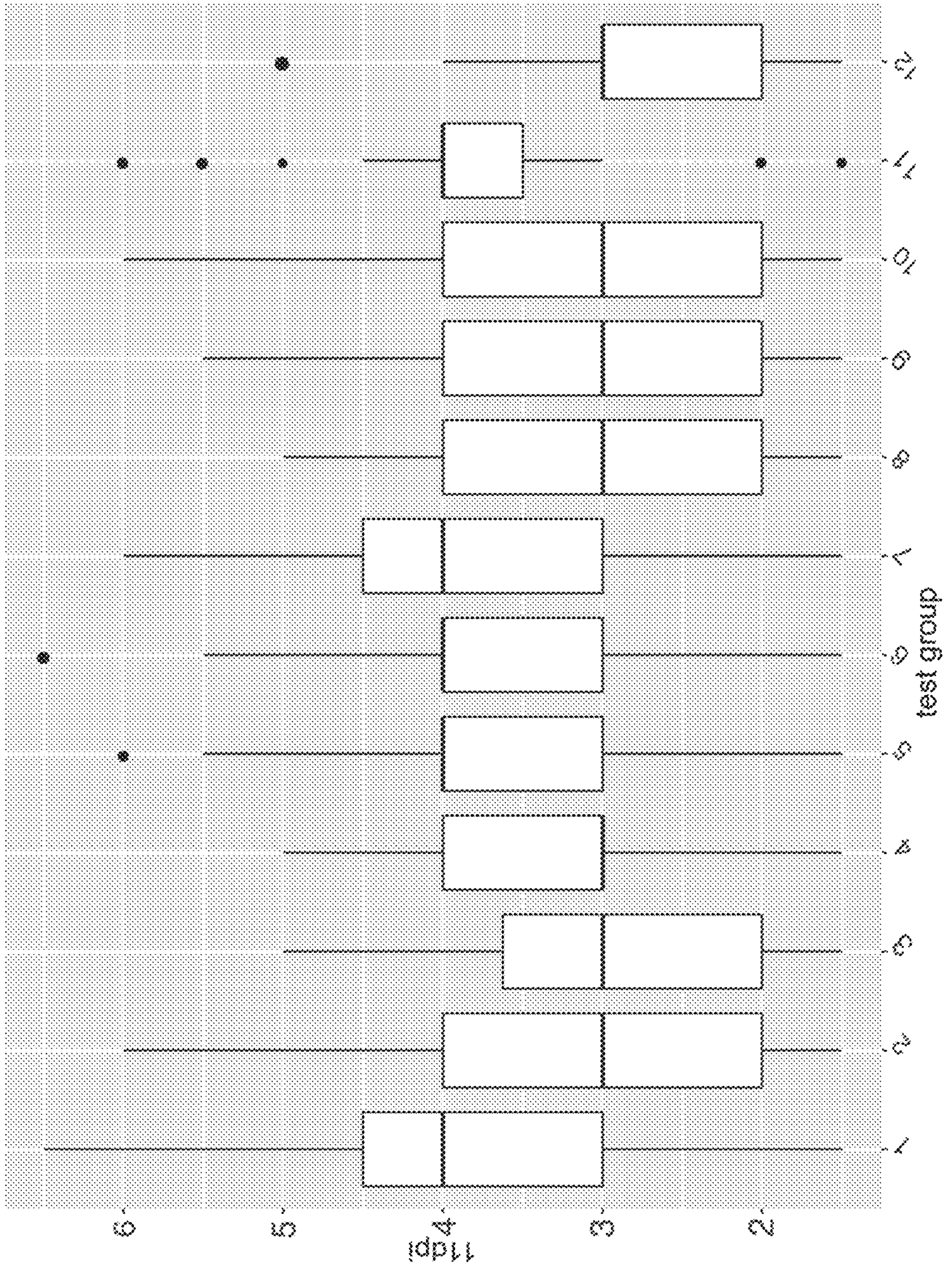
FIG. 5: Statistical box-plot evaluation of the data generated eleven days post infection during the transgenic verification of the resistance gene.
Figure 6:
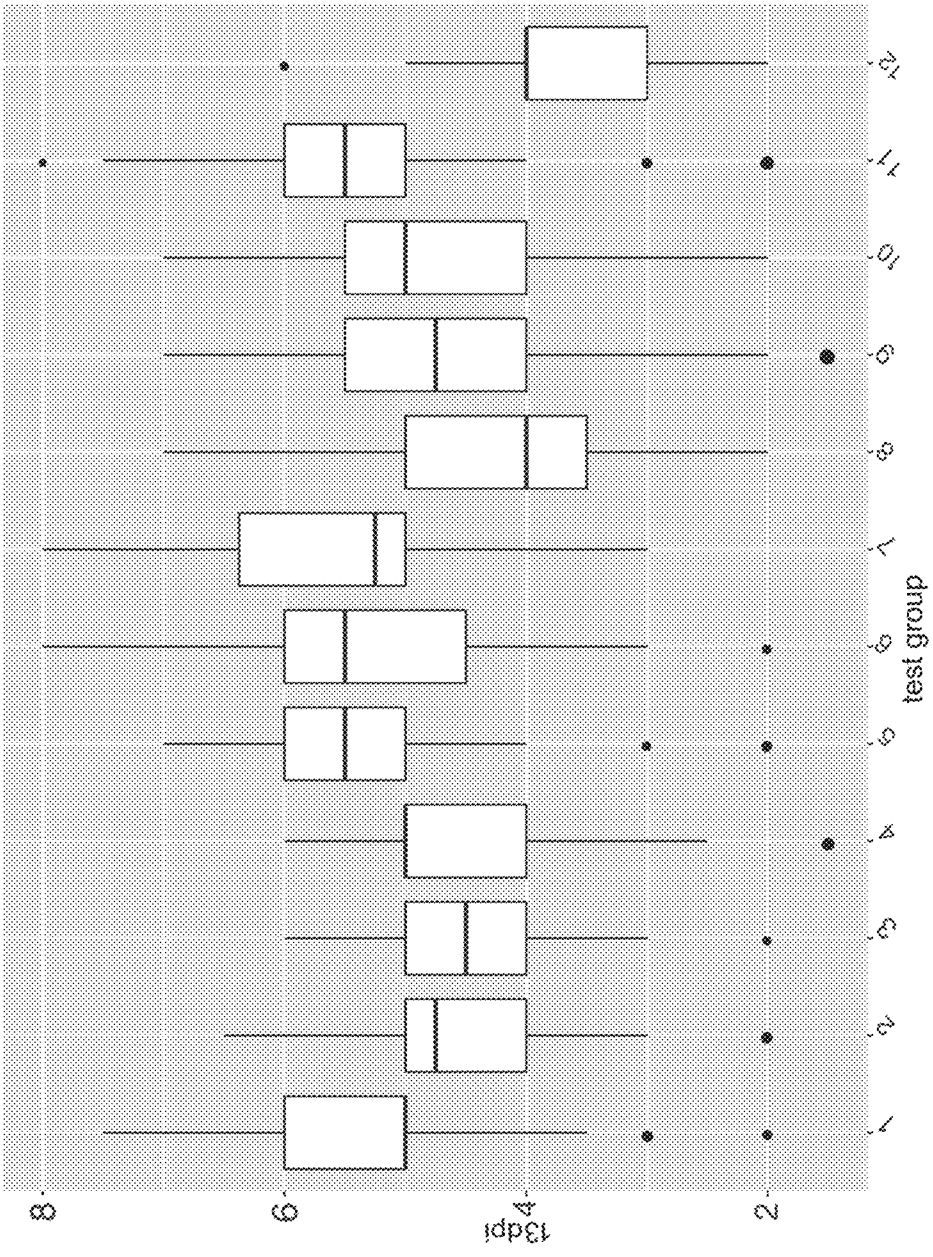
FIG. 6: Statistical box-plot evaluation of the data generated eight days post infection during the transgenic verification of the resistance gene.
Figure 7:
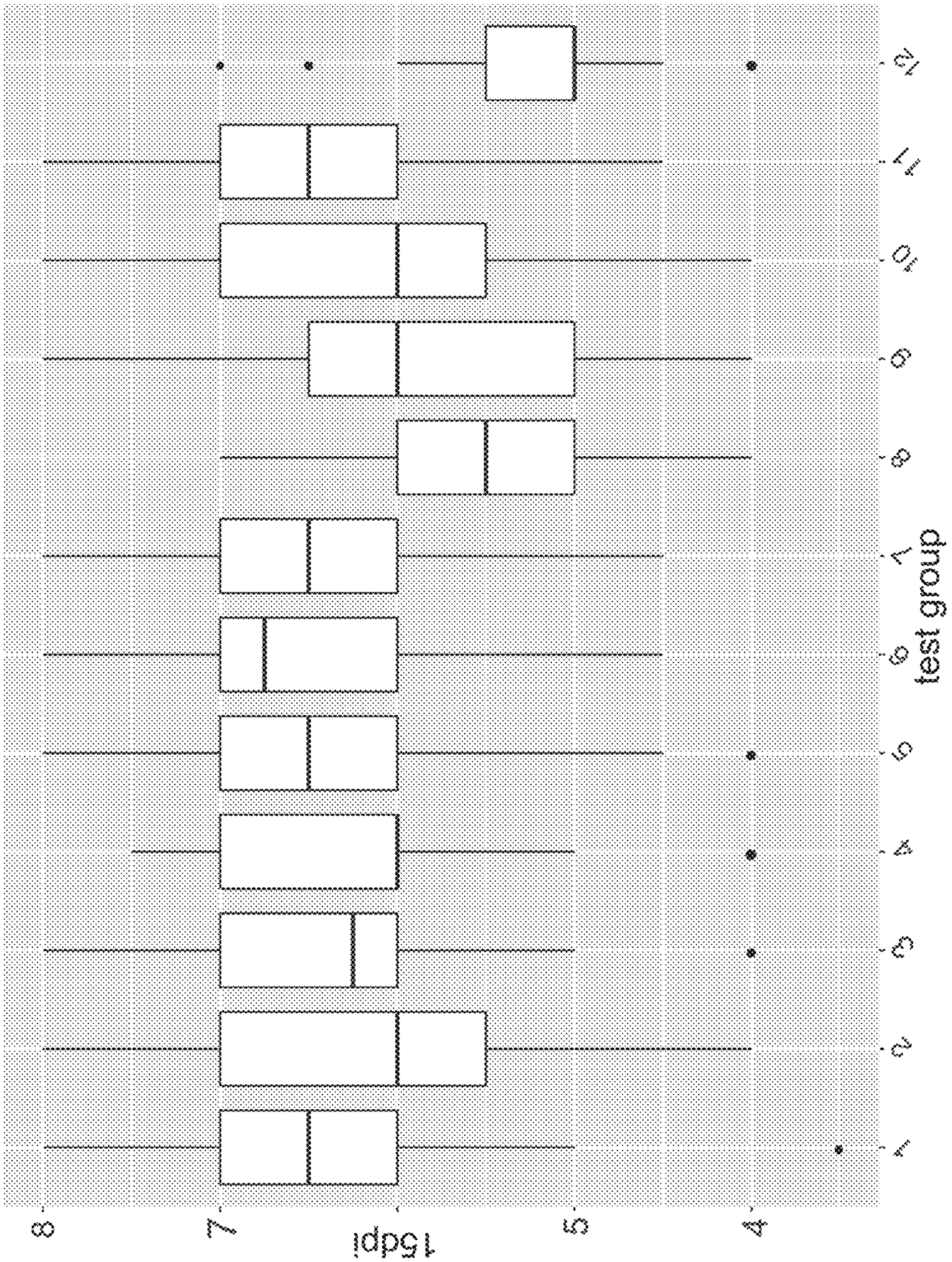
FIG. 7: Statistical box-plot evaluation of the data generated fifteen days post infection during the transgenic verification of the resistance gene.

The transformation of the sugar beets took place according to Lindsey & Gallois (1990), "Transformation of sugarbeet (*Beta vulgaris*) by *Agrobacterium tumefaciens*." Journal of experimental botany 41.5, 529-536). For this, "micropropagated shoots" of genotype 04E05B1DH5, which did not carry the resistance gene according to the invention, were used as starting material. Shoots were multiplied in the corresponding medium according to Lindsey & Gallois (1990). In order to induce as many meristems as possible, the "shoots" were transferred into a different medium (see Lindsey & Gallois (1990)) and incubated in darkness for several weeks at approximately 30° C. *Agrobacterium* strain AGL-1 with vector pZFN-nptII-LRR (FIG. 3) was cultured in an additional medium (see Lindsey & Gallois (1990)), additionally provided with corresponding antibiotics for selection. Sections of meristematic tissue based upon the shoot to be treated were incubated with *agrobacterium* for several hours in an additional medium (see Lindsey & Gallois (1990)). Plant explants and agrobacteria were co-cultivated in darkness for at least 2 days in medium (see Lindsey & Gallois (1990)), and inoculated explants were subsequently incubated in darkness for approximately 2 weeks in an additional medium (see Lindsey & Gallois (1990)). The explants were thereupon further propagated in an additional medium (see Lindsey & Gallois (1990)) and sub-cultivated, in order to enable the selection of the transgenic tissue. In order to conclude the selection phase and to reduce the extent of chimera formation, green "shoots" were transferred to medium H, and all were propagated for 2 weeks. Leaf material was then extracted from the green, growing "shoots" and examined by means of PCT for the presence of the transgene. Suitable "shoots" were rooted in medium I and subsequently transferred to a greenhouse for production of TI seed stock. Furthermore, leaf material derived from these "shoots" was used to analyse the expression of the transformed resistance gene.

Analysis of the Expression Level

RNA was isolated from the leafes of the in vitro "shoots" and used within an qRT-PCR. The qRT-PCR was performed according to Weltmeier et al. 2011 (s. background of invention). Measured values were normalized against the reference gene PLT3_075_F09 (s. Weltmeier et al. 2011). The expression was determined by the use of the following primer sequences:

| Sequence | Size [No. nucleotides] | $T_m$ [C. °] | Size of amplification product [No. nucleotides] |
|---|---|---|---|
| SEQ ID No. 92 | 21 | 59.8 | 170 |
| SEQ ID No. 93 | 21 | 58.9 | 170 |

Resistance Test in Sugar Beet after Inoculation with *Cercospora beticola* Under Greenhouse Conditions:

A pure *Cercospora beticola* culture with a known high virulence was propagated on vegetable juice agar in Petri dishes (9 cm diameter) at 20° C. under near-ultraviolet (NUV) light. After 14 days, the surface of the agar on which the mold was grown was flooded with 10 ml of sterile water per Petri dish, and the conidia and mycelium fragments were carefully scraped off with the aid of a subject carrier. An inoculum density of 20,000 conidia/mycelium fragments per ml, plus 0.1% TWEEN 20, was used to inoculate the plants. At the point in time of the inoculation, the plants had been cultivated for 8 to 9 weeks under greenhouse conditions. The top side and underside of the leaves were treated with the inoculum. The plants were subsequently incubated for 5 to 7 days at 25° C., 18 h/6 h light/dark, and approximately 100% humidity. The first *Cercospora* symptoms on the sugar beet leaves occurred after 12 to 14 hours. An assessment of the symptoms of the individual plants was performed regularly, with the assistance of the assessment of the rating scores shown in Table IA. The results are shown below.

TABLE G

Results of transgenic verification of the function of the resistance gene according to the invention in transformed plants; LSD = least significant difference; dpi = days post infection

| Test group | Number of Individuals | Average rating score 8 dpi | 11 dpi | 13 dpi | 15 dpi | Function | Expression level of the resistance gene according to the invention |
|---|---|---|---|---|---|---|---|
| 1 | 57 | 1.60 | 3.82 | 5.24 | 6.46 | negative control | 0.0 |
| 2 | 38 | 1.28 | 3.07 | 4.42 | 6.04 | transgenic validation | 4.6 |
| 3 | 60 | 1.26 | 2.83 | 4.38 | 6.20 | transgenic validation | 12.5 |
| 4 | 45 | 1.50 | 3.40 | 4.62 | 6.18 | no validated expression in vitro | 0.0 |
| 5 | 60 | 1.44 | 3.62 | 5.29 | 6.38 | transgenic validation | 2.6 |
| 6 | 57 | 1.68 | 3.69 | 5.30 | 6.52 | transgenic validation | 3.3 |
| 7 | 66 | 1.58 | 3.84 | 5.43 | 6.57 | transgenic validation | 2.9 |
| 8 | 60 | 1.31 | 2.81 | 4.19 | 5.48 | transgenic validation | 11.3 |
| 9 | 72 | 1.25 | 3.07 | 4.61 | 5.97 | transgenic validation | 26.8 |
| 10 | 60 | 1.44 | 3.26 | 4.77 | 6.00 | transgenic validation | 10.7 |
| 11 | 57 | 1.60 | 3.83 | 5.48 | 6.64 | transgenic validation | 4.4 |
| 12 | 72 | 1.34 | 2.62 | 3.75 | 5.19 | resistant source plant | not determined |
| mean value overall | 58.66 | 1.44 | 3.32 | 4.8 | 6.13 | | |
| LSD value | — | 0.17 | 0.47 | 0.48 | 0.4 | | |

Results of the Transgenic Validation of the Resistance Gene According to the Invention (s. Table G)

Test group 1 represents a negative control. The genotype is the same as for test groups 2 to 11 but no transformation has taken place. Therefore, no expression could be detected. Test group 4 has been transformed but no expression could be detected. Test groups 2, 3 and 5 to 11 represent transformants which carry the resistance gene according to the invention only due to the transformation. Test group 12 represents a breeding line comprising the resistance gene according to the invention in a non-transgenic version. The rating scores of all lines has been established after inoculating the plant material with *Cercospora beticola* as described above. Test group 12 shows the highest resistance which is indicated by a final value of 5,19.

The transgenic lines showed a rating score according to the following table:

TABLE H

| Rating scores of the transgenic lines of table G | | | | |
|---|---|---|---|---|
| | 8 dpi | 11 dpi | 13 dpi | 15 dpi |
| mean value transgenic validation | 1.42 | 3.33 | 4.87 | 6.2 |
| mean value transgenic validation for lines having an expression level >10 | 1.315 | 2.99 | 4.48 | 5.91 |

Table H shows that the rating scores for transgenic validation groups only. First the mean value for all transgenic test groups (excluding group 4) are shown. Below the rating scores only for those transgenic lines which showed an expression level of at least 10 (groups 3, 8, 9, 10; s. Table G) are given. Here, the final rating score is 5,91. That is a significantly higher resistance than the negative control of group 1 which has a rating score of only 6.46 (least significant difference=0.4; s. Table G). The best transgenic test group (group 8) shows an even better resistance due to a rating score is 5.48 (s. Table G).

It is worth mentioning that the expression level of transgenic insertions may be influenced by the integration locus. As the expression level was measured in vitro the actual expression level under infection conditions could be higher—especially under when the resistance gene is under control of a pathogen inducible promoter.

Statistical Evaluation of the Results of the Transgenic Validation

TABLE I

| statistic clustering | | | | |
|---|---|---|---|---|
| test group | cluster 8 dpi | cluster 11 dpi | cluster 13 dpi | cluster 15 dpi |
| 1 | ab | a | a | ab |
| 2 | e | de | bc | cd |
| 3 | e | ef | c | bcd |
| 4 | bc | bcd | bc | bcd |
| 5 | cd | abc | a | abc |
| 6 | a | ab | a | ab |
| 7 | ab | a | a | a |
| 8 | de | ef | c | e |
| 9 | e | de | bc | d |
| 10 | cd | cd | b | d |
| 11 | ab | a | a | a |
| 12 | de | f | d | e |

Table I shows a statistical evaluation of the rating scores contained in Table G. Each letter symbolizes the allocation to a statistical group. For example, it is evident that after the final evaluation (15 dpi) test group 8 (transgenic verification) is in the same cluster as test group 12 (resistant source) but in a different cluster than test group 1 (negative control). According to this test group 8 is significantly different from test group 1 but not significantly different than test group 12.

In addition, a box-plot analysis has been performed. The illustration of the box-plots is available from FIG. 4-7.

Example 3: Production of a Resistant Sugar Beet Plant According to the Invention on the Basis of Genetic Material Accessed from *Beta vulgaris* Subsp. *Maritime*

The process described hereafter was based on pooling wild beet material to generate a *Cercospora* resistance genepool. The *Beta vulgaris* subsp. *maritima* accessions used as starting material for the breeding program are listed in the following table.

TABLE 2

Accessions of Beta vulgaris subsp. maritima and their resistance rating scores towards Cercospora used in a breeding program; the first 4 columns on the right present the accession numbers wherein a certain accession may have different accession numbers depending on the deposition facility (USDA GRIN = US Department of Agriculture Germplasm Resources Information Network; IDBBNR = International Database for Beta; DEU001 = Plant Genetic Resource Collection; IPK = Leibnitz-Institut für Pflanzengenetik und Kulturpflanzenforschung)

| Accession denomination | | | | Resistance rating score for Cercospora | | | | | | | |
|---|---|---|---|---|---|---|---|---|---|---|---|
| | | | | GRIN studies | | | | | | | |
| | | | | SUGAR-BEET_ | SUGAR-BEET_ | SUGAR-BEET_CERCOS-PORA_ | SUGAR-BEET_CERCOS-PORA_ | SUGAR-BEET_CERCOS-PORA_ | SUGAR-BEET_CERCOS-PORA_ | SUGAR-BEET_CERCOSPORA_ | SUGAR-BEET_RICHARDSON_ |
| USDA GRIN | IDBBNR | DEU001 | IPK | CAC_CERCO_1 | CAC_WBITALY | 1989_RUPPEL | 1992_RUPPEL | 1994_RUPPEL | 1997_RUPPEL | 1000_PANELLA | 2010_TEST1910 |
| PI 120704 | 5191 | | | 1 | | | | | 9 | | |
| PI 169020 | 5265 | | | 1 | | | | | 8 | | |
| PI 169023 | 5268 | | | 1 | | | | | 7 | | |
| PI 169030 | 5274 | | | 1 | | | | | 8 | | |
| PI 546536 | 9703 | | | | | | 3 | | 8 | | |
| PI 546539 | 9706 | | | | | | 3 | | 6 | | |
| PI 518303 | 5797 | | | | | | | | | 4 | 2 |
| PI 518303 | 5797 | | | | | | | | | 4 | 2 |
| PI 546534 | 9701 | | | | | | 3 | | | | 8 |
| PI 590763 | 4587 | | | | | | | | | 4 | |
| PI 590766 | 4591 | | | | | | | | | 4 | |
| PI 109038 | 5160 | | | 1 | | 5 | | | 7 | | |
| | | 28894 | BETA 1521 | | | | | | | | |
| | 2195 | 32375 | BETA 1429 | | | | | | | | |
| | 3555 | 48819 | | | | | | | | | |
| | | 64088 | BETA 2157 | | | | | | | | |
| | 8535 | 58260 | BETA 1987 | | | | | | | | |
| | 3358 | 36542 | BETA 1228 | | | | | | | | |
| | 3744 | 51437 | BETA 1083 | | | | | | | | |
| | 6071 | 54762 | BETA 1655 | | | | | | | | |
| | 2649 | 54832 | BETA 992 | | | | | | | | |
| | 7103 | 57737 | BETA 1127 | | | | | | | | |
| | 8634 | 62120 | BETA 1057 | | | | | | | | |

TABLE 2-continued

Accessions of Beta vulgaris subsp. maritima and their resistance rating scores towards Cercospora used in a breeding program; the first 4 columns on the right present the accession numbers wherein a certain accession may have different accession numbers depending on the deposition facility (USDA GRIN = US Department of Agriculture Germplasm Resources Information Network; IDBBNR = International Database for Beta; DEU001 = Plant Genetic Resource Collection; IPK = Leibnitz-Institut für Pflanzengenetik und Kulturpflanzenforschung)

| Accession denomination | | | | Resistance rating score for Cercospora | | | | | | | | | | | | |
|---|---|---|---|---|---|---|---|---|---|---|---|---|---|---|---|---|
| USDA | | | | IDBB studies | | | | | | | | | | | | |
| GRIN | IDBBNR | DEU001 | IPK | 202 | 237 | 238 | 244 | 248 | 249 | 250 | 252 | 254 | 259 | 263 | 270 | 288 |
| | 8635 | 62121 | BETA 1447 | | | | | | | | | | | | | |
| | 8636 | 62122 | BETA 1014 | | | | | | | | | | | | | |
| | 8637 | 62123 | BETA 1432 | | | | | | | | | | | | | |
| | 8638 | 62124 | BETA 1090 | | | | | | | | | | | | | |
| | 8640 | 62126 | BETA 1377 | | | | | | | | | | | | | |
| | 8642 | 62128 | BETA 1558 | | | | | | | | | | | | | |
| | 8643 | 62130 | BETA 1348 | | | | | | | | | | | | | |
| | 8644 | 62131 | BETA 1610 | | | | | | | | | | | | | |
| | 2212 | 28931 | BETA 1666 | | | | | | | | | | | | | |
| | 3546 | 48810 | BETA 1304 | | | | | | | | | | | | | |
| PI 504196 | | | | | 3 | | | | | | | 7 | | | | 8 |
| PI 546409 | | | | | | | | | | 3 | | | | | | |
| | 3401 | 45516 | BETA 2174 | | | | | | | | | | | | | |
| PI 504245 | 5726 | | | | | | | | | | | | | | | 8 |
| PI 120704 | 5191 | | | | | | | | | | | | | | | |
| PI 169020 | 5265 | | | | | | | | | | | | | | | |
| PI 169023 | 5268 | | | | | | | | | | | | | | | |
| PI 169030 | 5274 | | | | | | | | | | | | | | | |
| PI 546536 | 9703 | | | | | | | | | | | | | | | |
| PI 546539 | 9706 | | | | | | | | | | | | | | | |
| PI 518303 | 5797 | | | | | | | | | | | | | | | |
| PI 518303 | 5797 | | | | | | | | | | | | | | | |
| PI 546534 | 9701 | | | | | | | | | | | | | | | |
| PI 590763 | 4587 | | | | | | | | | | | | | | | |
| PI 590766 | 4591 | | | | | | | | | | | | | | | |
| PI 109038 | 5160 | | | | | | | | | | | | | | | 8 |
| | | 28894 | BETA 1521 | | | | 3 | | | | | 1 | | | | |
| | 2195 | 32375 | BETA 1429 | 2 | | | | | | | | | | | | |

TABLE 2-continued

Accessions of Beta vulgaris subsp. maritima and their resistance rating scores towards Cercospora used in a breeding program; the first 4 columns on the right present the accession numbers wherein a certain accession may have different accession numbers depending on the deposition facility (USDA GRIN = US Department of Agriculture Germplasm Resources Information Network; IDBBNR = International Database for Beta; DEU001 = Plant Genetic Resource Collection; IPK = Leibnitz-Institut für Pflanzengenetik und Kulturpflanzenforschung)

| | | | | | | | | | | | | |
|---|---|---|---|---|---|---|---|---|---|---|---|---|
| | 3555 | 48819<br>64088 | BETA 2157 | | | | 4 | | | 4 | | |
| | 8535 | 58260 | BETA 1987 | | | | | | | 1 | | |
| | 3358 | 36542 | BETA 1228 | | 6 | | | | | 3 | | |
| | 3744 | 51437 | BETA 1083 | 6 | | | | | | | 7 | |
| | 6071 | 54762 | BETA 1655 | | | | | | | | | 2 |
| | 2649 | 54832 | BETA 992 | | | 8 | | | | | | 5 |
| | 7103 | 57737 | BETA 1127 | | | | | | | | 3 | |
| | 8634 | 62120 | BETA 1057 | | | | | | 5 | | | |
| | 8635 | 62121 | BETA 1447 | | | | | | 1 | | | |
| | 8636 | 62122 | BETA 1014 | | | | | | 3 | | | |
| | 8637 | 62123 | BETA 1432 | | | | | | 3 | | | |
| | 8638 | 62124 | BETA 1090 | | | | | | 2 | | | |
| | 8640 | 62126 | BETA 1377 | | | | | | 2 | | | |
| | 8642 | 62128 | BETA 1558 | | | | | | 2 | | | |
| | 8643 | 62130 | BETA 1348 | | | | | | 4 | | | |
| | 8644 | 62131 | BETA 1610 | | | | | | 2 | | | |
| | 2212 | 28931 | BETA 1666 | | 2 | | | | | 7 | | |
| | 3546 | 48810 | BETA 1304 | | | | | | | 3 | 3 | |
| PI 504196 | | | | | | | | | | | | |
| PI 546409 | | | | | | | | | | | | |
| | 3401 | 45516 | BETA 2174 | | | | | 3 | | | | |
| PI 504245 | 5726 | | | | | | | | | | | 1 |

As it is apparent from Table 2 the accessed genetic material had shown previously a non-uniform resistance level against *Cercospora* and the degree of resistance varied throughout the different studies. For example, the accession "PI 120704" showed a score of 1 in one study and a score of 9 in another study. As this publicly available data seemed to be unreliable, seed material from the accessions has been planted and the resulting plants were screened phenotypically for *Cercospora* resistance. About 150 partial resistant plants have been selected. However, as the seen resistance in each plant could have been the result of a plenty of genes all having a small contribution the chances to identify a single gene suitable for establishing a resistance or increasing the resistance level in a measurable manner was limited. It was decided to cross the about 150 resistant plants among each other using an open pollination scenario. This approach also allowed for the generation of recombinations within the genetic material. Crossing and selection have been repeated for several generations to improve the resistance level. The best descendants have been cloned and prepared for a genetic mapping approach. The mapping of the herein described resistance was coupled with intensive phenotyping. With the aid of the setup of a population of over 4,000 dividing descendants and the development of special recombination screens, the target region was reduced, and thus ever further isolated, via analysis of informative recombinants (genotypical and phenotypical) in a series of resistance tests. This genetic mapping, as well as the creation of physical maps accompanied by WHG sequencing ("whole genome sequencing"), comparative BAC (Bac-by-Bac) sequencing, and bioinformatic analyses, led to the identification of three recombinant genotypes that confirmed the resistance gene (1 recombinant in the neighboring gene, on the one hand, and 2 recombinants in the neighboring gene, on the other). In light of particular requirements, the inventors placed the highly repetitive structure in the target region, which, among other things, contains tandem repeats with very high sequence homology, which made the marker development, and thus the identification of informative recombinants, enormously more difficult. The following steps were particularly decisive for the location of the genetic structure of the resistance gene:

- development of the markers s4p0264s01, s4p2271s01, sxh0678s01, s4p4293s01, s4p4295s01, s4p4301s01 (see Table 1B).
- Fine mapping coupled with intensive phenotyping. The phenotypes were verified with 90-180 descendants per plant in a greenhouse test, and with intensive statistical methods (for example, t-test, power analysis, etc.).
- BAC clone identification and sequencing from BAC pools of the resistant genotype.
- Sequence evaluation, as well as sequence and protein comparison between RR (i.e., resistant) and ss (i.e., sensitive) genotypes; an unambiguous assembly of the RR and ss sequence data was thereby not always possible, due to the sequence complexity.

In the framework of the breeding program, the *Beta vulgaris* subsp. *maritima* derived resistance was crossed with an elite sugar beet line. Several back crossings via marker assisted selection allowed to transfer the resistance gene in established sugar beet germplasm. Surprisingly, no undesired effects towards sugar yield etc. could be observed. Subsequently, a proof of concept for the resistance gene within sugar beet has been established via transformation and the generation of sugar beets which were transgenic for the resistance gene (s. above). After this successful proof of concept the generated sugar beet germplasm comprising the resistance gene could be used for the generation of a *Cercospora* resistant sugar beet variety.

Example 4: Screening the Starting Accessions for the Identified Resistance Gene After the resistance gene has been identified the genetic source material (accessions according to Table 2) was screened by the help of markers to identify the accession which carried the resistance gene. The number of the analyzed plants per accession was dependent on the availability of seeds and is given in the table below.

TABLE 3

Number of plants per accession analyzed for the presence of the identified resistance gene

| Accession denomination | | | | |
|---|---|---|---|---|
| USDA GRIN | IDBBNR | DEU001 | IPK | Plants [No.] |
| PI 120704 | 5191 | | | 40 |
| PI 169020 | 5265 | | | 40 |
| PI 169023 | 5268 | | | 18 |
| PI 169030 | 5274 | | | 18 |
| PI 546536 | 9703 | | | 50 |
| PI 546539 | 9706 | | | 34 |
| PI 518303 | 5797 | | | 2 |
| PI 518303 | 5797 | | | 16 |
| PI 546534 | 9701 | | | 40 |
| PI 590763 | 4587 | | | 12 |
| PI 590766 | 4591 | | | 28 |
| PI 109038 | 5160 | | | 23 |
| | | 28894 | BETA 1521 | 40 |
| | 2195 | 32375 | BETA 1429 | 40 |
| | 3555 | 48819 | | 14 |
| | | 64088 | BETA 2157 | 12 |
| | 8535 | 58260 | BETA 1987 | 40 |
| | 3358 | 36542 | BETA 1228 | 40 |
| | 3744 | 51437 | BETA 1083 | 31 |
| | 6071 | 54762 | BETA 1655 | 40 |
| | 2649 | 54832 | BETA 992 | 12 |
| | 7103 | 57737 | BETA 1127 | 40 |
| | 8634 | 62120 | BETA 1057 | 18 |
| | 8635 | 62121 | BETA 1447 | 40 |
| | 8636 | 62122 | BETA 1014 | 40 |
| | 8637 | 62123 | BETA 1432 | 37 |
| | 8638 | 62124 | BETA 1090 | 11 |
| | 8640 | 62126 | BETA 1377 | 40 |
| | 8642 | 62128 | BETA 1558 | 40 |
| | 8643 | 62130 | BETA 1348 | 40 |
| | 8644 | 62131 | BETA 1610 | 40 |
| | 2212 | 28931 | BETA 1666 | 36 |
| | 3546 | 48810 | BETA 1304 | 40 |
| PI 504196 | | | | 37 |
| PI 546409 | | | | |
| | 3401 | 45516 | BETA 2174 | 40 |
| PI 504245 | 5726 | | | 40 |

Each of the given plants of each accession has been screened by the use of 572 SNP markers which were located 5' as well as 3' to the resistance gene. Due to the large amount of markers a haplotype pattern could be derived. However, none of the accessions used as starting material showed the haplotype of the line CRBM which carried the identified resistance gene. Most similarities have been found to the accession 48819 (DEU001 denomination)/3555 (IDBBNR) (s. Tables 2 and 3). The following table shows an extract of the entire marker analysis including positions 5' and 3' of the resistance gene.

TABLE 4

Comparison of a resistant line according to the invention and 14 plants of accession 48819 via SNP marker analysis (del = deletion, ins = insertion, Pos start = starting position of molecular marker on genetic strand, * = Position of resistance gene according to SEQ ID NO 1)

| | Marker | | | | | | |
|---|---|---|---|---|---|---|---|
| | s4e5628s03 | s4e5628s02 | s4p2272s01 | s4p2273s01 | s4p4291s01 | s4p4293s01 | sxh6264s01 |
| | Pos start | | | | | | |
| | 62,81 | 62,82 | 62,83 | 62,83 | 62,84 | 62,84 | 62,84 |
| CRBM comprising SEQ ID NO: 1 | A | A | A | A | A | A | G |
| 48819_1 | A | G | T | C | G | G | G |
| 48819_2 | A | G | T | C | G | G | G |
| 48819_3 | A | G | T | C | G | G | G |
| 48819_4 | A | G | T | C | G | G | G |
| 48819_5 | A | G | T | C | G | G | G |
| 48819_6 | A | G | T | A/C | G | A | G |
| 48819_7 | A | G | T | C | G | G | A/G |
| 48819_8 | A | G | T | A/C | G | G | G |
| 48819_9 | A | G | T | C | G | G | G |
| 48819_10 | A | G | T | C | G | G | G |
| 48819_11 | A | G | T | C | G | G | G |
| 48819_12 | A | G | T | C | G | G | G |
| 48819_13 | A | G | T | A/C | G | A | G |
| 48819_14 | A | G | A/T | A/C | G | G | G |

| | Marker | | | | | | |
|---|---|---|---|---|---|---|---|
| | sxh3116s01 | s4p4295s01 | s4p8772s01 | s4p8783s01 | s4p4301s01 | sxh0678s01 | s4p2276s01 |
| | Pos start | | | | | | |
| | 62,84 | 62,85 | 62,86 | 62,94 | 62,94 | 62,97 | 62,97 |
| CRBM comprising SEQ ID NO: 1 | C | A | T | * C/T | A | A | G |
| 48819_1 | C | T | A | C | A | A | G |
| 48819_2 | C | T | A | C | A | A | G |
| 48819_3 | C | A/T | A/T | C | A/T | A/C | A/G |
| 48819_4 | C | A/T | A/T | C | A/T | A/C | A/G |
| 48819_5 | C | A/T | T | C | T | A/C | A |
| 48819_6 | C | A/T | A/T | C | A/T | C | G |
| 48819_7 | A/C | NA | A | C | T | C | G |
| 48819_8 | A/C | NA | A | C | A/T | A/C | G |
| 48819_9 | A/C | A | A/T | C | T | C | A/G |
| 48819_10 | C | A | T | C | T | C | A |
| 48819_11 | C | A | T | C | T | C | A |
| 48819_12 | C | A/T | T | C | T | A/C | A |
| 48819_13 | C | A/T | A/T | C | A/T | C | A/G |
| 48819_14 | C | T | A | C | A/T | A/C | G |

| | Marker | | | | | |
|---|---|---|---|---|---|---|
| | s4p4305d01 | s4p4306s01 | s4e9714s01 | s4e7895s01 | s4p4307s01 | s4p4309s01 |
| | Pos start | | | | | |
| | 62,98 | 62,98 | 62,98 | 62,98 | 62,99 | 63,01 |
| CRBM comprising SEQ ID NO: 1 | del | G | G | C | C | T |
| 48819_1 | ins | G | G | C | C | T |
| 48819_2 | ins | G | G | C | C | T |
| 48819_3 | ins | A/G | C/G | C/G | C/T | C/T |
| 48819_4 | ins | A/G | C/G | C/G | C/T | C/T |
| 48819_5 | ins | A | C/G | G | C/T | C |
| 48819_6 | ins | G | G | C | C | C/T |

TABLE 4-continued

Comparison of a resistant line according to the invention and 14 plants of accession 48819 via SNP marker analysis (del = deletion, ins = insertion, Pos start = starting position of molecular marker on genetic strand, * = Position of resistance gene according to SEQ ID NO 1)

| | | | | | | |
|---|---|---|---|---|---|---|
| 48819_7 | ins | G | G | C | C | C/T |
| 48819_8 | ins | G | G | NA | C | C |
| 48819_9 | ins | A/G | C/G | G | C/T | C |
| 48819_10 | ins | A | C | G | T | C |
| 48819_11 | ins | A | C | G | T | C |
| 48819_12 | ins | A | C/G | G | C/T | C |
| 48819_13 | ins | A/G | C/G | C/G | C/T | C/T |
| 48819_14 | ins | A/G | C/G | C/G | C/T | C/T |

The results of the marker analysis (as exemplified by the data given in Table 4) show that the resistance gene according to the invention could not be traced back to one of the accessions according to Table 2. Even plants of the accession 48819 which shared the strongest marker overlap with the resistant line according to the invention had significant differences. Noticeable, was the detection of a deletion within the resistant line whereas accession 48819 showed a deletion at the same position. This could be an indication that a significant genetic restructuring at this locus took place during the generation of the resistance gene according to the invention. This assumption would also explain why it was not possible to trace back the resistance gene back to the starting material of the breeding program.

Example 5: Creation of *Cercospora* Resistant Seed Stock

The generated sugar beet germplasm comprising the resistance gene (outcome of Example 3) could be used for the generation of a *Cercospora* resistant sugar beet variety. For this purpose the gene was transmitted via crossing into a DH parent line which was crossed with a DH parent line originating from the other hybrid breeding pool. The result was a hybrid variety comprising the resistance towards *Cercospora* according to the present invention. The seeds of the variety were separated from each other (singularized), cleaned and polished. Afterwards, the seeds have been subjected to priming and pelleting as described in EP2002702A1. The resulting seed stock has been filed in a packaging made of cardboard which comprised an interlayer as vapor barrier. The resulting seed stock was suitable for sowing, growing, harvesting and subsequent industrial sugar production.

While several possible embodiments are disclosed above, embodiments of the present invention are not so limited. These exemplary embodiments are not intended to be exhaustive or to unnecessarily limit the scope of the invention, but instead were chosen and described in order to explain the principles of the present invention so that others skilled in the art may practice the invention. Indeed, various modifications of the invention in addition to those described herein will become apparent to those skilled in the art from the foregoing description. Such modifications are intended to fall within the scope of the appended claims.

What is claimed is:

1. A plant or portion thereof of the subspecies *Beta vulgaris* subsp. *vulgaris* comprising:

a nucleic acid molecule encoding a polypeptide that is able to confer resistance to *Cercospora beticola* in a plant in which the polypeptide is expressed, wherein the nucleic acid molecule comprises a nucleotide sequence that encodes a polypeptide having the amino acid sequence according to SEQ ID NO:3; and a promoter comprising SEQ ID NO:7.

2. The plant or portion thereof according to claim 1, wherein the plant is a hybrid plant.

3. The plant or portion thereof according to claim 1, wherein the plant is a double haploid plant.

4. The plant or portion thereof according to claim 1, wherein the resistance is dominant.

5. The plant or portion thereof according to claim 1, wherein the nucleic acid molecule is homozygous.

6. The plant or portion thereof according to claim 1, wherein the nucleic acid molecule is heterozygous.

7. The plant or portion thereof according to claim 1, wherein the plant or portion thereof comprises the nucleic acid molecule as an introgression.

8. The plant or portion thereof according to claim 1, wherein the plant is a variety.

9. The plant or portion thereof according to claim 1, wherein the nucleic acid molecule is positioned between a first marker selected from the group consisting of s4p0264s01, s4p2271s01, s4p4293s01, and s4p4295s01 and a second marker selected from the group consisting of sxh0678s01 and s4p4301s01 of the genome of the plant.

10. The plant or portion thereof according to claim 1, wherein the nucleic acid molecule is positioned between marker s4p4293s01 and marker sxh0678s01 of the genome of the plant.

11. The plant or portion thereof according to claim 1, wherein the nucleic acid molecule is positioned between marker s4p4293s01 and marker s4p4301s01 of the genome of the plant.

12. The plant or portion thereof according to claim 1, wherein the nucleic acid molecule is positioned between marker s4p4295s01 and marker sxh0678s01 of the genome of the plant.

13. The plant or portion thereof according to claim 1, wherein the nucleic acid molecule is positioned between marker s4p4295s01 and marker s4p4301s01 of the genome of the plant.

14. The plant or portion thereof according to claim 9, wherein the nucleic acid molecule positioned between the markers comprise confers the *Cercospora beticola* resistant genotype.

15. The plant or portion thereof according to claim 14, wherein the markers are selected from the group consisting of SEQ ID NOs: 55, 57, 59, 61, 63, and 65.

16. A storage organ of the plant according to claim 1, wherein the storage organ comprises the nucleic acid molecule.

17. A seed of the plant according to claim 1, wherein the seed comprises the nucleic acid molecule.

* * * * *

SEQUENCE LISTING

```
Sequence total quantity: 100
SEQ ID NO: 1            moltype = DNA  length = 3720
FEATURE                 Location/Qualifiers
source                  1..3720
                        mol_type = unassigned DNA
                        organism = Beta vulgaris
SEQUENCE: 1
atgaacatga aaatcctcct tttgtttgtc ttccttcatc acctccacta cttcatccat  60
ggcagaacac ttacagaacg ccaagcttta ctaagtatca aatctgccat tacttatgat  120
tattataact ctctctcctc atggaaaaac acaacacacc actgcagttg gccatacatc  180
acttgctcct cctcttcttc ttcttcttct gttatttctc tcaacttcac catgttattt  240
ctcgaaggaa ttctctcccc tgatataggc ttcctcacca acctgcaaaa cctctctatt  300
cgatctaacc tttttctgg cccactcccc cattctctct ctctcctcac ccaactccgc  360
tatctcgacg tttcccaaaa cagtttcaca ggtccaatcc catcttctct ctctctcctc  420
acccaactcc gctatctcca cgtttccggc aacagtttca caggtccaat cccatctttt  480
ctctctctcc tcacccaact ccgctatctc gacgtttccg acaacagttt cacaggtcca  540
atcccatctt ctctctctct cctcacccaa ctccgctatc tcgacgtttc ctacaacaat  600
ctaaatggca ctcttccctt atcggtcgtt gagaagatgt cggagctcag ctaccttaac  660
cttaggtata actctttcta cggtgagatt ccaccggagt ttgggaaact taagaagctt  720
gaaacattga atcttggtaa caacactctt tctgggagtc ttccatctga gttgggttca  780
ttaaagagtt tgaaacatat ggacttttct agtaatatgc tatttggtga gatcccacaa  840
tcttattctc ttcttcgaaa cttaatcgat attgatctta atagaaacaa gttatatggg  900
agtatacctg attatattgg agattttccg gagttggaat cacttttatt agactcgaat  960
aacttcacag ggagtatccc acaaaagtta ggtacaaacg ggaagttgca atatctagat  1020
ataagtaaca acaattttag tggtagtttg ccactaagtc tttgcaaagg agacaaactc  1080
caagatctgg acgcatccta taatttgttg gttgggtcaa ttcctgagag tttgggaagt  1140
tgcaagtcac ttgaaggagt gtacatggga aataatttct taaacgggtc gattcctaag  1200
ggcttgtttg ggagtgatgt ttcacttaat gacaaacttc ttagtggagg tctcgatgag  1260
aaattcggtg attgcgttaa tcttcgggac attgatctct ctaataataa gctatcaggg  1320
aagttacctg cgaccatcgg aaactgtatt catcttcggt ccttgacgct ttataataac  1380
```

```
acctgtaccg gacgtatccc tcaagagatt agcaagtgta agcagctaca gaccctcgat  1440
ctcagccaaa atcagttctc tggtgtgata cccaatgata ttacaggtaa gaaagtatat  1500
taaacttgtt actttgaaa atattcgctc tagtttttgt ttcagttggt ccattctcac  1560
tttgtattat tgaaatatat cccaaaaaag taaatataat tatataaaag aatcttgcta  1620
aaaataatat gaattatttt tgtatgtgca aaataatgta caaatctaac taatttgttg  1680
tggataataa tattaattgt gtgaaatagt aaatgtgtgg agatatataa ctttatttat  1740
catattcact caggttttta ggtatttatt atgagttttg cattggagat atccaacttg  1800
acaatagtat ttttgtaata taccaatata taaagattac tgtacataac caaaatgtat  1860
acttttctta tttttataaa cttatatatt cctcttcttt gtatttatca caacattttt  1920
tataccctttt tgcctcatat taatagcaac acttataatt tatttattta ctttttattt  1980
cttggtctat aacctcatct acccacatat gacacaccct ataaaggacc cacatgatta  2040
accaaaatat acaaatatct tcaatgaaat taactttaac actaatatga taaaaatcat  2100
gtcccgcttt ttatcctcta actaagactc tgcataaagg tatattgcaa ttaatatgag  2160
atggaagagg tataataatt atatgatcaa attcctggat tgaaaaaataa atatgagatt  2220
aaaagtggta tgtttttggt taaaagaaac tatccataaa gtatgttttt ggttaaaaga  2280
aactatgcaa cataccaatc aaatgtttat acgcttacaa tttatgtacc actttttttgt  2340
cattgttttt ctattgtttg ccatacgtac gttactaaat catgttgtct tttcacattt  2400
taactaacaa taaattacta ttgatacacc aaaaaaatct atgagcattg gagtacgttg  2460
tttgatagaa gcttcgtgct attatttctt gtcaaagaat ttcatatctc aatatcttct  2520
aatttaacaa tctaacgaaa tttttttgac ccaggaaaca aatccatttg caatctggaa  2580
aagatacaaa cacttaaatt atcaaacaat gctttgactg gtgaaatccc tcattgtgtt  2640
ggaaatatcg agctcatagc attatttctc caatcaaaca aactgaacgg taccataccc  2700
gcaaacttct caaagttatg tgattcattg atatatctag atcttagtga caatcaactc  2760
gaaggagttc tacctaagtc cttgtccaaa tgtcaaagtc tagaactcct aaatgtcggg  2820
aacaataggc taagagataa atttccttca tggttagaca acctcccacg tctccaagtt  2880
ttcagtgtgc gttttaacgc cttctacggt cctataacta gctcaccaaa agttagtcac  2940
ccatttccta tgctacaaat tatcgaccta tctaacaata agttttgtgg caagttgcca  3000
agaagatata tcaaaaactt tgcaaccatg cgcaatatga atgagtctgg tgttgggaat  3060
ccacagtacc tgggggactc atcaatatat agtattacgt actctatggt attgacattc  3120
aatgggttac aacaaaaata tgaaaagctt attgtgacga tgtcgacctt tgatatatcc  3180
agcaacaact ttactggaca gattccatat gttatagggg gattacgctc acttcgtaac  3240
cttaatctct ctcataatgt cttaaccggg aacattcctc catcaattgc aaaattgtct  3300
ttgcttcaag atttggacct ttcatcaaac agacttactg gtcgtatccc tcaagaatta  3360
gttagtttaa catttcttgg gagtttcaat gtttcgaaca atctattgga ggggtctata  3420
cctcatggtt tcaacttcga cacgtacaca gctaattcat accaggggaa tctcgaatta  3480
tgtggaaaac cattacctga gtgtggagaa agaagggcaa aaggcaccac taataatcaa  3540
gatgatccta aaaatgataa tgaacgaatg ttgtcgatgt ccgaaatcgt agttatgggg  3600
tttggcagtg gtgtactagt tgggttggct tggggatact atatgtttc agtgggaaag  3660
cccttttggt ttatcaagat ggctagcaaa atggaatcaa tattgattgg ttttttctga  3720

SEQ ID NO: 2            moltype = DNA  length = 2652
FEATURE                 Location/Qualifiers
source                  1..2652
                        mol_type = other DNA
                        organism = synthetic construct
                        note = cDNA sequence of the Cercospora
                         resistance-conferring gene
SEQUENCE: 2
atgaacatga aaatcctcct tttgtttgtc ttccttcatc acctccacta cttcatccat  60
ggcagaacac ttacagaacg ccaagcttta ctaagtatca aatctgccat tacttatgat  120
tattataact ctctctcctc atggaaaaac acaacacacc actgcagttg gccatacatc  180
acttgctcct cctcttcttc ttcttcttct gttatttctc tcaacttcac catgttattt  240
ctcgaaggaa ttctctcccc tgatataggc ttcctcacca acctgcaaaa cctctctatt  300
cgatctaacc ttttttctgg cccactcccc cattctctct ctctcctcac ccaactccgc  360
tatctcgacg tttcccaaaa cagtttcaca ggtccaatcc catcttctct ctctctcctc  420
acccaactcc gctatctcca cgtttccggc aacagtttca caggtccaat cccatctttt  480
ctctctctcc tcacccaact ccgctatctc gacgtttccg acaacagttt cacaggtcca  540
atcccatctt ctctctctct cctcacccaa ctccgctatc tcgacgtttc ctacaacaat  600
ctaaatggca ctcttccctt atcggtcggt gagaagatgt cggagctcag ctaccttaac  660
cttaggtata actctttcta cggtgagatt ccaccggagt ttgggaaact taagaagctt  720
gaaacattga atcttggtaa caacactctt tctgggagtc ttccatctga gttgggttca  780
ttaaagagtt tgaaacatat ggacttttct agtaatatgc tatttggtga gatcccacaa  840
tcttattctc ttcttcgaaa cttaatcgat attgatctta atagaaacaa gttatatggg  900
agtatacctg attatattgg agattttccg gagttggaat cacttttatt agactcgaat  960
aacttcacag ggagtatccc acaaaagtta ggtacaaacg ggaagttgca atatctagat  1020
ataagtaaca acaattttag tggtagtttg ccactaagtc tttgcaaagg agacaaactc  1080
caagatctgg acgcatccta taatttgttg gttgggtcaa ttcctgagag tttgggaagt  1140
tgcaagtcac ttgaaggagt gtacatggga aataatttct taaacgggtc gattcctaag  1200
ggcttgtttg ggagtgatgt ttcacttaat gacaaacttc ttagtggagg tctcgatgag  1260
aaattcggtg attgcgttaa tcttcgggac attgatctct ctaataataa gctatcaggg  1320
aagttacctg cgaccatcgg aaactgtatt catcttcggt ccttgacgct ttataataac  1380
acctgtaccg gacgtatccc tcaagagatt agcaagtgta agcagctaca gaccctcgat  1440
ctcagccaaa atcagttctc tggtgtgata cccaatgata ttacaggaaa caaatccatt  1500
tgcaatctgg aaaagataca aacacttaaa ttatcaaaca atgctttgac tggtgaaatc  1560
cctcattgtg ttggaaatat cgagctcata gcattatttc tccaatcaaa caaactgaac  1620
ggtaccatac ccgcaaactt ctcaaagtta tgtgattcat tgatatatct agatcttagt  1680
gacaatcaac tcgaaggagt tctacctaag tccttgtcca aatgtcaaag tctagaactc  1740
ctaaatgtcg ggaacaatag gctaagagat aaatttcctt catggttaga caacctccca  1800
cgtctccaag ttttcagtgt gcgttttaac gccttctacg gtcctataac tagctcacca  1860
```

```
aaagttagtc acccatttcc tatgctacaa attatcgacc tatctaacaa taagttttgt  1920
ggcaagttgc caagaagata tatcaaaaac tttgcaacca tgcgcaatat gaatgagtct  1980
ggtgttggga atccacagta cctgggggac tcatcaatat atagtattac gtactctatg  2040
gtattgacat tcaatgggtt acaacaaaaa tatgaaaagc ttattgtgac gatgtcgacc  2100
tttgatatat ccagcaacaa ctttactgga cagattccat atgttatagg gggattacgc  2160
tcacttcgta accttaatct ctctcataat gtcttaaccg ggaacattcc tccatcaatt  2220
gcaaaattgt ctttgcttca agatttggac ctttcatcaa acagacttac tggtcgtatc  2280
cctcaagaat tagttagttt aacatttctt gggagtttca atgtttcgaa caatctattg  2340
gaggggtcta tacctcatgg tttcaacttc gacacgtaca cagctaattc ataccagggg  2400
aatctcgaat tatgtggaaa accattacct gagtgtggag aaagaagggc aaaaggcacc  2460
actaataatc aagatgatcc taaaaatgat aatgaacgaa tgttgtcgat gtccgaaatc  2520
gtagttatgg ggtttggcag tggtgtacta gttgggttgg cttggggata ctatatgttt  2580
tcagtgggaa agccctttttg gtttatcaag atggctagca aaatggaatc aatattgatt  2640
ggtttttttct ga                                                     2652
```

```
SEQ ID NO: 3           moltype = AA  length = 883
FEATURE                Location/Qualifiers
source                 1..883
                       mol_type = protein
                       organism = Beta vulgaris
SEQUENCE: 3
MNMKILLLFV FLHHLHYFIH GRTLTERQAL LSIKSAITYD YYNSLSSWKN TTHHCSWPYI  60
TCSSSSSSSS VISLNFTMLF LEGILSPDIG FLTNLQNLSI RSNLFSGPLP HSLSLLTQLR  120
YLDVSQNSFT GPIPSSLSLL TQLRYLHVSG NSFTGPIPSF LSLLTQLRYL DVSDNSFTGP  180
IPSSLSLLTQ LRYLDVSYNN LNGTLPLSVV EKMSELSYLN LRYNSFYGEI PPEFGKLKKL  240
ETLNLGNNTL SGSLPSELGS LKSLKHMDFS SNMLFGEIPQ SYSLLRNLID IDLNRNKLYG  300
SIPDYIGDFP ELESLLLDSN NFTGSIPQKL GTNGKLQYLD ISNNNFSGSL PLSLCKGDKL  360
QDLDASYNLL VGSIPESLGS CKSLEGVYMG NNFLNGSIPK GLFGSDVSLN DKLLSGGLDE  420
KFGDCVNLRD IDLSNNKLSG KLPATIGNCI HLRSLTLYNN TCTGRIPQEI SKCKQLQTLD  480
LSQNQFSGVI PNDITGNKSI CNLEKIQTLK LSNNALTGEI PHCVGNIELI ALFLQSNKLN  540
GTIPANFSKL CDSLIYLDLS DNQLEGVLPK SLSKCQSLEL LNVGNNRLRD KFPSWLDNLP  600
RLQVFSVRFN AFYGPITSSP KVSHPFPMLQ IIDLSNNKFC GKLPRRYIKN FATMRNMNES  660
GVGNPQYLGD SSIYSITYSM VLTFNGLQQK YEKLIVTMST FDISSNNFTG QIPYVIGGLR  720
SLRNLNLSHN VLTGNIPPSI AKLSLLQDLD LSSNRLTGRI PQELVSLTFL GSFNVSNNLL  780
EGSIPHGFNF DTYTANSYQG NLELCGKPLP ECGERRAKGT TNNQDDPKND NERMLSMSEI  840
VVMGFGSGVL VGLAWGYYMF SVGKPFWFIK MASKMESILI GFF                    883
```

```
SEQ ID NO: 4           moltype = DNA  length = 4748
FEATURE                Location/Qualifiers
source                 1..4748
                       mol_type = unassigned DNA
                       organism = Beta vulgaris
SEQUENCE: 4
ttactatgaa caatacccta atatcattag gttttcccct tctctctcct aagtgccaaa  60
ctgccaaccc cctcccatct ttatttcaat aagagcacca ttaaattatt gtgtaacaaa  120
gaccattatt ttaagatcac taataaggtt gctctaatta ttcctagaat tctagtgaaa  180
aaagaaagat aaaagatgaa catggggtga tgactgatga ctgagagaca acagacaaca  240
cttggttgag ttgatatttg acgcaaagac ttggcgtgtt ggaaggttca ttacacattt  300
tatccaagtc aactttgaag tcttcttagc tagagactaa tagagtgaac gtgttggaag  360
gttcatgttc atgacattat aaaagtaata atagtgaaat ttcacaaagt atttataaac  420
ccaggacaga ctcaagagct ctacttatta tattagtgaa aaacaaacat acacacgaca  480
ataacacaac ataaacaata atgaacatga aaatcctcct tttgtttgtc ttccttcatc  540
acctccacta cttcatcaat ggcagaacac taacagaaca tcaagcttta ctaagtatca  600
aatctgccat tactaatgat acgaatagct atctctcctt atggaaaaac acaacacacc  660
actgcagttg gccatacatc acttgctcct cctcttcttc ttctgtcatt tctctcgata  720
tctcctactt agagctcacc ggaattctct cccctgatat aggcttcctc accaacctcc  780
aaaacctcac tattcaatgg aacgattttt ctggcccccct ccccacttct ctctctctcc  840
tcacccaact ccgccatctc gacgtttcct acaacaattt cacaggtcca atcccatctt  900
ctctctctct cctcacccaa ctccgccatc tcgacgtttc cttcaacagt ttcacaggtc  960
caatcccatc ttctctctct ctcctcaccc aactccgcta tctcgacgtt tcccaaaaca  1020
gtttcacagg tccaatccca tcttctctct ctctcctcac ccaactccgc tatctcgacg  1080
tttccgacaa cagtttcaca ggtccaatcc catcttttct ctctctcctc acccaactcc  1140
gctatctaga cgtttcctac aacaatctaa atggcactct tcccttatcg gtcgttgaga  1200
tgtcggaact caggtacctt aaccttaagt ataactcttt ctacggtgag attccaccgg  1260
agtttgggaa acttaagaag cttcaaacat tggatcttgg taacaactat ctttctgggg  1320
gtcttccatt tgagttgggt tcattaaaga gtttgaaata tattgatctt agtataaaca  1380
atttatatgg gagtatacct gattatattg gagattttcc ggagttggaa tcacttttat  1440
tagactcgaa taacttcaca gggagtatcc cacaaaagtt aggtacaaac gggaagttgc  1500
aatatctaga tataagtaac aacaatttta gtgggagttt gccagcaagt ctttgcaaag  1560
gagacaaact ccaacatttg ggagtatccg ataatttgtt ggttgggcca attcctgaga  1620
gtttgggaag ttgcaagtca cttgaagaag tgaacatggg aaataatttc tttaacgggt  1680
cgattcctaa gggcttgttt ggcctcccaa acattattga tgtttcactc aatgacaatc  1740
ttcttagcgg aggtctcgat gagaaatttg gtgattgtgt taatcttttc aacattgatc  1800
tctctaataa taagctatca gggaagttac ctgcgactat tggaaactgt tctaatcttc  1860
agttgttgat gcttaatcag aataacttca ccggaagtat ccctcaagag attagcaagt  1920
gtaagcagct acgggccctc gatctcagcc aaaatcagtt ctctggtgtg atacccaatg  1980
atattacagg taagaaagta tattaaactt gttacttttg aaaatattcg ctctagtttt  2040
ctttcagttg gtccattctc acttttgcat tattgaaata tatccctaaa aaagtaaatg  2100
taattatata aaagaatctt gctcaaaata atatgaatta tttttgtatg tgcaaaataa  2160
```

-continued

```
tgtacaatct aactaatttg ttgtgaaaaa taatataatt gtgtgaaata gtaaatgtgt  2220
ggagatatat aactttattt atcatattca ctaagggttt taggtatttt actatgactt  2280
ttgcattatg gagatatcca acttgacaat agtattttg taatatactt cctccgtttc  2340
taaataagtg caacatttac atagtgttta ctattcacag tttaaacttt aattagcttt  2400
ggtgatttac attttaggaa aaacatagtc atgtgggatc ttattagatt cgtctgaatg  2460
tgaatttttt taatatcaac tttttataat ttttacttat tgacaattga agatattaat  2520
ggttaaaata atgcattggc aaacgtgcaa acaagaaatg ttgcacttat ttagaaacgg  2580
aggaagtatc atatatgaag attattgtac ataacacttt tcttattttt ataaactata  2640
tattcttctt ctttgtattt atcacaacac tttttatatc tttgcctcat attaatggca  2700
acacttttaa tttatctatt tactttttat ttcttggtct atagcccatt tacatactta  2760
tgacacacct cataaaggac ccacacgatt aaccaaaata tacaaatatc ttcaatgaaa  2820
ttaacttcaa tactaatatg ataaaaatca tgccccgctg tttatcctca tcctaagact  2880
ctgcataaaa ttattatttc ttgtccatac ttaatcatgt tgtgttttca cattttaact  2940
aataataaat tacaattgat acaccaaaaa actctatgag cattgggtat gttgtttgat  3000
agaagcttca tgctattatt tcttgtcaaa gaatttcata tctcgatatc ttctatacca  3060
tctaacgaac aattattttc tgcaggaaac aaaaccattt gcaattttga agaaattaaa  3120
ttacttgatt tatcaaacaa tattttgacc ggtgaaatcc ctcgttgtct tggaaatact  3180
agtactcaac tcgaaacatt atttcttcaa tcaaacaaac tgaacggtac catacccgca  3240
aacttctcaa agttatgtga ttcattgatg tatctagatc ttagtgacaa tcaactcgaa  3300
ggagttctac ctaagtcatt gtccaaatgt caaaatttga aactcctaaa tgtcgggaac  3360
aacaggctaa gagataaatt tccctcatgg ctagacaacc tcccacatct ccaagttttc  3420
agtgtgcgtt tcaatgcctt ctacggtcct ataactagct catcaaaggt taatcaccca  3480
tttcctatgc tacaaattat cgacctatct aacaatgagt tttgtggcaa gttgccaaga  3540
agatatatca aaaattttgc aaccatgcgc aatatgaatg agtctggtgt tggggatcca  3600
cagtacctgg aggactcata tagtccgtac tctatggtat tgacattcaa tgggttacaa  3660
caaaaatatg aaaagcttat tgtgacgatg tcgacctttg atatatccaa caacaacttt  3720
actggacaga ttccatatgt tataggggga ttacactcac ttcgtaacct taatctctcg  3780
cataatgtct taaccgggaa cattcctcca tcaattgcaa aattgtcttt gcttcaggat  3840
ttggaccttt catcaaacag acttattggt cgtatccctc aagaattagt tagtttaaca  3900
tttcttggga gcttcaatgt ttcgaacaat ctattggagg ggcctatacc tattggtaac  3960
aacttcaata cattctcgaa taattcatac caggggaatg tcggattgtg tggaaaacca  4020
ttacctgagt gtggagaaag aagggcaaaa agcaccacta ataatcaaga tgttcctaaa  4080
aatgataatg aacgaatgtt gtcgatgtcc gaaatcgtag ttatggggtt tggcagtggt  4140
gtactagttg ggttggcttg gggatactat atgttttcag tgggaaagcc cttttggttt  4200
atcaagatgg ctagcaaaat ggaatcaata ttgattggtt ttttctgacc aacaatttgt  4260
tagccgatga agagcatcaa aaccaaaaaa acaaaaaaat tgagtaatat gcatgagtgt  4320
gaccttgttt tccaaagttt agcattacta ttagtgtctc aattcataat aataaaaaaa  4380
ttagcttgtt caagatttgt attttattca aagatttttt atgtctcttg tgcttctttt  4440
atcttatata tattttttgt atggtttgtt tttgtttaat attagtccct ccgctcaaaa  4500
tgatctttca cgcttgagat tggcattaag gtcaagagat gttgctaagc tttagaataa  4560
aaaaattcca aatgcataga gggaaagaaa gcgagacaaa atgttggaga aggcagagta  4620
aatgatgtga tggaggataa atagtagaag tgtgataccg aaagtttgaa aataataagg  4680
aattttattt cttgctggca cttcgttcta gtacaggttt ttggcccttc aaaatgctta  4740
taatgtag                                                           4748

SEQ ID NO: 5           moltype = DNA  length = 2460
FEATURE                Location/Qualifiers
source                 1..2460
                       mol_type = other DNA
                       organism = synthetic construct
                       note = cDNA sequence of the sensitive variant of the
                        Cercospora resistance-mediating gene
SEQUENCE: 5
atgaacatga aaatcctcct tttgtttgtc ttccttcatc acctccacta cttcatcaat  60
ggcagaacac taacagaaca tcaagcttta ctaagtatca aatctgccat tactaatgat  120
acgaatagct atctctcctt atggaaaaac acaacacacc actgcagttg gccatacatc  180
acttgctcct cctcttcttc ttctgtcatt tctctcgata tctcctactt agagctcacc  240
ggaattctct cccctgatat aggcttcctc accaacctcc aaaacctcac tattcaatgg  300
aacgattttt ctggcccct ccccacttct ctctctctcc tcacccaact ccgccatctc  360
gacgtttcct acaacaattt cacaggtcca atcccatctt ctctctctct cctcacccaa  420
ctccgccatc tcgacgtttc cttcaacagt ttcacaggtc caatcccatc ttctctctct  480
ctcctcaccc aactccgcta tctcgacgtt tcccaaaaca gtttcacagg tccaatccca  540
tcttctctct ctctcctcac ccaactccgc tatctcgacg tttccgacaa cagtttcaca  600
ggtccaatcc catcttttct ctctctcctc acccaactcc gctatctaga cgtttcctac  660
aacaatctaa atggcactct tcccttatcg gtcgttgaga tgtcggaact caggtacctt  720
aaccttaagt ataactcttt ctacggtgag attccaccgg agtttgggaa acttaagaag  780
cttcaaacat tggatcttgg taacaactat ctttctgggg gtcttccatt tgagttgggt  840
tcattaaaga gtttgaaata tattgatctt agtataaaca atttatatgg gagtatacct  900
gattatattg gagattttcc ggagttggaa tcacttttat tagactcgaa taacttcaca  960
gggagtatcc cacaaaagtt aggtacaaac gggaagttgc aatatctaga tataagtaac  1020
aacaatttta gtgggagttt gccagcaagt ctttgcaaag gagacaaact ccaacatttg  1080
ggagtatccg ataatttgtt ggttgggcca attcctgaga gtttgggaag ttgcaagtca  1140
cttgaagaag tgaacatggg aaataatttc tttaacgggt cgattcctaa gggcttgttt  1200
ggcctcccaa acattattga tgtttcactc aatgacaatc ttcttagcgg aggtctcgat  1260
gagaaatttg gtgattgtgt taatcttttc aacattgatc tctctaataa taagctatca  1320
gggaagttac ctgcgactat tggaaactgt tctaatcttc agttgttgat gcttaatcag  1380
aataacttca ccggaagtat ccctcaagag attagcaagt gtaagcagct acgggccctc  1440
gatctcagcc aaaatcagtt ctctggtgtg atacccaatg atattacaga tcttagtgac  1500
aatcaactcg aaggagttct acctaagtca ttgtccaaat gtcaaaattt gaaactccta  1560
```

-continued

```
aatgtcggga acaacaggct aagagataaa tttccctcat ggctagacaa cctcccacat  1620
ctccaagttt tcagtgtgcg tttcaatgcc ttctacggtc ctataactag ctcatcaaag  1680
gttaatcacc catttcctat gctacaaatt atcgacctat ctaacaatga gttttgtggc  1740
aagttgccaa gaagatatat caaaaatttt gcaaccatgc gcaatatgaa tgagtctggt  1800
gttggggatc cacagtacct ggaggactca tatagtccgt actctatggt attgacattc  1860
aatgggttac aacaaaaata tgaaaagctt attgtgacga tgtcgacctt tgatatatcc  1920
aacaacaact ttactggaca gattccatat gttatagggg gattacactc acttcgtaac  1980
cttaatctct cgcataatgt cttaaccggg aacattcctc catcaattgc aaaattgtct  2040
ttgcttcagg atttggacct ttcatcaaac agacttattg gtcgtatccc tcaagaatta  2100
gttagtttaa catttcttgg gagcttcaat gtttcgaaca atctattgga ggggcctata  2160
cctattggta acaacttcaa tacattctcg aataattcat accaggggaa tgtcggattg  2220
tgtggaaaac cattacctga gtgtggagaa agaagggcaa aaagcaccac taataatcaa  2280
gatgttccta aaaatgataa tgaacgaatg ttgtcgatgt ccgaaatcgt agttatgggg  2340
tttggcagtg gtgtactagt tggttggct tggggatact atatgtttc agtgggaaag  2400
ccctttggt ttatcaagat ggctagcaaa atggaatcaa tattgattgg ttttttctga  2460

SEQ ID NO: 6           moltype = AA  length = 819
FEATURE                Location/Qualifiers
source                 1..819
                       mol_type = protein
                       organism = Beta vulgaris
SEQUENCE: 6
MNMKILLLFV FLHHLHYFIN GRTLTEHQAL LSIKSAITND TNSYLSLWKN TTHHCSWPYI  60
TCSSSSSSVI SLDISYLELT GILSPDIGFL TNLQNLTIQW NDFSGPLPTS LSLLTQLRHL  120
DVSYNNFTGP IPSSLSLLTQ LRHLDVSFNS FTGPIPSSLS LLTQLRYLDV SQNSFTGPIP  180
SSLSLLTQLR YLDVSDNSFT GPIPSFLSLL TQLRYLDVSY NNLNGTLPLS VVEMSELRYL  240
NLKYNSFYGE IPPEFGKLKK LQTLDLGNNY LSGGLPFELG SLKSLKYIDL SINNLYGSIP  300
DYIGDFPELE SLLLDSNNFT GSIPQKLGTN GKLQYLDISN NNFSGSLPAS LCKGDKLQHL  360
GVSDNLLVGP IPESLGSCKS LEEVNMGNNF FNGSIPKGLF GLPNIIDVSL NDNLLSGGLD  420
EKFGDCVNLF NIDLSNNKLS GKLPATIGNC SNLQLLMLNQ NNFTGSIPQE ISKCKQLRAL  480
DLSQNQFSGV IPNDITDLSD NQLEGVLPKS LSKCQNLKLL NVGNNRLRDK FPSWLDNLPH  540
LQVFSVRFNA FYGPITSSSK VNHPFPMLQI IDLSNNEFCG KLPRRYIKNF ATMRNMNESG  600
VGDPQYLEDS YSPYSMVLTF NGLQQKYEKL IVTMSTFDIS NNNFTGQIPY VIGGLHSLRN  660
LNLSHNVLTG NIPPSIAKLS LLQDLDLSSN RLIGRIPQEL VSLTFLGSFN VSNNLLEGPI  720
PIGNNFNTFS NNSYQGNVGL CGKPLPECGE RRAKSTTNNQ DVPKNDNERM LSMSEIVVMG  780
FGSGVLVGLA WGYYMFSVGK PFWFIKMASK MESILIGFF                        819

SEQ ID NO: 7           moltype = DNA  length = 1998
FEATURE                Location/Qualifiers
source                 1..1998
                       mol_type = unassigned DNA
                       organism = Beta vulgaris
misc_feature           1..1998
                       note = promoter - native promoter of the Cercospora
                        resistance-conferring gene Beta vulgaris subsp. maritima
SEQUENCE: 7
gagcatagtg agtgcaaaag ccatggaagc tagattaaaa aggccatcat tctaagttag  60
acaattggaa acaacatcga gatacacgta cacataaggg ctgctcttct ctattactcc  120
ctctgttcct aatcatttgc ttttttagcg ggttccaaag gcctatgttt gaccactaat  180
atatttaaat taaaactggt gatatatatt aaaagaaaat tatgatgaat ttaacaaaaa  240
ccatatatgt tatgtccttt tttttcctat attaatgaat ttttacagtc aaagttggtg  300
aactttgacc caaaaaaaga aatggagcaa aaaaaaaaaa aaaaaaaaaa aactagggac  360
aatgagtaac atttttatct atgtcttttt aatatgaata tacgtaacaa attctgcaaa  420
aatagagata gcaactaata acacgcatga aaatgacaag ttatattata ccttttttttc  480
tcaatatatg aatatacgta acaaattaac tccagtagtt tttagtaaaa ctattagatt  540
attgtgtaac atatactctg gaaatagtac taagatccat tacaatcttt attgagaaat  600
ttcctcatgt accccctgag gtttggcgta atttccaaat acccctcata tttgaggaat  660
ttctcaaata ccctgatgtt tttgtttaga ctcaaaatac ctttactatg gacagtaccc  720
taatgtcatt aagttttccc cttctctctc cccaattttc tctctcctcc cattcccccca  780
cccactaccc actgcccact gccaagtagg ggtgtaagtg gattggactg gattggactt  840
tgccaaattc aaatccagtc caaagttttt tggactcgag aaattgagtc caagtccgat  900
ccaaatattt tttgagtcca gtccaatcta gtccgataat tttttcttga gtccgaatcc  960
agtccagtcc agtccgatta ttatatcttt tttcccgatt taggttcaat gattcacaac  1020
attttttgag atgcttgagc atttgacatc tgattcaatt atcaatatcc acaaataaga  1080
ttgaaagctt aaattaaagt aaaatactat gaataaaaag ttgaattaga tgcttacctt  1140
gatctaagtt gagaggaagc atagagactg agaattaatc tgagggacaa atagagaatg  1200
cgagagtcga gacagtgagg tagaaagaaa atgaagagta agaggaagtg agtattaagg  1260
actgaggagt aaagtaagat agaattagtt ggctactagc ctactaatgc agtattgcta  1320
gtataattta cttatttaac aaatggagct aagtgcaata gtttagcgcc aattgacata  1380
tttagagaga gaaggctgaa aaatccaata tttttaaaat agtatcatta tttttaatat  1440
atacattata tataaaaata tttttggact ggactggaca tattggactc caaagggatg  1500
agtccaaatc cagacaaaaa atatttggac ttgaaaattt aagtccgagt ccagtccgaa  1560
aaattttcag tccaatccag tccgacaaat ttggactgga ctggattgga ctctgaactt  1620
ttcgtagtcc gcttacaccc ctactgccaa gtgccaaact gccaaccccc ttttggttga  1680
gttgatattt gacgcaaaga cttggcgtgt tggaaggttc attacacatt ttatccaagt  1740
caactttgaa gtcttcttag ctagagacta gagtgaacgt gttggaaggt tcattacaca  1800
ttttatccaa tcaaactttg aagtcttctt agctagagac tagagtgaac gtgttggaag  1860
gttcatgttc atgacattat aaaagtaata atagtgaaat ttcacaaagt atttataaac  1920
ccaggacaga ctcaagagct ctacttatta ttagtgaaaa acaaacatac acacgacaat  1980
```

```
aacacaacat aaacaata                                                1998

SEQ ID NO: 8           moltype = DNA  length = 2000
FEATURE                Location/Qualifiers
source                 1..2000
                       mol_type = unassigned DNA
                       organism = Beta vulgaris
misc_feature           1..2000
                       note = terminator - native terminator of the Cercospora
                        resistance-conferring gene from Beta vulgaris subsp.
                        maritima
SEQUENCE: 8
ccaacaattt gttagccgat gaagagcatc aaaaccaaaa aaaacaaaaa aaattgatta  60
atatgcatga gtgtgacctt gttttccaaa gtttagcatt actattagtg tctcaattca  120
taataataaa aaaattagct tgttcaagat ttgtattttt attcaaagat tttttttgtc  180
tcttgtgctt cttttatctt atatatattt tttgtatggt ttgtttttgt ttaatattag  240
tccctccgct caaaatgatc tttcacgctt gagattggca ttaaggtcaa gagatgttgc  300
taagctttag aataaaaaaa ttccaaatgc atagagggaa agaaagcgag acaaaatgtt  360
ggagaaggca gagtaaatga tgtgatggag gataaatagt agaagtgtga taccgaaagt  420
ttgaaaataa taaggaattt tatttcttgc tggcactttg ttctagtaca ggtttttagc  480
ccttcaaaat gtttataatg tagagtcaaa attaatatcc ttaactagtt tttaagtccg  540
ggttatatcc tagatattaa taatattcat ttattagtaa cattttattt tataaatata  600
atactaagca ttatttggtt tgctggttaa gactttagtg tatatctatt tctttttttt  660
tttattgtat gcgtgtttac ataaactaaa gactataagg gatagtacca cgtggcgcag  720
ttccttgctt aggaacgtct tttaatatat taactagtat ttgggcccgg gcgttgctcc  780
gggttggtat tgtgtttccg aacatgatgt gcagtttttc ccattcccac taaaatatat  840
aaaggaaaac tcaacattta aaagatacaa atataataat atggacactt aaaacatgat  900
taaaagttga ttgagatggt aattgtgtca tgttataata gtaagaggtt gcctaattga  960
ggttgaggtg gtggagtagt ggtatcgctt cccatctgtt atccctgagg tataaggatc  1020
aaacctcata ggactcattt gagtaatttc ccatatcctc ctctcaaatg agtccttttc  1080
atctgacaaa aaaaaagagt ctaattttaa attaaaatta gacgatcttt tataaaatcg  1140
gcactttctg cacataggtc acaatttttt tgtttctatc tctctgcttt ctttaatttc  1200
acagtctcca actctccatc aacatcttac ttattttaga atagatgatg tatggtagta  1260
ttaaatggta aagtactaaa gctcctataa tacacagaag cttacatagt atagattcgt  1320
acatgagaca aggttacaat atactttctc cgttcttttt atattacaat aattactatt  1380
ttaagtagtt tcacatctat tgtaacaatt ccaattttgt tatagaaagc aactttaata  1440
attgacaata ttgcccttac tttatcttat taaaaccatc attaattact cactttctct  1500
tataaaattg cttttatttt ctaaggatga tttctctcct attctagtta attaaagagt  1560
tacttttgtg ctaaactgct catttattcc aaatccttaa aaattgtgtc caaacgtatt  1620
gttgtaatat aaaaagaaca gaggtactat tagtttgaat aaattttgat cagattaggt  1680
cacctttagg gggcgtttgg ttaggggtat tctggaaagg gtaagggaat caacttactt  1740
aattccctta cttgttgttt gtttgctcaa tttaatgatt ccctttaccc acccccttact  1800
cccaaagtcc tttactctca ttctccccac cccccaaggt ttcacttacc ctttcttgat  1860
tcatcattga ccatatcttt gaccacccaa ctaccaccac cacttgacca cctaatcacc  1920
taaccaccta attacccaac cactattacc acccaacccc tccacctgcc caccaatcgg  1980
caccataact gcccaaccgt                                              2000

SEQ ID NO: 9           moltype = AA  length = 911
FEATURE                Location/Qualifiers
source                 1..911
                       mol_type = protein
                       organism = Beta vulgaris
REGION                 1..911
                       note = PEPTIDE - Konsensus Sequenz aus Abbildung 1
VARIANT                20
                       note = N or H
VARIANT                27
                       note = H or R
VARIANT                39
                       note = N or Y
VARIANT                41
                       note = T or Y
VARIANT                42
                       note = N or Y
VARIANT                43
                       note = S or N
VARIANT                44
                       note = Y or S
VARIANT                47
                       note = L or S
VARIANT                75
                       note = D or N
VARIANT                76
                       note = I or F
VARIANT                77
                       note = S or T
VARIANT                78
                       note = Y or M
VARIANT                80
```

| | |
|---|---|
| | note = E or F |
| VARIANT | 82 |
| | note = T or E |
| VARIANT | 99 |
| | note = T or S |
| VARIANT | 101 |
| | note = Q or R |
| VARIANT | 102 |
| | note = W or S |
| VARIANT | 104 |
| | note = D or L |
| VARIANT | 111 |
| | note = T or H |
| VARIANT | 121 |
| | note = H or Y |
| VARIANT | 126 |
| | note = Y or Q |
| VARIANT | 171 |
| | note = D or H |
| VARIANT | 174 |
| | note = Q or G |
| VARIANT | 184 |
| | note = S or F |
| VARIANT | 208 |
| | note = F or S |
| VARIANT | 241 |
| | note = K or R |
| VARIANT | 246 |
| | note = Q or E |
| VARIANT | 265 |
| | note = D or N |
| VARIANT | 268 |
| | note = G or S |
| VARIANT | 273 |
| | note = F or S |
| VARIANT | 277 |
| | note = Y or H |
| VARIANT | 280 |
| | note = S or N |
| VARIANT | 290 |
| | note = I or R |
| VARIANT | 318 |
| | note = N or K |
| VARIANT | 319 |
| | note = A or L |
| VARIANT | 321 |
| | note = H or D |
| VARIANT | 376 |
| | note = G or D |
| VARIANT | 386 |
| | note = V or A |
| VARIANT | 388 |
| | note = D or Y |
| VARIANT | 389 |
| | note = P or S |
| VARIANT | 391 |
| | note = E or G |
| VARIANT | 397 |
| | note = N or Y |
| VARIANT | 410 |
| | note = F or L |
| VARIANT | 412 |
| | note = L or S |
| VARIANT | 418 |
| | note = N or K |
| VARIANT | 429 |
| | note = F or R |
| VARIANT | 440 |
| | note = N or D |
| VARIANT | 457 |
| | note = S or I |
| VARIANT | 458 |
| | note = N or H |
| VARIANT | 478 |
| | note = Q or R |
| VARIANT | 479 |
| | note = L or S |
| VARIANT | 481 |
| | note = M or T |

```
VARIANT                 482
                        note = N or Y
VARIANT                 484
                        note = Q or N
VARIANT                 486
                        note = N or T
VARIANT                 487
                        note = F or C
VARIANT                 489
                        note = S or R
VARIANT                 490
                        note = R or Q
VARIANT                 493
                        note = A or T
VARIANT                 505
                        note = R or Q
VARIANT                 506
                        note = K or E
VARIANT                 605
                        note = H or R
VARIANT                 607
                        note = S or P
VARIANT                 629
                        note = N or S
VARIANT                 648
                        note = E or K
VARIANT                 651
                        note = D or N
VARIANT                 666
                        note = E or G
VARIANT                 692
                        note = P or T
VARIANT                 697
                        note = H or R
VARIANT                 705
                        note = N or S
VARIANT                 733
                        note = H or R
VARIANT                 748
                        note = I or T
VARIANT                 785
                        note = P or S
VARIANT                 811
                        note = I or H
VARIANT                 814
                        note = N or F
VARIANT                 816
                        note = N or D
VARIANT                 819
                        note = F or Y
VARIANT                 821
                        note = S or T
VARIANT                 822
                        note = N or A
VARIANT                 823
                        note = N or A
VARIANT                 830
                        note = V or L
VARIANT                 831
                        note = G or E
VARIANT                 847
                        note = S or G
VARIANT                 854
                        note = V or D
SEQUENCE: 9
MNMKILLLFV FLHHLHYFIX GRTLTEXQAL LSIKSAITXD XXXXLSXWKN TTHHCSWPYI  60
TCSSSSSSS VISLXXXXLX LXGILSPDIG FLTNLQNLXI XXNXFSGPLP XSLSLLTQLR  120
XLDVSXNNFT GPIPSSLSLL TQLRHLDVSF NSFTGPIPSS LSLLTQLRYL XVSXNSFTGP  180
IPSXLSLLTQ LRYLDVSDNS FTGPIPSXLS LLTQLRYLDV SYNNLNGTLP LSVVEKMSEL  240
XYLNLXYNSF YGEIPPEFGK LKKLXTLXLG NNXLSGXLPX ELGSLKSLKX MDFSSNMLFG  300
EIPQSYSLLR NLIDIDLXXN XLYGSIPDYI GDFPELESLL LDSNNFTGSI PQKLGTNGKL  360
QYLDISNNNF SGSLPXSLCK GDKLQXLXXS XNLLVGXIPE SLGSCKSLEX VXMGNNFXNG  420
SIPKGLFGXP NIIDVSLNDX LLSGGLDEKF GDCVNLXXID LSNNKLSGKL PATIGNCXXL  480
XXLXLXXNXX TGXIPQEISK CKQLXXLDLS QNQFSGVIPN DITGNKSICN LEKIQTLKLS  540
NNALTGEIPH CVGNIELIAL FLQSNKLNGT IPANFSKLCD SLIYLDLSDN QLEGVLPKSL  600
SKCQXLXLLN VGNNRLRDKF PSWLDNLPXL QVFSVRFNAF YGPITSSXKV XHPFPMLQII  660
DLSNNXFCGK LPRRYIKNFA TMRNMNESGV GXPQYLXDSS IYSIXYSMVL TFNGLQQKYE  720
KLIVTMSTFD ISXNNFTGQI PYVIGGLXSL RNLNLSHNVL TGNIPPSIAK LSLLQDLDLS  780
SNRLXGRIPQ ELVSLTFLGS FNVSNNLLEG XIPXGXNFXT XXXNSYQGNX XLCGKPLPEC  840
```

```
GERRAKXTTN NQDXPKNDNE RMLSMSEIVV MGFGSGVLVG LAWGYYMFSV GKPFWFIKMA  900
SKMESILIGF F                                                      911

SEQ ID NO: 10          moltype = DNA  length = 201
FEATURE                Location/Qualifiers
source                 1..201
                       mol_type = unassigned DNA
                       organism = Beta vulgaris
SEQUENCE: 10
agagcagatt ggcatacttr tgaatattct cactggctat taaattctca gaagaaaaat  60
caacaccaag attatgacat gcttgtgcaa agacacaccc rgtcatgaat gcatcatagc  120
cagcttcatg cttagcccca gagttccaat ttgaggayct gcaagaaaac atgggagtaa  180
gatggtttca cataaaacat g                                           201

SEQ ID NO: 11          moltype = DNA  length = 201
FEATURE                Location/Qualifiers
source                 1..201
                       mol_type = unassigned DNA
                       organism = Beta vulgaris
SEQUENCE: 11
gggtttcttc gaagtttgat tttgttacat ttttcaaaga gaaattagtt gttgatgttg  60
aataatgatg ataagtagtt agggttcgta gtaaggtgga sgaragagaa aatggcgtca  120
ctctgayrag cttcttcatt ttgttcttct tccttagctc tgttttcagt cactgcgcca  180
tttttttttt aaaaggaaga t                                           201

SEQ ID NO: 12          moltype = DNA  length = 134
FEATURE                Location/Qualifiers
source                 1..134
                       mol_type = unassigned DNA
                       organism = Beta vulgaris
SEQUENCE: 12
caagcacaaa atcaaataat gagaatcaca ctatccaaag aaaatttcca tccacattta  60
tccaacacar ttatctctct tttacaccca aattatgtca accaaaaaca staaaacaag  120
tgagtgcagt agct                                                   134

SEQ ID NO: 13          moltype = DNA  length = 134
FEATURE                Location/Qualifiers
source                 1..134
                       mol_type = unassigned DNA
                       organism = Beta vulgaris
SEQUENCE: 13
taagtaaaaa gtggtaaaag aattaccaaa arcgcacara ataaattaat tagytggatw  60
taactawtta acctattcct tttttctgtc gctataacta cttttgctta acttattgat  120
ggtttgatcg ttga                                                   134

SEQ ID NO: 14          moltype = DNA  length = 150
FEATURE                Location/Qualifiers
source                 1..150
                       mol_type = unassigned DNA
                       organism = Beta vulgaris
SEQUENCE: 14
ttataatgta gagtcaaaat taatatcctt aactagtttt taagtccggg ttatatccta  60
gatattwata atattcattt attagtaaca ttttatttta taaatataat actaagcatt  120
atttggtttg ctggttaaga ctttagtgta                                  150

SEQ ID NO: 15          moltype = DNA  length = 201
FEATURE                Location/Qualifiers
source                 1..201
                       mol_type = unassigned DNA
                       organism = Beta vulgaris
SEQUENCE: 15
acatctacac tgggagactg ataaggacgt ttgcagatgt caagtatggg aatcatcatc  60
taacatgggt ggagattgtg tacaatgtta tttcattcat mgtggcaata attaccattg  120
ttgcgtttac tgtatatgcc aagagagcct tcgaagaact taagagggca gaagctaagg  180
aggatcgaga agaagaaacc t                                           201

SEQ ID NO: 16          moltype = DNA  length = 28
FEATURE                Location/Qualifiers
source                 1..28
                       mol_type = other DNA
                       organism = synthetic construct
                       note = genomic target sequence with 5'-flanking PAM (4 bp)
                        5'crRNA # 1
SEQUENCE: 16
tttatttcga tttcgattct tggattat                                    28

SEQ ID NO: 17          moltype = DNA  length = 28
FEATURE                Location/Qualifiers
source                 1..28
```

```
                        mol_type = other DNA
                        organism = synthetic construct
                        note = genomic target sequence with 5'-flanking PAM (4 bp)
                         5'crRNA # 2
SEQUENCE: 17
tttcaaccca gtatccttat ccgtcact                                      28

SEQ ID NO: 18           moltype = DNA  length = 28
FEATURE                 Location/Qualifiers
source                  1..28
                        mol_type = other DNA
                        organism = synthetic construct
                        note = genomic target sequence with 5'-flanking PAM (4 bp)
                         5'crRNA # 3
SEQUENCE: 18
tttatttaaa catgatacgt atcatatt                                      28

SEQ ID NO: 19           moltype = DNA  length = 28
FEATURE                 Location/Qualifiers
source                  1..28
                        mol_type = other DNA
                        organism = synthetic construct
                        note = genomic target sequence with 5'-flanking PAM (4 bp)
                         5'crRNA # 4
SEQUENCE: 19
tttaaacatg atacgtatca tattgagt                                      28

SEQ ID NO: 20           moltype = DNA  length = 28
FEATURE                 Location/Qualifiers
source                  1..28
                        mol_type = other DNA
                        organism = synthetic construct
                        note = genomic target sequence with 5'-flanking PAM (4 bp)
                         3'crRNA # 1
SEQUENCE: 20
tttgtgggtg ggtggttttc acgtgtgt                                      28

SEQ ID NO: 21           moltype = DNA  length = 28
FEATURE                 Location/Qualifiers
source                  1..28
                        mol_type = other DNA
                        organism = synthetic construct
                        note = genomic target sequence with 5'-flanking PAM (4 bp)
                         3'crRNA # 2
SEQUENCE: 21
tttcccctcc ctttgccgct gcgaagtt                                      28

SEQ ID NO: 22           moltype = DNA  length = 28
FEATURE                 Location/Qualifiers
source                  1..28
                        mol_type = other DNA
                        organism = synthetic construct
                        note = genomic target sequence with 5'-flanking PAM (4 bp)
                         3'crRNA # 3
SEQUENCE: 22
tttcttcttc ttgcttccac cataacac                                      28

SEQ ID NO: 23           moltype = DNA  length = 28
FEATURE                 Location/Qualifiers
source                  1..28
                        mol_type = other DNA
                        organism = synthetic construct
                        note = Mutagenesis primer 1
SEQUENCE: 23
tcagtgcagc cgtcgtctga aaacgaca                                      28

SEQ ID NO: 24           moltype = DNA  length = 28
FEATURE                 Location/Qualifiers
source                  1..28
                        mol_type = other DNA
                        organism = synthetic construct
                        note = Mutagenesis primer 2
SEQUENCE: 24
tgtcgttttc agacgacggc tgcactga                                      28

SEQ ID NO: 25           moltype = DNA  length = 20
FEATURE                 Location/Qualifiers
source                  1..20
                        mol_type = other DNA
```

```
                        organism = synthetic construct
                        note = pSeq_CRBM4_F1
SEQUENCE: 25
agcgcaacgc aattaatgtg                                                20

SEQ ID NO: 26           moltype = DNA  length = 20
FEATURE                 Location/Qualifiers
source                  1..20
                        mol_type = other DNA
                        organism = synthetic construct
                        note = pSeq_CRBM4_R1
SEQUENCE: 26
gatgaagctg aggtagtacc                                                20

SEQ ID NO: 27           moltype = DNA  length = 21
FEATURE                 Location/Qualifiers
source                  1..21
                        mol_type = other DNA
                        organism = synthetic construct
                        note = pSeq_CRBM4_F2
SEQUENCE: 27
aggaaggtta gcaagctcga g                                              21

SEQ ID NO: 28           moltype = DNA  length = 20
FEATURE                 Location/Qualifiers
source                  1..20
                        mol_type = other DNA
                        organism = synthetic construct
                        note = pSeq_CRBM4_R2
SEQUENCE: 28
tctcgtcgac cttctggatg                                                20

SEQ ID NO: 29           moltype = DNA  length = 21
FEATURE                 Location/Qualifiers
source                  1..21
                        mol_type = other DNA
                        organism = synthetic construct
                        note = pSeq_CRBM4_F3
SEQUENCE: 29
atgctgagta cgatgacatc c                                              21

SEQ ID NO: 30           moltype = DNA  length = 22
FEATURE                 Location/Qualifiers
source                  1..22
                        mol_type = other DNA
                        organism = synthetic construct
                        note = pSeq_CRBM4_R3
SEQUENCE: 30
tagacctgct tctcaacctt ca                                             22

SEQ ID NO: 31           moltype = DNA  length = 20
FEATURE                 Location/Qualifiers
source                  1..20
                        mol_type = other DNA
                        organism = synthetic construct
                        note = pSeq_CRBM4_F4
SEQUENCE: 31
accactcact cctcgataag                                                20

SEQ ID NO: 32           moltype = DNA  length = 21
FEATURE                 Location/Qualifiers
source                  1..21
                        mol_type = other DNA
                        organism = synthetic construct
                        note = pSeq_CRBM4_R4
SEQUENCE: 32
aacgacaatc tgatcgggta c                                              21

SEQ ID NO: 33           moltype = DNA  length = 28
FEATURE                 Location/Qualifiers
source                  1..28
                        mol_type = other DNA
                        organism = synthetic construct
                        note = Oligonucleotide fw for the generation of short 24-bp
                         protospacers (5'crRNA # 1)
SEQUENCE: 33
agattttcga tttcgattct tggattat                                       28

SEQ ID NO: 34           moltype = DNA  length = 28
```

```
FEATURE                Location/Qualifiers
source                 1..28
                       mol_type = other DNA
                       organism = synthetic construct
                       note = Oligonucleotide rev for the generation of short
                        24-bp protospacers (5'crRNA # 1)
SEQUENCE: 34
ggccataatc caagaatcga aatcgaaa                                    28

SEQ ID NO: 35          moltype = DNA  length = 28
FEATURE                Location/Qualifiers
source                 1..28
                       mol_type = other DNA
                       organism = synthetic construct
                       note = Oligonucleotide fw for the generation of short 24-bp
                        protospacers (5'crRNA # 2)
SEQUENCE: 35
agataaccca gtatccttat ccgtcact                                    28

SEQ ID NO: 36          moltype = DNA  length = 28
FEATURE                Location/Qualifiers
source                 1..28
                       mol_type = other DNA
                       organism = synthetic construct
                       note = Oligonucleotide rev for the generation of short
                        24-bp protospacers (5'crRNA # 2)
SEQUENCE: 36
ggccagtgac ggataaggat actgggtt                                    28

SEQ ID NO: 37          moltype = DNA  length = 28
FEATURE                Location/Qualifiers
source                 1..28
                       mol_type = other DNA
                       organism = synthetic construct
                       note = Oligonucleotide fw for the generation of short 24-bp
                        protospacers (5'crRNA # 3)
SEQUENCE: 37
agattttaaa catgatacgt atcatatt                                    28

SEQ ID NO: 38          moltype = DNA  length = 28
FEATURE                Location/Qualifiers
source                 1..28
                       mol_type = other DNA
                       organism = synthetic construct
                       note = Oligonucleotide rev for the generation of short
                        24-bp protospacers (5'crRNA # 3)
SEQUENCE: 38
ggccaatatg atacgtatca tgtttaaa                                    28

SEQ ID NO: 39          moltype = DNA  length = 28
FEATURE                Location/Qualifiers
source                 1..28
                       mol_type = other DNA
                       organism = synthetic construct
                       note = Oligonucleotide fw for the generation of short 24-bp
                        protospacers (5'crRNA # 4)
SEQUENCE: 39
agataacatg atacgtatca tattgagt                                    28

SEQ ID NO: 40          moltype = DNA  length = 28
FEATURE                Location/Qualifiers
source                 1..28
                       mol_type = other DNA
                       organism = synthetic construct
                       note = Oligonucleotide rev for the generation of short
                        24-bp protospacers (5'crRNA # 4)
SEQUENCE: 40
ggccactcaa tatgatacgt atcatgtt                                    28

SEQ ID NO: 41          moltype = DNA  length = 28
FEATURE                Location/Qualifiers
source                 1..28
                       mol_type = other DNA
                       organism = synthetic construct
                       note = Oligonucleotide fw for the generation of short 24-bp
                        protospacers (3'crRNA # 1)
SEQUENCE: 41
agattgggtg ggtggttttc acgtgtgt                                    28
```

```
SEQ ID NO: 42          moltype = DNA  length = 28
FEATURE                Location/Qualifiers
source                 1..28
                       mol_type = other DNA
                       organism = synthetic construct
                       note = Oligonucleotide rev for the generation of short
                        24-bp protospacers (3'crRNA # 1)
SEQUENCE: 42
ggccacacac gtgaaaacca cccaccca                                     28

SEQ ID NO: 43          moltype = DNA  length = 28
FEATURE                Location/Qualifiers
source                 1..28
                       mol_type = other DNA
                       organism = synthetic construct
                       note = Oligonucleotide fw for the generation of short 24-bp
                        protospacers (3'crRNA # 2)
SEQUENCE: 43
agatccctcc ctttgccgct gcgaagtt                                     28

SEQ ID NO: 44          moltype = DNA  length = 28
FEATURE                Location/Qualifiers
source                 1..28
                       mol_type = other DNA
                       organism = synthetic construct
                       note = Oligonukleotid rev fuer die Generierung kurzer 24-bp
                        Protospacer (3'crRNA#2)
SEQUENCE: 44
ggccaacttc gcagcggcaa agggaggg                                     28

SEQ ID NO: 45          moltype = DNA  length = 28
FEATURE                Location/Qualifiers
source                 1..28
                       mol_type = other DNA
                       organism = synthetic construct
                       note = Oligonucleotide fw for the generation of short 24-bp
                        protospacers (3'crRNA # 3)
SEQUENCE: 45
agatttcttc ttgcttccac cataacac                                     28

SEQ ID NO: 46          moltype = DNA  length = 28
FEATURE                Location/Qualifiers
source                 1..28
                       mol_type = other DNA
                       organism = synthetic construct
                       note = Oligonucleotide rev for the generation of short
                        24-bp protospacers (3'crRNA # 3)
SEQUENCE: 46
ggccgtgtta tggtggaagc aagaagaa                                     28

SEQ ID NO: 47          moltype = DNA  length = 24
FEATURE                Location/Qualifiers
source                 1..24
                       mol_type = other DNA
                       organism = synthetic construct
                       note = Primer pCRBM4_F1
SEQUENCE: 47
cacattttat ccaatcaaac tttg                                         24

SEQ ID NO: 48          moltype = DNA  length = 23
FEATURE                Location/Qualifiers
source                 1..23
                       mol_type = other DNA
                       organism = synthetic construct
                       note = Primer pCRBM4_R1
SEQUENCE: 48
ccttcgagaa ataacatggt gaa                                          23

SEQ ID NO: 49          moltype = DNA  length = 25
FEATURE                Location/Qualifiers
source                 1..25
                       mol_type = other DNA
                       organism = synthetic construct
                       note = Primer pCRBM4_F2
SEQUENCE: 49
gtacagtgac ggataaggat actgg                                        25

SEQ ID NO: 50          moltype = DNA  length = 25
FEATURE                Location/Qualifiers
```

```
source                  1..25
                        mol_type = other DNA
                        organism = synthetic construct
                        note = Primer pCRBM4_R2
SEQUENCE: 50
ttagtggtca aacataggcc tttgg                                         25

SEQ ID NO: 51           moltype = DNA  length = 23
FEATURE                 Location/Qualifiers
source                  1..23
                        mol_type = other DNA
                        organism = synthetic construct
                        note = Primer pCRBM4_F3
SEQUENCE: 51
agtaagaggt tgcctaattg agg                                           23

SEQ ID NO: 52           moltype = DNA  length = 23
FEATURE                 Location/Qualifiers
source                  1..23
                        mol_type = other DNA
                        organism = synthetic construct
                        note = Primer pCRBM4_R3
SEQUENCE: 52
ttgccgctgc gaagttccct ctc                                           23

SEQ ID NO: 53           moltype = DNA  length = 32767
FEATURE                 Location/Qualifiers
source                  1..32767
                        mol_type = unassigned DNA
                        organism = Beta vulgaris
SEQUENCE: 53
aaatgataca ggggtatatt tgactctatg aatttcagaa atctaatcaa atttgctaag  60
cttccaatga ttctactaag ccctacaaat tacaagaatt agttactttc atctctctgt  120
cggcttcaga accagaagtg tacaatatct tgtcaaacaa actctgctta gaggagctct  180
ttcgatcatc ttttttcgat ttggaagttc ccggtgatag gattgacatt gctgttttct  240
cggtcaattc ttctggatct tggttctgtc catctatctc tggctccatt aatctggtct  300
tccaattaat tccgatagcc tcagcttgct ctgcaaacaa gacctttgag atcggggagc  360
tgcagatatc cttataaact tcataaccag cagcacaggt tttcccacct tccaacaact  420
ttgataaagg atgtaggaga gagatagaat catcactcgt ttctaaccta tccttcaagg  480
caaggaagtt aacagccaag tctgccttac taaactgaac aaatactgca gtttcatcca  540
agttatagat gcaagcaact gagtatatac caaacacttt acagatgcat tgttttatgt  600
cacttgcctt gagttttggg gagaatcccc aaatcaaaac tatgttagga tgcaaaatgt  660
taagaaacct ccttttagct gaactgataa cgggaatttc attcatatca ccagtgctta  720
gattgatcac atctccactg ttccaactaa gatagagcag attggcatac ttgtgaatat  780
tctcactggc tattaaattc tcagaagaaa aatcaacacc aagattatga catgcttgtg  840
caaagacaca cccggtcatg aatgcatcat agccagcttc atgcttagcc ccagagttcc  900
aatttgagga cctgcaagaa aacatgggag taagatggtt tcacataaaa catgtgtaga  960
agtgcagtga acactggcga aaacaatcta attttacgaa ttcattcact cactcagctt  1020
caaattaagt ttccccttta tttagggtgc cccaaaaaga tacactcttc tgtttacctt  1080
ctctctccaa gcgaccaatc ttttctctct tctccaacat cgttttcttt ttctctctct  1140
acccactatc cattttgtcc tcctacattt gataactatt cttaatctcc aagaaaatcc  1200
aatgtgtgaa ataattacgg gacagggagt atacagaagc agccccccttg ccaatatagt  1260
ttacaaatta ccctcagaat taggcttacc tttcccaaag gagcaataaa ttcaaacaaa  1320
tctaaaaggt acaaggcatt aagtgccgaa cctcatgtca tcaacctgga cctccacctt  1380
cacacatgga tgtacaccac cattagagga ttgtccagag gctatctcag ggcacaacag  1440
agaaaatgct gaggccaatg acgtgctggc tttattcaag aatttttgaa ggctcgtgtc  1500
tgcattcaaa agtattttcg tgtcgacaac atgaggaaaa tacttgtgga tctcgagaac  1560
aaactcttca acagttgatg gaagaggacc aaagaattta tggtaaatat gtgccatatc  1620
tgcaaaaaat tataatggat aagatgacaa gaaaagatac taggaaggcc ttcaagtaca  1680
aatattatat catgatgctg gacgaccgat gctcccacaa ttatgtttgt taccaaatgc  1740
ttcgaaggat aattactaaa ttatgtgaat ggtggttacc aagtgtcccg gaccatgcaa  1800
taacttctcc tttcagtgac caacaagaag aagacgtacc taaaaagcaa ttgtgaccta  1860
caattagctt cttttcagca gcgagaaggt caaggacatg ccggaaacct gcagctgctt  1920
ttattttgcg agttgcttgc tggtgagacc catacttcac ctcctcctac aagaacaaac  1980
agaacaatca cacatgcaga aagttcccca cataccaagt tgctgtctgc taaacactga  2040
aactaactta tctctacaaa caatgaagga agttcctcac cagaaggttg atcttatcat  2100
tgtcagattc tacaaaaaca ataagcttct gcaagatggc actgccgtca tgagcacaca  2160
caaaaacaag atccttgaag tgcttccttg taacctgtaa ttgcagatca ttagtatata  2220
ttcaagatgt tataaattta ttgaaaagca gcgtctaaaa caataaaagt catgcttaag  2280
gcatagagcg atagagcata gacacttcag agtttaataa gagcaaatac tccaggagaa  2340
cataaatata tttcatatca caaatcctag taccaactgg caacggctaa ctgccaattt  2400
atgtactgct caaaaaggcc aagcatctaa aagatggctt aaaagtcgga ttttataaga  2460
aagtcgtcac atgattgcta ttacattgac atatcaaagg tcaaatgctg aaatttggtt  2520
cagcttgata tatattaagc atacaaacga tacgttgaca agaaagccta acaagacatg  2580
aagcatcagg cacataacat tcaaaagatt accaattcaa tcaacttcag ctgatgagaa  2640
gtaaatccat tcaatcgaag agcaggacgc atactaaaaa atatggtttc aaattgttgt  2700
ttagattcaa cagcacttgg aagctcggca tttctgttct gtagcaacat atcatgccaa  2760
tcactgagcc gaattttcat ccgttcggag aataaaatat cagctacatt gcccaaaggt  2820
aaatctctaa cttcattaga atatgcccat ttcccgttat atactgaatt caagcgactc  2880
```

```
aaagcctcgt cttcctgtcg tctagataaa taagacacgc ctgagattat acaatgtgta  2940
aatttaccac aataatgaca tcatactgac aaaatctcaa acaaatagtt ctaataaagt  3000
catgttatct gaaatttcta tgaataggaa attgaacaaa accttcatgc ttttttccaa  3060
ctaaaattga catcttctac attaccttca tgtatgcatg cattgaagtc aaactggtat  3120
tttgccaaga agtcaatcga agttgtttgg cacaggaatt catatgatgg gccatcagtg  3180
ggaagctctt gacgtggaaa tatataaaaa ttatgcctga caatgaacca ttgtaaaatt  3240
attagatgga gtatctctat ttattgttta cagccaattg agcttttaac aattactata  3300
ggtagtgttt ggaaacttgt atttcatttc aaataatgga attgaaatct ggaatttaaa  3360
gtttgtattt caattcctaa tcactgtttt gtaaaggggg tttgatagaa gagagagaaa  3420
tagaggttta atggaggaga gagaaaaagt gtgggtttac taaaaaaaag agaaataaat  3480
attagaaagt gtgggtttac tcatagagtt gggatatgta tgaggagaga attttcaaat  3540
gccaaggtaa tagcttgaat gacaaattta ataatttcaa attccatgtc atccaaacaa  3600
tagatttcat ccaaatccaa gatttgaaat gaaatcttgc tatccaaaca tatcataaat  3660
taattagtaa tttagacttg ctttctgctg cacttactta tggaaataat tttacttcag  3720
tccttaaata acccgcaatt tacatcaaag gcactaatat aaacacctag ttacgaaatg  3780
gaaatatcag atatacctgt aaaagtaaag aaacaaaaat acaaccctga gcatgaaggt  3840
atccttcaaa agtgcaatat ctgcatactt agaaccggaa ttagaagtgc gaatgcagac  3900
aataaccatc ccaggatcag aaacgtccaa gaaagttgag attcatcatc cattctcttt  3960
agcaaattta tgaactctaa tatataaatc atacccccccc ccccatccaa aagcaattgt  4020
caagctgcct gaacccctca taatttagga tacaacaaag taatcctaaa agacccttta  4080
caatactagt actcgggtat ttccacaatc ttctcatcat tgaatccaaa gcattgcatt  4140
tgaagaaatc aaatcataat ccattactat attagagcaa aatctatgtc attatagtat  4200
tggagagcaa gtatgactat taccccttta cactaggcaa aacacattgt cacaatgcta  4260
acttagtcat taaccaatat caatatggga ctgtggatat tcataaaatc gaagtttttc  4320
gcttgctcat aaactatctt tcattccagc acagtacaag agagaaaaga cagcattttc  4380
atacacttct ttctttagtt caaattcaca cagcagcaaa aaattcactt cttcatagct  4440
ttagctcagc aaacaaagca caaagcatgc aattactctc acacatagca caccaaaaaa  4500
acaaaaacca ctaaaaattc acacaaaaaa aaccaacaaa aattccatcg caatttcaac  4560
aatcaaaaca atcttctaag ttaaaaagag agataaagat gagaagaaaa actaacggat  4620
gagcaacgaa ggaattcttc gaagaatccc atcgaaatgg acaaacacca aattgaacaa  4680
cggcgaattt ctcagcagaa tctttcattt taaggtatcg aacatcgtgc cgatcaaact  4740
cgaacgattc gcgccaaggt gagcttgtaa ttccagtcat ttcgagatca atggcgacaa  4800
aatcggcaga ttttacatgc gtagtgaggt caattagggt ttcttcgaag tttgattttg  4860
ttacattttt caaagagaaa ttagttgttg atgttgaata atgatgataa gtagttaggg  4920
ttcgtagtaa ggtggaggaa agagaaaatg gcgtcactct gacaagcttc ttcattttgt  4980
tcttcttcct tagctctgtt ttcagtcact gcgccatttt tttaaaaaaa aggaagatga  5040
acaaagcaaa tattgaaccc aaattttgta attttggccc actttatatg taccccctccg  5100
tttcaaaata tggagcacgc cgcacacacg acatttaggg tcgaattttg aacattcttc  5160
aagatgatct aatggtataa tctctataat ttatatgtgg catattataa taagagtttt  5220
atgaagtcaa aaagtggatg tcatatattt aatgcatggt aagtttttcc taaatctgta  5280
tactagggta acatacatat gttgacttga agtatatata attcttgtag tataaatatg  5340
gctttggcca taagtagtaa tacacaacaa ctagaaaaat tgaaatcagt ccactgttat  5400
cttgtactct ataattttct gtttcctttt gtttcgcaac aaagacatat ttgtggtgaa  5460
agataatttt cgtaaattga atgacttata ttttgaaata aagagagtat taggtaaggt  5520
tacgtgcttt tcgcttgaat ttgttagacc tcaaatgtat atgtgattag aacggattgg  5580
ctctagtttt tattttatag aagtatatat gcatttttct tagagcacac tcgaaattac  5640
tttcggatag atatattcgg gaaaaaaaga ggttgaaggg aagttcatca ataattatgg  5700
taaaggaaaa aggacatcgt tacaattcta aattctagat aggatgtgat gataatccaa  5760
aagtcatctg aaaaactaaa caagtccaag atgctaatga ttcgagtaga gattgaatga  5820
gtgaccctaa ggattgtcaa ccctcttatt ctaacgtgtg taaaagaatt gacaactcta  5880
agagttactc aaacattttt cgattcgagt ggttaatata ccaatttgaa actattgaca  5940
ggagttattt taatgagtat aatggtcaat ggagcactga attccatctc acatagtcac  6000
atatttcatc tcaagttctg atgatttcaa acattgaaaa aagatgatac aagcaattaa  6060
ttcctaggga aacatattgt ggttttcatg gatacaagag tgagaataaa tcaaaactta  6120
ggctctaaca tttcttttct ctactagtaa ttgctaatta tatcaattca attgtcagtg  6180
taatcagtta atcaccaaat ctcttgtata gtcagtaaac tatacactgt ttagtcctct  6240
ggattttgcc cggtcgaatt atgcagcata accaaacttt gaagtttagt acttcctttg  6300
cacccaagtt agcttcacgg cccctgcctt ctggtggatg gtcaccctat gctttgagca  6360
ttctctgcaa tgcgcacgat attcaatgag aacgtcgcct tgaaaatcta aattgcaact  6420
aaaaattaga ttgaaatgaa acccacaaga gttgtttttc tgagtagttg gtgtagaatt  6480
cacaagtctt gctccattgt ttgaagatat gaagacaata atgtgctatg taaagtgcag  6540
ccgctagcta acagtggaag tggaaacttg atcattttac actcgcacaa gcgaaagctc  6600
ggctgacgtt gcaaactgaa gaaaaacctc tcaaaccaat tcgacttttg ctcaaagttg  6660
caaactaaag aaaaaggctg aatgcaaagc aagttcacca atgaacaata gatcggtgtt  6720
ggcctgaggc cacatcaagt gaagttgcct aattgcggcc ctctcatctg ttcacaggaa  6780
tcattttcca tatagaatca ctccaaaata aaagagcaaa gctgcaccag atgcagaagc  6840
ataactttca agacaactga tgacagataa atagcaaaag aatgcttaag aaatgatcaa  6900
aattgaatgg ctctggaatt acctcatcag ctgattttcc tttctctcta tctctctatc  6960
tctttactcg tctatggagc taccacatca catggcgttt catatgcttt ctgccgtcga  7020
actagacgtg cagcaaaagc tccatccatt gaatgcttca ctgggcatga gcgataaaac  7080
ccatcttcag ttaaaaagtc agatggaaca tatctgctta cagaatctct ttggaagtcc  7140
tatcacccaa caaagaatat attaaaatag agaaggagaa aagaacgtat ctatctgtca  7200
gcatccatat gaggtggaaa ctaggagtac tatataaagc cagtgcagta gctcctaccg  7260
gatgtctaag aaggaaggca gaaaccctat cttcgttttc ttcaagatca atggagcagg  7320
tactgtacac aagcacgcca tctggtttga ccagcctgta gatgttaaac aatcccacag  7380
acaaaaggga ataatatgag tgaaacaagt caacaggggg aaataaccaa taattctagg  7440
actgtcaaac tcaagctctt caaaaacaaa gatagctctt aatctcactt gcaagcagca  7500
tcgaacagct cgtcctgcaa cttctttagc tcttccatat cctctgactt tctattccaa  7560
cgcaaatccg gcctcttcag caaaaatata aagttggaac aaggctctta gatacaagaa  7620
```

```
ctgaaaaacc ttcgacatat aatggactct atcaagggca caatgacaaa ttctaaacat  7680
gagcatgtat atcaataaaa tactaagaac cctttcaatg gtactgctag aaggtttatt  7740
gctacacttt ttagtacacc atctataggt tttatagtac catcaaaatg gttcatggtg  7800
ccataagaaa attttatgta tttatggtac tatctaccat atctaatttt ctctgtaaaa  7860
atgtatttgt agatagagac cacgagttcc tcttttagat actgactttt ttttttctac  7920
atgatggcca acagacttct caaacaaaaa gaaaaagaaa atatttagat aatatgagca  7980
acaaaatagc aaccacctac ttttgatagt acacccaggc ccgaacaagg aacatctaaa  8040
agaactttat caaacttcga agtgttgctg tcctgaaaag aatagaaagt aactgcttca  8100
acaaagaaga agaggcagaa agcaaagcta gtacgcattt tgcaatgact tactgaaaag  8160
gagcgaagat cagcatggat gcaagtgatc acattatcaa cacgctgcag cttggctgtt  8220
tcttcaagta tccgtaaccg acctttattt atgtccattg ctgatatcat acctgaaaag  8280
ctacacattt agaatgcaga accagcatca ttggtagtta agttatcact ataccttggc  8340
cattcaagcg agatgccatg aagagtgtct tccctccagg agcagcacag caatcaatga  8400
tgtgatcacc aggctgtgga tccagaacag aaacagctag acctgcagcg aagtatagat  8460
gtaaacttgg gttgggctgt cacatttttt cacatcttat cttcctttct attctttcaa  8520
aactgaggag aaatggttgg gatttctata aacgtgagaa aaatggcatc agattagatg  8580
gttttactgc atgaaaaaaa ttgaatgtgt ttcggcatca cattactaca aggtcaaaag  8640
cactatcttt gaaaatgtag gacataatgg gacagagatg tgctgacctg cactctcatc  8700
ctggactgag cataaacctt cttttagaag tccagtttgt atcacaatct aggatatgag  8760
aaaacaactc aagatgtaat tgctcctaag atatcaatca tttcataata aacataaaag  8820
ttattattac aagacagcac ctgcatccca cttctgatgc agacaaagtc atccaaatgc  8880
aaggaaggct catgcgggac ctgcggacaa agtgttgtga tgcgcataga tatcgaaaga  8940
aggccctgta tagcactaat gagataagat tcagtaacct tcagcatgtt gagcttcaca  9000
acaaggtcat ctcgagttaa tccttttgca atattggccc tagtaccaag aaaaccatat  9060
gtattaacaa gagaaaagtg gcatagggat ctttatgact taggtaagca gttggcaatt  9120
agagagaata aaaccccaa acctcaagct gaaactcgga acactattgt tccacatcat  9180
caatttgata gctccttctt gcccaagata cttggtccac cgtcttacca tccactgaaa  9240
ggaaggtatt aaaagggaga aaagactcgt cagcatagaa aattgtacat cttaaatttt  9300
agaagtatag caccatcttc aggcatcagt caacgtaaat aaataccaca tctacaaata  9360
gaaccatact ttctggacag tcgggatcat gagcacagac aatactgcat gattattgcc  9420
tcgtattctc atgtatacaa gtatatgtaa cattaaatag cagtatttct tgagaaactc  9480
accacgggat gggaataagt tgtagcaagg gcacgtgctt gtgaacgatc atcaccctcc  9540
aatttgggta caggaaggga gtcattatcc tataaagaga aacagctttt gttttcaacc  9600
atatcaagac aaacagttta ttaaactata aacaacaaca atacacatgc acacacctac  9660
tgggaacaag atatatacta ctgataagta ttttctgatt gaagaaaaaa aatctcattt  9720
atttgcaaat atagatttaa tgacaagaaa gctttgaacc ttaaggaaaa ctagctttcg  9780
gaggatccca ttcaccatgt ttcctgcgcc tggtctaaga gcatacttgg caagattcac  9840
attctgcaat ataatccaac agtaagaaca cgacatggat ttagactcaa gtctctgaac  9900
ctatagaaca agtaaaatta gatcttatct catttgacaa tttaaaatta gatagtgcaa  9960
tattctgcag ttataagact tcatgtgtgc atactgcaca agtcatctta aaggtgttat  10020
taaagcttta attgccattt gacatcccct tgctcaactt tagcatgttt ttaggctaca  10080
acaatacgca ctgtctacat ggacatacaa attacaagcg tatggaaaag caataagcgc  10140
aaggaagtct tcagccagaa actctctatg agtccaacaa tatgcaacta aatatccaag  10200
taccgtgaat gagtaagaac taacctcgtc aacaacagca tatggtggca tttccagttt  10260
cacaatctca tagcatccaa tcctgaggat ctaaaattaa agataaatca atacacaaca  10320
tatgatatgg gtcggagcgt atataacaag tatagcaact acatttgaac agataacagc  10380
ctttgagaca ataaggaact ccgacattcc agtatatgcc agatttcata tctttagctc  10440
taaattgcca cgcaaaatgt tattgggcaa tatacctgta gcaggagagg ttccatgttc  10500
ctaaaggagc tttcatcatg gcatgaagaa acaataagat aatccagata ttttctccaa  10560
cgaattgaac caccaacaat gtcagtgacc tacaaagaca agttgtcaac ttaaaacttt  10620
tgaagcgtca tttcacttct gtagaccaat acaaaagcta ctactgcttt acatcataaa  10680
acctttagtc cttaggttca tctgattggc aaaaaaggtc cagatgcaag aaaagcaagt  10740
agctgtaatg ctgtattata tcagcattat tcagaacaga ataataaata tctacagatt  10800
ttgggtggaa gcttgatgat agagtatctc cacaaagaga actcgcttga gtcccaactc  10860
ccaaatctac ttttttggag tcacattatc agtcattttt tctggactct tataggaata  10920
gtgtgctatg taatgattta tggagcaggg gcatttcatg aatagcttta taagttagta  10980
tgggtgtctt ggggaataag ttaaagggtt agttagaggg aagaagtaca acatatatat  11040
agagcttttg taagaagggt ggttatgttg aaaatagatg agaaattggg tgagctcata  11100
gtagttcaat ttggactttg ggagagaatt aagcctcttg aaagcttgaa tatcatttac  11160
atttgttgtt tttactctta ttaatcaacc aaagttcatt ttcttccttt aatttctcca  11220
ttttagcact atgatttgtc caagctaagt gatttcttag catagtgcac agtgtagtat  11280
atcggagaac tcatttgagt cctgaaaggt cccacaagtt acatttttcc tactactact  11340
tgcaccaaaa caataagcat cattaagaca ttgtcactgg tccttcttag gttcttttgg  11400
aggggattcc tcagatgggg gaggcaccca tgaaggaaca tgttaccaag caatgggaca  11460
atgcaaaatg caccaataca gtagcttcac ttcattgatt gcatctatgt cacggaaaac  11520
tgaagaaaga agcaacacct caactttatc caggacagat atccactaac ctaggatgca  11580
agcttgagac tatttagcaa ttgcctctgg gatattaaat cagattacga ctatatttct  11640
acagttattg cttaagaaaa aggtacgatt tgaagcttgg gaagaaagag aacaagagta  11700
aaagaccaat ctgagatctc tttcatccag gtctctggtg cgaaatccaa gagtcctctc  11760
aacatattcc atctcattgt tccctgaacc ctttcctctc tcatttagaa gatcagcgaa  11820
ggcaccacca aactctatcc gcatcaatct cacagcagcc actggattta cacatgaaag  11880
caaaccagga gaaccataaa aatcacaaca aacttcctga tagcctactc actagcatca  11940
accattgtgt tcagcctaaa atgagcggct gttttcaatt gaacagcaac ttacatggac  12000
cactgcataa aagtgatttc ttaatccaga caaacaaaaa tgtttacttc aaccaactga  12060
atttgcatca gctcattagt gatttgacaa gttctaattt atgtatcaac aaacaagacc  12120
atatagctag gaaacaagag gcttaggcta agcttaatgc gtgaacaatg ttagatttca  12180
acctatcagc actgtggata actgcaaact gcgacttaaa taaggaagat aaaggaactg  12240
aatatgcaat ttcaaggtgc tcagcatttg aatcaacagt tacttcagat aattcagaac  12300
ataaaagatt tgaacattct aaggctacct catgattgca agcaatgtta cctgattcgc  12360
```

```
taaccctcac aagccacaag ccaaagaagc aatttggtaa atggttcatg gtacaactgt  12420
tcgcttttgg actaatctaa caatactagg tggtaaatta tgttcccata tctattacca  12480
taatgtacag caaattaggc agcactaatt ccaaatgacc caacaaaaaa agaggaagaa  12540
aatccaaaaa ttcaagccaa catatgcact aaaattacaa gcacaaaatc aaataatgag  12600
aatcacacta tccaaagaaa atttccatcc acatttatcc aacacaatta tctctctttt  12660
acacccaaat tatgtcaacc aaaaacacta aaacaagtga gtgcagtagc ttcacatcaa  12720
agaatatcaa tcacaaacac cacataataa aatttcaact cctgcccaaa caaaaaaaat  12780
ataaagaaaa aaaaacagca aaatttcaaa gataaaatag aaaaaaaaaa atcaaaatac  12840
agggggaaaa aaagtaaatt taccagctct atgaggcgaa acctgcaaat tcagcttctg  12900
ggttttctct gaaatatcaa gcacaataac cagcaattaa aaaaaattat aaataaaatt  12960
aaaaagaaaa gattgataat taaaatcaaa agagagcaat ttaaagcaca atcctttttt  13020
taccattttt tctgggagga agagcatcct tcgttttggg tttagacgaa aaaaatgaga  13080
gttgttgtat ttgtgcgcat gagtgatcat tgctggaaat gaaagtggga aagtggtaaa  13140
tgagtgcttt gtgaaattgg gttttgagga aaagtagaaa gaagaagaag ggtcgatgtc  13200
agagaagaga gagagtggat ggaaagtagt gatgattgcc tccattgttg ccggtgaagt  13260
gagctttctg caaatatttc actggactag tttttttttag cagataacgc taaaacagag  13320
aaagatgttc ggttaatttt aattttgga catttaaatg actattcaat atgtttcaac  13380
cttttttttt taaaacaaag gaacaatact agtattagat tacgttaatg tttagtacat  13440
ccaatactta tgtgtgtttg acctaactta aaatcgtaag ttgtttaaaa tgtcggtgtc  13500
ttgtttttaa gagatatcat acttactatc tttggttttt actcttccat tgttaacaga  13560
aactgtattt atttgggtaa ggggtttgag tgaattcctg taagtatgag aaagttttga  13620
gtgaagcaag agaaagagag aagaaaggaa cttcgagtga agattgagag aaacaacagt  13680
tagtgggaac tgttgttggg aacttgagtt taggagctca ggttgtaccc cgagagaatt  13740
aataggtttg taacagagtc ggtggcctat tatagtggaa agtttgagtc aaaatccatt  13800
gtggccgatg tcgtttcttc ttattgggcc taggaagttt ttcctcgcta aaatttcctg  13860
tgttcccatt gtgtgttcct tagctagctt tcaattccgc aaaaagttac gtttattctc  13920
tcactataat tcaccccccct cttatagtgc tcatattata caacaattga tatcaaagca  13980
ggaactctaa aaatacagaa atcatgttga gttcaagatc ttggaaaata tgaatactac  14040
agaaaaactg gaagaaaggt actctactca gagaccaccg atgttcaatg gcaaattcta  14100
cacaaactgg aagaactgaa tgaagatctt catcaaagcc gacaaatatc aggtttgtag  14160
aatcatagag gcaggcgatt ttgaagtcac taccactaat gacacatatg aggtaattcc  14220
taaattcata actcatttcg ataaagtata tttcgaaaag ttggaaatta acgttcttgc  14280
tattaaactg cttcattgtg gtcttagacc tcatgaacac aatcatgtca tgggatgcaa  14340
aatcgcaaaa caaatttggg atcttcttga agtcactcat gaaggtacgg gtaaagttaa  14400
gagatcaaaa atcgatcttt taatgaatca atatgaactt tttcaaatga aatataagga  14460
gtccactcaa gagatgttta cacgctttac taatactatt aatgagctaa cctctcttgg  14520
aaaagaaatt acatatgatg aacaggtaag aaaggtccca aggatcgttg gatggctaag  14580
gttacgcctt acaaaaaact aaggacttta cgaagttcaa tccggaacaa cttactggct  14640
cccttatgac tcacgagcta cacttggaca ctgagaatgg tgacttgtcc aaacagaagt  14700
cgattgcctt gaaagccatt tttgtcatac cgtcaattaa ttaagtaaaa agtggtaaaa  14760
gaattaccaa aaacgcacaa aataaattaa ttagttggat ataactaatt aacctattcc  14820
tttttctgt cgctataact acttttgctt aacttattga tggtttgatc gttgaatcca  14880
agttttctcc acccacaaag atattataga ctttacttta aaaggtacga taaataatgt  14940
ttaatcaggt atgcatcaac cttgaaatta ttaatttatt aagatcaaat tatgcatatt  15000
tatattaaac gtacaggact tgtgcacaat ccatggatga tattgtagat tttgttgtaa  15060
aggagttagg gacaaatgat gttgaattaa gaatgatgag gaacaacatt gaggtaccta  15120
atggcataca agattatgtg gtaacaaagg tgaagaagtt ggttgtacca ggcaatacag  15180
cagcggcaag ccatatatag gatgagctac catacccctta tgttgtgaac tattgtcacc  15240
accaacaaga cattggtcat tacgacatca ctttagttga ggaatgataa acctcttttt  15300
gctagatatt tgcaaacatc tagcagataa agaggaataa aacactattt atatttcatg  15360
aacactattt gttagttgca tgaacactat ttttagttac acgaacacta gttttagtag  15420
catcatgaac actatttttt agcatcggaa ttttcacgac tactttttgg tttgactgac  15480
actctgcaat tttcgagata actttttggt gatatgggtc ccatgaaata gaagatttat  15540
atttcatgaa cactatttgt tagttgcatg aacaatattt ttagttacac gaacactagt  15600
tttagtagca tgaacactat tttttagcat cggaatcttt gcgactactt tttggtttga  15660
ctgacacttt gcaattttcg agataacttt tttgtttgac tgacaactat ttcctatata  15720
tattgacagt tttacccctg ttagatgttt gcaaacatct agcaaaaaga ggtttatcat  15780
tcctccactt tagttagccc aacctccagt aacgccatcc agaccactgt cgtttgtcac  15840
tacgacactt acgcttggca accctatgtc ctagcccttc gatacctcga tatccgtccg  15900
ggcaatgtcc ccagtttgtc acttctctgc cattaatgac atattttgga gtatcaaacc  15960
caactccaag tatatatcgc aacatggctc agtaaagaga gtcatataat catgacgtag  16020
tttctatatg ccatcctacg tagtatcttg taacatgaat aacagcctgg tttgcaggtt  16080
gatggtacat ggtataaatt ggtattactc cctccggtct ttattagttt aatcctttct  16140
tttgtacaga gttataggag aaataatatt gtgggtcata gaaggaaaga gaaattatta  16200
ttttatgtta aagttgaatg tatgtgtgat gaaaagttag tagtcccatt tcaaaataga  16260
aaaaaaaaag gtaaactaat aagggacatc ccaaaaagga atacgggtaa actaataaat  16320
atccatgcag gttgttggta catggtacat gaagccgtcc aaaaccttca aaagcagtaa  16380
gtcctgctgc tatgccatat tcaaatattc aactccaaaa aaaaaaaaaa aaaaaatcaa  16440
aaatccgctt ttcagcgaaa atataggaaa taatccaaga atcgaaatcg aaataaagtc  16500
atgatgcaag tttggagagc tgaagttaca ctatatcgga gtacttactc aaatgttgat  16560
tagtactccg tgcgtttgaa gtaaagtcac atatggagta gttccaagct aggttgtaca  16620
gtgacggata aggatactgg gttgaaaagg tgaacgtcga gatttatacg tgtatttatt  16680
taaacaggat acgtatcata ttgggttctc atacgcgtac cagctgtgac ttagaaaaat  16740
taaccacgct atataggttc caagccctca tgattacctt ttcatagtgt aaatttcatg  16800
tagttgaatg gtgggaatcc aatcacaaaa acactgcagg taatggaaat gttccaactt  16860
tttccaagca ttttaaaata agacatgtga ttactaatta gggcgtgttc ggcaacagta  16920
attgtggtga tagtttttag ctgtgagagt agttgttagc tgtgctatta gcttttagtg  16980
gttggtgtgt agctgttagc tgttagatgt ccaagtagcg gtgtaaaata ttgatgttcg  17040
gtaaaagaag ctgtcaaagt agctgtctaa gaataactag ttaaaaattc aaataaaact  17100
```

-continued

```
ttaacatata atttatacac cactaaaagc tacccaaaag ctacaaattg tagcttttga  17160
caaacactac taaaacacta cttgtaccac taaaagctac ttacaccact atcttgccaa  17220
acactcttat tttttctaat tagtgttttg acctagtcaa gacactaaaa gctacttaaa  17280
aagcttgtgc cgaacatgcc aattctgaac caaggaacaa actataacaa aaaagtgcta  17340
tgtgaaactt ttgtaggcaa cagaagtaag gcatttttgg aatgtactaa caaatccgta  17400
ttaagacttg tacatgaaaa ttaccgtggt aacatttacc cacacttcct cattcacgta  17460
ctccgattca ttcttataag ggcataaccg cataaggcac atcaagatcc atgtatctaa  17520
tagtttaatt tgcctctgtg tttctgtatt aacaatgagc atagtgagtg caaaagccat  17580
ggaagctaga ttaaaaaggc catcattcta agttagacaa ttggaaacaa catcgagata  17640
cacgtacaca taagggctgc tcttctctat tactccctct gttcctaatc atttgctttt  17700
ttagcgggtt ccaaaggcct atgtttgacc actaatatat ttaaattaaa actggtgata  17760
tatattaaaa gaaaattatg atgaatttaa caaaaaccat atatgttatg tccttttttt  17820
tcctatatta atgaattttt acagtcaaag ttggtgaact ttgacccaaa aaaagaaatg  17880
gagcaaaaaa aaaaaaaaaa aaaaaaaact agggacaatg agtaacattt ttatctatgt  17940
ctttttaata tgaatatacg taacaaattc tgcaaaaata gagatagcaa ctaataacac  18000
gcatgaaaat gacaagttat attataccctt tttttctcaa tatatgaata tacgtaacaa  18060
attaactcca gtagttttta gtaaaactat tagattattg tgtaacatat actctggaaa  18120
tagtactaag atccattaca atctttattg agaaatttcc tcatgtaccc cctgaggttt  18180
ggcgtaattt ccaaataccc ctcatatttg aggaatttct caaataccct gatgtttttg  18240
tttagactca aaataccttt actatggaca gtaccctaat gtcattaagt tttccccttc  18300
tctctcccca attttctctc tcctcccatt cccccaccca ctacccactg cccactgcca  18360
agtaggggtg taagtggatt ggactggatt ggactttgcc aaattcaaat ccagtccaaa  18420
gtttttttgga ctcgagaaat tgagtccaag tccgatccaa atatttttttg agtccagtcc  18480
aatctagtcc gataattttt tcttgagtcc gaatccagtc cagtccagtc cgattattat  18540
atcttttttc ccgatttagg ttcaatgatt cacaacattt tttgagatgc ttgagcattt  18600
gacatctgat tcaattatca atatccacaa ataagattga aagcttaaat taaagtaaaa  18660
tactatgaat aaaaagttga attagatgct taccttgatc taagttgaga ggaagcatag  18720
agactgagaa ttaatctgag ggacaaatag agaatgcgag agtcgagaca gtgaggtaga  18780
aagaaaatga agagtaagag gaagtgagta ttaaggactg aggagtaaag taagatagaa  18840
ttagttggct actagcctac taatgcagta ttgctagtat aatttactta tttaacaaat  18900
ggagctaagt gcaatagttt agcgccaatt gacatattta gagagagaag gctgaaaaat  18960
ccaatatttt taaaatagta tcattatttt taatatatac attatatata aaaatatttt  19020
tggactggac tggacatatt ggactccaaa gggatgagtc caaatccaga caaaaaaatat  19080
ttggacttga aaatttaagt ccgagtccag tccgaaaaat tttcagtcca atccagtccg  19140
acaaatttgg actggactgg attggactct gaacttttcg tagtccgctt acaccccctac  19200
tgccaagtgc caaactgcca acccccttt ggttgagttg atatttgacg caaagacttg  19260
gcgtgttgga aggttcatta cacattttat ccaagtcaac tttgaagtct tcttagctag  19320
agactagagt gaacgtgttg gaaggttcat tacacatttt atccaatcaa actttgaagt  19380
cttcttagct agagactaga gtgaacgtgt tggaaggttc atgttcatga cattataaaa  19440
gtaataatag tgaaatttca caaagtattt ataaacccag gacagactca agagctctac  19500
ttattattag tgaaaaacaa acatacacac gacaataaca caacataaac aataatgaac  19560
atgaaaatcc tccttttgtt tgtcttcctt catcacctcc actacttcat ccatggcaga  19620
acacttacag aacgccaagc tttactaagt atcaaatctg ccattactta tgattattat  19680
aactctctct cctcatggaa aaacacaaca caccactgca gttggccata catcacttgc  19740
tcctcctctt cttcttcttc ttctgttatt tctctcaact tcaccatgtt atttctcgaa  19800
ggaattctct cccctgatat aggcttcctc accaacctgc aaaacctctc tattcgatct  19860
aaccttttt ctggcccact cccccattct ctctctctcc tcacccaact ccgctatctc  19920
gacgtttccc aaaacagttt cacaggtcca atcccatctt ctctctctct cctcacccaa  19980
ctccgctatc tccacgtttc cggcaacagt ttcacaggtc caatcccatc ttttctctct  20040
ctcctcaccc aactccgcta tctcgacgtt tccgacaaca gtttcacagg tccaatccca  20100
tcttctctct ctctcctcac ccaactccgc tatctcgacg tttcctacaa caatctaaat  20160
ggcactcttc ccttatcggt cgttgagaag atgtcggagc tcagctacct taaccttagg  20220
tataactctt tctacggtga gattccaccg gagtttggga aacttaagaa gcttgaaaca  20280
ttgaatcttg gtaacaacac tctttctggg agtcttccat ctgagttggg ttcattaaag  20340
agtttgaaac atatggactt ttctagtaat atgctatttg gtgagatccc acaatcttat  20400
tctcttcttc gaaacttaat cgatattgat cttaatagaa acaagttata tgggagtata  20460
cctgattata ttggagattt tccggagttg gaatcacttt tattagactc gaataacttc  20520
acagggagta tcccacaaaa gttaggtaca aacgggaagt tgcaatatct agatataagt  20580
aacaacaatt ttagtggtag tttgccacta agtctttgca aaggagacaa actccaagat  20640
ctggacgcat cctataattt gttggttggg tcaattcctg agagtttggg aagttgcaag  20700
tcacttgaag gagtgtacat gggaaataat ttcttaaacg ggtcgattcc taagggcttg  20760
tttgggagtg atgtttcact taatgacaaa cttcttagtg gaggtctcga tgagaaattc  20820
ggtgattgcg ttaatcttcg ggacattgat ctctctaata ataagctatc agggaagtta  20880
cctgcgacca tcggaaactg tattcatctt cggtccttga cgctttataa taacacctgt  20940
accggacgta tccctcaaga gattagcaag tgtaagcagc tacagaccct cgatctcagc  21000
caaaatcagt tctctggtgt gatacccaat gatattacag gtaagaaagt atattaaact  21060
tgttactttt gaaaatattc gctctagttt ttgtttcagt tggtccattc tcactttgta  21120
ttattgaaat atatcccaaa aaagtaaata taattatata aaagaatctt gctaaaaata  21180
atatgaatta tttttgtatg tgcaaaataa tgtacaaatc taactaattt gttgtggata  21240
ataatattaa ttgtgtgaaa tagtaaatgt gtggagatat ataactttat ttatcatatt  21300
cactcaggtt tttaggtatt tattatgagt tttgcattgg agatatccaa cttgacaata  21360
gtatttttgt aatataccaa tatataaaga ttactgtaca taaccaaaat gtatactttt  21420
cttattttta taaacttata tattcctctt ctttgtattt atcacaacat tttttatacc  21480
cttttgcctc atattaatag caacacttat aatttattta tttacttttt atttcttggt  21540
ctataacctc atctacccac atatgacaca ccctataaag gacccacatg attaaccaaa  21600
atatacaaat atcttcaatg aaattaactt taacactaat atgataaaaa tcatgtcccg  21660
ctttttatcc tctaactaag actctgcata aaggtatatt gcaattaata tgagatggaa  21720
gaggtataat aattatatga tcaaattcct ggattgaaaa ataaatatga gattaaaagt  21780
ggtatgtttt tggttaaaag aaactatcca taaagtatgt ttttggttaa aagaaactat  21840
```

```
gcaacatacc aatcaaatgt ttatacgctt acaatttatg taccactttt ttgtcattgt  21900
ttttctattg tttgccatac gtacgttact aaatcatgtt gtcttttcac attttaacta  21960
acaataaatt actattgata caccaaaaaa atctatgagc attggagtac gttgtttgat  22020
agaagcttcg tgctattatt tcttgtcaaa gaatttcata tctcaatatc ttctaattta  22080
acaatctaac gaaatttttt tgacccagga aacaaatcca tttgcaatct ggaaaagata  22140
caaacactta aattatcaaa caatgctttg actggtgaaa tccctcattg tgttggaaat  22200
atcgagctca tagcattatt tctccaatca aacaaactga acggtaccat acccgcaaac  22260
ttctcaaagt tatgtgattc attgatatat ctagatctta gtgacaatca actcgaagga  22320
gttctaccta agtccttgtc caaatgtcaa agtctagaac tcctaaatgt cgggaacaat  22380
aggctaagag ataaatttcc ttcatggtta gacaacctcc cacgtctcca agttttcagt  22440
gtgcgtttta acgccttcta cggtcctata actagctcac caaaagttag tcacccattt  22500
cctatgctac aaattatcga cctatctaac aataagtttt gtggcaagtt gccaagaaga  22560
tatatcaaaa actttgcaac catgcgcaat atgaatgagt ctggtgttgg gaatccacag  22620
tacctggggg actcatcaat atatagtatt acgtactcta tggtattgac attcaatggg  22680
ttacaacaaa aatatgaaaa gcttattgtg acgatgtcga cctttgatat atccagcaac  22740
aactttactg gacagattcc atatgttata gggggattac gctcacttcg taaccttaat  22800
ctctctcata atgtcttaac cgggaacatt cctccatcaa ttgcaaaatt gtctttgctt  22860
caagatttgg acctttcatc aaacagactt actggtcgta tccctcaaga attagttagt  22920
ttaacatttc ttgggagttt caatgtttcg aacaatctat tggaggggtc tatacctcat  22980
ggtttcaact tcgacacgta cacagctaat tcataccagg ggaatctcga attatgtgga  23040
aaaccattac ctgagtgtgg agaaagaagg gcaaaaggca ccactaataa tcaagatgat  23100
cctaaaaatg ataatgaacg aatgttgtcg atgtccgaaa tcgtagttat ggggtttggc  23160
agtggtgtac tagttgggtt ggcttgggga tactatatgt tttcagtggg aaagcccttt  23220
tggtttatca agatggctag caaaatggaa tcaatattga ttggtttttt ctgaccaaca  23280
atttgttagc cgatgaagag catcaaaacc aaaaaaaaca aaaaaaattg attaatatgc  23340
atgagtgtga ccttgtttc caaagtttag cattactatt agtgtctcaa ttcataataa  23400
taaaaaaatt agcttgttca agatttgtat ttttattcaa agattttttt tgtctcttgt  23460
gcttctttta tcttatatat attttttgta tggtttgttt ttgtttaata ttagtccctc  23520
cgctcaaaat gatctttcac gcttgagatt ggcattaagg tcaagagatg ttgctaagct  23580
ttagaataaa aaaattccaa atgcatagag ggaaagaaag cgagacaaaa tgttggagaa  23640
ggcagagtaa atgatgtgat ggaggataaa tagtagaagt gtgataccga aagtttgaaa  23700
ataataagga attttatttc ttgctggcac tttgttctag tacaggtttt tagcccttca  23760
aaatgtttat aatgtagagt caaaattaat atccttaact agtttttaag tccgggttat  23820
atcctagata ttaataatat tcatttatta gtaacatttt attttataaa tataatacta  23880
agcattattt ggtttgctgg ttaagacttt agtgtatatc tatttctttt ttttttattt  23940
gtatgcgtgt ttacataaac taaagactat aagggatagt accacgtggc gcagttcctt  24000
gcttaggaac gtcttttaat atattaacta gtatttgggc ccgggcgttg ctccgggttg  24060
gtattgtgtt tccgaacatg atgtgcagtt tttcccattc ccactaaaat atataaagga  24120
aaactcaaca tttaaaagat acaaatataa taatatggac acttaaaaca tgattaaaag  24180
ttgattgaga tggtaattgt gtcatgttat aatagtaaga ggttgcctaa ttgaggttga  24240
ggtggtggag tagtggtatc gcttcccatc tgttatccct gaggtataag gatcaaacct  24300
cataggactc atttgagtaa tttcccatat cctcctctca aatgagtcct tttcatctga  24360
caaaaaaaaa gagtctaatt ttaaattaaa attagacgat cttttataaa atcggcactt  24420
tctgcacata ggtcacaatt tttttgtttc tatctctctg ctttctttaa tttcacagtc  24480
tccaactctc catcaacatc ttacttattt tagaatagat gatgtatggt agtattaaat  24540
ggtaaagtac taaagctcct ataatacaca gaagcttaca tagtatagat tcgtacatga  24600
gacaaggtta caatatactt tctccgttct ttttatatta caataattac tattttaagt  24660
agtttcacat ctattgtaac aattccaatt ttgttataga aagcaacttt aataattgac  24720
aatattgccc ttactttatc ttattaaaac catcattaat tactcacttt ctcttataaa  24780
attgctttta ttttctaagg atgatttctc tcctattcta gttaattaaa gagttacttt  24840
tgtgctaaac tgctcattta ttccaaatcc ttaaaaattg tgtccaaacg tattgttgta  24900
atataaaaag aacagaggta ctattagttt gaataaattt tgatcagatt aggtcacctt  24960
tagggggcgt ttggttaggg gtattctgga aagggtaagg gaatcaactt acttaattcc  25020
cttacttgtt gtttgtttgc tcaatttaat gattcccttt acccacccct tactcccaaa  25080
gtcctttact ctcattctcc ccaccccccca aggtttcact taccctttct tgattcatca  25140
ttgaccatat ctttgaccac ccaactacca ccaccacttg accacctaat cacctaacca  25200
cctaattacc caaccactat taccacccaa cccctccacc tgcccaccaa tcggcaccat  25260
aactgcccaa ccgtcgccca atcaagccac ccaaccggca ccataaccgc ccaaccaagc  25320
cacccaaccg gcaccagaaa ttgtaccaag ctacccacac acgtgaaaac cacccaccca  25380
caagccctag aaaaaatgga agaatcgaga gaaagggagg ggagagaaaa gatgcagcga  25440
ctagaagggg agggggagga tgtgacggca aggggagagg gaacttcgca gcggcaaagg  25500
gaggggaaac gtcgcgtcgg caaagggcta aggtggaatt gacggggttg cagcaacaag  25560
gggagggcat ggagacgtcg taaccgcaag gggaggggca gcggcagtgg aactggggtg  25620
gagaggggta gtggcggcac tagggtgtgg gagaggtggc gggggatatc aagagagggg  25680
ggatatggtg gtgttatggt ggaagcaaga agaagaaaga ggaaagacaa tgtactaacc  25740
aaacaacaca ttaaatctaa gggttttggt ttcctttccc catctacccc tttcttgatt  25800
ccattccctt taccccttta caaccaaact ccccccttagt ttttactact tataaccttc  25860
aattttggct gttttttgtg acatttttta cttctccgag cctggtcata ttttctcccg  25920
aaacatttcg aggaaagtcg aagtgacttg tgaagttgtg cgggtgcttg gcaccatttg  25980
tgttgcctcg aaaagcatct gaataccccca tttattcctt tctcctgaaa cccaaaatta  26040
cctcgcaata aacgaaaaga tatccatata tttgttccaa gccacatgac tcctttccaa  26100
cgacctccca tgtgaccatg tccttagaag gcatcccgtg gcgttcgaag ctcggacccc  26160
cggaaagtcc gaaagtgtgt attataactt tcaattttgg ctgtttttgg gatatttttt  26220
acttcttcgg gccttgtcat attttctctc gaaacattca taggattgtc aatgtgactt  26280
gtaagttgta acgttgcacg ggtgcttggc acaatttgca ttgcctcgaa aagcctctga  26340
acaccccatt tgttcatttc tcgtgaaatc caaaattgcc tcgaaaaaaa cgtaaaggca  26400
tccacatatt cgttccaagc cacataactc atttccaatg acctcccata gagtccgtag  26460
ctcggacccc aggaaagtcc aaaaacgtgt actataacct tcaattttgg ctgtttttgg  26520
gacatgtttg gacttcaccg gcctggtcat attatcttcc gaagcattcc tacaaaatcc  26580
```

```
gacgagacta gtaacgttgt tacgcgggtg cttgacacca tatgtgttgc cttagaaagc  26640
ctttaaacac cccatttgtt catttttcgt gaaacccaaa attgtcccga aatgaacata  26700
aatgcatcca tgtattcgtt gcaagccaca tgatttcttt ccaatgacct cccatatcct  26760
taggaggcat gcatcatgtg gcgttcggcg agcgggtctc gggaaagtcc gaaagcctgt  26820
gttataacct tcaattttgg ctatttttgg gacattttg gcctttttca agcgtgttca  26880
tattttctcc cgaagcattc ctaggttagg cgatgtgact tgtaaagcgt gggtacttgg  26940
caccattttc tttgcctcga aaagtctttg agcaccacat ttgttcattt ctcgtgaaat  27000
tcaaaattgc ctcgaaatga acgtaaagac attcacatat tcattccaag ccacacatga  27060
ctcctttcca atgacctccc aagcccctag gagtcgtccc gtggcgttcg gatccggagc  27120
tcgggccccc gagaatgtcc gaaaccgtgt attatgacct tcaattttg ctgtttttgg  27180
aacatttttt gacttctctg ggctggtcat attttctccc gaaacatttg taggactacc  27240
gacgtgactt gtaatgttgc gtgggtgctt ggcacaattt gcattgcctc gaaaaacctt  27300
taaacaccgc atttgttcat ttctcgtgac acccaaaact gcctcgaaat gaacgtaaag  27360
gcatccatat attcgtttca tgccacatga ctcctttcca ctgacctccc atgtccctag  27420
aaagcacccc atatccgaaa gcttgtatta taaccttcaa ttttggctgt ttttgggaca  27480
cttggacttt ttcggttcgt tcatattttc tctcgaaatg ttcctagaaa aggtgacgtg  27540
agttgtaacg ttgcgcgggt acatggaacc atttgccttg cctcgaaaaa cctctgaaca  27600
ccgcatttgt tcatttctcg tgaaactcat aattacctca aaatgaacgt aaatgcatcc  27660
atatattttt tccaagccac ttgactctta tccaatgaca ttctatgtcc ttagaaggca  27720
ctgcttgtcg tccataattc gggccaggga aatgtatgaa agtgtgtatt ataaccttca  27780
attttggctg tttttgagac aattttttac ttctccggga ctggtcatat tttctcccga  27840
aaaaatactt cgagtgccga cgtgacttgt aacgtcgcgc ggatgcttga caccatttgt  27900
gttacctcga aaagcctttg aacaccacat ttgttcattt ctcgtgaaac ccaaaattgc  27960
ctcgaaatga acgtaaaggc atccacatat ttgttccaag ccacatgact catttccaat  28020
tctctcccat gtccctagga ggcatcccgt ggcgttcgga gctcggaccc tgggaaagtc  28080
cgaaagcgtg tattataacc ttcaattttg gctgttttg ggtcattttt tgacgtctct  28140
tggcttggtc atattttgtg ccgaaacatt cccaggattg ccgacttgac ttgtaacatt  28200
gctcgagtgc ttggcacaat ttgcattgcc tcaaaaagac tctaaacacc ccatttgttc  28260
atttctcggg aaacccaaaa ttacctcgaa atgaacgtaa aggcatccac atattcgttc  28320
catgccacat gactcttttc caatgacctc ccatgtccct aggaggcatc ccatggcatt  28380
cggagctcga acactgggaa agtccgaaag cgtgtattgt aaccttcaat tttggttgtt  28440
tgtgggacat tttgggctt ctccgggcct ggccatattt tctcccgaaa cgttccttgg  28500
aaagccgaag tgagttgtaa cattgcacgg gtgtttggca ccattagtgt tgcctcgaaa  28560
agcctttaac caacccattt gttcatttct cgtgaaacct aaaactgcct cgaaatgaac  28620
gtaaatgcat ccacatattc gttccaagcc acatgactcc tttccaatga ccttccaggc  28680
ccctaggagt catcttgtgg cgtttggagc tcagtccccg gtaaagtctg aaagcgtgta  28740
ttataacctt caattttggt tgtttttaag acattatttg acttctccgg gactgggcat  28800
attatctccc gaaacattac taggagtgcc gacgtgactt gtaacgccgc gtgggtgctt  28860
ggcgcaattg tgttgcctcg aaaagccatt gaacaccccc atttgttcat ttctcgagaa  28920
acccaaaatt gcctcgaaat gaatgtaaag gcatcgacat attcattcca agccacatgg  28980
ctcatttcca atgacctccc atatccctag gtgtacaccc catttgtctg atgttataat  29040
agcaagaggt cacgggttca aatcttgtta caagctaatt ttacttttgt taattgacat  29100
gacttatgta cacattggac aattatagtg gagtaacaaa ggtgacatgt gacgcgtata  29160
cattatcaca cacgtctttt aatatatttg tatagatcta gatttaagag taattttttt  29220
aatgcgcaat acttggccaa tttcttctgt atcaaatcat aggtctttgg ttggttcata  29280
agagtaaaga ccaaaataat aatctgaact gcaaaaattt tctccaagag ttaaaagttt  29340
gtataagtta gattaaaaaa attaatgaca tatgatgtag ttggacatta aatatgtaag  29400
tttagaagta attgtgttaa cataaaaaaa gattcgatta taacataaaa actaaagaaa  29460
cacaaaggcg ccgtacaaca atcaatatta cccaagtccc ctcattaata ttaagggatg  29520
acctagctcg tacatattta attatctttg aaaattcgtt gttcagactt gctagttgct  29580
attctatatt tgtatattca ttaatcaatt tttcaatatg tgagcattta cattttaaac  29640
tagagcaaat attgtctctt ttactatttt gttgttgtca aattttcaaa aataaattgc  29700
tcaaatactt ttcctagtga cataaaaaat agagcaaata atcaaacagt agcagaccca  29760
ggaactttta cataatgtag acggcataat gtgttaattt ttgcttcttt tttctaatat  29820
catccaataa cacaattctg cttctattag tttgtagttt cagatgatga tacccaaaca  29880
ataagaccaa gcaacaaatt gataagattt tgcttctctt tcttccactt ggtgtaactg  29940
taacagcttt gaagtttaac ttcagtaatc agttgcatat ttggcatatg atcaaaacaa  30000
tcaaattatt atgtatggaa aagcaaaaaa cttccaggtt tccatctgaa caaggaggcc  30060
aagagggtgg aagcaagcaa ggatatatga tcataaaatc ctatgaatat gatgtacaaa  30120
ccttttctac tgcaattagg taacctaaat gataccacct aggaacagca acaacttatt  30180
tacagcacta aacctaaatc aggttaaagt taatcagacc accatgtatc tgggtggtct  30240
ctcgagggaa agcgtctcca tctgtatccg ggtaacagag gtttcttctt ctcgatcctc  30300
cttggcttct gccctcttaa gttcttcgaa ggctctcttg gcatatacag taaacgcaac  30360
aatggtaatt attgccacta tgaatgaaat aacattgtac acaatctcca cccatgttag  30420
atgatgattc ccatacttga catctgcgaa cgtccttatc agtctcccac tgcaaatgaa  30480
tgctatcagc gtcaatattc gagataccaa ctcatttaac tattgaattg ccaaaaacag  30540
atatctttga ccatatattt gttactaaaa ataacgattg ataatgtgaa actatcactg  30600
atagatttaa aagaactttt ataaaagtat agtttctcta atgtataact gcagaaaata  30660
gaatggggta gacaaatgaa gtaattgttt tgaagaatgc aaaaggtcaa ttcagtaata  30720
cttttatacg tgattggggg aagcattaaa aatcccttct aagataaaga tgacctcatt  30780
ggcaatggaa tcgacatcca cagacccttg cattagaaca gagtggaagt ttctgtgaac  30840
ttacgtgtag atgtaaagaa aagcttctgg caccatccct gcaattgatc cccatagata  30900
aggccaaaac gtcatacttg tcaccacaac tgcgtagttg aagatagtat agggaaatgg  30960
tgaaacccta aagagtgcca ccacgcggaa ctgatgaaac cagctacctt cggcagcaag  31020
cctaagcata gcagccttat ccggccatct ttgcaaccat tgctaacaag gtacaaaaac  31080
ataaacattg tggacttaat tagacaagaa agttaaatta aaatcaacat tagataatca  31140
ataaatcaaa tgtaagcagg gaacatattt cttacatgga ttctatcccg gaagagcaat  31200
ccaagtaaat agggaagaat cattccaata gtagttccaa ccatgattat cacaaaacca  31260
agaccataac caaagatcat gcctgcaagc cacatggatg ggccagaagg aatcagaaat  31320
```

```
acagggaaga ttgctaggga agtaacaagg accacagcaa gaaccggacg gccaaaggca  31380
gtggcttccc attgcatcat tggaacaaga acctgcagag aaagtaccaa aaactttgag  31440
gcaaaaattt cctgcttgta tattgcaaaa agtagtacag cgaaggcatt ccgtgcagaa  31500
tggcttatag attggaaata cggagaacaa tgcaactata agcacaggcc catctcttga  31560
cttttgggac aataacatgg acccccagat tgatttataa gttctcacac catagctaga  31620
ttttgttgga actttcataa atcatagtga cataagtata gcataatatt catgccttcg  31680
acagaagttt tcgcatatgg taaggctact attgaaaaaa ttcccttgtg tttgaagtac  31740
gcataaaaat atctagtggc agtcaaccaa ataaaacatt ctaggagtcc ctcaaaaaat  31800
taaagagtca tcagttcaga agactttaat atcaatactt tctattatcc gggtttggca  31860
tgcagtaaat ttcatgagaa aaggaaaaat cagctatttg attatataag gaactaattc  31920
ggatgtatca ctaagctttc catcgactgg aacatcggga gctagtctcc aatactcgtc  31980
aaggatctaa cataaacatc ttctccgcaa tcaaaaagcc aaggtcacat acatctaggc  32040
ctctgtctca ttctgatggc atggtatgat gcaagttaga caacactatt atttggcaga  32100
tgacacttag ggtctaata tttaagctca ttcaagataa tcaagtaatc aagttcaatc  32160
tcaaggtttc agttgcgcta aaaaatgtaa tacttggctc attcagaatt agtttgttga  32220
agctggttgg tatttgcttc atttgttaat ggaaccaggc tcataaacaa gctttcatta  32280
ggctaaactt atttaacaaa atcaaaagct taatactata atttttgata ggatttcttt  32340
tgggcagtta tacatgagta atgaacaagc tctacacaat ctttttaat gaacaagctt  32400
taatcgagct agggtacgtt ctattcaact tattggacct gaacttattg gaacttatct  32460
gaactgaact tattgaacct gaactgaact tattggaact tattaaacct gattggacct  32520
gattcaactt attggacctg attgaacctg attggaactt attggacctg attgaacctg  32580
attgacctta ttggacctta ttggaactta ttgaccctga ttgaaactta ttagacctta  32640
ttggacctga ttgaaactta ttagacctta ttgaacctga ttgaaactta tttgacctta  32700
ttagacaaaa acattattat tattattgtt attattatta ttattattat tattattatt  32760
attatta                                                            32767

SEQ ID NO: 54          moltype = DNA  length = 201
FEATURE                Location/Qualifiers
source                 1..201
                       mol_type = unassigned DNA
                       organism = Beta vulgaris
SEQUENCE: 54
agagcagatt ggcatacttr tgaatattct cactggctat taaattctca gaagaaaaat  60
caacaccaag attatgacat gcttgtgcaa agacacaccc agtcatgaat gcatcatagc  120
cagcttcatg cttagcccca gagttccaat ttgaggayct gcaagaaaac atgggagtaa  180
gatggtttca cataaaacat g                                            201

SEQ ID NO: 55          moltype = DNA  length = 201
FEATURE                Location/Qualifiers
source                 1..201
                       mol_type = unassigned DNA
                       organism = Beta vulgaris
SEQUENCE: 55
agagcagatt ggcatacttr tgaatattct cactggctat taaattctca gaagaaaaat  60
caacaccaag attatgacat gcttgtgcaa agacacaccc ggtcatgaat gcatcatagc  120
cagcttcatg cttagcccca gagttccaat ttgaggayct gcaagaaaac atgggagtaa  180
gatggtttca cataaaacat g                                            201

SEQ ID NO: 56          moltype = DNA  length = 201
FEATURE                Location/Qualifiers
source                 1..201
                       mol_type = unassigned DNA
                       organism = Beta vulgaris
SEQUENCE: 56
gggtttcttc gaagtttgat tttgttacat ttttcaaaga gaaattagtt gttgatgttg  60
aataatgatg ataagtagtt agggttcgta gtaaggtgga cgaragagaa aatggcgtca  120
ctctgayrag cttcttcatt ttgttcttct tccttagctc tgttttcagt cactgcgcca  180
ttttttttt aaaaggaaga t                                             201

SEQ ID NO: 57          moltype = DNA  length = 201
FEATURE                Location/Qualifiers
source                 1..201
                       mol_type = unassigned DNA
                       organism = Beta vulgaris
SEQUENCE: 57
gggtttcttc gaagtttgat tttgttacat ttttcaaaga gaaattagtt gttgatgttg  60
aataatgatg ataagtagtt agggttcgta gtaaggtgga ggaragagaa aatggcgtca  120
ctctgayrag cttcttcatt ttgttcttct tccttagctc tgttttcagt cactgcgcca  180
ttttttttt aaaaggaaga t                                             201

SEQ ID NO: 58          moltype = DNA  length = 134
FEATURE                Location/Qualifiers
source                 1..134
                       mol_type = unassigned DNA
                       organism = Beta vulgaris
SEQUENCE: 58
caagcacaaa atcaaataat gagaatcaca ctatccaaag aaaatttcca tccacattta  60
tccaacacag ttatctctct tttacaccca aattatgtca accaaaaaca staaaacaag  120
tgagtgcagt agct                                                    134
```

```
SEQ ID NO: 59           moltype = DNA  length = 134
FEATURE                 Location/Qualifiers
source                  1..134
                        mol_type = unassigned DNA
                        organism = Beta vulgaris
SEQUENCE: 59
caagcacaaa atcaaataat gagaatcaca ctatccaaag aaaatttcca tccacattta  60
tccaacacaa ttatctctct tttacaccca aattatgtca accaaaaaca staaaacaag  120
tgagtgcagt agct                                                     134

SEQ ID NO: 60           moltype = DNA  length = 134
FEATURE                 Location/Qualifiers
source                  1..134
                        mol_type = unassigned DNA
                        organism = Beta vulgaris
SEQUENCE: 60
taagtaaaaa gtggtaaaag aattaccaaa arcgcacara ataaattaat tagytggatw  60
taactattta acctattcct tttttctgtc gctataacta cttttgctta acttattgat  120
ggtttgatcg ttga                                                     134

SEQ ID NO: 61           moltype = DNA  length = 134
FEATURE                 Location/Qualifiers
source                  1..134
                        mol_type = unassigned DNA
                        organism = Beta vulgaris
SEQUENCE: 61
taagtaaaaa gtggtaaaag aattaccaaa arcgcacara ataaattaat tagytggatw  60
taactaatta acctattcct tttttctgtc gctataacta cttttgctta acttattgat  120
ggtttgatcg ttga                                                     134

SEQ ID NO: 62           moltype = DNA  length = 150
FEATURE                 Location/Qualifiers
source                  1..150
                        mol_type = unassigned DNA
                        organism = Beta vulgaris
SEQUENCE: 62
ttataatgta gagtcaaaat taatatcctt aactagtttt taagtccggg ttatatccta  60
gatatttata atattcattt attagtaaca ttttatttta taaatataat actaagcatt  120
atttggtttg ctggttaaga ctttagtgta                                    150

SEQ ID NO: 63           moltype = DNA  length = 150
FEATURE                 Location/Qualifiers
source                  1..150
                        mol_type = unassigned DNA
                        organism = Beta vulgaris
SEQUENCE: 63
ttataatgta gagtcaaaat taatatcctt aactagtttt taagtccggg ttatatccta  60
gatattaata atattcattt attagtaaca ttttatttta taaatataat actaagcatt  120
atttggtttg ctggttaaga ctttagtgta                                    150

SEQ ID NO: 64           moltype = DNA  length = 201
FEATURE                 Location/Qualifiers
source                  1..201
                        mol_type = unassigned DNA
                        organism = Beta vulgaris
SEQUENCE: 64
acatctacac tgggagactg ataaggacgt ttgcagatgt caagtatggg aatcatcatc  60
taacatgggt ggagattgtg tacaatgtta tttcattcat cgtggcaata attaccattg  120
ttgcgtttac tgtatatgcc aagagagcct tcgaagaact taagagggca gaagctaagg  180
aggatcgaga agaagaaacc t                                             201

SEQ ID NO: 65           moltype = DNA  length = 201
FEATURE                 Location/Qualifiers
source                  1..201
                        mol_type = unassigned DNA
                        organism = Beta vulgaris
SEQUENCE: 65
acatctacac tgggagactg ataaggacgt ttgcagatgt caagtatggg aatcatcatc  60
taacatgggt ggagattgtg tacaatgtta tttcattcat agtggcaata attaccattg  120
ttgcgtttac tgtatatgcc aagagagcct tcgaagaact taagagggca gaagctaagg  180
aggatcgaga agaagaaacc t                                             201

SEQ ID NO: 66           moltype = DNA  length = 21
FEATURE                 Location/Qualifiers
source                  1..21
                        mol_type = other DNA
                        organism = synthetic construct
                        note = Primer pCRBM4_S2
```

```
SEQUENCE: 66
gtagttgaat ggtgggaatc c                                          21

SEQ ID NO: 67           moltype = DNA  length = 21
FEATURE                 Location/Qualifiers
source                  1..21
                        mol_type = other DNA
                        organism = synthetic construct
                        note = Primer pCRBM4_S3
SEQUENCE: 67
caatattgcc cttactttat c                                          21

SEQ ID NO: 68           moltype = DNA  length = 20
FEATURE                 Location/Qualifiers
source                  1..20
                        mol_type = other DNA
                        organism = synthetic construct
                        note = Primer pSeq_LbCpf1_F4
SEQUENCE: 68
accactcact cctcgataag                                            20

SEQ ID NO: 69           moltype = DNA  length = 22
FEATURE                 Location/Qualifiers
source                  1..22
                        mol_type = other DNA
                        organism = synthetic construct
                        note = SEQ 70: pSeq_LbCpf1_R3
SEQUENCE: 69
tagacctgct tctcaacctt ca                                         22

SEQ ID NO: 70           moltype = DNA  length = 21
FEATURE                 Location/Qualifiers
source                  1..21
                        mol_type = other DNA
                        organism = synthetic construct
                        note = Primer pSeq_Ribozyme_F
SEQUENCE: 70
tgcagcggat ccaaattact g                                          21

SEQ ID NO: 71           moltype = DNA  length = 18
FEATURE                 Location/Qualifiers
source                  1..18
                        mol_type = other DNA
                        organism = synthetic construct
                        note = Primer pSeq_Ribozyme_R
SEQUENCE: 71
cctggtccca ttcgccat                                              18

SEQ ID NO: 72           moltype = DNA  length = 20
FEATURE                 Location/Qualifiers
source                  1..20
                        mol_type = other DNA
                        organism = synthetic construct
                        note = Primer pSeq_tDT_F
SEQUENCE: 72
ttacaagaag ctgtccttcc                                            20

SEQ ID NO: 73           moltype = DNA  length = 20
FEATURE                 Location/Qualifiers
source                  1..20
                        mol_type = other DNA
                        organism = synthetic construct
                        note = Primer pSeq_tDT_R
SEQUENCE: 73
gtactgttcc acgatggtgt                                            20

SEQ ID NO: 74           moltype = DNA  length = 19956
FEATURE                 Location/Qualifiers
source                  1..19956
                        mol_type = unassigned DNA
                        organism = Beta vulgaris
SEQUENCE: 74
aaatgataca ggggtatatt tgactctatg aatttcagaa atctaatcaa atttgctaag  60
cttccaatga ttctactaag ccctacaaat tacaagaatt agttactttc atctctctgt  120
cggcttcaga accagaagtg tacaatatct tgtcaaacaa actctgctta gaggagctct  180
ttcgatcatc ttttttcgat ttggaagttc ccggtgatag gattgacatt gctgttttct  240
cggtcaattc ttctggatct tggttctgtc catctatctc tggctccatt aatctggtct  300
tccaattaat tccgatagcc tcagcttgct ctgcaaacaa gacctttgag atcggggagc  360
tgcagatatc cttataaact tcataaccag cagcacaggt tttcccacct tccaacaact  420
```

-continued

```
ttgataaagg atgtaggaga gagatagaat catcactcgt ttctaaccta tccttcaagg  480
caaggaagtt aacagccaag tctgccttac taaactgaac aaatactgca gtttcatcca  540
agttatagat gcaagcaact gagtatatac caaacacttt acagatgcat tgttttatgt  600
cacttgcctt gagttttggg gagaatcccc aaatcaaaac tatgttagga tgcaaaatgt  660
taagaaacct ccttttagct gaactgataa cgggaatttc attcatatca ccagtgctta  720
gattgatcac atctccactg ttccaactaa gatagagcag attggcatac ttgtgaatat  780
tctcactggc tattaaattc tcagaagaaa aatcaacacc aagattatga catgcttgtg  840
caaagacaca cccggtcatg aatgcatcat agccagcttc atgcttagcc ccagagttcc  900
aatttgagga cctgcaagaa aacatgggag taagatggtt tcacataaaa catgtgtaga  960
agtgcagtga acactggcga aaacaatcta attttacgaa ttcattcact cactcagctt  1020
caaattaagt ttccccttta tttagggtgc cccaaaaaga tacactcttc tgtttacctt  1080
ctctctccaa gcgaccaatc ttttctctct tctccaacat cgttttcttt ttctctctct  1140
acccactatc cattttgtcc tcctacattt gataactatt cttaatctcc aagaaaatcc  1200
aatgtgtgaa ataattacgg gacagggagt atacagaagc agccccccttg ccaatatagt  1260
ttacaaatta ccctcagaat taggcttacc tttcccaaag gagcaataaa ttcaaacaaa  1320
tctaaaaggt acaaggcatt aagtgccgaa cctcatgtca tcaacctgga cctccacctt  1380
cacacatgga tgtacaccac cattagagga ttgtccagag gctatctcag ggcacaacag  1440
agaaaatgct gaggccaatg acgtgctggc tttattcaag aatttttgaa ggctcgtgtc  1500
tgcattcaaa agtattttcg tgtcgacaac atgaggaaaa tacttgtgga tctcgagaac  1560
aaactcttca acagttgatg gaagaggacc aaagaattta tggtaaatat gtgccatatc  1620
tgcaaaaaat tataatggat aagatgacaa gaaaagatac taggaaggcc ttcaagtaca  1680
aatattatat catgatgctg gacgaccgat gctcccacaa ttatgtttgt taccaaatgc  1740
ttcgaaggat aattactaaa ttatgtgaat ggtggttacc aagtgtcccg gaccatgcaa  1800
taacttctcc tttcagtgac caacaagaag aagacgtacc taaaaagcaa ttgtgaccta  1860
caattagctt cttttcagca gcgagaaggt caaggacatg ccggaaacct gcagctgctt  1920
ttattttgcg agttgcttgc tggtgagacc catacttcac ctcctcctac aagaacaaac  1980
agaacaatca cacatgcaga aagttcccca cataccaagt tgctgtctgc taaacactga  2040
aactaactta tctctacaaa caatgaagga agttcctcac cagaaggttg atcttatcat  2100
tgtcagattc tacaaaaaca ataagcttct gcaagatggc actgccgtca tgagcacaca  2160
caaaaacaag atccttgaag tgcttccttg taacctgtaa ttgcagatca ttagtatata  2220
ttcaagatgt tataaattta ttgaaaagca gcgtctaaaa caataaaagt catgcttaag  2280
gcatagagcg atagagcata gacacttcag agtttaataa gagcaaatac tccaggagaa  2340
cataaatata tttcatatca caaatcctag taccaactgg caacggctaa ctgccaattt  2400
atgtactgct caaaaaggcc aagcatctaa aagatggctt aaaagtcgga ttttataaga  2460
aagtcgtcac atgattgcta ttacattgac atatcaaagg tcaaatgctg aaatttggtt  2520
cagcttgata tatattaagc atacaaacga tacgttgaca agaaagccta acaagacatg  2580
aagcatcagg cacataacat tcaaaagatt accaattcaa tcaacttcag ctgatgagaa  2640
gtaaatccat tcaatcgaag agcaggacgc atactaaaaa atatggtttc aaattgttgt  2700
ttagattcaa cagcacttgg aagctcggca tttctgttct gtagcaacat atcatgccaa  2760
tcactgagcc gaattttcat ccgttcggag aataaaatat cagctacatt gcccaaaggt  2820
aaatctctaa cttcattaga atatgcccat ttcccgttat atactgaatt caagcgactc  2880
aaagcctcgt cttcctgtcg tctagataaa taagacacgc ctgagattat acaatgtgta  2940
aatttaccac aataatgaca tcatactgac aaaatctcaa acaaatagtt ctaataaagt  3000
catgttatct gaaatttcta tgaataggaa attgaacaaa accttcatgc tttttttccaa  3060
ctaaaattga catcttctac attaccttca tgtatgcatg cattgaagtc aaactggtat  3120
tttgccaaga agtcaatcga agttgtttgg cacaggaatt catatgatgg gccatcagtg  3180
ggaagctctt gacgtggaaa tatataaaaa ttatgcctga caatgaacca ttgtaaaatt  3240
attagatgga gtatctctat ttattgttta cagccaattg agcttttaac aattactata  3300
ggtagtgttt ggaaacttgt atttcatttc aaataatgga attgaaatct ggaatttaaa  3360
gtttgtattt caattcctaa tcactgtttt gtaaaggggg tttgatagaa gagagagaaa  3420
tagaggttta atggaggaga gagaaaaagt gtgggtttac taaaaaaaag agaaataaat  3480
attagaaagt gtgggtttac tcatagagtt gggatatgta tgaggagaga attttcaaat  3540
gccaaggtaa tagcttgaat gacaaattta ataatttcaa attccatgtc atccaaacaa  3600
tagatttcat ccaaatccaa gatttgaaat gaaatcttgc tatccaaaca tatcataaat  3660
taattagtaa tttagacttg ctttctgctg cacttactta tggaaataat tttacttcag  3720
tccttaaata acccgcaatt tacatcaaag gcactaatat aaacacctag ttacgaaatg  3780
gaaatatcag atatacctgt aaaagtaaag aaacaaaaat acaaccctga gcatgaaggt  3840
atccttcaaa agtgcaatat ctgcatactt agaaccggaa ttagaagtgc gaatgcagac  3900
aataaccatc ccaggatcag aaacgtccaa gaaagttgag attcatcatc cattctcttt  3960
agcaaattta tgaactctaa tatataaatc atacccccccc ccccatccaa aagcaattgt  4020
caagctgcct gaacccctca taatttagga tacaacaaag taatcctaaa agacccttta  4080
caatactagt actcgggtat ttccacaatc ttctcatcat tgaatccaaa gcattgcatt  4140
tgaagaaatc aaatcataat ccattactat attagagcaa aatctatgtc attatagtat  4200
tggagagcaa gtatgactat taccccttta cactaggcaa aacacattgt cacaatgcta  4260
acttagtcat taaccaatat caatatggga ctgtggatat tcataaaatc gaagtttttc  4320
gcttgctcat aaactatctt tcattccagc acagtacaag agagaaaaga cagcattttc  4380
atacacttct ttctttagtt caaattcaca cagcagcaaa aaattcactt cttcatagct  4440
ttagctcagc aaacaaagca caaagcatgc aattactctc acacatagca caccaaaaaa  4500
acaaaaacca ctaaaaattc acacaaaaaa aaccaacaaa aattccatcg caatttcaac  4560
aatcaaaaca atcttctaag ttaaaaaagag agataaagat gagaagaaaa actaacggat  4620
gagcaacgaa ggaattcttc gaagaatccc atcgaaatgg acaaacacca aattgaacaa  4680
cggcgaattt ctcagcagaa tctttcattt taaggtatcg aacatcgtgc cgatcaaact  4740
cgaacgattc gcgccaaggt gagcttgtaa ttccagtcat ttcgagatca atggcgacaa  4800
aatcggcaga ttttacatgc gtagtgaggt caattagggt ttcttcgaag tttgattttg  4860
ttacattttt caaagagaaa ttagttgttg atgttgaata atgatgataa gtagttaggg  4920
ttcgtagtaa ggtggaggaa agagaaaatg gcgtcactct gacaagcttc ttcattttgt  4980
tcttcttcct tagctctgtt ttcagtcact gcgccatttt tttaaaaaaa aggaagatga  5040
acaaagcaaa tattgaaccc aaattttgta attttggccc actttatatg taccccctccg  5100
tttcaaaata tggagcacgc cgcacacacg acatttaggg tcgaattttg aacattcttc  5160
```

-continued

```
aagatgatct aatggtataa tctctataat ttatatgtgg catattataa taagagtttt  5220
atgaagtcaa aaagtggatg tcatatattt aatgcatggt aagtttttcc taaatctgta  5280
tactagggta acatacatat gttgacttga agtatatata attcttgtag tataaatatg  5340
gctttggcca taagtagtaa tacacaacaa ctagaaaaat tgaaatcagt ccactgttat  5400
cttgtactct ataattttct gtttcctttt gtttcgcaac aaagacatat ttgtggtgaa  5460
agataatttt cgtaaattga atgacttata ttttgaaata aagagagtat taggtaaggt  5520
tacgtgcttt tcgcttgaat ttgttagacc tcaaatgtat atgtgattag aacggattgg  5580
ctctagtttt tattttatag aagtatatat gcatttttct tagagcacac tcgaaattac  5640
tttcggatag atatattcgg gaaaaaaaga ggttgaaggg aagttcatca ataattatgg  5700
taaaggaaaa aggacatcgt tacaattcta aattctagat aggatgtgat gataatccaa  5760
aagtcatctg aaaaactaaa caagtccaag atgctaatga ttcgagtaga gattgaatga  5820
gtgaccctaa ggattgtcaa ccctcttatt ctaacgtgtg taaaagaatt gacaactcta  5880
agagttactc aaacattttt cgattcgagt ggttaatata ccaatttgaa actattgaca  5940
ggagttattt taatgagtat aatggtcaat ggagcactga attccatctc acatagtcac  6000
atatttcatc tcaagttctg atgatttcaa acattgaaaa aagatgatac aagcaattaa  6060
ttcctaggga aacatattgt ggttttcatg gatacaagag tgagaataaa tcaaaactta  6120
ggctctaaca tttcttttct ctactagtaa ttgctaatta tatcaattca attgtcagtg  6180
taatcagtta atcaccaaat ctcttgtata gtcagtaaac tatacactgt ttagtcctct  6240
ggatttgcc cggtcgaatt atgcagcata accaaacttt gaagtttagt acttcctttg  6300
cacccaagtt agcttcacgg cccctgcctt ctggtggatg gtcaccctat gctttgagca  6360
ttctctgcaa tgcgcacgat attcaatgag aacgtcgcct tgaaaatcta aattgcaact  6420
aaaaattaga ttgaaatgaa acccacaaga gttgtttttc tgagtagttg gtgtagaatt  6480
cacaagtctt gctccattgt ttgaagatat gaagacaata atgtgctatg taaagtgcag  6540
ccgctagcta acagtggaag tggaaacttg atcattttac actcgcacaa gcgaaagctc  6600
ggctgacgtt gcaaactgaa gaaaaacctc tcaaaccaat tcgacttttg ctcaaagttg  6660
caaactaaag aaaaaggctg aatgcaaagc aagttcacca atgaacaata gatcggtgtt  6720
ggcctgaggc cacatcaagt gaagttgcct aattgcggcc ctctcatctg ttcacaggaa  6780
tcattttcca tatagaatca ctccaaaata aaagagcaaa gctgcaccag atgcagaagc  6840
ataactttca agacaactga tgacagataa atagcaaaag aatgcttaag aaatgatcaa  6900
aattgaatgg ctctggaatt acctcatcag ctgattttcc tttctctcta tctctctatc  6960
tctttactcg tctatggagc taccacatca catggcgttt catatgcttt ctgccgtcga  7020
actagacgtg cagcaaaagc tccatccatt gaatgcttca ctgggcatga gcgataaaac  7080
ccatcttcag ttaaaaagtc agatggaaca tatctgctta cagaatctct ttggaagtcc  7140
tatcacccaa caaagaatat attaaaatag agaaggagaa aagaacgtat ctatctgtca  7200
gcatccatat gaggtggaaa ctaggagtac tatataaagc cagtgcagta gctcctaccg  7260
gatgtctaag aaggaaggca gaaaccctat cttcgttttc ttcaagatca atggagcagg  7320
tactgtacac aagcacgcca tctggtttga ccagcctgta gatgttaaac aatcccacag  7380
acaaaaggga ataatatgag tgaaacaagt caacaggggg aaataaccaa taattctagg  7440
actgtcaaac tcaagctctt caaaaacaaa gatagctctt aatctcactt gcaagcagca  7500
tcgaacagct cgtcctgcaa cttctttagc tcttccatat cctctgactt tctattccaa  7560
cgcaaatccg gcctcttcag caaaaatata aagttggaac aaggctctta gatacaagaa  7620
ctgaaaaacc ttcgacatat aatggactct atcaagggca caatgacaaa ttctaaacat  7680
gagcatgtat atcaataaaa tactaagaac cctttcaatg gtactgctag aaggtttatt  7740
gctacacttt ttagtacacc atctataggt tttatagtac catcaaaatg gttcatggtg  7800
ccataagaaa attttatgta tttatggtac tatctaccat atctaatttt ctctgtaaaa  7860
atgtatttgt agatagagac cacgagttcc tcttttagat actgactttt tttttctac  7920
atgatggcca acagacttct caaacaaaaa gaaaaagaaa atatttagat aatatgagca  7980
acaaaatagc aaccacctac ttttgatagt acacccaggc ccgaacaagg aacatctaaa  8040
agaactttat caaacttcga agtgttgctg tcctgaaaag aatagaaagt aactgcttca  8100
acaaagaaga agaggcagaa agcaaagcta gtacgcattt tgcaatgact tactgaaaag  8160
gagcgaagat cagcatggat gcaagtgatc acattatcaa cacgctgcag cttggctgtt  8220
tcttcaagta tccgtaaccg acctttattt atgtccattg ctgatatcat acctgaaaag  8280
ctacacattt agaatgcaga accagcatca ttggtagtta agttatcact ataccttggc  8340
cattcaagcg agatgccatg aagagtgtct tccctccagg agcagcacag caatcaatga  8400
tgtgatcacc aggctgtgga tccagaacag aaacagctag acctgcagcg aagtatagat  8460
gtaaacttgg gttgggctgt cacatttttt cacatcttat cttcctttct attctttcaa  8520
aactgaggag aaatggttgg gatttctata aacgtgagaa aaatggcatc agattagatg  8580
gttttactgc atgaaaaaaa ttgaatgtgt ttcggcatca cattactaca aggtcaaaag  8640
cactatcttt gaaaatgtag gacataatgg gacagagatg tgctgacctg cactctcatc  8700
ctggactgag cataaacctt cttttagaag tccagtttgt atcacaatct aggatatgag  8760
aaaacaactc aagatgtaat tgctcctaag atatcaatca tttcataata aacataaaag  8820
ttattattac aagacagcac ctgcatccca cttctgatgc agacaaagtc atccaaatgc  8880
aaggaaggct catgcgggac ctgcggacaa agtgttgtga tgcgcataga tatcgaaaga  8940
aggccctgta tagcactaat gagataagat tcagtaacct tcagcatgtt gagcttcaca  9000
acaaggtcat ctcgagttaa tccttttgca atattggccc tagtaccaag aaaaccatat  9060
gtattaacaa gagaaaagtg gcatagggat ctttatgact taggtaagca gttggcaatt  9120
agagagaata aaacccccaa acctcaagct gaaactcgga acactattgt tccacatcat  9180
caatttgata gctccttctt gcccaagata cttggtccac cgtcttacca tccactgaaa  9240
ggaaggtatt aaaagggaga aaagactcgt cagcatagaa aattgtacat cttaaatttt  9300
agaagtatag caccatcttc aggcatcagt caacgtaaat aaataccaca tctacaaata  9360
gaaccatact ttctggacag tcgggatcat gagcacagac aatactgcat gattattgcc  9420
tcgtattctc atgtatacaa gtatatgtaa cattaaatag cagtatttct tgagaaactc  9480
accacgggat gggaataagt tgtagcaagg gcacgtgctt gtgaacgatc atcaccctcc  9540
aatttgggta caggaaggga gtcattatcc tataaagaga aacagctttt gttttcaacc  9600
atatcaagac aaacagttta ttaaactata aacaacaaca atacacatgc acacacctac  9660
tgggaacaag atatatacta ctgataagta ttttctgatt gaagaaaaaa aatctcattt  9720
atttgcaaat atagatttaa tgacaagaaa gctttgaacc ttaaggaaaa ctagctttcg  9780
gaggatccca ttcaccatgt ttcctgcgcc tggtctaaga gcatacttgg caagattcac  9840
attctgcaat ataatccaac agtaagaaca cgacatggat ttagactcaa gtctctgaac  9900
```

```
ctatagaaca agtaaaatta gatcttatct catttgacaa tttaaaatta gatagtgcaa  9960
tattctgcag ttataagact tcatgtgtgc atactgcaca agtcatctta aaggtgttat  10020
taaagcttta attgccattt gacatcccct tgctcaactt tagcatgttt ttaggctaca  10080
acaatacgca ctgtctacat ggacatacaa attacaagcg tatggaaaag caataagcgc  10140
aaggaagtct tcagccagaa actctctatg agtccaacaa tatgcaacta aatatccaag  10200
taccgtgaat gagtaagaac taacctcgtc aacaacagca tatggtggca tttccagttt  10260
cacaatctca tagcatccaa tcctgaggat ctaaaattaa agataaatca atacacaaca  10320
tatgatatgg gtcggagcgt atataacaag tatagcaact acatttgaac agataacagc  10380
ctttgagaca ataaggaact ccgacattcc agtatatgcc agatttcata tctttagctc  10440
taaattgcca cgcaaaatgt tattgggcaa tatacctgta gcaggagagg ttccatgttc  10500
ctaaaggagc tttcatcatg gcatgaagaa acaataagat aatccagata ttttctccaa  10560
cgaattgaac caccaacaat gtcagtgacc tacaaagaca agttgtcaac ttaaaacttt  10620
tgaagcgtca tttcacttct gtagaccaat acaaaagcta ctactgcttt acatcataaa  10680
acctttagtc cttaggttca tctgattggc aaaaaaggtc cagatgcaag aaaagcaagt  10740
agctgtaatg ctgtattata tcagcattat tcagaacaga ataataaata tctacagatt  10800
ttgggtggaa gcttgatgat agagtatctc cacaaagaga actcgcttga gtcccaactc  10860
ccaaatctac ttttttggag tcacattatc agtcattttt tctggactct tataggaata  10920
gtgtgctatg taatgattta tggagcaggg gcatttcatg aatagcttta taagttagta  10980
tgggtgtctt ggggaataag ttaaagggtt agttagaggg aagaagtaca acatatatat  11040
agagcttttg taagaagggt ggttatgttg aaaatagatg agaaattggg tgagctcata  11100
gtagttcaat ttggactttg ggagagaatt aagcctcttg aaagcttgaa tatcatttac  11160
atttgttgtt tttactctta ttaatcaacc aaagttcatt ttcttccttt aatttctcca  11220
ttttagcact atgatttgtc caagctaagt gatttcttag catagtgcac agtgtagtat  11280
atcggagaac tcatttgagt cctgaaaggt cccacaagtt acatttttcc tactactact  11340
tgcaccaaaa caataagcat cattaagaca ttgtcactgg tccttcttag gttcttttgg  11400
aggggattcc tcagatgggg gaggcaccca tgaaggaaca tgttaccaag caatgggaca  11460
atgcaaaatg caccaataca gtagcttcac ttcattgatt gcatctatgt cacggaaaac  11520
tgaagaaaga agcaacacct caactttatc caggacagat atccactaac ctaggatgca  11580
agcttgagac tatttagcaa ttgcctctgg gatattaaat cagattacga ctatatttct  11640
acagttattg cttaagaaaa aggtacgatt tgaagcttgg gaagaaagag aacaagagta  11700
aaagaccaat ctgagatctc tttcatccag gtctctggtg cgaaatccaa gagtcctctc  11760
aacatattcc atctcattgt tccctgaacc ctttcctctc tcatttagaa gatcagcgaa  11820
ggcaccacca aactctatcc gcatcaatct cacagcagcc actggattta cacatgaaag  11880
caaaccagga gaaccataaa aatcacaaca aacttcctga tagcctactc actagcatca  11940
accattgtgt tcagcctaaa atgagcggct gttttcaatt gaacagcaac ttacatggac  12000
cactgcataa aagtgatttc ttaatccaga caaacaaaaa tgtttacttc aaccaactga  12060
atttgcatca gctcattagt gatttgacaa gttctaattt atgtatcaac aaacaagacc  12120
atatagctag gaaacaagag gcttaggcta agcttaatgc gtgaacaatg ttagatttca  12180
acctatcagc actgtggata actgcaaact gcgacttaaa taaggaagat aaaggaactg  12240
aatatgcaat ttcaaggtgc tcagcatttg aatcaacagt tacttcagat aattcagaac  12300
ataaaagatt tgaacattct aaggctacct catgattgca agcaatgtta cctgattcgc  12360
taaccctcac aagccacaag ccaaagaagc aatttggtaa atggttcatg gtacaactgt  12420
tcgcttttgg actaatctaa caatactagg tggtaaatta tgttcccata tctattacca  12480
taatgtacag caaattaggc agcactaatt ccaaatgacc caacaaaaaa agaggaagaa  12540
aatccaaaaa ttcaagccaa catatgcact aaaattacaa gcacaaaatc aaataatgag  12600
aatcacacta tccaaagaaa atttccatcc acatttatcc aacacaatta tctctctttt  12660
acacccaaat tatgtcaacc aaaaacacta aaacaagtga gtgcagtagc ttcacatcaa  12720
agaatatcaa tcacaaacac cacataataa aatttcaact cctgcccaaa caaaaaaaat  12780
ataaagaaaa aaaaacagca aaatttcaaa gataaaatag aaaaaaaaaa atcaaaatac  12840
agggggaaaa aaagtaaatt taccagctct atgaggcgaa acctgcaaat tcagcttctg  12900
ggttttctct gaaatatcaa gcacaataac cagcaattaa aaaaaattat aaataaaatt  12960
aaaaagaaaa gattgataat taaaatcaaa agagagcaat ttaaagcaca atcctttttt  13020
taccattttt tctgggagga agagcatcct tcgttttggg tttagacgaa aaaaatgaga  13080
gttgttgtat ttgtgcgcat gagtgatcat tgctggaaat gaaagtggga aagtggtaaa  13140
tgagtgcttt gtgaaattgg gttttgagga aaagtagaaa gaagaagaag ggtcgatgtc  13200
agagaagaga gagagtggat ggaaagtagt gatgattgcc tccattgttg ccggtgaagt  13260
gagctttctg caaatatttc actggactag tttttttag cagataacgc taaaacagag  13320
aaagatgttc ggttaatttt aatttttgga catttaaatg actattcaat atgtttcaac  13380
cttttttttt taaaacaaag gaacaatact agtattagat tacgttaatg tttagtacat  13440
ccaatactta tgtgtgtttg acctaactta aaatcgtaag ttgtttaaaa tgtcggtgtc  13500
ttgtttttaa gagatatcat acttactatc tttggttttt actcttccat tgttaacaga  13560
aactgtattt atttgggtaa ggggtttgag tgaattcctg taagtatgag aaagttttga  13620
gtgaagcaag agaaagagag aagaaaggaa cttcgagtga agattgagag aaacaacagt  13680
tagtgggaac tgttgttggg aacttgagtt taggagctca ggttgtaccc cgagagaatt  13740
aataggtttg taacagagtc ggtggcctat tatagtggaa agtttgagtc aaaatccatt  13800
gtggccgatg tcgtttcttc ttattgggcc taggaagttt ttcctcgcta aaatttcctg  13860
tgttcccatt gtgtgttcct tagctagctt tcaattccgc aaaaagttac gtttattctc  13920
tcactataat tcaccccccct cttatagtgc tcatattata caacaattga tatcaaagca  13980
ggaactctaa aaatacagaa atcatgttga gttcaagatc ttggaaaata tgaatactac  14040
agaaaaactg gaagaaaggt actctactca gagaccaccg atgttcaatg gcaaattcta  14100
cacaaactgg aagaactgaa tgaagatctt catcaaagcc gacaaatatc aggtttgtag  14160
aatcatagag gcaggcgatt ttgaagtcac taccactaat gacacatatg aggtaattcc  14220
taaattcata actcatttcg ataaagtata tttcgaaaag ttggaaatta acgttcttgc  14280
tattaaactg cttcattgtg gtcttagacc tcatgaacac aatcatgtca tgggatgcaa  14340
aatcgcaaaa caaatttggg atcttcttga agtcactcat gaaggtacgg gtaaagttaa  14400
gagatcaaaa atcgatcttt taatgaatca atatgaactt tttcaaatga aatataagga  14460
gtccactcaa gagatgttta cacgctttac taatactatt aatgagctaa cctctcttgg  14520
aaaagaaatt acatatgatg aacaggtaag aaaggtccca aggatcgttg gatggctaag  14580
gttacgcctt acaaaaaact aaggacttta cgaagttcaa tccggaacaa cttactggct  14640
```

```
cccttatgac tcacgagcta cacttggaca ctgagaatgg tgacttgtcc aaacagaagt  14700
cgattgcctt gaaagccatt tttgtcatac cgtcaattaa ttaagtaaaa agtggtaaaa  14760
gaattaccaa aaacgcacaa aataaattaa ttagttggat ataactaatt aacctattcc  14820
ttttttctgt cgctataact acttttgctt aacttattga tggtttgatc gttgaatcca  14880
agttttctcc acccacaaag atattataga ctttacttta aaaggtacga taaataatgt  14940
ttaatcaggt atgcatcaac cttgaaatta ttaatttatt aagatcaaat tatgcatatt  15000
tatattaaac gtacaggact tgtgcacaat ccatggatga tattgtagat tttgttgtaa  15060
aggagttagg gacaaatgat gttgaattaa gaatgatgag gaacaacatt gaggtaccta  15120
atggcataca agattatgtg gtaacaaagg tgaagaagtt ggttgtacca ggcaatacag  15180
cagcggcaag ccatatatag gatgagctac catacccta tgttgtgaac tattgtcacc  15240
accaacaaga cattggtcat tacgacatca ctttagttga ggaatgataa acctcttttt  15300
gctagatatt tgcaaacatc tagcagataa agaggaataa aacactattt atatttcatg  15360
aacactattt gttagttgca tgaacactat ttttagttac acgaacacta gttttagtag  15420
catcatgaac actatttttt agcatcggaa ttttcacgac tactttttgg tttgactgac  15480
actctgcaat tttcgagata actttttggt gatatgggtc ccatgaaata gaagatttat  15540
atttcatgaa cactatttgt tagttgcatg aacaatattt ttagttacac gaacactagt  15600
tttagtagca tgaacactat tttttagcat cggaatcttt gcgactactt tttggtttga  15660
ctgacacttt gcaattttcg agataacttt tttgtttgac tgacaactat ttcctatata  15720
tattgacagt tttaccctg ttagatgttt gcaaacatct agcaaaaaga ggtttatcat  15780
tcctccactt tagttagccc aacctccagt aacgccatcc agaccactgt cgtttgtcac  15840
tacgacactt acgcttggca accctatgtc ctagcccttc gatacctcga tatccgtccg  15900
ggcaatgtcc ccagtttgtc acttctctgc cattaatgac atattttgga gtatcaaacc  15960
caactccaag tatatatcgc aacatggctc agtaaagaga gtcatataat catgacgtag  16020
tttctatatg ccatcctacg tagtatcttg taacatgaat aacagcctgg tttgcaggtt  16080
gatggtacat ggtataaatt ggtattactc cctccggtct ttattagttt aatcctttct  16140
tttgtacaga gttataggag aaataatatt gtgggtcata gaaggaaaga gaaattatta  16200
ttttatgtta aagttgaatg tatgtgtgat gaaaagttag tagtcccatt tcaaaataga  16260
aaaaaaaaag gtaaactaat aagggacatc ccaaaaagga atacgggtaa actaataaat  16320
atccatgcag gttgttggta catggtacat gaagccgtcc aaaaccttca aaagcagtaa  16380
gtcctgctgc tatgccatat tcaaatattc aactccaaaa aaaaaaaaaa aaaaaatcaa  16440
aaatccgctt ttcagcgaaa atataggaaa taatccaaga atcgaaatcg aaataaagtc  16500
atgatgcaag tttggagagc tgaagttaca ctatatcgga gtacttactc aaatgttgat  16560
tagtactccg tgcgtttgaa gtaaagtcac atatggagta gttccaagct aggttgtaca  16620
gtgacggata aggatactgg gttgaaaagg tgaacgtcga gatttatacg tgtatttatt  16680
taaacaggat acgtatcata ttgggttctc atacgcgtac cagctgtgac ttagaaaaat  16740
taaccacgct atataggttc caagccctca tgattacctt ttcatagtgt aaatttcatg  16800
tagttgaatg gtgggaatcc aatcacaaaa acactgcagg taatggaaat gttccaactt  16860
tttccaagca ttttaaaata agacatgtga ttactaatta gggcgtgttc ggcaacagta  16920
attgtggtga tagtttttag ctgtgagagt agttgttagc tgtgctatta gcttttagtg  16980
gttggtgtgt agctgttagc tgttagatgt ccaagtagcg gtgtaaaata ttgatgttcg  17040
gtaaaagaag ctgtcaaagt agctgtctaa gaataactag ttaaaaattc aaataaaact  17100
ttaacatata atttatacac cactaaaagc tacccaaaag ctacaaattg tagcttttga  17160
caaacactac taaaacacta cttgtaccac taaaagctac ttacaccact atcttgccaa  17220
acactcttat tttttctaat tagtgttttg acctagtcaa gacactaaaa gctacttaaa  17280
aagcttgtgc cgaacatgcc aattctgaac caaggaacaa actataacaa aaaagtgcta  17340
tgtgaaactt ttgtaggcaa cagaagtaag gcatttttgg aatgtactaa caaatccgta  17400
ttaagacttg tacatgaaaa ttaccgtggt aacatttacc cacacttcct cattcacgta  17460
ctccgattca ttcttataag ggcataaccg cataaggcac atcaagatcc atgtatctaa  17520
tagtttaatt tgcctctgtg tttctgtatt aacaatgagc atagtgagtg caaaagccat  17580
ggaagctaga ttaaaaaggc catcattcta agttagacaa ttggaaacaa catcgagata  17640
cacgtacaca taagggctgc tcttctctat tactccctct gttcctaatc atttgctttt  17700
ttagcgggtt ccaaaggcct atgtttgacc actaatatat ttaaattaaa actggtgata  17760
tatattaaaa gaaaattatg atgaatttaa caaaaaccat atatgttatg tcctttttttt  17820
tcctatatta atgaattttt acagtcaaag ttggtgaact ttgacccaaa aaaagaaatg  17880
gagcaaaaaa aaaaaaaaaa aaaaaaaact agggacaatg agtaacattt ttatctatgt  17940
ctttttaata tgaatatacg taacaaattc tgcaaaaata gagatagcaa ctaataacac  18000
gcatgaaaat gacaagttat attatacctt tttttctcaa tatatgaata tacgtaacaa  18060
attaactcca gtagttttta gtaaaactat tagattattg tgtaacatat actctggaaa  18120
tagtactaag atccattaca atctttattg agaaatttcc tcatgtaccc cctgaggttt  18180
ggcgtaattt ccaaataccc ctcatatttg aggaatttct caaataccct gatgtttttg  18240
tttagactca aaataccttt actatggaca gtaccctaat gtcattaagt tttccccttc  18300
tctctcccca attttctctc tcctcccatt cccccaccca ctacccactg cccactgcca  18360
agtaggggtg taagtggatt ggactggatt ggactttgcc aaattcaaat ccagtccaaa  18420
gttttttgga ctcgagaaat tgagtccaag tccgatccaa atattttttg agtccagtcc  18480
aatctagtcc gataattttt tcttgagtcc gaatccagtc cagtccagtc cgattattat  18540
atcttttttc ccgatttagg ttcaatgatt cacaacattt tttgagatgc ttgagcattt  18600
gacatctgat tcaattatca atatccacaa ataagattga aagcttaaat taaagtaaaa  18660
tactatgaat aaaaagttga attagatgct taccttgatc taagttgaga ggaagcatag  18720
agactgagaa ttaatctgag ggacaaatag agaatgcgag agtcgagaca gtgaggtaga  18780
aagaaaatga agagtaagag gaagtgagta ttaaggactg aggagtaaag taagatagaa  18840
ttagttggct actagcctac taatgcagta ttgctagtat aatttactta tttaacaaat  18900
ggagctaagt gcaatagttt agcgccaatt gacatattta gagagagaag gctgaaaaat  18960
ccaatatttt taaaatagta tcattatttt taatatatac attatatata aaaatatttt  19020
tggactggac tggacatatt ggactccaaa gggatgagtc caaatccaga caaaaaatat  19080
ttggacttga aaatttaagt ccgagtccag tccgaaaaat tttcagtcca atccagtccg  19140
acaaatttgg actggactgg attggactct gaacttttcg tagtccgctt acacccctac  19200
tgccaagtgc caaactgcca accccctttt ggttgagttg atatttgacg caaagacttg  19260
gcgtgttgga aggttcatta cacattttat ccaagtcaac tttgaagtct tcttagctag  19320
agactagagt gaacgtgttg gaaggttcat tacacatttt atccaatcaa actttgaagt  19380
```

```
cttcttagct agagactaga gtgaacgtgt tggaaggttc atgttcatga cattataaaa  19440
gtaataatag tgaaatttca caaagtattt ataaacccag gacagactca agagctctac  19500
ttattattag tgaaaaacaa acatacacac gacaataaca caacataaac aataatgaac  19560
atgaaaatcc tccttttgtt tgtcttcctt catcacctcc actacttcat ccatggcaga  19620
acacttacag aacgccaagc tttactaagt atcaaatctg ccattactta tgattattat  19680
aactctctct cctcatggaa aaacacaaca caccactgca gttggccata catcacttgc  19740
tcctcctctt cttcttcttc ttctgttatt tctctcaact tcaccatgtt atttctcgaa  19800
ggaattctct cccctgatat aggcttcctc accaacctgc aaaacctctc tattcgatct  19860
aacctttttt ctggcccact cccccattct ctctctctcc tcacccaact ccgctatctc  19920
gacgtttccc aaaacagttt cacaggtcca atccca                           19956

SEQ ID NO: 75          moltype = DNA  length = 19206
FEATURE                Location/Qualifiers
source                 1..19206
                       mol_type = unassigned DNA
                       organism = Beta vulgaris
SEQUENCE: 75
ccaacaattt gttagccgat gaagagcatc aaaaccaaaa aaaacaaaaa aaattgatta  60
atatgcatga gtgtgacctt gttttccaaa gtttagcatt actattagtg tctcaattca  120
taataataaa aaaattagct tgttcaagat ttgtattttt attcaaagat ttttttgtc  180
tcttgtgctt cttttatctt atatatattt tttgtatggt ttgtttttgt ttaatattag  240
tccctccgct caaaatgatc tttcacgctt gagattggca ttaaggtcaa gagatgttgc  300
taagctttag aataaaaaaa ttccaaatgc atagagggaa agaaagcgag acaaaatgtt  360
ggagaaggca gagtaaatga tgtgatggag gataaatagt agaagtgtga taccgaaagt  420
ttgaaaataa taaggaattt tatttcttgc tggcactttg ttctagtaca ggtttttagc  480
ccttcaaaat gtttataatg tagagtcaaa attaatatcc ttaactagtt tttaagtccg  540
ggttatatcc tagatattaa taatattcat ttattagtaa cattttattt tataaatata  600
atactaagca ttatttggtt tgctggttaa gactttagtg tatatctatt tctttttttt  660
tttattgtat gcgtgtttac ataaactaaa gactataagg gatagtacca cgtggcgcag  720
ttccttgctt aggaacgtct tttaatatat taactagtat ttgggcccgg gcgttgctcc  780
gggttggtat tgtgtttccg aacatgatgt gcagtttttc ccattcccac taaaatatat  840
aaaggaaaac tcaacattta aaagatacaa atataataat atggacactt aaaacatgat  900
taaaagttga ttgagatggt aattgtgtca tgttataata gtaagaggtt gcctaattga  960
ggttgaggtg gtggagtagt ggtatcgctt cccatctgtt atccctgagg tataaggatc  1020
aaacctcata ggactcattt gagtaatttc ccatatcctc ctctcaaatg agtccttttc  1080
atctgacaaa aaaaaagagt ctaattttaa attaaaatta gacgatcttt tataaaatcg  1140
gcactttctg cacataggtc acaatttttt tgtttctatc tctctgcttt ctttaatttc  1200
acagtctcca actctccatc aacatcttac ttattttaga atagatgatg tatggtagta  1260
ttaaatggta aagtactaaa gctcctataa tacacagaag cttacatagt atagattcgt  1320
acatgagaca aggttacaat atactttctc cgttcttttt atattacaat aattactatt  1380
ttaagtagtt tcacatctat tgtaacaatt ccaattttgt tatagaaagc aactttaata  1440
attgacaata ttgcccttac tttatcttat taaaaccatc attaattact cactttctct  1500
tataaaattg cttttatttt ctaaggatga tttctctcct attctagtta attaaagagt  1560
tacttttgtg ctaaactgct catttattcc aaatccttaa aaattgtgtc caaacgtatt  1620
gttgtaatat aaaaagaaca gaggtactat tagtttgaat aaattttgat cagattaggt  1680
cacctttagg gggcgtttgg ttaggggtat tctggaaagg gtaagggaat caacttactt  1740
aattccctta cttgttgttt gtttgctcaa tttaatgatt ccctttaccc accccttact  1800
cccaaagtcc tttactctca ttctccccac cccccaaggt ttcacttacc ctttcttgat  1860
tcatcattga ccatatcttt gaccacccaa ctaccaccac cacttgacca cctaatcacc  1920
taaccaccta attacccaac cactattacc acccaacccc tccacctgcc caccaatcgg  1980
caccataact gcccaaccgt cgcccaatca agccacccaa ccggcaccat aaccgcccaa  2040
ccaagccacc caaccggcac cagaaattgt accaagctac ccacacacgt gaaaaccacc  2100
cacccacaag ccctagaaaa aatggaagaa tcgagagaaa gggaggggag agaaaagatg  2160
cagcgactag aaggggaggg ggaggatgtg acggcaaggg gagagggaac ttcgcagcgg  2220
caaagggagg ggaaacgtcg cgtcggcaaa gggctaaggt ggaattgacg gggttgcagc  2280
aacaagggga gggcatggag acgtcgtaac cgcaaggggga ggggcagcgg cagtggaact  2340
ggggtggaga ggggtagtgg cggcactagg gtgtgggaga ggtggcgggg gatatcaaga  2400
gagggggat atggtggtgt tatggtggaa gcaagaagaa gaaagaggaa agacaatgta  2460
ctaaccaaac aacacattaa atctaagggt tttggtttcc tttccccatc taccccttc  2520
ttgattccat tccctttacc cctttacaac caaactcccc cttagttttt actacttata  2580
accttcaatt ttggctgttt tttgtgacat tttttacttc tccgagcctg gtcatatttt  2640
ctcccgaaac atttcgagga aagtcgaagt gacttgtgaa gttgtgcggg tgcttggcac  2700
catttgtgtt gcctcgaaaa gcatctgaat accccattta ttcctttctc ctgaaaccca  2760
aaattacctc gcaataaacg aaaagatatc catatatttg ttccaagcca catgactcct  2820
ttccaacgac ctcccatgtg accatgtcct tagaaggcat cccgtggcgt tcgaagctcg  2880
gacccccgga aagtccgaaa gtgtgtatta taactttcaa ttttggctgt ttttgggata  2940
ttttttactt cttcgggcct tgtcatattt tctctcgaaa cattcatagg attgtcaatg  3000
tgacttgtaa gttgtaacgt tgcacgggtg cttggcacaa tttgcattgc ctcgaaaagc  3060
ctctgaacac cccatttgtt catttctcgt gaaatccaaa attgcctcga aaaaaacgta  3120
aaggcatcca catattcgtt ccaagccaca taactcattt ccaatgacct cccatagagt  3180
ccgtagctcg gaccccagga aagtccaaaa acgtgtacta taaccttcaa ttttggctgt  3240
ttttgggaca tgtttggact tcaccggcct ggtcatatta tcttccgaag cattcctaca  3300
aaatccgacg agactagtaa cgttgttacg cgggtgcttg acaccatatg tgttgcctta  3360
gaaagccttt aaacacccca tttgttcatt tttcgtgaaa cccaaaattg tcccgaaatg  3420
aacataaatg catccatgta ttcgttgcaa gccacatgat ttctttccaa tgacctccca  3480
tatccttagg aggcatgcat catgtggcgt tcggcgagcg ggtctcggga aagtccgaaa  3540
gcctgtgtta taaccttcaa ttttggctat ttttgggaca tttttggcct ttttcaagcg  3600
tgttcatatt ttctcccgaa gcattcctag gttaggcgat gtgacttgta aagcgtgggt  3660
acttggcacc attttctttg cctcgaaaag tctttgagca ccacatttgt tcatttctcg  3720
```

-continued

```
tgaaattcaa aattgcctcg aaatgaacgt aaagacattc acatattcat tccaagccac  3780
acatgactcc tttccaatga cctcccaagc ccctaggagt cgtcccgtgg cgttcggatc  3840
cggagctcgg gcccccgaga atgtccgaaa ccgtgtatta tgaccttcaa tttttgctgt  3900
ttttggaaca ttttttgact tctctgggct ggtcatattt tctcccgaaa catttgtagg  3960
actaccgacg tgacttgtaa tgttgcgtgg gtgcttggca caatttgcat tgcctcgaaa  4020
aacctttaaa caccgcattt gttcatttct cgtgacaccc aaaactgcct cgaaatgaac  4080
gtaaaggcat ccatatattc gtttcatgcc acatgactcc tttccactga cctcccatgt  4140
ccctagaaag caccccatat ccgaaagctt gtattataac cttcaatttt ggctgttttt  4200
gggacacttg gactttttcg gttcgttcat attttctctc gaaatgttcc tagaaaaggt  4260
gacgtgagtt gtaacgttgc gcgggtacat ggaaccattt gccttgcctc gaaaaacctc  4320
tgaacaccgc atttgttcat ttctcgtgaa actcataatt acctcaaaat gaacgtaaat  4380
gcatccatat attttttcca agccacttga ctcttatcca atgacattct atgtccttag  4440
aaggcactgc ttgtcgtcca taattcgggc cagggaaatg tatgaaagtg tgtattataa  4500
ccttcaattt tggctgtttt tgagacaatt ttttacttct ccgggactgg tcatattttc  4560
tcccgaaaaa atacttcgag tgccgacgtg acttgtaacg tcgcgcggat gcttgacacc  4620
atttgtgtta cctcgaaaag cctttgaaca ccacatttgt tcatttctcg tgaaacccaa  4680
aattgcctcg aaatgaacgt aaaggcatcc acatatttgt tccaagccac atgactcatt  4740
tccaattctc tcccatgtcc ctaggaggca tcccgtggcg ttcggagctc ggaccctggg  4800
aaagtccgaa agcgtgtatt ataaccttca attttggctg tttttgggtc atttttgac  4860
gtctcttggc ttggtcatat tttgtgccga aacattccca ggattgccga cttgacttgt  4920
aacattgctc gagtgcttgg cacaatttgc attgcctcaa aaagactcta aacaccccat  4980
ttgttcattt ctcgggaaac ccaaaattac ctcgaaatga acgtaaaggc atccacatat  5040
tcgttccatg ccacatgact cttttccaat gacctcccat gtccctagga ggcatcccat  5100
ggcattcgga gctcgaacac tgggaaagtc cgaaagcgtg tattgtaacc ttcaattttg  5160
gttgtttgtg ggacattttt gggcttctcc gggcctggcc atatttctc ccgaaacgtt  5220
ccttggaaag ccgaagtgag ttgtaacatt gcacgggtgt ttggcaccat tagtgttgcc  5280
tcgaaaagcc tttaaccaac ccatttgttc atttctcgtg aaacctaaaa ctgcctcgaa  5340
atgaacgtaa atgcatccac atattcgttc caagccacat gactcctttc caatgacctt  5400
ccaggcccct aggagtcatc ttgtggcgtt tggagctcag tccccggtaa agtctgaaag  5460
cgtgtattat aaccttcaat tttggttgtt tttaagacat tatttgactt ctccgggact  5520
gggcatatta tctcccgaaa cattactagg agtgccgacg tgacttgtaa cgccgcgtgg  5580
gtgcttggcg caattgtgtt gcctcgaaaa gccattgaac acccccattt gttcatttct  5640
cgagaaaccc aaaattgcct cgaaatgaat gtaaaggcat cgacatattc attccaagcc  5700
acatggctca tttccaatga cctcccatat ccctaggtgt acaccccatt tgtctgatgt  5760
tataatagca agaggtcacg ggttcaaatc ttgttacaag ctaattttac ttttgttaat  5820
tgacatgact tatgtacaca ttggacaatt atagtggagt aacaaaggtg acatgtgacg  5880
cgtatacatt atcacacacg tcttttaata tatttgtata gatctagatt taagagtaat  5940
ttttttaatg cgcaatactt ggccaatttc ttctgtatca aatcataggt ctttggttgg  6000
ttcataagag taaagaccaa aataataatc tgaactgcaa aaattttctc caagagttaa  6060
aagtttgtat aagttagatt aaaaaaatta atgacatatg atgtagttgg acattaaata  6120
tgtaagttta gaagtaattg tgttaacata aaaaaagatt cgattataac ataaaaacta  6180
aagaaacaca aaggcgccgt acaacaatca atattaccca agtcccctca ttaatattaa  6240
gggatgacct agctcgtaca tatttaatta tctttgaaaa ttcgttgttc agacttgcta  6300
gttgctattc tatatttgta tattcattaa tcaatttttc aatatgtgag catttacatt  6360
ttaaactaga gcaaatattg tctcttttac tattttgttg ttgtcaaatt ttcaaaaata  6420
aattgctcaa atacttttcc tagtgacata aaaaatagag caaataatca aacagtagca  6480
gacccaggaa cttttacata atgtagacgg cataatgtgt taatttttgc ttctttttc  6540
taatatcatc caataacaca attctgcttc tattagtttg tagtttcaga tgatgatacc  6600
caaacaataa gaccaagcaa caaattgata agattttgct tctctttctt ccacttggtg  6660
taactgtaac agctttgaag tttaacttca gtaatcagtt gcatatttgg catatgatca  6720
aaacaatcaa attattatgt atggaaaagc aaaaaacttc caggtttcca tctgaacaag  6780
gaggccaaga gggtggaagc aagcaaggat atatgatcat aaaatcctat gaatatgatg  6840
tacaaacctt ttctactgca attaggtaac ctaaatgata ccacctagga acagcaacaa  6900
cttatttaca gcactaaacc taaatcaggt taaagttaat cagaccacca tgtatctggg  6960
tggtctctcg agggaaagcg tctccatctg tatccgggta acagaggttt cttcttctcg  7020
atcctccttg gcttctgccc tcttaagttc ttcgaaggct ctcttggcat atacagtaaa  7080
cgcaacaatg gtaattattg ccactatgaa tgaaataaca ttgtacacaa tctccaccca  7140
tgttagatga tgattcccat acttgacatc tgcgaacgtc cttatcagtc tcccactgca  7200
aatgaatgct atcagcgtca atattcagaa taccaactca tttaactatt gaattgccaa  7260
aaacagatat ctttgaccat atatttgtta ctaaaaataa cgattgataa tgtgaaacta  7320
tcactgatag atttaaaaga acttttataa aagtatagtt tctctaatgt ataactgcag  7380
aaaatagaat ggggtagaca aatgaagtaa ttgttttgaa gaatgcaaaa ggtcaattca  7440
gtaatacttt tatacgtgat tgggggaagc attaaaaatc ccttctaaga taaagatgac  7500
ctcattggca atggaatcga catccacaga cccttgcatt agaacagagt ggaagtttct  7560
gtgaacttac gtgtagatgt aaagaaaagc ttctggcacc atccctgcaa ttgatcccca  7620
tagataaggc caaaacgtca tacttgtcac cacaactgcg tagttgaaga tagtataggg  7680
aaatggtgaa accctaaaga gtgccaccac gcggaactga tgaaaccagc taccttcggc  7740
agcaagccta agcatagcag ccttatccgg ccatctttgc aaccattgct aacaaggtac  7800
aaaaacataa acattgtgga cttaattaga caagaaagtt aaattaaaat caacattaga  7860
taatcaataa atcaaatgta agcagggaac atatttctta catggattct atcccggaag  7920
agcaatccaa gtaaataggg aagaatcatt ccaatagtag ttccaaccat gattatcaca  7980
aaaccaagac cataaccaaa gatcatgcct gcaagccaca tggatgggcc agaaggaatc  8040
agaaatacag ggaagattgc tagggaagta acaaggacca cagcaagaac cggacggcca  8100
aaggcagtgg cttcccattg catcattgga acaagaacct gcagagaaag taccaaaaac  8160
tttgaggcaa aaatttcctg cttgtatatt gcaaaaagta gtacagcgaa ggcattccgt  8220
gcagaatggc ttatagattg gaaatacgga gaacaatgca actataagca caggcccatc  8280
tcttgacttt tgggacaata acatggaccc ccagattgat ttataagttc tcacaccata  8340
gctagatttt gttggaactt tcataaatca tagtgacata agtatagcat aatattcatg  8400
ccttcgacag aagttttcgc atatggtaag gctactattg aaaaaattcc cttgtgtttg  8460
```

```
aagtacgcat aaaaatatct agtggcagtc aaccaaataa aacattctag gagtccctca  8520
aaaaattaaa gagtcatcag ttcagaagac tttaatatca atactttcta ttatccgggt  8580
ttggcatgca gtaaatttca tgagaaaagg aaaaatcagc tatttgatta tataaggaac  8640
taattcggat gtatcactaa gctttccatc gactggaaca tcgggagcta gtctccaata  8700
ctcgtcaagg atctaacata aacatcttct ccgcaatcaa aaagccaagg tcacatacat  8760
ctaggcctct gtctcattct gatggcatgg tatgatgcaa gttagacaac actattattt  8820
ggcagatgac acttaggggt ctaatattta agctcattca agataatcaa gtaatcaagt  8880
tcaatctcaa ggtttcagtt gcgctaaaaa atgtaatact tggctcattc agaattagtt  8940
tgttgaagct ggttggtatt tgcttcattt gttaatggaa ccaggctcat aaacaagctt  9000
tcattaggct aaacttattt aacaaaatca aaagcttaat actataattt ttgataggat  9060
ttcttttggg cagttataca tgagtaatga acaagctcta cacaatcttt tttaatgaac  9120
aagctttaat cgagctaggg tacgttctat tcaacttatt ggacctgaac ttattggaac  9180
ttatctgaac tgaacttatt gaacctgaac tgaacttatt ggaacttatt aaacctgatt  9240
ggacctgatt caacttattg gacctgattg aacctgattg gaacttattg gacctgattg  9300
aacctgattg accttattgg accttattgg aacttattga ccctgattga aacttattag  9360
accttattgg acctgattga aacttattag accttattga acctgattga aacttatttg  9420
accttattag acaaaaacat tattattatt attgttatta ttattattat tattattatt  9480
attattatta ttattattat tattattatt attattgtta acctgattga taacatttat  9540
atctttcata gttattagta acgaaaacat gttatctcta gttattcaaa gacgaattgc  9600
aaaatattgt aataataata ataataatat attattatta ttattattgt taaccttaat  9660
tatttgacca tgattataat attattcaat agcaatatga ataatcaaat aatagacaat  9720
aatacaagta taatactata cattgtggta ctttaataaa aaaattctaa taataacata  9780
atcagctaat agtaatatga ataataaaat aatagacata atacaaataa ataataaaat  9840
aatagacata atacagataa ataataaaat aatttacact aatacaagta taatactata  9900
taatcattgt ggtactttaa ttaaaattct aataataaca taatccgcta atagtgatat  9960
gaaattatga ataacaaaat agtggacaat aatacaaatg tttattaaac attgactatt  10020
tggaccttat tggaccttat tagacctgat tggaacttat tggaccttat tagacctgat  10080
tggaacttat tgcacctgat tggaacttat tacacctgat tggaacttat tgcacctgat  10140
tggaacttat tgcacctgat tggaacttat tgcacttatt agaccttatt gcaacttatc  10200
tgaacttatc tgaacttatt ggacctgaaa cttaattttt taagttgaac agaacgcacc  10260
cctagtatcc acgaacatag ttagttgttc atcgacaagg gtgttaattc cttgactata  10320
aaaaaaatat ctgctaatat gtcctccata ccatgtcttg atctgattcc caaaatcacg  10380
tgttttcgtg tctggtgacc acgttgctag acatggaaga caggtctaat tgttcagttt  10440
caagtcaggt tgattaaaca tatgttagca atatacaatc attattagtc aaactaattc  10500
aactcgggtt tggtttgatt caggttatgt cgaggatcag gtccaaatcg ggttaatcct  10560
tccaggtcaa atatatctaa gtctgttttg ccaaagtcta ctttttgtat ccgtgtccat  10620
gctaaatgac aaacaaaaag cagcttttac caagctcgaa tcagatttgt tcgcttaaag  10680
agtcacttcg ctcatttaca gcaacaatta aaggacaaaa cattgtccat tcaactactt  10740
acggatatta acttattggc aactgctagc gtaataaggc aatcaacagc actcggcctc  10800
aataatgaac ctacaaggag tccaatgacc aatacaaatt atcactggca tcatctagca  10860
cgacaatctc ttaactctaa gagtctaagt gccttgacat acaaaagtat tccttttaaa  10920
agtacccccg tgtggatatt ctgccaagca aatgcaatcg atacacccaa ttagggcttt  10980
tccattatga gtcctcagag cctcagattg taaaacaggt cagtaaaaga ggaaaatagt  11040
atttgattct tttgctaaac ccttggatat aagaatggtg acttgtattg tcacgccaag  11100
cttctttcat aaaagctgat catattatta tatgagagtt ctgagtttca aggtccgcat  11160
tcgatctaac tagacatcac ttccaattaa agttgagaaa cgaaactagg tgtcctcttt  11220
gtttcccaaa ggtgaacttt agatacttat tataagcata ttttgttatg aatcgggcta  11280
aggagagggc tactcttggt attgcataat tagttaatta cttagtagta gcttgaggaa  11340
taaggaagca agtaagttag aggaaagagt atgaaaatct gctataaagt gaggagagga  11400
gggatagaag gataatcaca aaattattga gttaactttg gttttagttg cttaggttgg  11460
gagtgtccag ccactcgaat gtcttgggac tgtaaacacc attgttcatg atctaattgc  11520
atcaatatta caattaactc atttctcttc ttatccatat tcatcttctt acaatcacaa  11580
ctatttccag atcatccatc caaatcttca tccacttgcc ttagtttcta ctccagattt  11640
cagtctatta caaattgatt tctacaatat gtcaattcat cacaaattat catgttttct  11700
gaacaaaagt tcactgtttc aggacaaata cagaaagaac tactttgatg cttagaacag  11760
atatattgta aaattgtatt cggaatttgg gatacaactg gagaagatat gaataaatag  11820
gcattcaggg agctcagaaa aacagaccgt gccatatggt gctctgctgc ataacaggaa  11880
ataatggata aagtatgaat aacgttataa cttcttaaaa acctagatga caagtatttt  11940
ggttgctttt tattattggt aggcaaggag aatactcaac aacagtttag ccttaaactg  12000
cttcttattt ctcctcttcc cctttttcct gatgatttgg ggttgtcact cagttctttt  12060
acctctcatt tccaggtact ttagagttat attacacaaa ggattgcaag agaagaacag  12120
gtcgccctgg catgcactca gaaagtatac gacccttcac aggaaatgtg gtgctccaag  12180
acttatatct caggctctca tgagtcatgt caaggaccat ctttaatcat ttgtattcta  12240
ggtttctcag gcgatgcggt gtgctggtgt gtctctccct cccacttgag tgtgtgtatt  12300
gtttgtgccc ctaagttttt atcttaacaa tcactactag tcaattagtc attaccaacc  12360
ctacccacct ctcttgttac tgttgttctt ggagatattt catatatgtc agcttagaac  12420
ttatattacg tttcttatta catattctct taagctcgcg cacatactct gtgatcgaag  12480
ggatccatat tagttatctt ttagtggagt tgttgtgaaa aaagactgca tagaaaaatt  12540
aagatagctc atagttgtaa atgtaattga acttttagat tgatagcctt gaggctgctt  12600
gcattgaacc aaccaaattc agccaggcta gtctatgcct ctttggtgtc acctggtagg  12660
ttgaatttgt gtagctgtag ttctacaaga gactgattta aaaatgtttt cgcactgaaa  12720
cagcttaaac cacaaaacag gaaagtgcag aacaaactcc agaaaatggt gcagaacata  12780
ccttctcaaa aaggaaagga actccccatt ttaacagtac gaggacaact gctacagcac  12840
taatggagga gatcaagatt ttgatccacc agatgaagga ttctgatctt gtttcagcct  12900
gagaatgtaa ggttgaagct tcaggcctct ttgtaatagc agatgtcacc agactaacaa  12960
attcactgtc gtcttgcata gcaggcccaa catctatgtc atgcttagtt agctccattg  13020
aatttggcat ctccaagaga tctcaagagc tgcccaaaaa gacggtacaa tattatgagc  13080
atacatgaca tgatgacaac ccataaagaa tatcataacc tgtcacattt tttattcaaa  13140
gttcaacagc cctcttacaa catgattgag aatggagggg aagagagaga gagttggtct  13200
```

-continued

```
cagacattga tcacataatc atttcaatta gttttaaagg tgctcatgaa atagaactag  13260
tgtcttaagc tggagacttc tgtatttttc atggttttag attatcaatc atattcttag  13320
aatctttgat ctctagaact ctttcctttc ctcccaatat tttttccact ttgtcttttg  13380
ttaattacgg cttcgctgca ggcctgcaat aaatctttta aatttttaca gatactatgt  13440
agagttgtat acataagctc taatctgaag acgattggtt tcgatgctag ttaatacaaa  13500
taaatatatt atggatataa tatgcagtaa attgggccat gggcaccagg gacaacttag  13560
acaagtatag tgcaactacc aggaaattta agctgggtac ctctgattca tcatgctggt  13620
tgataatatt attgcttcca caagtgttcg ctacggctca accaaactaa gtcacaactc  13680
acaagctgca caacccaact gacaattatc gcctattgtc taagctatac attacattac  13740
cccaatgcca caacgtggct cacgcctagg catggtaagg aagttcagat gtacgcagcc  13800
ttaccctttt aataacaaag aggctgtttc caggtgaccc ttaaatctta attgcaaaca  13860
ccatctgctg cttcacataa ataagcgact tcaaaattgt aaattaaaga atttgaatgc  13920
aaattgtgtg aaaaacaact ccatcaagaa tccattaagc acgctttact attagtatca  13980
ataataggaa acccttatat ccccttttgac gaaggcacac atgcaacact aatgtgtcct  14040
tataaacttc atgaaagtat atctctacga aacccttta gtcttatgtg attctttaag  14100
tgtccaactg atgattggtt acaaggtatt tagcccaaag tagcatttca gagagatggt  14160
gtagaatgag tagcttataa accgaggttg aggtgtaatc ctaataaatt aggaactaat  14220
accacaagag agatggacat gtagagatac aatatagtac agaataagat tatttgaaat  14280
ctttttacca gggaaactcc agaggtgttc cataaaacac aataccatat aactgggaga  14340
tcaatatttt agattaaaaa atataaaaat ctatttgggt tgagtatata gttggttagt  14400
ccaataatat ataaatttat aaggtggagg tcttcggtat atgacattcc aaatttgagt  14460
atcaaatgat atatatggtt ttccatactt gaatcccttt tcatgtacta cctctgtttc  14520
aaattaatag ttacacttac acttttcacg catgccaatg cagaactttg aggacatata  14580
tctttagttt tgtatttgta aaaattataa aaagtacata ttaataaaat acatattaat  14640
acgaatctaa caagatccca catgactatg attttattca cgtataaatc acaaacgagg  14700
gtcaaaatgc aattgtgaat agtgtaaaat gtcaaagtgt aactattaat ttgaaacgga  14760
ggtagtatgt gtttatgcaa cacttttcct ttttcccttt ttgctattta gtaatttatg  14820
taaaatactt ccattgaccc aaaagttggg tgattatagt ttacatctat cattattatt  14880
tatcattact atagattatt caccattgta atcaacttta taaaagtata cacaggtaac  14940
tcaggagtca ggggtgctgg gccaaacact tttatagttt aaggtgaaaa atctcgagaa  15000
tcttctcctg ccacgcaaaa tgagtgttct tccactttaa agatgttata acacttatct  15060
taacctacta ttcgtaaata acacttatct taacctacta ttcgtcaaga catacttgct  15120
tcatctcact aagaacgtct tagttttcat ttgaaattcg taccagaaag attcacttca  15180
aatctattta tttttagata aattgttatt aaaaacgacg aagaaacgtc agaggacaac  15240
aaatcctcta aactccaaat tataagtgag tccaactatg ttgacgtaag gtaattagag  15300
tatccataaa agccctggcc gctttggccc acaaagcagc ttagaatact acccaacccc  15360
aaatataatc aatcaggtga ggaagctcgc aacagatgcg agagttccac tccaatcaaa  15420
ggcaccagaa catagccatc gacatcttct cttctttacc cccttgaaa ccaacagatc  15480
ttaaggaagt ccactagtga acaaggacat aaccactact catgtggaat gccaatcagc  15540
ctctgtcaaa gggaagtcca ttagtgaaca aggacatacc cactgctcaa ggtagtcatg  15600
tggaaattgg aatcccaatc agcctttgtc aaaaggaata agccacatcg caatgaagaa  15660
aaaggtgcaa accagattta ttgcatctcc aacacgacat aaatatcgag aatgaggcct  15720
ttactgacaa aggaactctg gatttccaat ttccactgag cattggactc agttgagaag  15780
taattggtct tgctagattc tgtttacgca catactctta atgataaata aatgtaacag  15840
gccaattggt ctggaaaaaa acagttgata aaaggctagt ttgggccttg gggataaata  15900
taatctggta tgagttaata aatttctgtt taaggtaaag agaatgtgtt atgtgggata  15960
atttaatcaa gaaaatctta gtaagatgga ggtagtctaa cttccattcc tcaaaatgtg  16020
taattcctta taaaatcagt cagcctctag atacatagtt agcaaaaatg gaaggtatag  16080
aagtgggggt gagggaagag gaaggaaaga gaaccgcgat caatcatatt gttcgtgctc  16140
aagtttgagt tgtgcctata gctagttaga gtttgtctat ttcattgttt ttggtcagtg  16200
ttcatattct gagtgtcatc gtgtttgggt tctagaatgc tccttttcct aatgtcgaca  16260
tttctccact ttactctaga aaaatgatct cattgtagcc attccagctt caattttaat  16320
ggatactaag atccctttca ggaacaatgt taaggtagat gttagtgttt taacagccat  16380
gtggatgtta gtgtctagaa cgagtggtca aaacactact agcctcaaaa tattgtgatc  16440
agtctgaaaa ctctatgtta gatggttgct ttttttggta ggttcgcttg ttttgggggg  16500
ttagctttgt ttattttctt cacaatttgc ccttaaactt ttcacaaaat ctacaattga  16560
agattcttaa atagataaca gacgtgtcag ctacttcaac agctaattgt acgaaaaagt  16620
tcagctacct tgaaaccaaa ccactaacag ctagtacagt ttgtttctac tattacattt  16680
atctaatata acagctagta tttagtccaa cgatgtataa tatcaatgaa atggaactaa  16740
tctgtaaatt ggaccttagg cataagagtc gagttgagca ggtacactcc aatcaccaag  16800
ttatttaagc ttaaaatgtc taacttccaa tgctgtttga cgatactcat tgccaagtgt  16860
ttgttacaga tcaaccaagc aaataaagca acaagtgaac agctgcacta gtacccaact  16920
gcgaattttc gtcgattgcc aagtgcatgt ctgggacaca ataccatcat gtccataccc  16980
attaccttgc ttagccagct atcgtaatcc ataacacata aaaaccaaca aagtcttgat  17040
agtttcacaa atcaaaatgt tcacttttca ttccaaccaa aacaagcaat aaatctcttc  17100
atccatactc acaagaagaa caatctctca cactacccac ttgattagta aaaaccccaa  17160
tcaaaaacaa aatccaaccc acataaacaa atcaaattta gtaactaccc ataaactcaa  17220
aaacctcaaa tcacaatacc aataaaagag atatacaatc aatcaaaaaa aatacaacaa  17280
cagctaaaca aataacatca taaactaaag ttattcattt tatttcctaa ctagagatca  17340
attaagcagc ataaaacaac atcactaatt caagttaata atcatcaaat tctatactat  17400
aaaacataca taccttacca aaactaccca gctgaaaatt agggtagagc tccagaaatc  17460
ccggcgaaaa atccggtgag aaattcagct aaatttgaaa acttctttag gttaagtagt  17520
gtacacgatg aattgaagat ttttacaagc atatgaaaat ggtggttgaa attgaaatgg  17580
gggtttttga aaattgttgc gacgcgtaaa agtggaaaaa aaaaaggaga gaatcaaaga  17640
aatgagcaag tttttgtagg tgggtttact gttgttgctt ttgtttgtgc acattactga  17700
ctattcttaa ttcttccatg cgtgtggggg tgaaggaatt gtttcctaa gttgtttagc  17760
cacttcatag agtcattgga tttgaatat ctagggaata atgatcatgt gtttagtgta  17820
tctataaatt ataatttatg tatgtatatt gtatatgtgg tgaggcatag aggacaaggt  17880
ctaagaggaa tagaggattg tgagggagtg tttcatgctt ttaagaatga tgagtcattg  17940
```

```
agtgtattaa gttataagta gtatttgatc gagtagtaaa gtttgtatca cgtaaatcag  18000
agtgataatt aggaattggg atttgctcaa gtggtgagtt ttcccatctt tccgagcaag  18060
gtttctaggg ttcaattcct acctcaagca tttccttggg atttaagggg acggctcaga  18120
ggaattcttc ttaccaatat tttaaaaaaa aaaaaattaa gagtggtaat ttagttcaga  18180
tcctaccttt atccggttcg aaacgacttc aagaaaaaaa aatccgacat cgtttaaaat  18240
tttttacttc cgactcattt aatccgcctc caactttgaa acaagtagtc ttatttcttt  18300
tatgttaaga aaatttgcca aaaaaaccct ttttaaagtc cagttttgcg aaaaaaaaaa  18360
accttataaa gcattctttg tgaaaacaaa ccaaaaagta aattattttt gcaaaatgaa  18420
acctaatctc atttttcggt tttgaccatg gacttttcga cattgaccac ttctatttat  18480
cttcttcctc cataatcaca gcctagccac cactaccaac acctgccgct agccccccaca  18540
acctgcaccc ccacaacctc catccacccc ctcaagcggc aacccccctt attcccatac  18600
gcggcaaccc tacaccttat cctccacccc cctccgccct taccttttct cctctccctt  18660
cttccctcca tcacccctcc ccactctctt ctccctttgc cccccatcgt tgcaccaccc  18720
ataatccctc tctgtaaccc cctctcctcg cagctccccc tccctcccag ccaaggttga  18780
aaaattacag aggcagtcgc atatggggat gggggactat cgtctaaggg gtggagagag  18840
ggtttggggg ctgctggtgg gggtggggta ggctgaatgt ggtgggggct gagggtgggg  18900
ggtgaaggtg gggctgcagg tcgggctggc ggtatggaga aagaagggaa atagaagtgg  18960
ttaacaccgg aaagtccatg atcaacaccg aaaaatgaaa ttaggtttca tcttgcaaaa  19020
ataatttatt actttttgat ttgttttcgc aaagaatgct ttataaggtt ttttcgcata  19080
acatttagac ttttatcatc cctcttagat ttgacacata ttatacgaat tatactaaaa  19140
agactcctta tagtaattcg actaatgttt tattaaaatg aacctttaga ataactcggg  19200
taatat                                                            19206
```

```
SEQ ID NO: 76          moltype = DNA  length = 2000
FEATURE                Location/Qualifiers
source                 1..2000
                       mol_type = unassigned DNA
                       organism = Beta vulgaris
SEQUENCE: 76
tacgtaacaa attctgcaaa aatagagata gcaactaata acacgcatga aaatgacaag  60
ttatattata cctttttttc tcaatatatg aatatacgta acaaattaac tccagtagtt  120
tttagtaaaa ctattagatt attgtgtaac atatactctg gaaatagtac taagatccat  180
tacaatcttt attgagaaat ttcctcatgt acccccctgag gtttggcgta atttccaaat  240
acccctcata tttgaggaat ttctcaaata ccctgatgtt tttgtttaga ctcaaaatac  300
ctttactatg gacagtaccc taatgtcatt aagttttccc cttctctctc cccaattttc  360
tctctcctcc cattccccca cccactaccc actgcccact gccaagtagg ggtgtaagtg  420
gattggactg gattggactt tgccaaattc aaatccagtc caaagttttt tggactcgag  480
aaattgagtc caagtccgat ccaaatattt tttgagtcca gtccaatcta gtccgataat  540
tttttcttga gtccgaatcc agtccagtcc agtccgatta ttatatcttt tttcccgatt  600
taggttcaat gattcacaac attttttgag atgcttgagc atttgacatc tgattcaatt  660
atcaatatcc acaaataaga ttgaaagctt aaattaaagt aaaatactat gaataaaaag  720
ttgaattaga tgcttacctt gatctaagtt gagaggaagc atagagactg agaattaatc  780
tgagggacaa atagagaatg cgagagtcga gacagtgagg tagaaagaaa atgaagagta  840
agaggaagtg agtattaagg actgaggagt aaagtaagat agaattagtt ggctactagc  900
ctactaatgc agtattgcta gtataattta cttatttaac aaatggagct aagtgcaata  960
gtttagcgcc aattgacata tttagagaga gaaggctgaa aaatccaata tttttaaaat  1020
agtatcatta tttttaatat atacattata tataaaaata tttttggact ggactggaca  1080
tattggactc caaagggatg agtccaaatc cagacaaaaa atatttggac ttgaaaattt  1140
aagtccgagt ccagtccgaa aaattttcag tccaatccag tccgacaaat ttggactgga  1200
ctggattgga ctctgaactt ttcgtagtcc gcttacaccc ctactgccaa gtgccaaact  1260
gccaaccccc ttttggttga gttgatattt gacgcaaaga cttggcgtgt tggaaggttc  1320
attacacatt ttatccaagt caactttgaa gtcttcttag ctagagacta gagtgaacgt  1380
gttggaaggt tcattacaca ttttatccaa tcaaactttg aagtcttctt agctagagac  1440
tagagtgaac gtgttggaag gttcatgttc atgacattat aaaagtaata atagtgaaat  1500
ttcacaaagt atttataaac ccaggacaga ctcaagagct ctacttatta ttagtgaaaa  1560
acaaacatac acacgacaat aacacaacat aaacaataat gaacatgaaa atcctccttt  1620
tgtttgtctt ccttcatcac ctccactact tcatccatgg cagaacactt acagaacgcc  1680
aagctttact aagtatcaaa tctgccatta cttatgatta ttataactct ctctcctcat  1740
ggaaaaacac aacacaccac tgcagttggc catacatcac ttgctcctcc tcttcttctt  1800
cttcttctgt tatttctctc aacttcacca tgttatttct cgaaggaatt ctctcccctg  1860
atataggctt cctcaccaac ctgcaaaacc tctctattcg atctaacctt ttttctggcc  1920
cactccccca ttctctctct ctcctcaccc aactccgcta tctcgacgtt tcccaaaaca  1980
gtttcacagg tccaatccca                                              2000
```

```
SEQ ID NO: 77          moltype = DNA  length = 2000
FEATURE                Location/Qualifiers
source                 1..2000
                       mol_type = unassigned DNA
                       organism = Beta vulgaris
SEQUENCE: 77
ccaacaattt gttagccgat gaagagcatc aaaaccaaaa aaaacaaaaa aaattgatta  60
atatgcatga gtgtgacctt gttttccaaa gtttagcatt actattagtg tctcaattca  120
taataataaa aaaattagct tgttcaagat ttgtattttt attcaaagat tttttttgtc  180
tcttgtgctt cttttatctt atatatattt tttgtatggt ttgtttttgt ttaatattag  240
tccctccgct caaaatgatc tttcacgctt gagattggca ttaaggtcaa gagatgttgc  300
taagctttag aataaaaaaa ttccaaatgc atagagggaa agaaagcgag acaaaatgtt  360
ggagaaggca gagtaaatga tgtgatggag gataaatagt agaagtgtga taccgaaagt  420
ttgaaaataa taaggaattt tatttcttgc tggcactttg ttctagtaca ggtttttagc  480
ccttcaaaat gtttataatg tagagtcaaa attaatatcc ttaactagtt tttaagtccg  540
```

```
ggttatatcc tagatattaa taatattcat ttattagtaa cattttattt tataaatata  600
atactaagca ttatttggtt tgctggttaa gactttagtg tatatctatt tcttttttt  660
tttattgtat gcgtgtttac ataaactaaa gactataagg gatagtacca cgtggcgcag  720
ttccttgctt aggaacgtct tttaatatat taactagtat ttgggcccgg gcgttgctcc  780
gggttggtat tgtgtttccg aacatgatgt gcagtttttc ccattcccac taaaatatat  840
aaaggaaaac tcaacattta aaagatacaa atataataat atggacactt aaaacatgat  900
taaaagttga ttgagatggt aattgtgtca tgttataata gtaagaggtt gcctaattga  960
ggttgaggtg gtggagtagt ggtatcgctt cccatctgtt atccctgagg tataaggatc  1020
aaacctcata ggactcattt gagtaatttc ccatatcctc ctctcaaatg agtccttttc  1080
atctgacaaa aaaaaagagt ctaattttaa attaaaatta gacgatcttt tataaaatcg  1140
gcactttctg cacataggtc acaatttttt tgtttctatc tctctgcttt ctttaatttc  1200
acagtctcca actctccatc aacatcttac ttattttaga atagatgatg tatggtagta  1260
ttaaatggta aagtactaaa gctcctataa tacacagaag cttacatagt atagattcgt  1320
acatgagaca aggttacaat atactttctc cgttcttttt atattacaat aattactatt  1380
ttaagtagtt tcacatctat tgtaacaatt ccaattttgt tatagaaagc aactttaata  1440
attgacaata ttgcccttac tttatcttat taaaaccatc attaattact cactttctct  1500
tataaaattg cttttatttt ctaaggatga tttctctcct attctagtta attaaagagt  1560
tacttttgtg ctaaactgct catttattcc aaatccttaa aaattgtgtc caaacgtatt  1620
gttgtaatat aaaaagaaca gaggtactat tagtttgaat aaattttgat cagattaggt  1680
cacctttagg gggcgtttgg ttaggggtat tctggaaagg gtaagggaat caacttactt  1740
aattccctta cttgttgttt gtttgctcaa tttaatgatt ccctttaccc accccttact  1800
cccaaagtcc tttactctca ttctccccac cccccaaggt ttcacttacc ctttcttgat  1860
tcatcattga ccatatcttt gaccacccaa ctaccaccac cacttgacca cctaatcacc  1920
taaccaccta attacccaac cactattacc acccaacccc tccacctgcc caccaatcgg  1980
caccataact gcccaaccgt                                                2000

SEQ ID NO: 78           moltype = DNA  length = 5488
FEATURE                 Location/Qualifiers
source                  1..5488
                        mol_type = other DNA
                        organism = synthetic construct
                        note = Codon-optimized LBcpf1
SEQUENCE: 78
aagcttatcg atgtcgacag gccttaaggg ccagatcccc cgggctgcag gaattcgatc  60
tggcacgaca ggtttcccga ctggaaagcg ggcagtgagc gcaacgcaat taatgtgagt  120
tagctcactc attaggcacc ccaggcttta cactttatgc ttccggctcg tatgttgtgt  180
ggaattgtga gcggataaca atttcacaca ggaaacagct atgacatgat tacgaattca  240
aaaattacgg atatgaatat aggcatatcc gtatccgaat tatccgtttg acagctagca  300
acgattgtac aattgcttct ttaaaaaagg aagaaagaaa gaaagaaaag aatcaacatc  360
agcgttaaca aacggccccg ttacggccca aacggtcata tagagtaacg gcgttaagcg  420
ttgaaagact cctatcgaaa tacgtaaccg caaacgtgtc atagtcagat cccctcttcc  480
ttcaccgcct caaacacaaa aataatcttc tacagcctat atatacaacc ccccttcta  540
tctctccttt ctcacaattc atcatctttc tttctctacc cccaatttta agaaatcctc  600
tcttctcctc ttcattttca aggtaaatct ctctctctct ctctctctct gttattcctt  660
gttttaatta ggtatgtatt attgctagtt tgttaatctg cttatcttat gtatgcctta  720
tgtgaatatc tttatcttgt tcatctcatc cgtttagaag ctataaattt gttgatttga  780
ctgtgtatct acacgtggtt atgtttatat ctaatcagat atgaatttct tcatattgtt  840
gcgtttgtgt gtaccaatcc gaaatcgttg attttttca tttaatcgtg tagctaattg  900
tacgtataca tatggatcta cgtatcaatt gttcatctgt ttgtgtttgt atgtatacag  960
atctgaaaac atcacttctc tcatctgatt gtgttgttac atacatagat atagatctgt  1020
tatatcattt tttttattaa ttgtgtatat atatatgtgc atagatctgg attacatgat  1080
tgtgattatt tacatgattt tgttatttac gtatgtatat atgtagatct ggactttttg  1140
gagttgttga cttgattgta tttgtgtgtg tatatgtgtg ttctgatctt gatatgttat  1200
gtatgtgcag cgaattcggc gcgccatggc tcctaagaag aagaggaagg ttagcaagct  1260
cgagaagttt accaactgct acagcctctc taagaccctc aggttcaagg ctatccctgt  1320
gggaaagacc caagagaata tcgacaacaa gaggctcctc gtcgaggatg agaagagagc  1380
tgaagattac aagggcgtga agaagctcct cgacaggtac tacctcagct tcatcaacga  1440
tgtgctccac agcatcaagc tcaagaacct caacaactac atcagcctct tccgtaagaa  1500
aaccaggacc gagaaagaga acaaagagct tgagaacctc gagatcaacc tccgtaaaga  1560
gatcgccaag gctttcaagg gaaacgaggg atacaagagc ctcttcaaga aggatattat  1620
cgagacaatc ctgcctgagt tcctggacga taaggatgag atcgctctcg tgaacagctt  1680
caacggattc actactgcct tcaccggatt cttcgacaac agggaaaaca tgttcagcga  1740
agaggccaag agcacctcta tcgctttcag atgcatcaac gagaacctca cgcgttacat  1800
cagcaacatg gacatcttcg agaaggtgga cgccatcttc gataagcacg aggtgcaaga  1860
aatcaaagag aagatcctca acagcgacta cgacgtcgag gacttttttg aaggggagtt  1920
cttcaacttc gttctcaccc aagagggcat cgacgtgtac aacgctatta tcggaggatt  1980
cgtgaccgag tctggggaga agattaaggg actcaacgag tacatcaacc tgtacaacca  2040
gaaaacgaag cagaagctcc cgaagttcaa gccgctctac aagcaggttc tctctgatcg  2100
tgagagcctc tcattttacg gtgagggtta cacctctgac gaggaagtgc ttgaggtttt  2160
ccgtaacacc ctcaacaaga acagcgagat cttctcgtcc atcaagaagt tggagaaact  2220
tttcaagaac ttcgacgagt acagcagcgc tgggatcttc gttaagaacg gacctgctat  2280
cagcaccatc agcaaggata ttttcggcga gtggaacgtg atcagggaca agtggaatgc  2340
tgagtacgat gacatccacc tcaagaagaa ggctgtcgtc actgagaagt acgaggatga  2400
caggcgtaag tcgttcaaga agatcggctc tttcagcctc gagcagcttc aagaatacgc  2460
tgatgctgat ctcagcgtgg tcgagaagct caaagagatc atcatccaga aggtcgacga  2520
gatctacaag gtgtacgggt cctctgagaa gttgttcgat gctgatttcg tcctcgagaa  2580
gagtctgaag aagaacgacg ctgtcgtcgc gatcatgaag gatttgctcg acagcgtgaa  2640
gtccttcgag aactatatca aggccttctt cggagagggc aaagagacta atagggacga  2700
gtctttctac ggggatttcg tgctcgctta cgatatcctc ctcaaggtgg accatatcta  2760
```

```
cgacgccatc agaaactacg tgacccagaa gccttacagc aaggacaagt tcaagttgta  2820
ctttcagaac ccgcagttca tgggcggatg ggacaaagac aaagagacag attacagggc  2880
caccatcctc aggtacgggt ctaagtacta cctggccatc atggacaaga aatacgccaa  2940
gtgcctccaa aagatcgaca aggatgacgt gaacgggaac tatgagaaga tcaactacaa  3000
gctccttccg ggaccgaaca agatgcttcc taaggtgttc ttcagcaaga aatggatggc  3060
ctactacaac ccgtctgagg acatccagaa aatctacaag aacgggacct tcaagaaagg  3120
cgacatgttc aacctcaacg actgccacaa gctcatcgat ttcttcaagg acagcatctc  3180
gcgttacccg aagtggtcta acgcttacga ctttaacttc agcgagacag aaaagtacaa  3240
ggatatcgcc gggttctacc gtgaggttga ggaacagggt tacaaggtta gcttcgagag  3300
cgcctccaag aaagaggttg acaagttggt cgaagagggc aagctctaca tgttccagat  3360
ctataacaag gacttctccg acaagagcca cggaactcct aacctccata cgatgtactt  3420
caagctgctt ttcgacgaga acaaccacgg gcagatcaga ctttctggtg gtgctgaact  3480
cttcatgcgt agggcctcac tcaagaaaga agagttggtt gttcacccgg ccaactctcc  3540
aatcgctaac aagaatcctg acaacccgaa aaagaccacc acgctgtctt acgacgtcta  3600
caaggacaaa aggttcagcg aggaccagta cgagcttcat atcccgatcg ctatcaacaa  3660
gtgcccgaag aacatcttca agatcaatac cgaggtgagg gtgctgctca agcacgatga  3720
taaccettac gtgatcggaa tcgatcgtgg tgagagaaac ctcctctaca tcgttgtggt  3780
ggacggaaag ggaaacatcg tcgagcagta cagcctgaac gagattatca acaatttcaa  3840
cggcatcagg atcaagaccg actaccactc actcctcgat aagaaagaaa aagagcgttt  3900
cgaggccagg cagaactgga cttctatcga aaacatcaaa gagttgaagg ccggctacat  3960
ctctcaggtg gtgcataaga tctgcgagct ggtggaaaag tacgatgctg tgatcgctct  4020
tgaggacctc aactctgggt tcaagaacag tagagtgaag gttgagaagc aggtctacca  4080
aaagttcgag aagatgctca tcgacaagct caactacatg gtggacaaaa agagcaaccc  4140
ttgcgctacc ggtggtgctc ttaagggata ccagatcacg aacaagttcg agtccttcaa  4200
gagcatgagc acccagaacg gcttcatctt ctatatccct gcttggctca ccagcaagat  4260
cgatccttct actggtttcg tgaacctgct caagaccaag tacacctcga tcgccgacag  4320
caagaagttc atctcgtctt tcgacaggat catgtacgtg ccggaagagg atcttttcga  4380
gttcgctctc gactataaga acttcagcag gaccgacgcc gactacatta agaagtggaa  4440
gctctactcc tacgggaacc gtatcaggat cttccgaaat ccgaagaaaa acaacgtgtt  4500
cgactgggaa gaagtgtgcc tcacctctgc ctacaaagaa ctgttcaaca agtacggcat  4560
caactaccag cagggtgata tcagggctct tttgtgcgag cagagcgaca aggcattcta  4620
cagctcattc atggccctca tgtctctcat gctccagatg aggaactcta tcaccggaag  4680
gaccgatgtg gacttcctta tctctccggt caagaactct gacgggatct tctacgacag  4740
ccgtaactat gaggctcaag agaacgctat cctgccgaag aatgctgatg caaacggggc  4800
ttacaacatt gcgagaaagg ttctctgggc tatcgggcag tttaagaaag cggaagatga  4860
gaagctcgac aaggtgaaga tcgccatctc caacaaagag tggcttgagt acgctcagac  4920
ctccgttaag cacaagaggc ctgctgctac taagaaagct ggccaggcca aaaagaagaa  4980
gtgaggcgcg ccgagctcca ggcctcccag ctttcgtccg tatcatcggt ttcgacaacg  5040
ttcgtcaagt tcaatgcatc agtttcattg cccacacacc agaatcctac taagtttgag  5100
tattatggca ttggaaaagc tgttttcttc tatcatttgt tctgcttgta atttactgtg  5160
ttctttcagt ttttgttttc ggacatcaaa atgcaaatgg atggataaga gttaataaat  5220
gatatggtcc ttttgttcat tctcaaatta ttattatctg ttgtttttac tttaatgggt  5280
tgaatttaag taagaaagga actaacagtg tgatattaag gtgcaatgtt agacatataa  5340
aacagtcttt cacctctctt tggttatgtc ttgaattggt ttgtttcttc acttatctgt  5400
gtaatcaagt ttactatgag tctatgatca agtaattatg caatcaagtt aagtacagta  5460
taggcttgag ctccctagga tcaagctt                                     5488

SEQ ID NO: 79          moltype = DNA  length = 989
FEATURE                Location/Qualifiers
source                 1..989
                       mol_type = unassigned DNA
                       organism = Petroselinum crispum
SEQUENCE: 79
aattcgaatc caaaaattac ggatatgaat ataggcatat ccgtatccga attatccgtt  60
tgacagctag caacgattgt acaattgctt ctttaaaaaa ggaagaaaga aagaaagaaa  120
agaatcaaca tcagcgttaa caaacggccc cgttacggcc caaacggtca tatagagtaa  180
cggcgttaag cgttgaaaga ctcctatcga aatacgtaac cgcaaacgtg tcatagtcag  240
atcccctctt ccttcaccgc ctcaaacaca aaaataatct tctacagcct atatatacaa  300
ccccccttc tatctctcct ttctcacaat tcatcatctt tctttctcta cccccaattt  360
taagaaatcc tctcttctcc tcttcatttt caaggtaaat ctctctctct ctctctctct  420
ctgttattcc ttgttttaat taggtatgta ttattgctag tttgttaatc tgcttatctt  480
atgtatgcct tatgtgaata tctttatctt gttcatctca tccgtttaga agctataaat  540
ttgttgattt gactgtgtat ctacacgtgg ttatgtttat atctaatcag atatgaattt  600
cttcatattg ttgcgtttgt gtgtaccaat ccgaaatcgt tgattttttt catttaatcg  660
tgtagctaat tgtacgtata catatggatc tacgtatcaa ttgttcatct gtttgtgttt  720
gtatgtatac agatctgaaa acatcacttc tctcatctga ttgtgttgtt acatacatag  780
atatagatct gttatatcat tttttttatt aattgtgtat atatatatgt gcatagatct  840
ggattacatg attgtgatta tttacatgat tttgttattt acgtatgtat atatgtagat  900
ctggactttt tggagttgtt gacttgattg tatttgtgtg tgtatatgtg tgttctgatc  960
ttgatatgtt atgtatgtgc agctgaacc                                   989

SEQ ID NO: 80          moltype = DNA  length = 8726
FEATURE                Location/Qualifiers
source                 1..8726
                       mol_type = other DNA
                       organism = synthetic construct
                       note = Resistance gene expression cassette
SEQUENCE: 80
tttatttaaa catgatacgt atcatattga gtactcatac gcgtaccagc tgtgacttag  60
```

```
aaaaattaac cacgctatat aggttccaag ccctcatgat taccttttca tagtgtaaat  120
ttcatgtagt tgaatggtgg gaatccaatc acaaaaacac tgcaggtaat ggaaatgttc  180
caactttttc caagcatttt aaaataagac atgtgattac taattagggc gtgttcggca  240
acagtaactg tggtgatagt ttttagctgt gagaatagtt gttagctgtg ctgttagctt  300
ttagtggttg gtgtgtaact gttagctgtt agatgtccaa gtagcggtgt aaaatattga  360
tgttcgataa aagaagctgt caaagtagct gtttaagaat aactagttat aaattcaaat  420
aaatctttaa tatataattt atacaccact aaaagctacc caaaagctac aatctaccca  480
aaagctacaa tctacccaaa agctacaaat tgtagctttt gacaaacact actaaaacac  540
tacttgtacc actaaaagct acttacacca ctatcttgcc aaacgctctt attttttcta  600
attagtgttt tgacctaatc aagacactaa aagctactta aaaagcttgt gccgaacacg  660
ccaattctga accaaggaac aaactataac aaaaaagtgc tatgtggaac ttttgtaggc  720
aacagaagta aggcattttt ggaatgtact aacaaatccg tattaagact tgtacatgaa  780
aattaccgtg gtaacatttg cccacacttc ctcattcacg tactccgatt cattctgata  840
aggcacatca agatccatgt atctaatagt ttaatttgcc tctgtgtttc tgtattaaca  900
atgagcatag tgagtgcaaa agccatggaa gctagattaa aaaggccatc attctaagtt  960
agacaattgg aaacaacatc gagatacacg tacacataag ggctgctctt ctctattact  1020
ccctctgttc ctaatcattt gctttttag cgggttccaa aggcctatgt ttgaccacta  1080
atatatttaa attaaaactg gtgatatata ttaaaagaaa attatgatga atttaacaaa  1140
aaccatatat gttatgtcct ttttttcct atattaatga atttttacag tcaaagttgg  1200
tgaactttga cccaaaaaaa gaaatggagc aaaaaaaaaa aaaaaaaaaa aaaactaggg  1260
acaatgagta acatttttat ctatgtcttt ttaatatgaa tatacgtaac aaattctgca  1320
aaaatagaga tagcaactaa taacacgcat gaaaatgaca agttatatta tacctttttt  1380
tctcaatata tgaatatacg taacaaatta actccagtag tttttagtaa aactattaga  1440
ttattgtgta acatatactc tggaaatagt actaagatcc attacaatct ttattgagaa  1500
atttcctcat gtacccccctg aggtttggcg taatttccaa atacccctca tatttgagga  1560
atttctcaaa taccctgatg tttttgttta gactcaaaat acctttacta tggacagtac  1620
cctaatgtca ttaagttttc cccttctctc tccccaattt tctctctcct cccattcccc  1680
cacccactac ccactgccca ctgccaagta ggggtgtaag tggattggac tggattggac  1740
tttgccaaat tcaaatccag tccaaagttt tttggactcg agaaattgag tccaagtccg  1800
atccaaatat tttttgagtc cagtccaatc tagtccgata attttttctt gagtccgaat  1860
ccagtccagt ccagtccgat tattatatct tttttcccga tttaggttca atgattcaca  1920
acattttttg agatgcttga gcatttgaca tctgattcaa ttatcaatat ccacaaataa  1980
gattgaaagc ttaaattaaa gtaaaatact atgaataaaa agttgaatta gatgcttacc  2040
ttgatctaag ttgagaggaa gcatagagac tgagaattaa tctgagggac aaatagagaa  2100
tgcgagagtc gagacagtga ggtagaaaga aaatgaagag taagaggaag tgagtattaa  2160
ggactgagga gtaaagtaag atagaattag ttggctacta gcctactaat gcagtattgc  2220
tagtataatt tacttattta acaaatggag ctaagtgcaa tagtttagcg ccaattgaca  2280
tatttagaga gagaaggctg aaaaatccaa tatttttaaa atagtatcat tatttttaat  2340
atatacatta tatataaaaa tatttttgga ctggactgga catattggac tccaaaggga  2400
tgagtccaaa tccagacaaa aaatatttgg acttgaaaat ttaagtccga gtccagtccg  2460
aaaaatttc agtccaatcc agtccgacaa atttggactg gactggattg gactctgaac  2520
ttttcgtagt ccgcttacac ccctactgcc aagtgccaaa ctgccaaccc cctttggtt  2580
gagttgatat ttgacgcaaa gacttggcgt gttggaaggt tcattacaca ttttatccaa  2640
gtcaactttg aagtcttctt agctagagac tagagtgaac gtgttggaag gttcattaca  2700
cattttatcc aatcaaactt tgaagtcttc ttagctagag actagagtga acgtgttgga  2760
aggttcatgt tcatgacatt ataaaagtaa taatagtgaa atttcacaaa gtatttataa  2820
acccaggaca gactcaagag ctctacttat tattagtgaa aaacaaacat acacacgaca  2880
ataacacaac ataaacaata atgaacatga aaatcctcct tttgtttgtc ttccttcatc  2940
acctccacta cttcatccat ggcagaacac ttacagaacg ccaagcttta ctaagtatca  3000
aatctgccat tacttatgat tattataact ctctctcctc atggaaaaac acaacacacc  3060
actgcagttg gccatacatc acttgctcct cctcttcttc ttcttcttct gttatttctc  3120
tcaacttcac catgttattt ctcgaaggaa ttctctcccc tgatataggc ttcctcacca  3180
acctgcaaaa cctctctatt cgatctaacc ttttttctgg cccactcccc cattctctct  3240
ctctcctcac ccaactccgc tatctcgacg tttcccaaaa cagtttcaca ggtccaatcc  3300
catcttctct ctctctcctc acccaactcc gctatctcca cgtttccggc aacagtttca  3360
caggtccaat cccatctttt ctctctctcc tcacccaact ccgctatctc gacgtttccg  3420
acaacagttt cacaggtcca atcccatctt ctctctctct cctcacccaa ctccgctatc  3480
tcgacgtttc ctacaacaat ctaaatggca ctcttccctt atcggtcgtt gagaagatgt  3540
cggagctcag ctaccttaac cttaggtata actctttcta cggtgagatt ccaccggagt  3600
ttgggaaact taagaagctt gaaacattga atcttggtaa caacactctt tctgggagtc  3660
ttccatctga gttgggttca ttaaagagtt tgaaacatat ggacttttct agtaatatgc  3720
tatttggtga gatcccacaa tcttattctc ttcttcgaaa cttaatcgat attgatctta  3780
atagaaacaa gttatatggg agtatacctg attatattgg agattttccg gagttggaat  3840
cacttttatt agactcgaat aacttcacag ggagtatccc acaaaagtta ggtacaaacg  3900
ggaagttgca atatctagat ataagtaaca acaattttag tggtagtttg ccactaagtc  3960
tttgcaaagg agacaaactc caagatctgg acgcatccta taatttgttg gttgggtcaa  4020
ttcctgagag tttgggaagt tgcaagtcac ttgaaggagt gtacatggga aataatttct  4080
taaacgggtc gattcctaag ggcttgtttg ggagtgatgt ttcacttaat gacaaacttc  4140
ttagtggagg tctcgatgag aaattcggtg attgcgttaa tcttcgggac attgatctct  4200
ctaataataa gctatcaggg aagttacctg cgaccatcgg aaactgtatt catcttcggt  4260
ccttgacgct ttataataac acctgtaccg gacgtatccc tcaagagatt agcaagtgta  4320
agcagctaca gaccctcgat ctcagccaaa atcagttctc tggtgtgata cccaatgata  4380
ttacaggtaa gaaagtatat taaacttgtt actttttgaaa atattcgctc tagtttttgt  4440
ttcagttggt ccattctcac tttgtattat tgaaatatat cccaaaaaag taaatataat  4500
tatataaaag aatcttgcta aaaataatat gaattatttt tgtatgtgca aaataatgta  4560
caaatctaac taatttgttg tggataataa tattaattgt gtgaaatagt aaatgtgtgg  4620
agatatataa ctttatttat catattcact caggttttta ggtatttatt atgagttttg  4680
cattggagat atccaacttg acaatagtat ttttgtaata taccaatata taaagattac  4740
tgtacataac caaaatgtat acttttctta tttttataaa cttatatatt cctcttcttt  4800
```

```
gtatttatca caacattttt tatacccttt tgcctcatat taatagcaac acttataatt  4860
tatttattta ctttttattt cttggtctat aacctcatct acccacatat gacacaccct  4920
ataaaggacc cacatgatta accaaaatat acaaatatct tcaatgaaat taactttaac  4980
actaatatga taaaaatcat gtcccgcttt ttatcctcta actaagactc tgcataaagg  5040
tatattgcaa ttaatatgag atggaagagg tataataatt atatgatcaa attcctggat  5100
tgaaaaataa atatgagatt aaaagtggta tgtttttggt taaaagaaac tatccataaa  5160
gtatgttttt ggttaaaaga aactatgcaa cataccaatc aaatgtttat acgcttacaa  5220
tttatgtacc actttttttgt cattgttttt ctattgtttg ccatacgtac gttactaaat  5280
catgttgtct tttcacattt taactaacaa taaattacta ttgatacacc aaaaaaatct  5340
atgagcattg gagtacgttg tttgatagaa gcttcgtgct attatttctt gtcaaagaat  5400
ttcatatctc aatatcttct aatttaacaa tctaacgaaa ttttttttgac ccaggaaaca  5460
aatccatttg caatctggaa aagatacaaa cacttaaatt atcaaacaat gctttgactg  5520
gtgaaatccc tcattgtgtt ggaaatatcg agctcatagc attatttctc caatcaaaca  5580
aactgaacgg taccataccc gcaaacttct caaagttatg tgattcattg atatatctag  5640
atcttagtga caatcaactc gaaggagttc tacctaagtc cttgtccaaa tgtcaaagtc  5700
tagaactcct aaatgtcggg aacaataggc taagagataa atttccttca tggttagaca  5760
acctcccacg tctccaagtt ttcagtgtgc gttttaacgc cttctacggt cctataacta  5820
gctcaccaaa agttagtcac ccatttccta tgctacaaat tatcgaccta tctaacaata  5880
agttttgtgg caagttgcca agaagatata tcaaaaactt tgcaaccatg cgcaatatga  5940
atgagtctgg tgttgggaat ccacagtacc tgggggactc atcaatatat agtattacgt  6000
actctatggt attgacattc aatgggttac aacaaaaata tgaaaagctt attgtgacga  6060
tgtcgacctt tgatatatcc agcaacaact ttactggaca gattccatat gttatagggg  6120
gattacgctc acttcgtaac cttaatctct ctcataatgt cttaaccggg aacattcctc  6180
catcaattgc aaaattgtct ttgcttcaag atttggacct ttcatcaaac agacttactg  6240
gtcgtatccc tcaagaatta gttagtttaa catttcttgg gagtttcaat gtttcgaaca  6300
atctattgga ggggtctata cctcatggtt tcaacttcga cacgtacaca gctaattcat  6360
accaggggaa tctcgaatta tgtggaaaac cattacctga gtgtggagaa agaagggcaa  6420
aaggcaccac taataatcaa gatgatccta aaaatgataa tgaacgaatg ttgtcgatgt  6480
ccgaaatcgt agttatgggg tttggcagtg gtgtactagt tgggttggct tggggatact  6540
atatgttttc agtgggaaag cccttttggt ttatcaagat ggctagcaaa atggaatcaa  6600
tattgattgg ttttttctga ccaacaattt gttagccgat gaagagcatc aaaaccaaaa  6660
aaaacaaaaa aaattgatta atatgcatga gtgtgacctt gttttccaaa gtttagcatt  6720
actattagtg tctcaattca taataataaa aaaattagct tgttcaagat ttgtattttt  6780
attcaaagat ttttttgtc tcttgtgctt cttttatctt atatatattt tttgtatggt  6840
ttgtttttgt ttaatattag tccctccgct caaaatgatc tttcacgctt gagattggca  6900
ttaaggtcaa gagatgttgc taagctttag aataaaaaaa ttccaaatgc atagagggaa  6960
agaaagcgag acaaaatgtt ggagaaggca gagtaaatga tgtgatggag gataaatagt  7020
agaagtgtga taccgaaagt ttgaaaataa taaggaattt tatttcttgc tggcactttg  7080
ttctagtaca ggtttttagc ccttcaaaat gtttataatg tagagtcaaa attaatatcc  7140
ttaactagtt tttaagtccg ggttatatcc tagatattaa taatattcat ttattagtaa  7200
cattttattt tataaatata atactaagca ttatttggtt tgctggttaa gactttagtg  7260
tatatctatt tctttttttt tttattgtat gcgtgtttac ataaactaaa gactataagg  7320
gatagtacca cgtggcgcag ttccttgctt aggaacgtct tttaatatat taactagtat  7380
ttgggcccgg gcgttgctcc gggttggtat tgtgtttccg aacatgatgt gcagtttttc  7440
ccattcccac taaaatatat aaaggaaaac tcaacattta aaagatacaa atataataat  7500
atggacactt aaaacatgat taaaagttga ttgagatggt aattgtgtca tgttataata  7560
gtaagaggtt gcctaattga ggttgaggtg gtggagtagt ggtatcgctt cccatctgtt  7620
atccctgaga tataaggatc aaacctcata ggactcattt gagtaatttc ccatatcctc  7680
ctctcaaatg agtccttttc atctgacaaa aaaaaatgtc taattttaaa ttaaaattag  7740
acgatctttt ataaaatcgg cactttctgc acataggtca caattttttt gtttctatct  7800
ctctgctttc tttaattcta cagtctccaa ctctccatca acatcttact tattttagaa  7860
tagatgatgt atggtagtat taaatggtaa agtactaaag ctcctataat acacagaagc  7920
ttacatagta tagattcgta catgagacaa ggttacaata tactttctcc gttcttttta  7980
tattacaata attactattt taagtagttt cacatctatt gtaacaattc caattttgtt  8040
atagaaagca actttaataa ttgacaatat tgcccttact ttatcttatt aaaaccatca  8100
ttaattactc actttctctt ataaaattgc ttttattttc taaggataat ttctctccta  8160
ttctagttaa ttaaagagtt acttttgtgc taaactgctc atttgttcca aatccttaaa  8220
aattgtgtcc aaacgcattg ttgtaatata aaaagaacag aggtactatt agtttgaata  8280
aattttgatc ggattaggtc acctttaggg ggcgtttggt taggggtatt ctggaaacgg  8340
taagggaatc aacttactta attcccttac ttgttgtttg tttgctcaat ttaatgattc  8400
cctttaccca ccccttactc ccaaagtcct ttactctcat tccccccacc ccccaaggtt  8460
tcacttaccc tttcttgatt catcattgac catatctttg accacccaac taccaccacc  8520
acttgaccac ctaatcacct aaccacctaa cccaaccact attaccaccc aacccctcca  8580
cctgcccacc aatcggcacc agaactgccc aaccgtcgcc caatcaagcc acccaaccgg  8640
caccataacc gcccaaccaa gccacccaac cggcaccaga aattgtacca agctacccac  8700
acacgtgaaa accacccacc cacaaa                                   8726

SEQ ID NO: 81          moltype = DNA  length = 20
FEATURE                Location/Qualifiers
source                 1..20
                       mol_type = other DNA
                       organism = synthetic construct
                       note = Primer
SEQUENCE: 81
atgttatctt taccacagtt                                    20

SEQ ID NO: 82          moltype = DNA  length = 24
FEATURE                Location/Qualifiers
source                 1..24
```

```
                        mol_type = other DNA
                        organism = synthetic construct
                        note = Primer
SEQUENCE: 82
gtccctaaat gaaatacgta aaac                                          24

SEQ ID NO: 83           moltype = DNA  length = 3706
FEATURE                 Location/Qualifiers
source                  1..3706
                        mol_type = other DNA
                        organism = synthetic construct
                        note = PCR Product
SEQUENCE: 83
atgttatctt taccacagtt tgttgctctg acacaaccgg taaatgcatt ggcctttgtt  60
tttgatggca tcaactttgg agcatctgat tttgcatatt cagccttttc catggtaatt  120
cttttacaag aattttcatt ctttcttaag tataaacact tagcttggga caaacttctg  180
atcctatttc ttaattttg caggtgatgg tggctgttat gagcattttg tgtttgatgt  240
ttctttcttc tcattacggt tttattggga tctgggtggc tctaactatt tacatgagcc  300
tccgcgcgtt tgctgaaggc gggaaacgac aatctgatcc ccatcaagct tgagctcagg  360
atttagcagc attccagatt gggttcaatc aacaaggtac gagccatatc actttattca  420
aattggtatc gccaaaacca agaaggaact cccatcctca aaggtttgta aggaagaatt  480
ctcagtccaa agcctcaaca aggtcagggt acagagtctc caaaccatta gccaaaagct  540
acaggagatc aatgaagaat cttcaatcaa agtaaactac tgttccagca catgcatcat  600
ggtcagtaag tttcagaaaa agacatccac cgaagactta aagttagtgg gcatctttga  660
aagtaatctt gtcaacatcg agcagctggc ttgtggggac cagacaaaaa aggaatggtg  720
cagaattgtt aggcgcacct accaaaagca tctttgcctt tattgcaaag ataaagcaga  780
ttcctctagt acaagtgggg aacaaaataa cgtggaaaag agctgtcctg acagcccact  840
cactaatgcg tatgacgaac gcagtgacga ccacaaaaga attccctcta tataagaagg  900
cattcattcc catttgaagg atcatcagat actcaaccaa tccttctaga agatctaagc  960
ttatcgataa gcttgatgta attggaggaa gatcaaaatt ttcaatcccc attcttcgat  1020
tgcttcaatt gaagtttctc cgatggcgca agttagcaga atctgcaatg gtgtgcagaa  1080
cccatctctt atctccaatc tctcgaaatc cagtcaacgc aaatctccct tatcggtttc  1140
tctgaagacg cagcagcatc cacgagctta tccgatttcg tcgtcgtggg gattgaagaa  1200
gagtgggatg acgttaattg gctctgagct tcgtcctctt aaggtcatgt cttctgtttc  1260
cacggcgtgc atgcttcacg gtgcaagcag ccgtccagca actgctcgta agtcctctgg  1320
tctttctgga accgtccgta ttccaggtga caagtctatc tcccacaggt ccttcatgtt  1380
tggaggtctc gctagcggtg aaacccgtat caccggtctt ttggaaggtg aagatgttat  1440
caacactggt aaggctatgc aagctatggg tgccagaatc cgtaaggaag gtgatacttg  1500
gatcattgat ggtgttggta acggtggact ccttgctcct gaggctcctc tcgatttcgg  1560
taacgctgca actggttgcc gtttgactat gggtcttgtt ggtgtttacg atttcgatag  1620
cactttcatt ggtgacgctt ctctcactaa gcgtccaatg ggtcgtgtgt tgaacccact  1680
tcgcgaaatg ggtgtgcagg tgaagtctga agacggtgat cgtcttccag ttaccttgcg  1740
tggaccaaag actccaacgc caatcaccta cagggtacct atggcttccg ctcaagtgaa  1800
gtccgctgtt ctgcttgctg gtctcaacac cccaggtatc accactgtta tcgagccaat  1860
catgactcgt gaccacactg aaaagatgct tcaaggtttt ggtgctaacc ttaccgttga  1920
gactgatgct gacggtgtgc gtaccatccg tcttgaaggt cgtggtaagc tcaccggtca  1980
agtgattgat gttccaggtg atccatcctc tactgctttc ccattggttg ctgccttgct  2040
tgttccaggt tccgacgtca ccatccttaa cgttttgatg aacccaaccc gtactggtct  2100
catcttgact ctgcaggaaa tgggtgccga catcgaagtg atcaacccac gtcttgctgg  2160
tggagaagac gtggctgact tgcgtgttcg ttcttctact ttgaagggtg ttactgttcc  2220
agaagaccgt gctccttcta tgatcgacga gtatccaatt ctcgctgttg cagctgcatt  2280
cgctgaaggt gctaccgtta tgaacggttt ggaagaactc cgtgttaagg aaagcgaccg  2340
tctttctgct gtcgcaaacg gtctcaagct caacggtgtt gattgcgatg aaggtgagac  2400
ttctctcgtc gtgcgtggtc gtcctgacgg taagggtctc ggtaacgctt ctggagcagc  2460
tgtcgctacc cacctcgatc accgtatcgc tatgagcttc ctcgttatgg gtctcgtttc  2520
tgaaaaccct gttactgttg atgatgctac tatgatcgct actagcttcc cagagttcat  2580
ggatttgatg gctggtcttg gagctaagat cgaactctcc gacactaagg ctgcttgatg  2640
agctcaagaa ttcgagctcg gtaccggatc ctctagctag agctttcgtt cgtatcatcg  2700
gtttcgacaa cgttcgtcaa gttcaatgca tcagtttcat tgcgcacaca ccagaatcct  2760
actgagtttg agtattatgg cattgggaaa actgtttttc ttgtaccatt tgttgtgctt  2820
gtaatttact gtgtttttta ttcggttttc gctatcgaac tgtgaaatgg aaatggatgg  2880
agaagagtta atgaatgata tggtcctttt gttcattctc aaattaatat tatttgtttt  2940
ttctcttatt tgttgtgtgt tgaatttgaa attataagag atatgcaaac attttgtttt  3000
gagtaaaaat gtgtcaaatc gtggcctcta atgaccgaag ttaatatgag gagtaaaaca  3060
cttgtagttg taccattatg cttattcact aggcaacaaa tatattttca gacctagaaa  3120
agctgcaaat gttactgaat acaagtatgt cctcttgtgt tttagacatt tatgaacttt  3180
cctttatgta attttccaga atccttgtca gattctaatc attgctttat aattatagtt  3240
atactcatgg atttgtagtt gagtatgaaa atatttttta atgcatttta tgacttgcca  3300
attgattgac aacatgcatc aatcgacctg cagccactcg aagcggccgc cactcgagtg  3360
gtggccgcat cgatcgtgaa gtttctcatc taagcccccca tttggacgtg aatgtagaca  3420
cgtcgaaata aagatttccg aattagaata atttgtttat tgctttcgcc tataaatacg  3480
acggatcgta atttgtcgtt ttatcaaaat gtactttcat tttataataa cgctgcggac  3540
atctacattt ttgaattgaa aaaaattggt aattactctt tctttttctc catattgacc  3600
atcatactca ttgctgatcc atgtagattt cccggacatg aagccattta caattgaata  3660
tatcctaagt aaaacctcat aggttttacg tatttcattt agggac                 3706

SEQ ID NO: 84           moltype = DNA  length = 26
FEATURE                 Location/Qualifiers
source                  1..26
```

```
                         mol_type = other DNA
                         organism = synthetic construct
                         note = Primer
SEQUENCE: 84
cgctgcggac atctacattt ttgaat                                          26

SEQ ID NO: 85            moltype = DNA  length = 28
FEATURE                  Location/Qualifiers
source                   1..28
                         mol_type = other DNA
                         organism = synthetic construct
                         note = Primer
SEQUENCE: 85
agttaacttt ccacttatcg gggcactg                                        28

SEQ ID NO: 86            moltype = DNA  length = 751
FEATURE                  Location/Qualifiers
source                   1..751
                         mol_type = other DNA
                         organism = synthetic construct
                         note = PCR Product
SEQUENCE: 86
cgctgcggac atctacattt ttgaattgaa aaaaaattgg taattactct ttctttttct  60
ccatattgac catcatactc attgctgatc catgtagatt tcccggacat gaagccattt  120
acaattgaat atatcctaag taaaacctca taggttttac gtatttcatt tagggactaa  180
aatggtttag gataattact ttagctaaca taagataata aataaataaa taaataaaaa  240
taaaatggtt gtagataaat aaggaaatca ataatgaata tgagtgtgag tgataggacg  300
ggaatgggaa acttttacac tactttaacg ctattgaacg agtatgagta tgttataaac  360
gtaaaatgtt ttatgtgtta gacaatggcc tcaagtgaaa gtgaccctat taatggagga  420
aatgcaaacc acgagtctga ggtcacgctc gaagaaatga gggcaaggat cgacgcattg  480
cgtagcgacc ctgtttttgg agatgccacg ggagatgcta gtgataaccg aatggattta  540
atgaggttga tgatgatgga gcttttacaa ggaaatcgac aaaggcctag aactgaacaa  600
gaagagtgct caaacatgtt caagaggttt tcggctcata agccccccaac ttatgatgga  660
aagccagacc ccactgagtt tgaagaatgg ctcaacggca tggaaaaatt gttcgatgcc  720
acccagtgcc ccgataagtg gaaagttaac t                                   751

SEQ ID NO: 87            moltype = DNA  length = 30
FEATURE                  Location/Qualifiers
source                   1..30
                         mol_type = other DNA
                         organism = synthetic construct
                         note = Primer
SEQUENCE: 87
gctctgacac aaccggtaaa tgcattggcc                                      30

SEQ ID NO: 88            moltype = DNA  length = 29
FEATURE                  Location/Qualifiers
source                   1..29
                         mol_type = other DNA
                         organism = synthetic construct
                         note = Primer
SEQUENCE: 88
gcagattctg ctaacttgcg ccatcggag                                       29

SEQ ID NO: 89            moltype = DNA  length = 1042
FEATURE                  Location/Qualifiers
source                   1..1042
                         mol_type = other DNA
                         organism = synthetic construct
                         note = PCR Product
SEQUENCE: 89
gctctgacac aaccggtaaa tgcattggcc tttgtttttg atggcatcaa ctttggagca  60
tctgattttg catattcagc cttttccatg gtaattcttt tacaagaatt ttcattcttt  120
cttaagtata aacacttagc ttgggacaaa cttctgatcc tatttcttaa tttttgcagg  180
cgatggtggc tgttatgagc attttgtgtt tgatgtttct ctcttctcat tacggtttta  240
ttgggatctg ggtggctcta actatttaca tgagcctccg cgcgtttgct gaaggcggga  300
aacgacaatc tgatccccat caagcttgag ctcaggattt agcagcattc cagattgggt  360
tcaatcaaca aggtacgagc catatcactt tattcaaatt ggtatcgcca aaaccaagaa  420
ggaactccca tcctcaaagg tttgtaagga agaattctca gtccaaagcc tcaacaaggt  480
cagggtacag agtctccaaa ccattagcca aaagctacag gagatcaatg aagaatcttc  540
aatcaaagta aactactgtt ccagcacatg catcatggtc agtaagtttc agaaaaagac  600
atccaccgaa gacttaaagt tagtgggcat ctttgaaagt aatcttgtca acatcgagca  660
gctggcttgt ggggaccaga caaaaaagga atggtgcaga attgttaggc gcacctacca  720
aaagcatctt tgcctttatt gcaaagataa agcagattcc tctagtacaa gtggggaaca  780
aaataacgtg gaaaagagct gtcctgacag cccactcact aatgcgtatg acgaacgcag  840
tgacgaccac aaaagaattc cctctatata agaaggcatt cattcccatt tgaaggatca  900
tcagatactg aaccaatcct tctagaagat ctaagcttat cgataagctt gatgtaattg  960
gaggaagatc aaaatttca atccccattc ttcgattgct tcaattgaag tttctccgat  1020
ggcgcaagtt agcagaatct gc                                             1042
```

```
SEQ ID NO: 90          moltype = AA  length = 665
FEATURE                Location/Qualifiers
source                 1..665
                       mol_type = protein
                       organism = Beta vulgaris
SEQUENCE: 90
MAATFTNPTF SPSSTPLTKT LKSQSSISST LPFSTPPKTP TPLFHRPLQI SSSQSHKSSA  60
IKTQTQAPSS PAIEDSSFVS RFGPDEPRKG SDVLVEALER EGVTNVFAYP GGASMEIHQA  120
LTRSKTIRNV LPRHEQGGVF AAEGYARATG KVGVCIATSG PGATNLVSGL ADALLDSVPL  180
VAITGQVPRR MIGTDAFQET PIVEVTRSIT KHNYLVLDVE DIPRIVKEAF FLANSGRPGP  240
VLIDLPKDIQ QQLVVPDWDR PFKLGGYMSR LPKSKFSTNE VGLLEQIVRL MSESKKPVLY  300
VGGGCLNSSE ELRRFVELTG IPVASTLMGL GSYPCNDELS LHMLGMHGTV YANYAVDKAD  360
LLLAFGVRFD DRVTGKLEAF ASRAKIVHID IDSAEIGKNK QPHVSICADV KLALRGMNKI  420
LESRIGKLNL DFSKWREELG EQKKEFPLSF KTFGDAIPPQ YAIQVLDELT NGNAIISTGV  480
GQHQMWAAQH YKYRNPRQWL TSGGLGAMGF GLPAAIGAAV ARPDAVVVDI DGDGSFIMNV  540
QELATIRVEN LPVKIMLLNN QHLGMVVQWE DRFYKANRAH TYLGNPSKSA DIFPDMLKFA  600
EACDIPSARV SNVADLRAAI QTMLDTPGPY LLDVIVPHQE HVLPMIPSGA GFKDTITEGD  660
GRTSY                                                              665

SEQ ID NO: 91          moltype = DNA  length = 1998
FEATURE                Location/Qualifiers
source                 1..1998
                       mol_type = other DNA
                       organism = synthetic construct
                       note = Acetolactate synthase with mutation
SEQUENCE: 91
atggcggcta ccttcacaaa cccaacattt tccccttcct caactccatt aaccaaaacc  60
ctaaaatccc aatcttccat ctcttcaacc ctcccctttt ccacccctcc caaaacccca  120
actccactct ttcaccgtcc cctccaaatc tcatcctccc aatcccacaa atcatccgcc  180
attaaaacac aaactcaagc accttcttct ccagctattg aagattcatc tttcgtttct  240
cgatttggcc ctgatgaacc cagaaaaggg tccgatgtcc tcgttgaagc tcttgagcgt  300
gaaggtgtta ccaatgtgtt tgcttaccct ggtggtgcat ctatggaaat ccaccaagct  360
ctcacacgct ctaaaaccat ccgcaatgtc ctccctcgcc atgaacaagg cggggttttc  420
gccgccgagg gatatgctag agctactgga aaggttggtg tctgcattgc gacttctggt  480
cctggtgcta ccaacctcgt atcaggtctt gctgacgctc tccttgattc tgtccctctt  540
gttgccatca ctggccaagt tccacgccgt atgattggca ctgatgcttt tcaggagact  600
ccaattgttg aggtgacaag gtctattact aagcataatt atttagtttt ggatgtagag  660
gatattccta gaattgttaa ggaagccttt tttttagcta attctggtag gcctggacct  720
gttttgattg atcttcctaa agatattcag cagcaattgg ttgttcctga ttgggatagg  780
ccttttaagt tgggtgggta tatgtctagg ctgccaaagt ccaagttttc gacgaatgag  840
gttggacttc ttgagcagat tgtgaggttg atgagtgagt cgaagaagcc tgtcttgtat  900
gtgggaggtg ggtgtttgaa ttctagtgag gagttgagga gatttgttga gttgacaggg  960
attccggtgg ctagtacttt gatggggttg ggtcttaccc cttgtaatga tgaactgtct  1020
cttcatatgt tggggatgca cgggactgtt tatgccaatt atgcggtgga taaggcggat  1080
ttgttgcttg ctttcggggt taggtttgat gatcgtgtga ccgggaagct cgaggcgttt  1140
gctagccgtg ctaagattgt gcatattgat attgactctg ctgagattgg gaagaacaag  1200
cagccccatg tgtccatttg tgctgatgtt aaattggcat tgcggggtat gaataagatt  1260
ctggagtcta gaatagggaa gctgaatttg gatttctcca agtggagaga agaattaggt  1320
gagcagaaga aggaattccc actgagtttt aagacatttg gggatgcaat tcctccacaa  1380
tatgccattc aggtgcttga tgagttgacc aatggtaatg ctattataag tactggtgtt  1440
gggcagcacc aaatgtgggc tgcgcagcat tacaagtaca gaaaccctcg ccaatggctg  1500
acctctggtg ggttgggggc tatggggttt gggctaccag ccgccattgg agctgcagtt  1560
gctcgaccag atgcagtggt tgtcgatatt gatggggatg gcagttttat tatgaatgtt  1620
caagagttgg ctacaattag ggtggaaaat ctcccagtta agataatgct gctaaacaat  1680
caacatttag gtatggttgt ccaattggaa gataggttct ataaagctaa ccgggcacat  1740
acataccttg gaaacccttc caaatctgct gatatcttcc ctgatatgct caaattcgct  1800
gaggcatgtg atattccttc tgcccgtgtt agcaacgtgg ctgatttgag ggccgccatt  1860
caaacaatgt tggatactcc agggccgtac ctgctcgatg tgattgtacc gcatcaagag  1920
catgtgttgc ctatgattcc aagtggtgcc ggtttcaagg ataccattac agagggtgat  1980
ggaagaacct cttattga                                                1998

SEQ ID NO: 92          moltype = DNA  length = 21
FEATURE                Location/Qualifiers
source                 1..21
                       mol_type = unassigned DNA
                       organism = Beta vulgaris
SEQUENCE: 92
cctgagagtt tgggaagttg c                                            21

SEQ ID NO: 93          moltype = DNA  length = 23
FEATURE                Location/Qualifiers
source                 1..23
                       mol_type = unassigned DNA
                       organism = Beta vulgaris
SEQUENCE: 93
atgtcccgaa gattaacgca atc                                          23

SEQ ID NO: 94          moltype = DNA  length = 3720
```

```
FEATURE                Location/Qualifiers
source                 1..3720
                       mol_type = other DNA
                       organism = synthetic construct
                       note = modified genomic sequence of the gene mediating
                        resistance towards cercospora
SEQUENCE: 94
atgaacatga aaatcttact tttgtttgtc ttccttcatc acctccacta cttcatccat  60
ggcagaacac ttacagaacg ccaagcttta ctaagtatca aatctgccat tacttatgat  120
tattataact ctctctcctc atggaaaaac acaacacacc actgcagttg gccatacatc  180
acttgctcct cctcttcttc ttcttcttct gttatttctc tcaacttcac catgttattt  240
ctcgaaggaa ttctctcccc tgatataggc ttcctcacca acctgcaaaa cctctctatt  300
cgatctaacc ttttttctgg cccactcccc cattctctct ctctcctcac ccaactccgc  360
tatctcgacg tttcccaaaa cagtttcaca ggtccaatcc catcttctct ctctctcctc  420
acccaactcc gctatctcca cgtttccggc aacagtttca caggtccaat cccatctttt  480
ctctctctcc tcacccaact ccgctatctc gacgtttccg acaacagttt cacaggtcca  540
atcccatctt ctctctctct cctcacccaa ctccgctatc tcgacgtttc ctacaacaat  600
ctaaatggca ctcttccctt atcggtcgtt gagaagatgt cggagctcag ctaccttaac  660
cttaggtata actctttcta cggtgagatt ccaccggagt ttgggaaact taagaagctt  720
gaaacattga atcttggtaa caacactctt tctgggagtc ttccatctga gttgggttca  780
ttaaagagtt tgaaacatat ggacttttct agtaatatgc tatttggtga gatcccacaa  840
tcttattctc ttcttcgaaa cttaatcgat attgatctta atagaaacaa gttatatggg  900
agtatacctg attatattgg agattttccg gagttggaat cacttttatt agactcgaat  960
aacttcacag ggagtatccc acaaaagtta ggtacaaacg ggaagttgca atatctagat  1020
ataagtaaca acaattttag tggtagtttg ccactaagtc tttgcaaagg agacaaactc  1080
caagatctgg acgcatccta taatttgttg gttgggtcaa ttcctgagag tttgggaagt  1140
tgcaagtcac ttgaaggagt gtacatggga aataatttct taaacgggtc gattcctaag  1200
ggcttgtttg ggagtgatgt ttcacttaat gacaaacttc ttagtggagg tctcgatgag  1260
aaattcggtg attgcgttaa tcttcgggac attgatctct ctaataataa gctatcaggg  1320
aagttacctg cgaccatcgg aaactgtatt catcttcggt ccttgacgct ttataataac  1380
acctgtaccg gacgtatccc tcaagagatt agcaagtgta agcagctaca gaccctcgat  1440
ctcagccaaa atcagttctc tggtgtgata cccaatgata ttacaggtaa gaaagtatat  1500
taaacttgtt acttttgaaa atattcgctc tagtttttgt ttcagttggt ccattctcac  1560
tttgtattat tgaaatatat cccaaaaaag taaatataat tatataaaag aatcttgcta  1620
aaaataatat gaattatttt tgtatgtgca aaataatgta caaatctaac taatttgttg  1680
tggataataa tattaattgt gtgaaatagt aaatgtgtgg agatatataa ctttatttat  1740
catattcact caggttttta ggtatttatt atgagttttg cattggagat atccaacttg  1800
acaatagtat ttttgtaata taccaatata taaagattac tgtacataac caaaatgtat  1860
acttttctta tttttataaa cttatatatt cctcttcttt gtatttatca caacattttt  1920
tataccottt tgcctcatat taatagcaac acttataatt tatttattta ctttttattt  1980
cttggtctat aacctcatct acccacatat gacacaccct ataaaggacc cacatgatta  2040
accaaaatat acaaatatct tcaatgaaat taactttaac actaatatga taaaaatcat  2100
gtcccgcttt ttatcctcta actaagactc tgcataaagg tatattgcaa ttaatatgag  2160
atggaagagg tataataatt atatgatcaa attcctggat tgaaaaataa atatgagatt  2220
aaaagtggta tgtttttggt taaaagaaac tatccataaa gtatgttttt ggttaaaaga  2280
aactatgcaa cataccaatc aaatgtttat acgcttacaa tttatgtacc actttttttgt  2340
cattgttttt ctattgtttg ccatacgtac gttactaaat catgttgtct tttcacattt  2400
taactaacaa taaattacta ttgatacacc aaaaaaatct atgagcattg gagtacgttg  2460
tttgatagaa gcttcgtgct attatttctt gtcaaagaat ttcatatctc aatatcttct  2520
aatttaacaa tctaacgaaa ttttttttgac ccaggaaaca aatccatttg caatctggaa  2580
aagatacaaa cacttaaatt atcaaacaat gctttgactg gtgaaatccc tcattgtgtt  2640
ggaaatatcg agctcatagc attatttctc caatcaaaca aactgaacgg taccataccc  2700
gcaaacttct caaagttatg tgattcattg atatatctag atcttagtga caatcaactc  2760
gaaggagttc tacctaagtc cttgtccaaa tgtcaaagtc tagaactcct aaatgtcggg  2820
aacaataggc taagagataa atttccttca tggttagaca acctcccacg tctccaagtt  2880
ttcagtgtgc gttttaacgc cttctacggt cctataacta gctcaccaaa agttagtcac  2940
ccatttccta tgctacaaat tatcgaccta tctaacaata agttttgtgg caagttgcca  3000
agaagatata tcaaaaactt tgcaaccatg cgcaatatga atgagtctgg tgttgggaat  3060
ccacagtacc tgggggactc atcaatatat agtattacgt actctatggt attgacattc  3120
aatgggttac aacaaaaata tgaaaagctt attgtgacga tgtcgacctt tgatatatcc  3180
agcaacaact ttactggaca gattccatat gttatagggg gattacgctc acttcgtaac  3240
cttaatctct ctcataatgt cttaaccggg aacattcctc catcaattgc aaaattgtct  3300
ttgcttcaag atttggacct ttcatcaaac agacttactg gtcgtatccc tcaagaatta  3360
gttagtttaa catttcttgg gagtttcaat gtttcgaaca atctattgga ggggtctata  3420
cctcatggtt tcaacttcga cacgtacaca gctaattcat accaggggaa tctcgaatta  3480
tgtggaaaac cattacctga gtgtggagaa agaagggcaa aaggcaccac taataatcaa  3540
gatgatccta aaaatgataa tgaacgaatg ttgtcgatgt ccgaaatcgt agttatgggg  3600
tttggcagtg gtgtactagt tgggttggct tggggatact atatgttttc agtgggaaag  3660
ccctttttggt ttatcaagat ggctagcaaa atggaatcaa tattgattgg ttttttctga  3720

SEQ ID NO: 95          moltype = DNA  length = 2652
FEATURE                Location/Qualifiers
source                 1..2652
                       mol_type = other DNA
                       organism = synthetic construct
                       note = modified cDNA sequence of the gene mediating
                        resistance towards cercospora
misc_feature           55..57
                       note = variation - Modified codon
```

SEQUENCE: 95
atgaacatga aaatcctcct tttgtttgtc ttccttcatc acctccacta cttcatacat 60
ggcagaacac ttacagaacg ccaagcttta ctaagtatca aatctgccat tacttatgat 120
tattataact ctctctcctc atggaaaaac acaacacacc actgcagttg gccatacatc 180
acttgctcct cctcttcttc ttcttcttct gttatttctc tcaacttcac catgttattt 240
ctcgaaggaa ttctctcccc tgatataggc ttcctcacca acctgcaaaa cctctctatt 300
cgatctaacc ttttttctgg cccactcccc cattctctct ctctcctcac ccaactccgc 360
tatctcgacg tttcccaaaa cagtttcaca ggtccaatcc catcttctct ctctctcctc 420
acccaactcc gctatctcca cgtttccggc aacagtttca caggtccaat cccatctttt 480
ctctctctcc tcacccaact ccgctatctc gacgtttccg acaacagttt cacaggtcca 540
atcccatctt ctctctctct cctcacccaa ctccgctatc tcgacgtttc ctacaacaat 600
ctaaatggca ctcttccctt atcggtcgtt gagaagatgt cggagctcag ctaccttaac 660
cttaggtata actctttcta cggtgagatt ccaccggagt ttgggaaact taagaagctt 720
gaaacattga atcttggtaa caacactctt tctgggagtc ttccatctga gttgggttca 780
ttaaagagtt tgaaacatat ggacttttct agtaatatgc tatttggtga gatcccacaa 840
tcttattctc ttcttcgaaa cttaatcgat attgatctta atagaaacaa gttatatggg 900
agtatacctg attatattgg agattttccg gagttggaat cacttttatt agactcgaat 960
aacttcacag ggagtatccc acaaaagtta ggtacaaacg ggaagttgca atatctagat 1020
ataagtaaca acaattttag tggtagtttg ccactaagtc tttgcaaagg agacaaactc 1080
caagatctgg acgcatccta taatttgttg gttgggtcaa ttcctgagag tttgggaagt 1140
tgcaagtcac ttgaaggagt gtacatggga aataatttct taaacgggtc gattcctaag 1200
ggcttgtttg ggagtgatgt ttcacttaat gacaaacttc ttagtggagg tctcgatgag 1260
aaattcggtg attgcgttaa tcttcgggac attgatctct ctaataataa gctatcaggg 1320
aagttacctg cgaccatcgg aaactgtatt catcttcggt ccttgacgct ttataataac 1380
acctgtaccg gacgtatccc tcaagagatt agcaagtgta agcagctaca gaccctcgat 1440
ctcagccaaa atcagttctc tggtgtgata cccaatgata ttacaggaaa caaatccatt 1500
tgcaatctgg aaaagataca aacacttaaa ttatcaaaca atgctttgac tggtgaaatc 1560
cctcattgtg ttggaaatat cgagctcata gcattatttc tccaatcaaa caaactgaac 1620
ggtaccatac ccgcaaactt ctcaaagtta tgtgattcat tgatatatct agatcttagt 1680
gacaatcaac tcgaaggagt tctacctaag tccttgtcca aatgtcaaag tctagaactc 1740
ctaaatgtcg ggaacaatag gctaagagat aaatttcctt catggttaga caacctccca 1800
cgtctccaag ttttcagtgt gcgttttaac gccttctacg gtcctataac tagctcacca 1860
aaagttagtc acccatttcc tatgctacaa attatcgacc tatctaacaa taagttttgt 1920
ggcaagttgc caagaagata tatcaaaaac tttgcaacca tgcgcaatat gaatgagtct 1980
ggtgttggga atccacagta cctgggggac tcatcaatat atagtattac gtactctatg 2040
gtattgacat tcaatgggtt acaacaaaaa tatgaaaagc ttattgtgac gatgtcgacc 2100
tttgatatat ccagcaacaa ctttactgga cagattccat atgttatagg gggattacgc 2160
tcacttcgta accttaatct ctctcataat gtcttaaccg ggaacattcc tccatcaatt 2220
gcaaaattgt ctttgcttca agatttggac ctttcatcaa acagacttac tggtcgtatc 2280
cctcaagaat tagttagttt aacatttctt gggagtttca atgtttcgaa caatctattg 2340
gaggggtcta tacctcatgg tttcaacttc gacacgtaca cagctaattc ataccagggg 2400
aatctcgaat tatgtggaaa accattacct gagtgtggag aaagaagggc aaaaggcacc 2460
actaataatc aagatgatcc taaaaatgat aatgaacgaa tgttgtcgat gtccgaaatc 2520
gtagttatgg ggtttggcag tggtgtacta gttgggttgg cttggggata ctatatgttt 2580
tcagtgggaa agccctttg gtttatcaag atggctagca aaatggaatc aatattgatt 2640
ggtttttct ga 2652

SEQ ID NO: 96 moltype = AA length = 883
FEATURE Location/Qualifiers
source 1..883
mol_type = protein
organism = synthetic construct
note = modified protein sequence of the gene mediating
resistance towards cercospora
SITE 209
note = VARIANT - position modified to leucine
SEQUENCE: 96
MNMKILLLFV FLHHLHYFIH GRTLTERQAL LSIKSAITYD YYNSLSSWKN TTHHCSWPYI 60
TCSSSSSSSS VISLNFTMLF LEGILSPDIG FLTNLQNLSI RSNLFSGPLP HSLSLLTQLR 120
YLDVSQNSFT GPIPSSLSLL TQLRYLHVSG NSFTGPIPSF LSLLTQLRYL DVSDNSFTGP 180
IPSSLSLLTQ LRYLDVSYNN LNGTLPLSVL EKMSELSYLN LRYNSFYGEI PPEFGKLKKL 240
ETLNLGNNTL SGSLPSELGS LKSLKHMDFS SNMLFGEIPQ SYSLLRNLID IDLNRNKLYG 300
SIPDYIGDFP ELESLLLDSN NFTGSIPQKL GTNGKLQYLD ISNNNFSGSL PLSLCKGDKL 360
QDLDASYNLL VGSIPESLGS CKSLEGVYMG NNFLNGSIPK GLFGSDVSLN DKLLSGGLDE 420
KFGDCVNLRD IDLSNNKLSG KLPATIGNCI HLRSLTLYNN TCTGRIPQEI SKCKQLQTLD 480
LSQNQFSGVI PNDITGNKSI CNLEKIQTLK LSNNALTGEI PHCVGNIELI ALFLQSNKLN 540
GTIPANFSKL CDSLIYLDLS DNQLEGVLPK SLSKCQSLEL LNVGNNRLRD KFPSWLDNLP 600
RLQVFSVRFN AFYGPITSSP KVSHPFPMLQ IIDLSNNKFC GKLPRRYIKN FATMRNMNES 660
GVGNPQYLGD SSIYSITYSM VLTFNGLQQK YEKLIVTMST FDISSNNFTG QIPYVIGGLR 720
SLRNLNLSHN VLTGNIPPSI AKLSLLQDLD LSSNRLTGRI PQELVSLTFL GSFNVSNNLL 780
EGSIPHGFNF DTYTANSYQG NLELCGKPLP ECGERRAKGT TNNQDDPKND NERMLSMSEI 840
VVMGFGSGVL VGLAWGYYMF SVGKPFWFIK MASKMESILI GFF 883

SEQ ID NO: 97 moltype = DNA length = 2652
FEATURE Location/Qualifiers
source 1..2652
mol_type = other DNA
organism = synthetic construct
note = modified cDNA of the gene mediating resistance

```
                       towards cercospora
misc_feature           625..627
                       note = variation - Modified codon
SEQUENCE: 97
atgaacatga aaatcctcct tttgtttgtc ttccttcatc acctccacta cttcatccat  60
ggcagaacac ttacagaacg ccaagcttta ctaagtatca aatctgccat tacttatgat  120
tattataact ctctctcctc atggaaaaac acaacacacc actgcagttg gccatacatc  180
acttgctcct cctcttcttc ttcttcttct gttatttctc tcaacttcac catgttattt  240
ctcgaaggaa ttctctcccc tgatataggc ttcctcacca acctgcaaaa cctctctatt  300
cgatctaacc ttttttctgg cccactcccc cattctctct ctctcctcac ccaactccgc  360
tatctcgacg tttcccaaaa cagtttcaca ggtccaatcc catcttctct ctctctcctc  420
acccaactcc gctatctcca cgtttccggc aacagtttca caggtccaat cccatctttt  480
ctctctctcc tcacccaact ccgctatctc gacgtttccg acaacagttt cacaggtcca  540
atcccatctt ctctctctct cctcacccaa ctccgctatc tcgacgtttc ctacaacaat  600
ctaaatggca ctcttccctt atcgctcgtt gagaagatgt cggagctcag ctaccttaac  660
cttaggtata actctttcta cggtgagatt ccaccggagt ttgggaaact taagaagctt  720
gaaacattga atcttggtaa caacactctt tctgggagtc ttccatctga gttgggttca  780
ttaaagagtt tgaaacatat ggacttttct agtaatatgc tatttggtga gatcccacaa  840
tcttattctc ttcttcgaaa cttaatcgat attgatctta atagaaacaa gttatatggg  900
agtatacctg attatattgg agattttccg gagttggaat cacttttatt agactcgaat  960
aacttcacag ggagtatccc acaaaagtta ggtacaaacg ggaagttgca atatctagat  1020
ataagtaaca acaattttag tggtagtttg ccactaagtc tttgcaaagg agacaaactc  1080
caagatctgg acgcatccta taatttgttg gttgggtcaa ttcctgagag tttgggaagt  1140
tgcaagtcac ttgaaggagt gtacatggga aataatttct taaacgggtc gattcctaag  1200
ggcttgtttg ggagtgatgt ttcacttaat gacaaacttc ttagtggagg tctcgatgag  1260
aaattcggtg attgcgttaa tcttcgggac attgatctct ctaataataa gctatcaggg  1320
aagttacctg cgaccatcgg aaactgtatt catcttcggt ccttgacgct ttataataac  1380
acctgtaccg gacgtatccc tcaagagatt agcaagtgta agcagctaca gaccctcgat  1440
ctcagccaaa atcagttctc tggtgtgata cccaatgata ttacaggaaa caaatccatt  1500
tgcaatctgg aaaagataca aacacttaaa ttatcaaaca atgctttgac tggtgaaatc  1560
cctcattgtg ttggaaatat cgagctcata gcattatttc tccaatcaaa caaactgaac  1620
ggtaccatac ccgcaaactt ctcaaagtta tgtgattcat tgatatatct agatcttagt  1680
gacaatcaac tcgaaggagt tctacctaag tccttgtcca aatgtcaaag tctagaactc  1740
ctaaatgtcg ggaacaatag gctaagagat aaatttcctt catggttaga caacctccca  1800
cgtctccaag ttttcagtgt gcgttttaac gccttctacg gtcctataac tagctcacca  1860
aaagttagtc acccatttcc tatgctacaa attatcgacc tatctaacaa taagttttgt  1920
ggcaagttgc caagaagata tatcaaaaac tttgcaacca tgcgcaatat gaatgagtct  1980
ggtgttggga atccacagta cctgggggac tcatcaatat atagtattac gtactctatg  2040
gtattgacat tcaatgggtt acaacaaaaa tatgaaaagc ttattgtgac gatgtcgacc  2100
tttgatatat ccagcaacaa ctttactgga cagattccat atgttatagg gggattacgc  2160
tcacttcgta accttaatct ctctcataat gtcttaaccg ggaacattcc tccatcaatt  2220
gcaaaattgt ctttgcttca agatttggac ctttcatcaa acagacttac tggtcgtatc  2280
cctcaagaat tagttagttt aacatttctt gggagtttca atgtttcgaa caatctattg  2340
gaggggtcta tacctcatgg tttcaacttc gacacgtaca cagctaattc ataccagggg  2400
aatctcgaat tatgtggaaa accattacct gagtgtggag aaagaagggc aaaaggcacc  2460
actaataatc aagatgatcc taaaaatgat aatgaacgaa tgttgtcgat gtccgaaatc  2520
gtagttatgg ggtttggcag tggtgtacta gttgggttgg cttggggata ctatatgttt  2580
tcagtgggaa agcccttttg gtttatcaag atggctagca aaatggaatc aatattgatt  2640
ggtttttct ga                                                      2652

SEQ ID NO: 98          moltype = DNA  length = 21
FEATURE                Location/Qualifiers
source                 1..21
                       mol_type = unassigned DNA
                       organism = Beta vulgaris
SEQUENCE: 98
cgtttccggc aacagtttca c                                           21

SEQ ID NO: 99          moltype = DNA  length = 21
FEATURE                Location/Qualifiers
source                 1..21
                       mol_type = unassigned DNA
                       organism = Beta vulgaris
SEQUENCE: 99
agagagagag aggagtgggt t                                           21

SEQ ID NO: 100         moltype = AA  length = 883
FEATURE                Location/Qualifiers
source                 1..883
                       mol_type = protein
                       organism = synthetic construct
SEQUENCE: 100
MNMKILLLFV FLHHLHYFIH GRTLTERQAL LSIKSAITYD YYNSLSSWKN TTHHCSWPYI  60
TCSSSSSSSS VISLNFTMLF LEGILSPDIG FLTNLQNLSI RSNLFSGPLP HSLSLLTQLR  120
YLDVSQNSFT GPIPSSLSLL TQLRYLHVSG NSFTGPIPSF LSLLTQLRYL DVSDNSFTGP  180
IPSSLSLLTQ LRYLDVSYNN LNGTLPLSLL EKMSELSYLN LRYNSFYGEI PPEFGKLKKL  240
ETLNLGNNTL SGSLPSELGS LKSLKHMDFS SNMLFGEIPQ SYSLLRNLID IDLNRNKLYG  300
SIPDYIGDFP ELESLLLDSN NFTGSIPQKL GTNGKLQYLD ISNNNFSGSL PLSLCKGDKL  360
QDLDASYNLL VGSIPESLGS CKSLEGVYMG NNFLNGSIPK GLFGSDVSLN DKLLSGGLDE  420
```

-continued

| | | | | | | |
|---|---|---|---|---|---|---|
| KFGDCVNLRD | IDLSNNKLSG | KLPATIGNCI | HLRSLTLYNN | TCTGRIPQEI | SKCKQLQTLD | 480 |
| LSQNQFSGVI | PNDITGNKSI | CNLEKIQTLK | LSNNALTGEI | PHCVGNIELI | ALFLQSNKLN | 540 |
| GTIPANFSKL | CDSLIYLDLS | DNQLEGVLPK | SLSKCQSLEL | LNVGNNRLRD | KFPSWLDNLP | 600 |
| RLQVFSVRFN | AFYGPITSSP | KVSHPFPMLQ | IIDLSNNKFC | GKLPRRYIKN | FATMRNMNES | 660 |
| GVGNPQYLGD | SSIYSITYSM | VLTFNGLQQK | YEKLIVTMST | FDISSNNFTG | QIPYVIGGLR | 720 |
| SLRNLNLSHN | VLTGNIPPSI | AKLSLLQDLD | LSSNRLTGRI | PQELVSLTFL | GSFNVSNNLL | 780 |
| EGSIPHGFNF | DTYTANSYQG | NLELCGKPLP | ECGERRAKGT | TNNQDDPKND | NERMLSMSEI | 840 |
| VVMGFGSGVL | VGLAWGYYMF | SVGKPFWFIK | MASKMESILI | GFF | | 883 |